`US011760736B2`

(12) United States Patent
Brak et al.

(10) Patent No.: US 11,760,736 B2
(45) Date of Patent: Sep. 19, 2023

(54) PROCESSES AND INTERMEDIATES FOR PREPARING MCL1 INHIBITORS

(71) Applicant: Gilead Sciences, Inc., Foster City, CA (US)

(72) Inventors: Katrien Brak, Belmont, CA (US); Kae M. Bullock, San Carlos, CA (US); Greg Cizio, San Mateo, CA (US); Kathy Dao, San Mateo, CA (US); Darryl D. Dixon, San Mateo, CA (US); Joshua R. Dunetz, Burlingame, CA (US); Luke D. Humphreys, Edmonton (CA); Valerie Huynh, Santa Clara, CA (US); Michael A. Ischay, San Mateo, CA (US); Trevor C. Johnson, San Mateo, CA (US); Jeffrey E. Merit, San Mateo, CA (US); Christopher S. Regens, San Francisco, CA (US); Eric A. Standley, Foster City, CA (US); Dietrich P. Steinhuebel, San Francisco, CA (US); Justin Y. Su, Foster City, CA (US); Tao Wu, Edmonton (CA); Marshall D. Young, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/701,404

(22) Filed: Mar. 22, 2022

(65) Prior Publication Data

US 2023/0013713 A1 Jan. 19, 2023

Related U.S. Application Data

(63) Continuation of application No. 17/100,107, filed on Nov. 20, 2020, now Pat. No. 11,325,891.

(60) Provisional application No. 62/940,387, filed on Nov. 26, 2019.

(51) Int. Cl.
| | | |
|---|---|---|
| C07D 267/16 | (2006.01) | |
| C07C 311/13 | (2006.01) | |
| C07D 317/30 | (2006.01) | |
| C07D 319/06 | (2006.01) | |
| C07D 413/12 | (2006.01) | |
| C07D 513/04 | (2006.01) | |

(52) U.S. Cl.
CPC .......... *C07D 267/16* (2013.01); *C07C 311/13* (2013.01); *C07D 317/30* (2013.01); *C07D 319/06* (2013.01); *C07D 413/12* (2013.01); *C07D 513/04* (2013.01)

(58) Field of Classification Search
CPC ............................. C07D 267/16; C07C 311/13
See application file for complete search history.

(56) References Cited

U.S. PATENT DOCUMENTS

| | | |
|---|---|---|
| 10,703,733 B2 | 7/2020 | Chu et al. |
| 10,988,451 B2 | 4/2021 | Chu et al. |
| 11,325,891 B2 | 5/2022 | Brak et al. |
| 2016/0068545 A1 | 3/2016 | Brown et al. |
| 2017/0088560 A1 | 3/2017 | Brown et al. |
| 2018/0289720 A1 | 10/2018 | Harrington et al. |
| 2019/0352271 A1 | 11/2019 | Chu et al. |
| 2020/0331870 A1 | 10/2020 | Chu et al. |
| 2021/0171543 A1 | 6/2021 | Chu et al. |
| 2021/0179570 A1 | 6/2021 | Brak et al. |
| 2022/0177409 A1 | 6/2022 | Dixon et al. |
| 2022/0340535 A1 | 10/2022 | Chu et al. |

FOREIGN PATENT DOCUMENTS

| | | | |
|---|---|---|---|
| WO | WO-2016/033486 A1 | 3/2016 | |
| WO | WO-2017/147410 A1 | 8/2017 | |
| WO | WO-2018/183418 A1 | 10/2018 | |
| WO | WO-2019/036575 A1 | 2/2019 | |
| WO | WO-2019/046150 A1 | 3/2019 | |
| WO | WO-2019/079578 A1 | 4/2019 | |
| WO | WO-2019/173181 A1 | 9/2019 | |
| WO | WO-2019/222112 A1 | 11/2019 | |
| WO | WO-2019/222266 A1 | 11/2019 | |
| WO | WO-2019/222269 A1 | 11/2019 | |
| WO | WO-2019222122 A1 * | 11/2019 | ............. E21B 44/00 |
| WO | WO-2020/023657 A1 | 1/2020 | |
| WO | WO-2020/097577 A1 | 5/2020 | |
| WO | WO-2020/147802 A1 | 7/2020 | |
| WO | WO-2021/005043 A1 | 1/2021 | |
| WO | WO-2021/096860 A1 | 5/2021 | |
| WO | WO-2021096860 A1 * | 5/2021 | ............. A61K 45/06 |
| WO | WO-2021/202452 A1 | 10/2021 | |
| WO | WO-2021/225823 A1 | 11/2021 | |
| WO | WO-2021/226168 A1 | 11/2021 | |
| WO | WO-2021/250102 A1 | 12/2021 | |
| WO | WO-2022/008674 A1 | 1/2022 | |
| WO | WO-2022/051317 A1 | 3/2022 | |
| WO | WO-2022/108984 A1 | 5/2022 | |

OTHER PUBLICATIONS

Invitation to Pay Additional Fees—Partial Intl. Search Report dated Feb. 26, 2021 for Intl. Appl. No. PCT/US2020/061517.
Office Action dated Dec. 17, 2021 for Taiwanese Appl. No. 109141559.
Intl. Search Report—Written Opinion dated Apr. 19, 2021 for Intl. Appl. No. PCT/US2020/061517.
Intl. Preliminary Report on Patentability dated Jun. 9, 2022 for Intl. Appl. No. PCT/US2020/061517.
Non-Final Office Action dated Sep. 27, 2021 for U.S. Appl. No. 17/100,107.
Notice of Allowance and Fees Due dated Mar. 18, 2022 for U.S. Appl. No. 17/100,107.
Notice of Allowance dated Jun. 17, 2022 for Taiwanese Appl. No. 109141559.

(Continued)

*Primary Examiner* — Matthew P Coughlin

(57) ABSTRACT

The present disclosure provides methods for preparing MCL1 inhibitors or a salt thereof and related key intermediates.

15 Claims, No Drawings

(56) References Cited

OTHER PUBLICATIONS

Examination Report dated Dec. 14, 2022 for Indian Appl. No. 202217030442.
Rombauts et al., (2021) CAPLUS AN 2021:114898.
Examination Report dated Mar. 31, 2023 for Australian Appl. No. 2020391106.
Jones, J. et al. (1982) "Enzymes in organic synthesis. 26. Synthesis of enantiomerically pure grandisol from an enzyme-generated chiral synthon", Canadian Journal of Chemistry, 60(15):2007-2011.
Pichon, C. et al. (2000) "Enzymatic acylation of cyclobutene and cyclobutane meso-diols at low temperature", Tetrahedron: Asymmetry, 11(11):2429-2434.
Office Action dated Apr. 20, 2023 for Japanese Appl. No. 2022-530220.

* cited by examiner

PROCESSES AND INTERMEDIATES FOR PREPARING MCL1 INHIBITORS

CROSS REFERENCE TO RELATED APPLICATIONS

This Application is a Continuation of application Ser. No. 17/100,107 filed on Nov. 20, 2020. Application Ser. No. 17/100,107 claims the benefit of U.S. Provisional Application 62/940,387 filed on Nov. 26, 2019. The entire contents of these applications are incorporated herein by reference in their entirety.

FIELD

The present disclosure relates to methods and intermediates for the synthesis of certain compounds which inhibit MCL1, for use in the treatment of cancers.

BACKGROUND

Apoptosis (programmed cell death) is a process for elimination of unwanted or potentially dangerous cells from an organism. Avoidance of apoptosis is critical for the development and sustained growth of tumors. Myeloid cell leukemia 1 protein (MCL1) is an antiapoptotic member of the Bcl-2 family of proteins. MCL1 is overexpressed in many cancers. Overexpression of MCL1 prevents cancer cells from undergoing apoptosis. Research has shown that MCL1 inhibitors can be used to treat cancers. Compounds that inhibit MCL1 have been disclosed, but there remains a need for synthetic methods for preparing such compounds on a manufacturing scale.

PCT Application No. PCT/US2019/032053 (WO 2019/222112) discloses novel compounds useful as MCL1 inhibitors. This patent publication discloses that compounds according to Formula (A), (A)

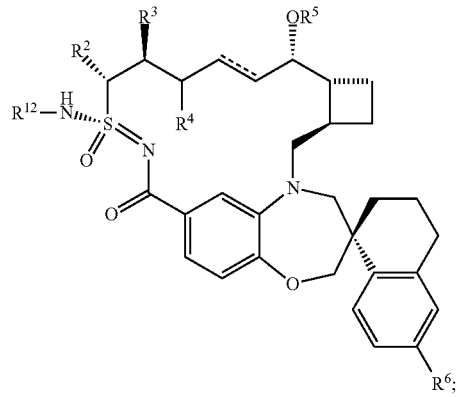

and pharmaceutically acceptable salts thereof, are effective as inhibitors of MCL1, and are useful in the treatment of cancers.

There is currently a need for synthetic methods and intermediates that can be used to prepare the compound of formula I and salts thereof. There is also a need for methods for preparing intermediate compounds that can be used to prepare the compound of formula I and salts thereof.

SUMMARY

The present disclosure provides methods for making compounds according to Formula (A), as shown above. In some embodiments, the present disclosure provides compounds according to Formula (I), (I)

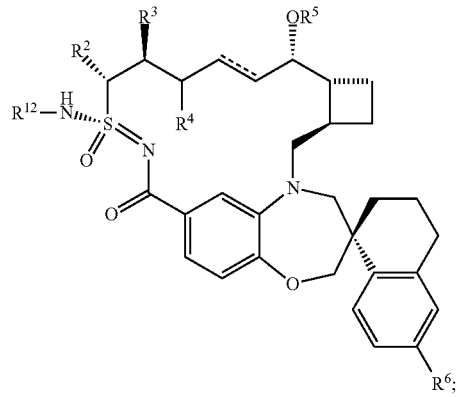

wherein: ═══ is a single or double bond;

$R^{12}$ is hydrogen or —C(O)$R^1$;

$R^1$ is $C_{1-6}$alkyl, $C_{1-6}$haloalkyl, $C_{2-6}$alkenyl, $C_{2-6}$alkynyl, $C_{3-10}$cycloalkyl, $C_{6-10}$aryl, 3-12 membered heterocycloalkyl, 5-10 membered heteroaryl, —O$R^7$, or —N$R^8R^9$, wherein said $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, and 5-10 membered heteroaryl are optionally substituted with 1-5 $R^{10}$ groups;

$R^2$ is hydrogen, $C_{1-6}$alkyl, $C_{1-6}$haloalkyl, $C_{3-10}$cycloalkyl, or 3-12 membered heterocycloalkyl, wherein said $C_{1-6}$alkyl, $C_{1-6}$haloalkyl, $C_{3-10}$cycloalkyl, and 3-12 membered heterocycloalkyl are optionally substituted with 1-5 $R^{10}$ groups;

$R^3$ is hydrogen, $C_{1-6}$alkyl, —O$R^7$, $C_{1-6}$haloalkyl, $C_{3-10}$cycloalkyl, 3-12 membered heterocycloalkyl, —C(O)$R^7$, or —CN, wherein said $C_{1-6}$alkyl, $C_{1-6}$haloalkyl, $C_{3-10}$cycloalkyl, and 3-12 membered heterocycloalkyl are optionally substituted with 1-5 $R^{10}$ groups;

$R^4$ is hydrogen;

$R^5$ is $C_{1-6}$alkyl, —(CH$_2$CH$_2$O)$_p$$R^7$, $C_{1-6}$haloalkyl, or $C_{3-10}$cycloalkyl, wherein said $C_{1-6}$alkyl, $C_{1-6}$haloalkyl, or $C_{3-10}$cycloalkyl, are optionally substituted with 1-5 $R^{10}$ groups;

$R^6$ is hydrogen or halogen;

each $R^7$ is independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, wherein said $C_{1-6}$alkyl, $C_{3-10}$ cycloalkyl, $C_{1-6}$haloalkyl, 3-12 membered heterocycloalkyl, $C_{6-10}$ aryl, and 5-10 membered heteroaryl are optionally substituted with from 1-5 $R^{10}$ groups;

each $R^8$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$ cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups;

each $R^{10}$ is independently $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_qR^a$, —$S(O)_2NR^aR^b$, —$NR^aS(O)_2R^b$, —$N_3$, —CN, or —$NO_2$, or two $R^{10}$ groups form a fused, spiro, or bridged $C_{3-10}$cycloalkyl or 3-12 membered heterocycloalkyl, wherein said $C_{1-6}$alkyl, $C_{1-6}$haloalkyl, $C_{2-6}$alkynyl, $C_{3-10}$cycloalkyl, $C_{6-10}$aryl, 3-12 membered heterocycle, and 5-10 membered heteroaryl is optionally substituted with 1-5 $R^{20}$ groups;

each $R^a$ and $R^b$ is independently hydrogen, $C_{1-6}$alkyl, $C_{2-6}$ alkenyl, $C_{3-10}$ cycloalkyl, $C_{1-6}$ haloalkyl, 3-12 membered heterocycloalkyl, $C_{6-10}$aryl, 5-10 membered heteroaryl, or $R^a$ and $R^b$ together with the atoms to which they are attached form a 3-12 membered heterocycloalkyl, wherein said $C_{1-6}$alkyl, $C_{2-6}$alkenyl, $C_{3-10}$cycloalkyl, $C_{1-6}$haloalkyl, 3-12 membered heterocycloalkyl, $C_{6-10}$aryl, 5-10 membered heteroaryl is optionally substituted with 1-5 $R^{20}$ groups;

each $R^{20}$ is independently $C_{1-6}$ alkyl, $C_{3-10}$ cycloalkyl, $C_{1-6}$haloalkyl, 3-12 membered heterocycloalkyl, $C_6$-$C_{10}$ aryl, 5-10 membered heteroaryl, hydroxyl, $C_{1-6}$ alkoxy, amino, —CN, —C(O)H, —C(O)$NH_2$, —C(O)NH($C_{1-6}$ alkyl), —C(O)N($C_{1-6}$ alkyl)$_2$, —COOH, —C(O)$C_{1-6}$ alkyl, —C(O)O$C_{1-6}$ alkyl, or halogen;

p is 0, 1, or 2; and q is 0, 1, or 2;

and pharmaceutically acceptable salts thereof. In some embodiments, the compound of Formula I is a compound according to Formula I(a):

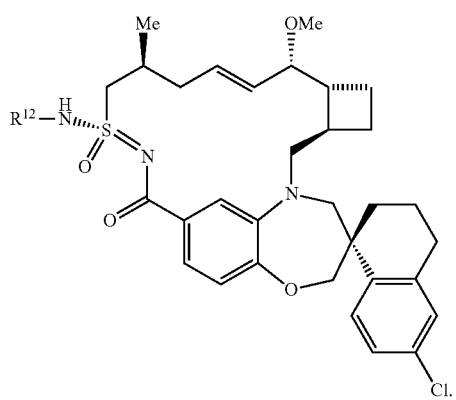

(Ia)

In particular embodiments, the present disclosure provides methods of making the Compound 1:

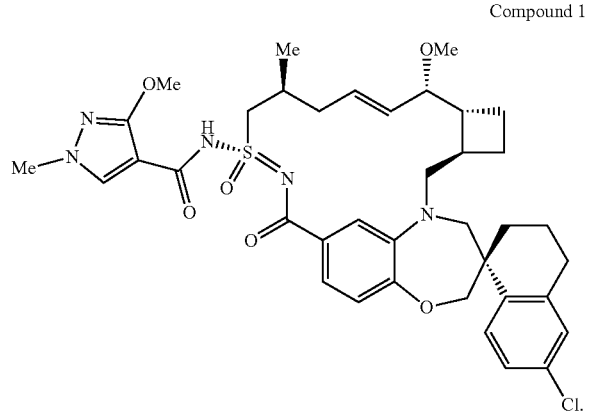 [SMILES: COc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Compound 1

Compounds of Formula A (as well as formulae I and I(a)) can be schematically divided into four functional regions, as shown below, each separated by one of four critical synthetic bonds (dotted lines):

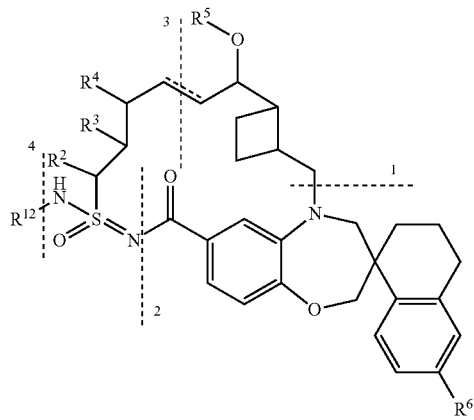

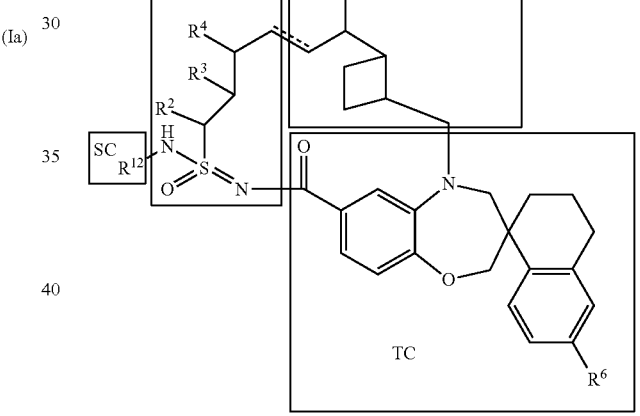

Thus, the Compounds of Formula A (as well as formulae I and I(a)) can be considered to contain four main subparts: a tetracyclic core (TC), and in particular, a 6'-substituted-3,4-dihydro-2H,2'H,4H-5λ²-spiro[benzo[b][1,4]oxazepane-3,1'-napthenelene-7-acyl moiety; a disubstituted cyclobutane moiety (CB); a multi-substituted sulfonimidamide moiety (SNO); and sn N-linked side-chain (SC).

In this structure, the TC and CB moieties are connected by a single N—C alkylamine bond (numbered 1), the TC and SNO moieties are connected by a single N—C acylamide bond (numbered 2), the CB and SNO moieties are connected by a C—C alkyl or C═C alkenyl bond (numbered 3), and the SC and SNO moieties are connected by an N—H or N—C single bond (numbered 4), depending on the identity of $R^{12}$.

WO 2019/222112 has disclosed a process of preparing the compounds of Formula A (including formula I and I(a)). In the process, the critical synthetic bonds are formed in the order 1, 2, 4 then 3. Thus, the process may be abbreviated schematically as follows:

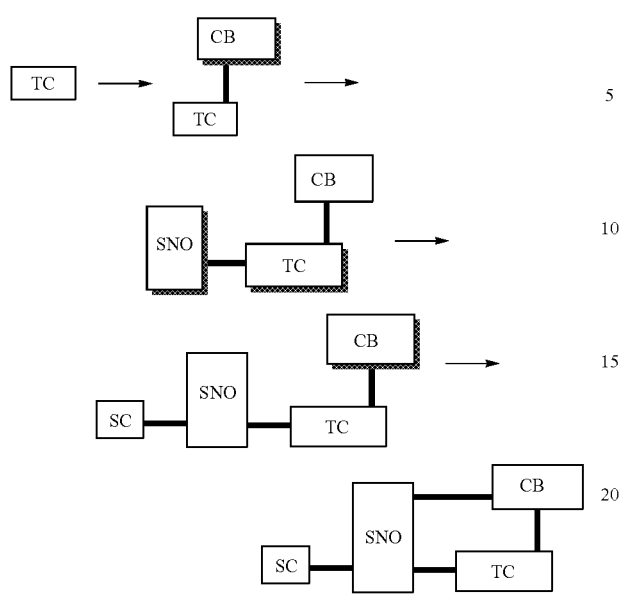

It is understood that in this nomenclature, when discussing a synthetic route which will build up and connect the key fragments in a stepwise manner, there may be protecting groups and other temporary substituents present in more intermediates which will not match the final substituents or structural motifs seen in the final compound of Formula A.

The process disclosed in WO 2019/222112

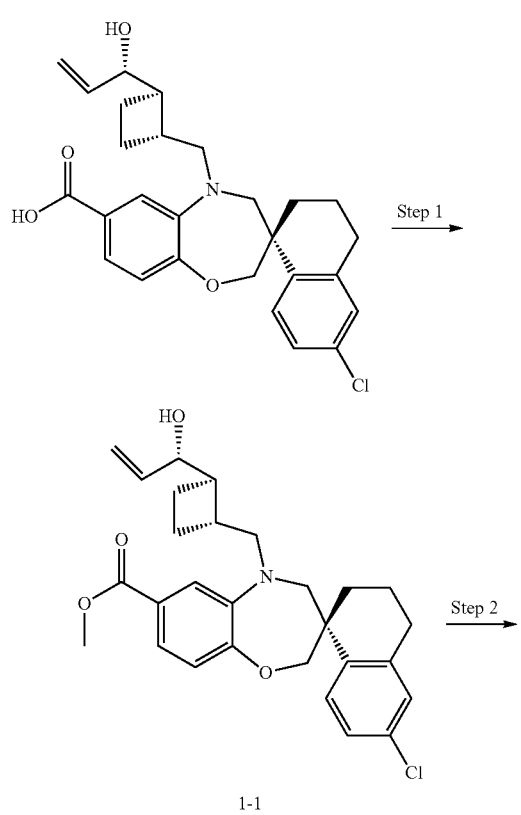

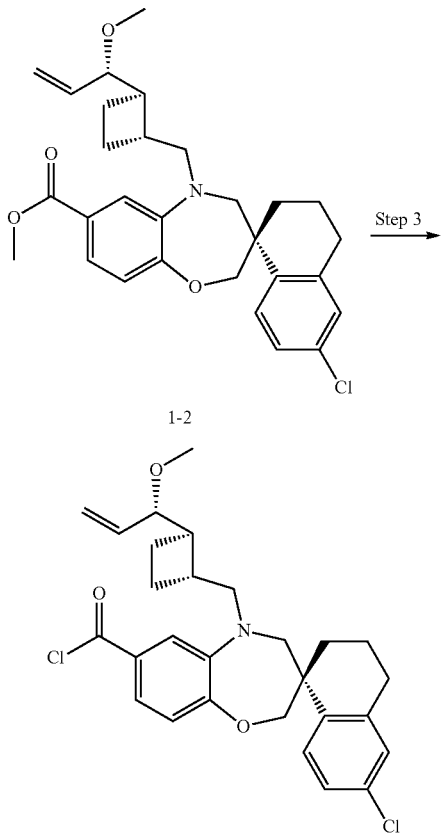

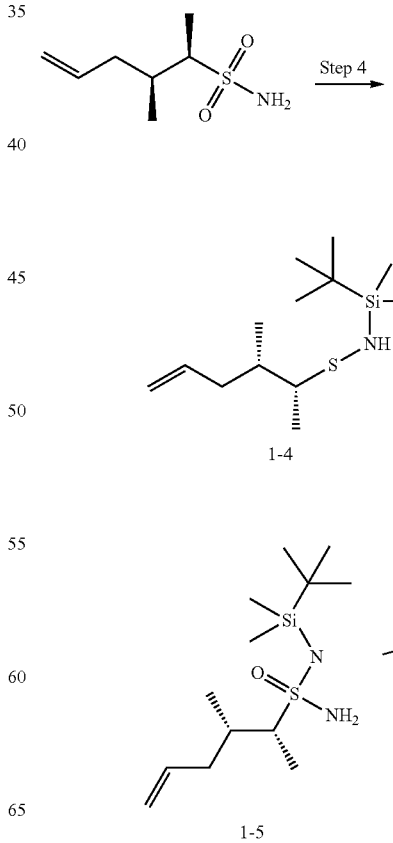

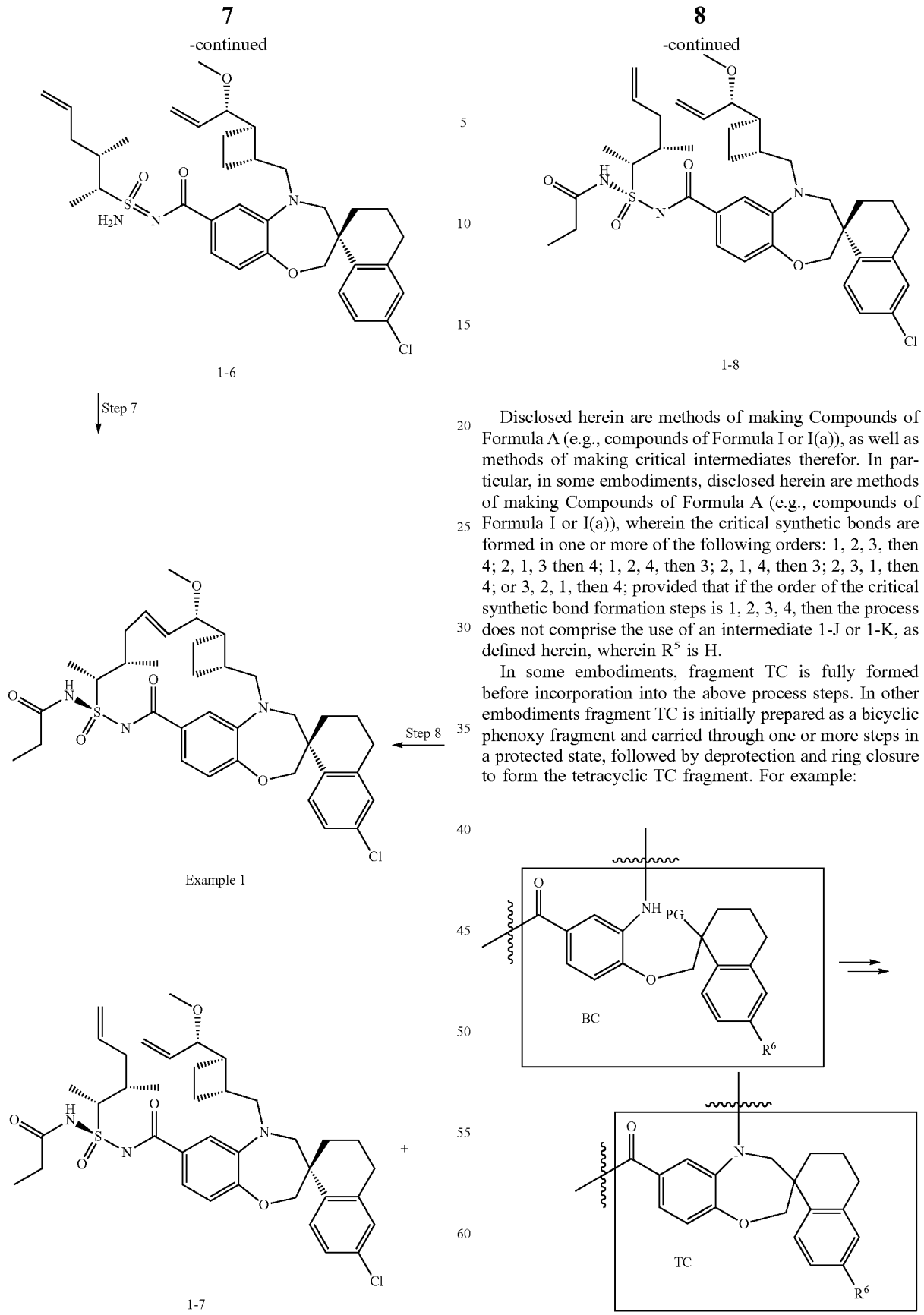

Disclosed herein are methods of making Compounds of Formula A (e.g., compounds of Formula I or I(a)), as well as methods of making critical intermediates therefor. In particular, in some embodiments, disclosed herein are methods of making Compounds of Formula A (e.g., compounds of Formula I or I(a)), wherein the critical synthetic bonds are formed in one or more of the following orders: 1, 2, 3, then 4; 2, 1, 3 then 4; 1, 2, 4, then 3; 2, 1, 4, then 3; 2, 3, 1, then 4; or 3, 2, 1, then 4; provided that if the order of the critical synthetic bond formation steps is 1, 2, 3, 4, then the process does not comprise the use of an intermediate 1-J or 1-K, as defined herein, wherein $R^5$ is H.

In some embodiments, fragment TC is fully formed before incorporation into the above process steps. In other embodiments fragment TC is initially prepared as a bicyclic phenoxy fragment and carried through one or more steps in a protected state, followed by deprotection and ring closure to form the tetracyclic TC fragment. For example:

wherein PG represents a protected aldehyde, for example, PG is $CH(OC_{1-6}alkyl)(OC_{1-6}alkyl)$ or $-O(C_{2-10}alkyl)O-$.

DETAILED DESCRIPTION

Therefore, in a first aspect, the present disclosure provides a Method (Method A) for making a Compound of Formula A (e.g., a compound of Formula I or I(a)), as described above, wherein the method comprises the steps of:

(a) (1) Synthesizing fragment TC (or BC), (2) synthesizing fragment CB, (3) joining fragment TC (or BC) to fragment CB by forming Bond 1, (4) synthesizing fragment SNO, (5) joining fragment TC-CB (or BC-CB) to fragment SNO by forming Bond 2, (6) connecting the CB moiety and the SNO moiety of the SNO-TC-CB (or SNO-BC-CB) fragment by forming Bond 3 intramolecularly, and (7) attaching the SC moiety to the SNO-TC-CB (or SNO-BC-CB) fragment by forming Bond 4 to form the compound of Formula A;

provided that at no point in the process is the TC-CB fragment a compound of formula intermediate 1-J or 1-K, as defined herein, wherein $R^5$ is H; or (b) (1) Synthesizing fragment SNO, (2) synthesizing fragment TC (or BC), (3) joining fragment SNO to fragment TC (or BC) by forming Bond 2, (4) synthesizing fragment CB, (5) joining fragment TC-SNO (or BC-SNO) to fragment CB by forming Bond 1, (6) connecting the CB moiety and the SNO moiety of the SNO-TC-CB (or SNO-BC-CB) fragment by forming Bond 3 intramolecularly, and (7) attaching the SC moiety to the SNO-TC-CB (or SNO-BC-CB) fragment by forming Bond 4 to form the compound of Formula A; or (c) (1) Synthesizing fragment TC (or BC), (2) synthesizing fragment CB, (3) joining fragment TC (or BC) to fragment CB by forming Bond 1, (4) synthesizing fragment CNO, (5) joining fragment TC-CB (or BC-CB) to fragment CNO by forming Bond 2, (6) attaching the SC moiety to the SNO-TC-CB (or SNO-BC-CB) fragment by forming Bond 4, and (7) connecting the CB moiety and the SNO moiety of the SC-SNO-TC-CB (or SNO-BC-CB) fragment by forming Bond 3 intramolecularly to form the compound of Formula A; or (d) (1) Synthesizing fragment SNO, (2) synthesizing fragment TC (or BC), (3) joining fragment SNO to fragment TC (or BC) by forming Bond 2, (4) synthesizing fragment CB, (5) joining fragment TC-SNO (or BC-SNO) to fragment CB by forming Bond 1, (6) attaching the SC moiety to the SNO-TC-CB (or SNO-BC-CB) fragment by forming Bond 4, and (7) connecting the CB moiety and the SNO moiety of the SC-SNO-TC-CB (or SC-SNO-BC-CB) fragment by forming Bond 3 intramolecularly to form the compound of Formula A; or (e) (1) Synthesizing fragment TC (or BC), (2) synthesizing fragment SNO, (3) joining fragment TC (or BC) to fragment SNO by forming Bond 2, (4) synthesizing fragment CB, (5) joining fragment TC-SNO (or BC-SNO) to fragment CB by forming Bond 3, (6) connecting the CB moiety and the SNO moiety of the SNO-TC-CB (or SNO-BC-CB) moiety by forming Bond 2 intramolecularly, and (7) attaching the SC moiety to the SNO-TC-CB (or SNO-BC-CB) fragment by forming Bond 4 to form the compound of Formula A; or (f) (1) Synthesizing fragment SNO, (2) synthesizing fragment CB, (3) joining fragment SNO to fragment CB by forming Bond 3, (4) synthesizing fragment TC (or BC), (5) joining fragment SNO-CB to fragment TC (or BC) by forming Bond 2, (6) connecting the CB moiety and the TC (or BC) moiety of the SNO-TC-CB (or SNO-BC-CB) fragment by forming Bond 1 intramolecularly, and (7) attaching the SC moiety to the SNO-TC-CB (or SNO-BC-CB) fragment by forming Bond 4 to form the compound of Formula A;

optionally wherein any of the preceding processes further comprises the step of converting any intermediate comprising a fragment BC into the same intermediate comprising a fragment TC, for example, if step (3) joins fragment SNO to fragment BC by forming Bond 2, then step (3') may convert fragment SNO-BC to fragment SNO-TC, followed by the remaining steps (e.g., in process (b) or process (d)); or if step (5) joins fragment SNO-CB to fragment BC to form fragment SNO-BC-CB, then step (5') may convert fragment SNO-BC-CB to fragment SNO-TC-CB (without Bond 1), followed by the remaining steps or, alternatively, step (6') may convert fragment SNO-BC-CB to fragment SNO-TC-CB (with Bond 1), followed by the remaining steps (e.g., in process (f));

wherein, fragment BC is:

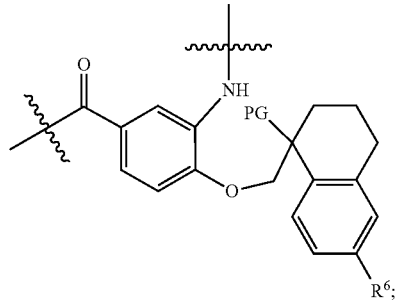

fragment TC is:

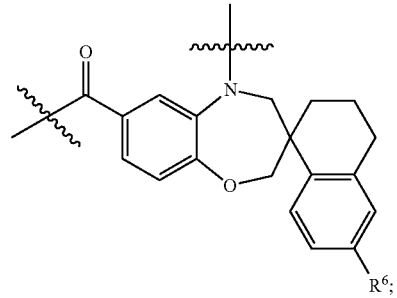

fragment CB is:

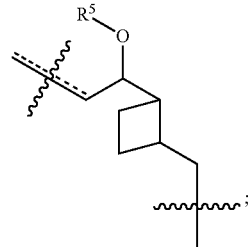

fragment SNO is:

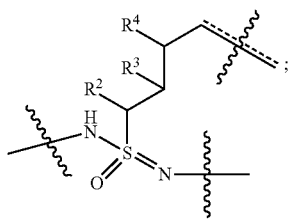

fragment SC is R[12]; and PG is a protecting group (e.g., CH(OC$_{1-6}$alkyl)(OC$_{1-6}$alkyl) or —O(C$_{2-10}$alkyl)O—); and wherein all other substituents are as defined for the compound of Formula A herein.

In some embodiments, the product of Method A is a Compound I, a Compound I(a), or Compound 1, as defined herein. In some embodiments, Method A may comprise one or more steps, in any order and any combination, as provided in any embodiments of Method 1, Method 2, Method 3, Method 4, and Method 5 as described herein.

In a second aspect, the present disclosure provides a method (Method 1) of making a compound selected from one or more of Compounds 1-B, 1-C, 1-D, 1-E, 1-F, 1-G, 1-H, 1-I, 1-J, 1-K, 2-B, 2-C, 2-D, 2-E, 3-A, 3-B, 3-C, 3-D, 9-A, 9-B, 9-C, 9-D, 9-E, and Compound I or I(a), as hereinbefore described, wherein the method comprises the step of reacting a precursor compound with one or more reagents in a suitable solvent for a time and under conditions effective to form the product compound. Method 1 generally pertains to formation of the cyclobutyl moiety (CB), including advanced intermediates 1-I, 1-J, and 1-K, as well as the evolution of those intermediates to Compound 1. Without being limited in the order or combination of steps employed, the potential embodiments of Method 1 may include any steps shown in Schemes 1, 2 and 3.

Scheme 1

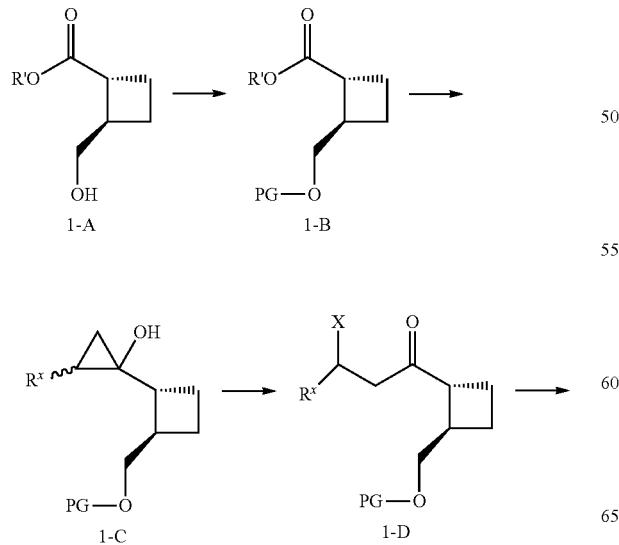

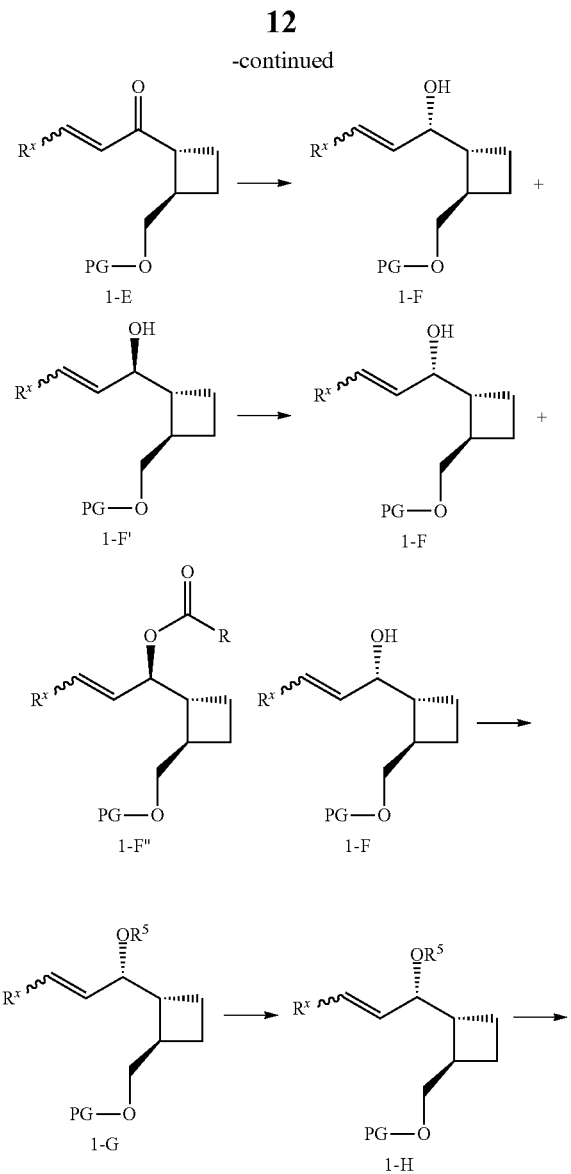

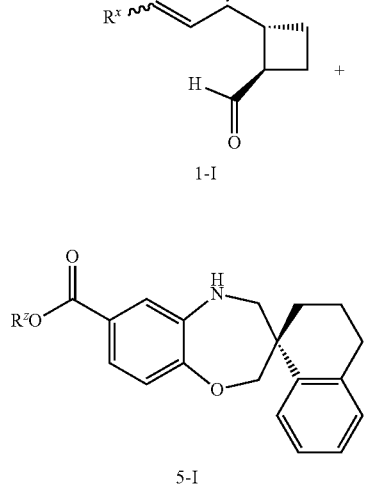

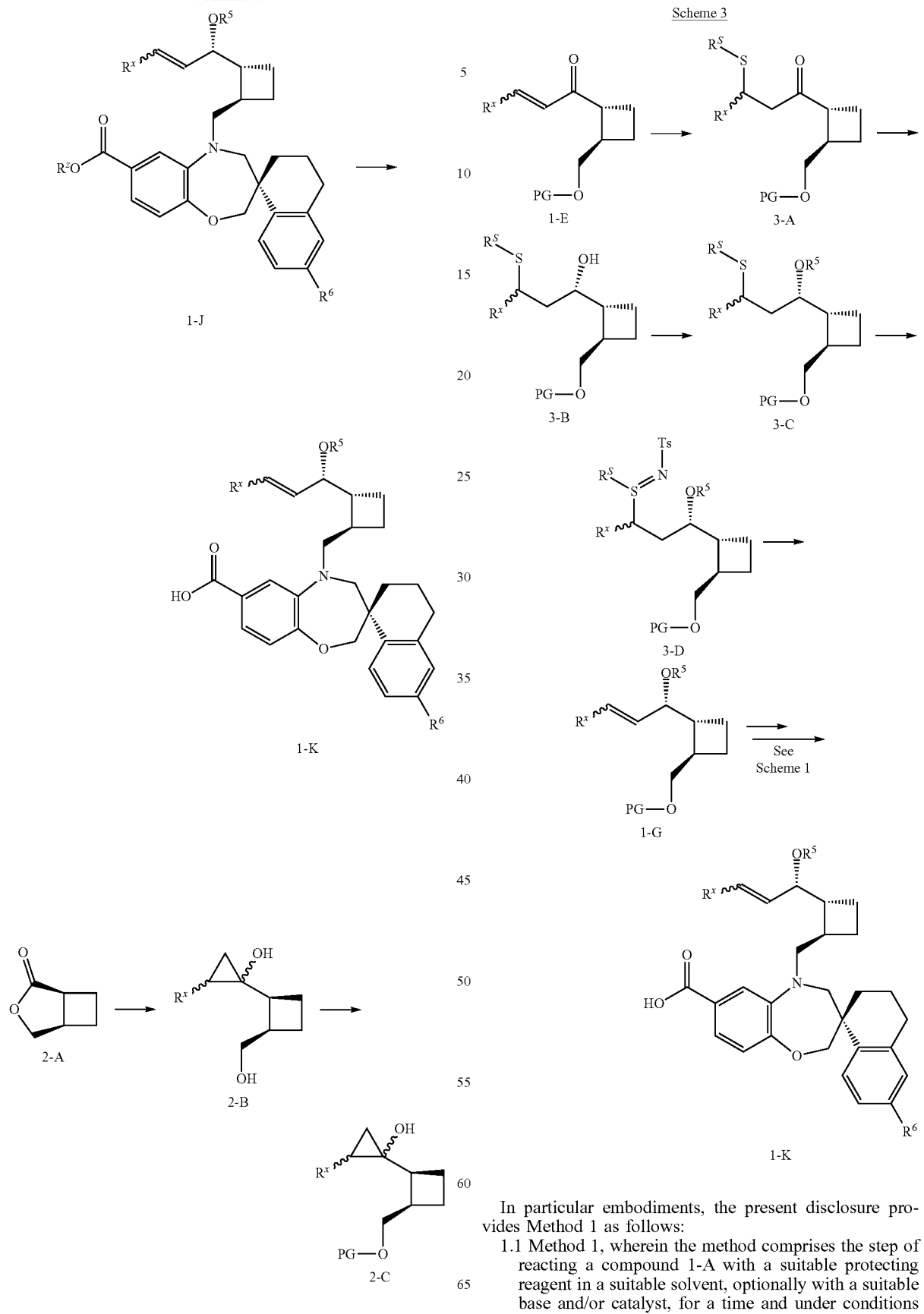
In particular embodiments, the present disclosure provides Method 1 as follows:
1.1 Method 1, wherein the method comprises the step of reacting a compound 1-A with a suitable protecting reagent in a suitable solvent, optionally with a suitable base and/or catalyst, for a time and under conditions effective to yield a compound 1-B; wherein R' is $C_{1-6}$alkyl (e.g., methyl, ethyl, propyl, isopropyl, n-butyl, or t-butyl), optionally R' is methyl;

1.2 Method 1.1, wherein the substituent PG is selected from a silyl group, an alkylcarbonyl group (e.g., —C(=O)—$C_{1-6}$alkyl, such as acetyl, isobutyryl, pivaloyl, adamantanecarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl), an aryloxycarbonyl group (e.g., phenoxycarbonyl), a tertiary alkyl group (e.g., t-butyl or trityl), an alkoxyalkyl group (e.g., methoxymethyl or ethoxymethyl), or a $C_{1-6}$alkylaryl group (e.g., benzyl, 3,5-dimethoxybenzyl);

1.3 Method 1.2, wherein the substituent PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

1.4 Method 1.3, wherein the substituent PG is a tert-butyldiphenyl silyl group, optionally wherein the protecting agent is tert-butyldiphenylsilyl chloride;

1.5 Any of Methods 1.1-1.4, wherein the protecting reagent is selected from silyl chlorides (e.g., chlorotrimethylsilane, chlorotriethylsilane, chlorotripropylsilane, triisopropylsilyl chloride, tert-butyldimethylsilyl chloride, chlorodimethylphenylsilane, chlorotriphenylsilane), silyl trifluoromethanesulfonates (e.g., trimethylsilyl trifluoromethanesulfonate, triethylsilyl trifluoromethanesulfonate, triisopropylsilyl trifluoromethanesulfonate, tert-butyldimethylsilyl trifluoromethanesulfonate, dimethylphenylsilyl trifluoromethanesulfonate, triphenylsilyl trifluoromethanesulfonate), silyl bromides (e.g., bromotrimethylsilane, bromotriethylsilane, bromotripropylsilane, triisopropylsilyl bromide, tert-butyldimethylsilyl bromide, bromodimethylphenylsilane, bromotriphenylsilane), N,O-bis(trimethylsilyl)acetamide, N,O-bis(trimethylsilyl) trifluoroacetamide, N-methyl-N-(trimethylsilyl) trifluoroacetamide, benzyl halides (e.g., 3,5-dimethoxybenzyl chloride, 3,5-dimethoxybenzyl bromide), dibenzyl carbonate, acid chlorides (e.g., pivaloyl chloride, 1-adamantanecarbonyl chloride), anhydrides (e.g., di-tert-butyl carbonate), chloroformates (e.g., methyl chloroformate, ethyl chloroformate, benzyl chloroformate, phenyl chloroformate), alkyl chlorides (e.g., trityl chloride), and alkoxymethyl chlorides (e.g., methoxymethyl chloride);

1.6 Any of Methods 1.1-1.5, wherein the reaction comprises a base;

1.7 Method 1.6, wherein the base is selected from tertiary amines (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane), aromatic amines (e.g., pyridine, 2,6-lutidine, collidine, 1-methylimidazole), and inorganic bases (e.g., lithium carbonate, sodium carbonate, potassium carbonate, calcium carbonate, potassium phosphate (monobasic, dibasic or tribasic), sodium phosphate (monobasic, dibasic or tribasic));

1.8 Method 1.7, wherein the base is triethylamine;

1.9 Any of Methods 1.1-1.8, wherein the reaction comprises a catalyst;

1.10 Method 1.9, wherein the catalyst is selected from 4-(dimethylamino)pyridine, N-methylimidazole, 4-pyrrolidinopyridine, 4-piperidinopyridine, and 9-azajulolidine;

1.11 Method 1.10, wherein the catalyst is 4-(dimethylamino)pyridine;

1.12 Any of Methods 1.1-1.11, wherein the suitable solvent is a nonpolar solvent or polar aprotic solvent;

1.13 Method 1.12, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

1.14 Method 1.12, wherein the polar aprotic solvent is selected from N,N-dimethylformamide, N,N-dimethylacetamide, N-methyl-2-pyrrolidinone, dimethyl sulfoxide, and nitriles (e.g., acetonitrile);

1.15 Method 1.12, wherein the nonpolar solvent is a halogenated solvent, optionally, wherein the solvent is dichloromethane;

1.16 Any of Methods 1.1-1.15, wherein the temperature of the reaction is from −30 to 40° C., e.g., from −10 to 30° C., or about 0° C. to 25° C.;

1.17 Method 1, or any of 1.1-1.16, wherein the method comprises the step of reacting a compound 1-B with an organometallic reagent in a suitable solvent for a time and under conditions effective to form a 1-hydroxycyclopropane compound 1-C, wherein R' is defined as in Method 1.1, and PG is defined as provided in Method 1.2, 1.3 or 1.4;

1.18 Method 1.17, wherein the substituent $R^x$ is selected from H, $C_{1-6}$alkyl (e.g., methyl), and $C_{6-10}$aryl (e.g. phenyl), wherein the alkyl is optionally substituted with $C_{6-10}$aryl (e.g., phenyl);

1.19 Method 1.18, wherein $R^x$ is H;

1.20 Method 1.17, 1.18 or 1.19 wherein the organometallic reagent is an organolithium reagent (e.g., $C_{1-6}$alkyl lithium) or a Grignard reagent (e.g., $C_{1-6}$alkylmagnesium halide);

1.21 Method 1.20, wherein the organometallic reagent is selected from ethylmagnesium bromide, ethylmagnesium chloride, n-propylmagnesium bromide and 2-phenylethylmagnesium bromide, each optionally provided as a solution in an ethereal solvent (e.g., tetrahydrofuran, methyl tert-butyl ether, diethyl ether, dibutyl ether, dioxane);

1.22 Any of Methods 1.17-1.21, wherein the reaction further comprises a transition metal promoter, such as a titanium(IV) compound;

1.23 Method 1.22, wherein the promoter is a titanium(IV) alkoxide (e.g., titanium(IV) methoxide, titanium(IV) ethoxide, titanium(IV) propoxide, titanium(IV) isopropoxide, or titanium(IV) butoxide);

1.24 Any of Methods 1.20-1.23, wherein the organometallic reagent is ethylmagnesium bromide and the promoter is titanium(IV) isopropoxide;

1.25 Any of Methods 1.17-1.24, wherein the suitable solvent is a nonpolar solvent or polar aprotic solvent;

1.26 Method 1.25, wherein the nonpolar solvent is selected from ethers (e.g., tetrahydrofuran, 2-methyltetrahydrofuran, methyl tert-butyl ether, cyclopentyl methyl ether. dioxane), hydrocarbon solvents (e.g., toluene, n-hexane, n-heptane), and halogenated solvents (e.g., 1,2-dichloroethane, chloroform, chlorobenzene);

1.27 Method 1.25, wherein the polar aprotic solvent is selected from N,N-dimethylformamide, N,N-dimethylacetamide, N-methyl-2-pyrrolidinone, dimethyl sulfoxide, and nitriles (e.g., acetonitrile);

1.28 Method 1.25, wherein the nonpolar solvent is an ethereal solvent, optionally, wherein the solvent is tetrahydrofuran;

1.29 Any of Methods 1.17-1.28, wherein the temperature of the reaction is from −20 to 30° C., e.g., from −5 to 15° C., or about 0° C. to 5° C.;

1.30 Method 1, or any of Methods 1.1-1.29, wherein the method comprises the step of reacting a compound 1-C with a halogenating agent in a suitable solvent for a time and under conditions effective to form beta-halo ketone compound 1-D, wherein PG is defined as provided in Method 1.2, 1.3 or 1.4, and $R^x$ is defined as in Method 1.18 or 1.19;

1.31 Method 1.30, wherein the substituent X is selected from bromo, chloro and iodo;

1.32 Method 1.31, wherein X is bromo;

1.33 Method 1.30, 1.31 or 1.32 wherein the halogenating agent is selected from N-bromosuccinimide, N-bromophthalimide, bromine, 1,3-dibromo-5,5-dimethylhydantoin, N-bromosaccharin, hypobromous acid, N-chlorophthalimide, N-chlorosuccinimide, N-chlorosaccharin, 1,3-dichloro-5,5-dimethylhydantoin, N-iodosucciminide, N-iodophthalimide, and iodine;

1.34 Method 1.33, wherein the halogenating agent is selected from N-bromosuccinimide, N-bromophthalimide, bromine, 1,3-dibromo-5,5-dimethylhydantoin, N-bromosaccharin, and hypobromous acid;

1.35 Method 1.34, wherein the halogenating agent is N-bromosuccinimide;

1.36 Any of Methods 1.30-1.35, wherein the suitable solvent is a nonpolar solvent;

1.37 Method 1.36, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

1.38 Method 1.37, wherein the nonpolar solvent is a halogenated solvent, optionally wherein the solvent is dichloromethane;

1.39 Any of Methods 1.30-1.38, wherein the temperature of the reaction is from −20 to 30° C., e.g., from −5 to 15° C., or about 0° C. to 5° C.;

1.40 Any of Methods 1.30-1.39, wherein the compound 1-C is mixed (e.g., stirred or agitated) in the suitable solvent with the halogenating agent for 0.25 to 5 hours, e.g., 0.5 to 3 hours, or 1 to 2 hours, or about 1.5 hours;

1.41 Method 1, or any of Methods 1.1-1.40, wherein the method comprises the step of reacting a compound 1-D with a base in a suitable solvent for a time and under conditions effective to form an alpha, beta-unsaturated ketone compound 1-E, wherein PG is defined as provided in Method 1.2, 1.3 or 1.4, and $R^x$ is defined as in Method 1.18 or 1.19, and wherein X is chloro, bromo or iodo;

1.42 Method 1.41, wherein the base is selected from tertiary amines (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, DABCO), and aromatic amines (e.g., pyridine, 2,6-lutidine, collidine, 1-methylimidazole);

1.43 Method 1.42, wherein the base is selected from triethylamine, N,N-diisopropylethylamine, N-methylmorpholine, and 1,8-diazabicyclo[5.4.0]undec-7-ene;

1.44 Method 1.43, wherein the base is triethylamine;

1.45 Any of Methods 1.41-1.44, wherein the suitable solvent is a nonpolar solvent;

1.46 Method 1.45, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

1.47 Method 1.46, wherein the nonpolar solvent is a halogenated solvent, optionally wherein the solvent is dichloromethane;

1.48 Any of Methods 1.41-1.47, wherein the temperature of the reaction is from −20 to 30° C., e.g., from −5 to 15° C., or about 0° C. to 5° C.;

1.49 Any of Methods 1.30 to 1.48, wherein the conversion of compound 1-C to compound 1-D and the conversion of compound 1-D to compound 1-E takes place consecutively in the same vessel without isolation of compound 1-D;

1.50 Method 1, or any of Methods 1.1-1.49, wherein the method comprises the step of reducing an alpha, beta-unsaturated ketone compound 1-E to an allylic alcohol compound 1-F and its stereoisomer 1-F', wherein PG is defined as provided in Method 1.2, 1.3 or 1.4, and $R^x$ is defined as in Method 1.18 or 1.19;

1.51 Method 1.50, wherein the reduction is carried out by reacting the compound 1-E with a reducing agent and a Lewis acid catalyst, in a suitable solvent;

1.52 Method 1.51, wherein the reducing agent is selected from a borane agent (e.g., borane, a borane complex [e.g., $BH_3$-THF, $BH_3$-DMS, $BH_3$-CBS], 9-BBN), a borohydride agent (e.g., sodium borohydride, lithium borohydride, lithium triethylborohydride), an aluminum hydride agent (e.g., lithium aluminum hydride, diisobutylaluminum hydride), a hydrogen source (e.g., isopropanol) with a transfer hydrogenation agent (e.g., RuCl[(R,R)-Tsdpen](p-cymene), RuCl[(S,S)-Tsdpen](p-cymene), an aluminum alkoxide agent in an alcoholic solvent (e.g., aluminum triisopropoxide in ethanol), and a reductase enzyme (e.g., a ketoreductase);

1.53 Method 1.52, wherein the reducing agent is sodium borohydride;

1.54 Method 1.51, 1.52, or 1.53, wherein the Lewis acid is selected from cerium(III) chloride, magnesium bromide, magnesium chloride, magnesium iodide, calcium chloride, calcium bromide, and calcium iodide;

1.55 Method 1.54, wherein the Lewis acid is cerium(III) chloride, e.g., cerium(III) chloride heptahydrate or anhydrous cerium(III) chloride;

1.56 Any of Methods 1.50-1.55, wherein the suitable solvent is a polar protic solvent or nonpolar solvent;

1.57 Method 1.56, wherein the polar protic solvent is an alcohol (e.g., methanol, ethanol, propanol, isopropanol, butanol);

1.58 Method 1.56, wherein the nonpolar solvent is an ether (e.g., tetrahydrofuran, 2-methyltetrahydrofuran, methyl tert-butyl ether, cyclopentyl methyl ether, dioxane), a hydrocarbon solvent (e.g., toluene, n-hexane, n-heptane), or a halogenated solvent (e.g., dichloromethane, 1,2-dichloroethane, chloroform, chlorobenzene); 1.59 Method 1.56, wherein the solvent is ethanol;

1.60 Any of Methods 1.50-1.59, wherein the temperature of the reaction is from −30 to 30° C., e.g., from −20 to 20° C., or −10 to 0° C.;

1.61 Any of Methods 1.50-1.60, wherein products 1-F and 1-F' are not separated before the next step of the method;

1.62 Any of Methods 1.50-1.60, wherein the products 1-F and 1-F' are separated before the next step in the method;

1.63 Method 1, or any of Methods 1.1-1.62, wherein the method comprises the step of treating a mixture of allylic alcohol compounds 1-F and 1-F' with an acyl donor and an esterase enzyme, wherein PG is defined as provided in Method 1.2, 1.3 or 1.4, and $R^x$ is defined as in Method 1.18 or 1.19, wherein the acyl donor is an ester of an acid of the formula RCOOH;

1.64 Method 1.63, wherein the esterase enzyme selectively esterifies the (R)-allylic alcohol moiety of compound 1-F' to form ester 1-F''';

1.65 Method 1.64, wherein the esterase is a bacterial esterase, e.g., *Pseudomonas stutzeri* lipase;

1.66 Method 1.63, 1.64 or 1.65 wherein R is selected from H, $C_{1-6}$alkyl (e.g., methyl, ethyl, propyl, isopropyl, n-butyl, isobutyl), halo$C_{1-6}$alkyl (e.g., trifluoromethyl, trichloromethyl), $C_{1-6}$ alkylcarboxylate (e.g., 3-propionate, 4-butyrate), optionally substituted aryl (e.g., phenyl, 4-bromophenyl), and optionally substituted heteroaryl (e.g., 2-pyridyl);

1.67 Any of Methods 1.63-1.66, wherein the acyl donor is a vinyl ester, isopropenyl ester, methyl ester, ethyl ester, 2,2,2-trifluoroethyl ester, 2,2,2-trichloroethyl ester, or methoxyvinyl ester of an acid RCOOH, or is an anhydride of an acid RCOOH (including mixed and unmixed linear anhydrides and cyclic anhydrides of dicarboxylic acids), wherein R is defined as in Method 1.66;

1.68 Method 1.67, wherein the acyl donor is selected from succinic anhydride, vinyl acetate, isopropenyl acetate, ethyl acetate, isopropyl acetate, acetic anhydride, 2,2,2-trifluoroethyl acetate, 2,2,2-trichloroethyl acetate, methoxyvinyl acetate, vinyl propionate, vinyl valerate, vinyl isobutyrate, vinyl trifluoroacetate, vinyl trichloroacetate, vinyl benzoate, vinyl 4-bromoacetate, vinyl picolinate, glutaric anhydride, vinyl formate, vinyl butyrate, and butyric anhydride;

1.69 Any of Methods 1.63-1.68, wherein the suitable solvent is a nonpolar solvent or polar aprotic solvent;

1.70 Method 1.69, wherein the nonpolar solvent is selected from ethers (e.g., tetrahydrofuran, 2-methyltetrahydrofuran, methyl tert-butyl ether, cyclopentyl methyl ether, dioxane), and hydrocarbon solvents (e.g., toluene, n-hexane, n-heptane);

1.71 Method 1.69, wherein the polar aprotic solvent is selected from N,N-dimethylformamide, N,N-dimethylacetamide, N-methyl-2-pyrrolidinone, dimethyl sulfoxide, and nitriles (e.g., acetonitrile);

1.72 Method 1.69, wherein the nonpolar solvent is an ethereal solvent, optionally, wherein the solvent is methyl tert-butyl ether;

1.73 Any of Methods 1.63-1.72, wherein the temperature of the reaction is from 0 to 50° C., e.g., from 10 to 30° C., or about 20° C.;

1.74 Any of Methods 1.63-1.73, wherein upon completion of the reaction, the product mixture is purified to isolate the compound 1-F and/or to remove and discard the compound 1-F''';

1.75 Method 1, or any of Methods 1.1-1.74, wherein the method comprises the step of reacting a compound 1-F with an alkylating agent, and optionally a base, in a suitable solvent for a time and under conditions effective to form an ether compound 1-G, wherein PG is defined as provided in Method 1.2, 1.3 or 1.4, and $R^x$ is defined as in Method 1.18 or 1.19, and wherein $R^5$ is selected from $C_{1-6}$alkyl, $-(CH_2CH_2O)_pR^7$, $C_{1-6}$haloalkyl, and $C_{3-10}$cycloalkyl, wherein said $C_{1-6}$alkyl, $C_{1-6}$haloalkyl, or $C_{3-10}$cycloalkyl, are optionally substituted with 1-5 $R^{10}$ groups ($R^7$ and $R^{10}$ are as defined for the Compound of Formula I);

1.76 Method 1.75, wherein $R^5$ is selected from $C_{1-6}$alkyl and $C_{1-6}$haloalkyl, each optionally substituted with 1-3 groups selected from halogen, oxo, $C_{3-6}$cycloalkyl, and 4-6 membered heterocycloalkyl;

1.77 Method 1.76, wherein $R^5$ is $C_{1-6}$alkyl (e.g., methyl, ethyl, isopropyl, propyl, tert-butyl) optionally substituted with 1-3 halogen (e.g., fluoro);

1.78 Method 1.77, wherein $R^5$ is methyl;

1.79 Any of Methods 1.75-1.78, wherein the alkylating agent is a compound of the formula $R^5$—X, wherein X is selected from Cl, Br, I, $OS(O)_2OR^5$, and $OSO_2$-L wherein L is $C_{1-6}$alkyl, optionally substituted aryl, or halo$C_{1-6}$alkyl;

1.80 Method 1.79, wherein the alkylating agent is selected from an alkyl bromide, alkyl chloride, alkyl iodide, alkyl triflate, alkyl tosylate, alkyl mesylate, alkyl nosylate, alkyl benzenesulfonate, and dialkyl sulfate;

1.81 Method 1.80, wherein the alkylating agent is selected from methyl iodide, methyl triflate, methyl tosylate and dimethyl sulfate;

1.82 Any of Methods 1.75-1.81, wherein the reaction further comprises a base selected from inorganic hydrides (e.g., sodium hydride, potassium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide), inorganic hydroxides (e.g., sodium hydroxide, potassium hydroxide, or lithium hydroxide), and amide bases (e.g., sodium hexamethyldisilazide, lithium hexamethyldisilazide, potassium hexamethyldisilazide, lithium diisopropylamide, sodium diisopropylamide, or potassium diisopropylamide);

1.83 Method 1.82, wherein the base is sodium t-butoxide;

1.84 Any of Methods 1.75-1.83, wherein the suitable solvent is a nonpolar solvent, polar protic solvent, or polar aprotic solvent;

1.85 Method 1.84, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, or chlorobenzene);

1.86 Method 1.84, wherein the polar protic solvent is an alcoholic solvent (e.g., tert-butanol, or tert-amyl alcohol), optionally in combination with water;

1.87 Method 1.84, wherein the polar aprotic solvent is selected from N,N-dimethylacetamide, N,N-dimethylformamide, N-methyl-2-pyrrolidinone, and dimethyl sulfoxide, optionally in combination with water;

1.88 Method 1.84, wherein the suitable solvent is tetrahydrofuran;

1.89 Any of Methods 1.75-1.88, wherein the temperature of the reaction is from −80 to 50° C., e.g., from −45 to 10° C., or −10° C. to 10° C., or about 0° C.;

1.90 Method 1, or any of Methods 1.1-1.89, wherein the method comprises the step of treating a compound 1-G in a suitable solvent with a deprotection reagent for a time and under conditions effective to form an alcohol compound 1-H, wherein PG is defined as provided in Method 1.2, 1.3 or 1.4, and $R^x$ is defined as in Method 1.18 or 1.19, and wherein $R^5$ is defined as in any of Methods 1.75-1.78;

1.91 Method 1.90, wherein $R^5$ is $C_{1-6}$alkyl (e.g., methyl, ethyl, isopropyl, propyl, tert-butyl) optionally substituted with 1-3 halogen (e.g., fluoro);

1.92 Method 1.91, wherein $R^5$ is methyl, ethyl, or isopropyl, optionally, wherein $R^5$ is methyl;

1.93 Any of Methods 1.90-1.92, wherein the deprotection reagent is selected from an inorganic base (e.g., an aqueous solution thereof), an acid (e.g., an aqueous solution thereof or a solution in an organic solvent), a fluoride agent (e.g., in an organic solvent), a hydrogenation agent (e.g., hydrogen in combination with a heterogenous catalyst (e.g., a transition metal catalyst) or a homogeneous catalyst (e.g., a soluble transition metal complex), or a phase transfer hydrogenation system), optionally further comprising a phase transfer agent;

1.94 Any of Methods 1.90-1.93, wherein the deprotection reagent is selected from sodium hydroxide, potassium hydroxide, lithium hydroxide, hydrochloric acid (e.g., aqueous HCl, HCl in ether, HCl in methanol, HCl in isopropanol), sulfuric acid, acetic acid, trifluoroacetic acid, phosphoric acid, methanesulfonic acid, 4-toluenesulfonic acid, hydrofluoric acid, hydrogen fluoride pyridine, hydrogen fluoride triethylamine, potassium fluoride, sodium fluoride, lithium fluoride, cesium fluoride, tetramethylammonium fluoride, tetraethylammonium fluoride, tetrabutylammonium fluoride, hydrogen in combination with a catalyst (e.g., Pd, Pd/C, Pt, Ru/C, Raney Nickel, Ru complexes, Rh complexes, $PtO_2$, Pt complexes, Pd complexes, Ir complexes), and ammonium formate in combination with a palladium or platinum catalyst (e.g., Pd, Pd/C, Pt, $PtO_2$);

1.95 Any of Methods 1.90-1.94, wherein the substituent PG is a silyl group, and the deprotection agent is a fluoride agent;

1.96 Method 1.95, wherein the substituent PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl), and the deprotection reagent is selected from hydrofluoric acid, hydrogen fluoride pyridine, hydrogen fluoride triethylamine, potassium fluoride, sodium fluoride, lithium fluoride, tetramethylammonium fluoride, tetraethylammonium fluoride, and tetrabutylammonium fluoride;

1.97 Method 1.96, wherein the substituent PG is tert-butyldiphenylsilyl and the deprotection agent is selected from tetramethylammonium fluoride, tetraethylammonium fluoride, and tetrabutylammonium fluoride;

1.98 Any of Methods 1.90-1.97, wherein the suitable solvent is a nonpolar solvent, polar protic solvent, or polar aprotic solvent;

1.99 Method 1.98, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

1.100 Method 1.98, wherein the polar protic solvent is an alcoholic solvent (e.g., methanol, ethanol, propanol, isopropanol, tert-butanol, tert-amyl alcohol), optionally in combination with water, or wherein the polar protic solvent is water;

1.101 Method 1.98, wherein the polar aprotic solvent is selected from N,N-dimethylacetamide, N,N-dimethylformamide, N-methyl-2-pyrrolidinone, and dimethyl sulfoxide, optionally in combination with water;

1.102 Method 1.98, wherein the suitable solvent is tetrahydrofuran;

1.103 Any of Methods 1.90-1.102, wherein the temperature of the reaction is from −15 to 50° C., e.g., from −5 to 40° C., or 0° C. to 30° C., or from 10° C. to 30° C.;

1.104 Method 1, or any of Methods 1.1-1.103, wherein the method comprises the step of treating a compound 1-H in a suitable solvent with an oxidizing agent to form an aldehyde compound 1-I, wherein $R^x$ is defined as in Method 1.18 or 1.19, and wherein $R^5$ is defined as in any of Methods 1.75-1.78;

1.105 Method 1.104, wherein the reaction further comprises an additive, a catalyst and/or a base;

1.106 Method 1.104 or 1.105, wherein the oxidizing agent is selected from sodium hypochlorite, sulfur trioxide pyridine, dimethyl sulfoxide/oxalyl chloride, DMSO/acetic anhydride, DMSO/trifluoroacetic anhydride, diacetoxyiodobenzene (DAIB), tetrapropylammonium perruthenate (TPAP)/N-methyl morpholine oxide, Dess-Martin Periodinane, pyridinium chlorochromate, N-chlorosuccinimide/dimethyl sulfide, iodosylbenzene, DMSO/dicyclohexylcarbodiimide, bis(trifluoroacetoxy)iodobenzene, and manganese dioxide;

1.107 Method 1.106, wherein the oxidizing agent is selected from diacetoxyiodobenzene (DAIB), Dess-Martin Periodinane, iodosylbenzene, and bis(trifluoroacetoxy)iodobenzene;

1.108 Method 1.107, wherein the oxidizing agent is diacetoxyiodobenzene (DAIB);

1.109 Any of Methods 1.104-1.108, wherein the reaction further comprises a catalyst selected from TEMPO ((2,2,6,6-tetramethylpiperidin-1-yl)oxyl), 4-hydroxy-TEMPO, polymer-supported TEMPO, 2-azaadamantane N-oxyl, 9-azabicyclo[3.3.1]nonane N-oxyl, and 9-azanoradamantane N-oxyl;

1.110 Any of Methods 1.104-1.109, wherein the reaction further comprises an additive selected from sodium bromide, lithium bromide and potassium bromide;

1.111 Any of Methods 1.104-1.110, wherein the reaction further comprises a base selected from an inorganic base (e.g., sodium phosphate dibasic, sodium bicarbonate, potassium bicarbonate, lithium hydroxide, sodium hydroxide, potassium hydroxide) and an organic amine base (e.g., triethylamine, N,N-diisopropylethylamine, pyridine, DBU, DBN);

1.112 Any of Methods 1.104-1.109, wherein the oxidizing agent is diacetoxyiodobenzene and the catalyst is TEMPO, wherein the reaction does not further comprise a base or an additive;

1.113 Any of Methods 1.104-1.112, wherein the suitable solvent is a nonpolar solvent, or polar aprotic solvent;

1.114 Method 1.113, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

1.115 Method 1.113, wherein the polar aprotic solvent is selected from N,N-dimethylacetamide, N,N-dimethylformamide, N-methyl-2-pyrrolidinone, and dimethyl sulfoxide, optionally in combination with water;

1.116 Method 1.113, wherein the suitable solvent is dichloromethane;

1.117 Any of Methods 1.104-1.116, wherein the temperature of the reaction is from −80 to 50° C., e.g., from −40 to 40° C., or 10° C. to 30° C.;

1.118 Method 1, or any of Methods 1.1-1.117, wherein the method comprises the step of treating a compound 1-I in a suitable solvent with a reducing agent and the compound 5-I, for a time and under conditions effective to form the tertiary amine compound 1-J, wherein $R^x$ is defined as in Method 1.18 or 1.19, wherein $R^5$ is defined as in any of Methods 1.75-1.78, and wherein $R^z$ is defined as in any of Methods 2.129-2.131, and wherein $R^6$ is hydrogen or halogen. In one embodiment, $R^x$ is H. In one embodiment, $R^5$ is methyl;

1.119 Method 1.118, wherein $R^6$ is selected from chloro, bromo, fluoro and iodo;

1.120 Method 1.119, wherein $R^6$ is chloro;

1.121 Any of Methods 1.118-1.120, wherein the reducing agent is selected from a hydride reducing agent, a silane reducing agent, and zinc in acid (e.g., zinc in acetic acid);

1.122 Method 1.121, wherein the reducing agent is a hydride reducing agent;

1.123 Method 1.122, wherein the hydride reducing agent is selected from sodium borohydride, lithium borohydride, sodium cyanoborohydride, zinc borohydride, sodium triacetoxyborohydride, and tetramethylammonium triacetoxyborohydride;

1.124 Method 1.123, wherein the hydride reducing agent is sodium triacetoxyborohydride or sodium cyanoborohydride;

1.125 Any of Methods 1.122-1.124, wherein the hydride reducing agent is combined with a reagent to modulate the hydride reducing activity (e.g., titanium isopropoxide, magnesium perchlorate, or zinc chloride);

1.126 Method 1.121, the reducing agent is selected from silanes (triisopropylsilane, triphenylsilane, diethylsilane, etc.), sodium borohydride, sodium borohydride/acetic acid, sodium triacetoxyborohydride, sodium cyanoborohydride, titanium isopropoxide/sodium cyanoborohydride, zinc/acetic acid, sodium borohydride/magnesium perchlorate, zinc borohydride/zinc chloride, tetramethylammonium triacetoxyborohydride. In one embodiment, the reducing agent is triethylsilane;

1.127 Any of Methods 1.121 to 1.126, wherein the reaction further comprises an acid (e.g., selected from acetic acid, trifluoroacetic acid, citric acid, pivalic acid, p-toluenesulfonic acid, methanesulfonic acid, and hydrochloric acid). In one embodiment, the acid is trifluoroacetic acid;

1.128 Any of Methods 1.118-1.128, wherein the suitable solvent is a nonpolar solvent, or polar aprotic solvent;

1.129 Method 1.128, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), acetonitrile, and halogenated solvents (e.g., dichloromethane, 1,2-dichloroethane, chloroform, chlorobenzene);

1.130 Method 1.128, wherein the polar aprotic solvent is selected from N,N-dimethylacetamide, N,N-dimethylformamide, N-methyl-2-pyrrolidinone, and dimethyl sulfoxide;

1.131 Method 1.128, wherein the suitable solvent is dichloromethane. In one embodiment, the solvent is acetonitrile;

1.132 Any of Methods 1.118-1.131, wherein the temperature of the reaction is from −30 to 50° C., e.g., from −30 to 0° C., or −30 to −10° C., or about −20° C. In one embodiment, the temperature is −10 to 30° C.;

1.133 Method 1, or any of Methods 1.1-1.132, wherein the method comprises the step of hydrolyzing the compound 1-J in a suitable solvent for a time and under conditions effective to form the carboxylic acid compound 1-K, wherein $R^x$ is defined as in Method 1.18 or 1.19, wherein $R^5$ is defined as in any of Methods 1.75-1.78, and wherein $R^z$ is defined as in any of Methods 2.129-2.131, and wherein $R^6$ is hydrogen or halogen;

1.134 Method 1.133, wherein the reaction comprises treating the compound 1-J in an organic and/or aqueous solvent with an aqueous acid or a base; or treating the compound 1-J with an enzyme (e.g., a bacterial or fungal lipase, such as lipase from *Rhizopus* species); or treating the compound 1-J with magnesium dibromide in a nonpolar solvent; or treating the compound 1-J with a fluoride source (e.g., hydrofluoric acid, hydrogen fluoride pyridine, hydrogen fluoride triethylamine, potassium fluoride, sodium fluoride, lithium fluoride, tetramethylammonium fluoride, tetraethylammonium fluoride, tetrabutylammonium fluoride), in a nonpolar solvent; or treating the compound 1-J with hydrogen in combination with a catalyst (e.g., Pd, Pd/C, Pt, Ru/C, Raney Nickel, Ru complexes, Rh complexes, $PtO_2$, Pt complexes, Pd complexes, Ir complexes), or ammonium formate in combination with a palladium or platinum catalyst (e.g., Pd, Pd/C, Pt, $PtO_2$);

1.135 Method 1.134, wherein the acid is selected from hydrochloric acid, hydrobromic acid, sulfuric acid, phosphoric acid, acetic acid, trifluoroacetic acid, methanesulfonic acid, benzenesulfonic acid, and toluenesulfonic acid;

1.136 Method 1.134, wherein the base is selected from sodium hydroxide, potassium hydroxide, lithium hydroxide, tetrabutylammonium hydroxide, sodium carbonate, potassium carbonate, lithium carbonate, sodium bicarbonate, potassium bicarbonate, lithium bicarbonate, cesium hydroxide, calcium hydroxide, magnesium hydroxide, ammonium hydroxide, tetramethylammonium hydroxide, alkoxides (lithium, sodium, potassium, magnesium, or calcium salts of methoxide, ethoxide, isopropoxide, t-butoxide, or t-pentoxide), trimethyltin hydroxide, sodium trimethylsilanolate, potassium trimethylsilanolate, and pyridine;

1.137 Any of Methods 1.133-1.136, wherein the solvent is selected from one or more of water, alcohols (e.g., methanol, ethanol, isopropanol, propanol, butanol, tert-butanol, tert-amyl alcohol), polar aprotic solvents (e.g., N,N-dimethylacetamide, N,N-dimethylformamide, N-methyl-2-pyrrolidinone, dimethyl sulfoxide, acetonitrile), ethers (e.g., 2-methyltetrahydrofuran, tetrahydrofuran, methyl tert-butyl ether, cyclopentyl methyl ether, dioxane), hydrocarbon solvents (e.g., toluene, n-heptane), and halogenated solvents (e.g., dichloromethane, 1,2-dichloroethane, chloroform, chlorobenzene);

1.138 Any of Methods 1.133-1.137, wherein the temperature of the reaction is from −10 to 100° C., e.g., from 10 to 80° C., or 20 to 80° C., or from 20 to 50° C. In one embodiment, the temperature is from 20 to 100° C. In one embodiment, the temperature is from 50 to 70° C.;

1.139 Method 1, or any of Methods 1.1-1.138, wherein the method comprises the step of treating (1S,5R)-3-oxabicyclo[3.2.0]heptan-2-one (compound 2-A) with an organometallic reagent in a suitable solvent for a time and under conditions effective to form a 1-hydroxycyclopropane compound 2-B, wherein the substituent $R^x$ is selected from H, $C_{1-6}$alkyl (e.g., methyl), and $C_{6-10}$aryl (e.g. phenyl), wherein the alkyl is optionally substituted aryl (e.g., phenyl);

1.140 Method 1.139, wherein $R^x$ is H;

1.141 Method 1.139 or 1.140 wherein the organometallic reagent is an organolithium reagent (e.g., $C_{1-6}$alkyl lithium) or a Grignard reagent (e.g., $C_{1-6}$alkylmagnsium halide);

1.142 Method 1.141, wherein the organometallic reagent is selected from ethylmagnesium bromide, ethylmagnesium chloride, ethylmagnesium iodide, n-propylmagnesium bromide and 2-phenylethylmagnesium bromide, each optionally provided as a solution in an ethereal solvent (e.g., tetrahydrofuran, methyl tert-butyl ether, diethyl ether, dibutyl ether, dioxane);

1.143 Any of Methods 1.139-1.142, wherein the reaction further comprises a transition metal promoter, such as a titanium(IV) compound;

1.144 Method 1.143, wherein the promoter is a titanium (IV) alkoxide (e.g., titanium(IV) methoxide, titanium (IV) ethoxide, titanium(IV) propoxide, titanium(IV) isopropoxide, titanium(IV) n-butoxide, titanium(IV) t-butoxide, titanium(IV) benzoxide);

1.145 Any of Methods 1.139-1.144, wherein the organometallic reagent is ethylmagnesium bromide and the promoter is titanium(IV) isopropoxide;

1.146 Any of Methods 1.139-1.145, wherein the suitable solvent is a nonpolar solvent or polar aprotic solvent;

1.147 Method 1.146, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., 1,2-dichloroethane, chloroform, chlorobenzene); or wherein the polar aprotic solvent is a nitrile (e.g., acetonitrile);

1.148 Method 1.147, wherein the nonpolar solvent is an ethereal solvent, optionally, wherein the solvent is tetrahydrofuran;

1.149 Any of Methods 1.139-1.148, wherein the temperature of the reaction is from −20 to 50° C., e.g., from −10 to 10° C., or about 0° C. to 5° C.;

1.150 Method 1, or any of 1.1-1.149, wherein the method comprises the step of reacting a compound 2-B with a suitable protecting reagent in a suitable solvent, optionally with a suitable base and/or catalyst, for a time and under conditions effective to yield a compound 2-C, wherein $R^x$ is defined as in Method 1.139 or 1.140;

1.151 Method 1.150, wherein the substituent PG is selected from a silyl group, an alkylcarbonyl group (e.g., —C(=O)—$C_{1-6}$alkyl, such as acetyl, isobutyryl, pivaloyl, adamantanecarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl), an aryloxycarbonyl group (e.g., phenoxycarbonyl), a tertiary alkyl group (e.g., t-butyl or trityl), an alkoxyalkyl group (e.g., methoxymethyl or ethoxymethyl), and a $C_{1-6}$alkylaryl group (e.g., benzyl, 3,5-dimethoxybenzyl);

1.152 Method 1.151, wherein the substituent PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

1.153 Method 1.152, wherein the substituent PG is a tert-butyldiphenyl silyl group, optionally wherein the protecting agent is TBDPS-chloride;

1.154 Any of Methods 1.150-1.153, wherein the protecting reagent is selected from silyl chlorides (e.g., chlorotrimethylsilane, chlorotriethylsilane, chlorotripropylsilane, triisopropylsilyl chloride, tert-butyldimethylsilyl chloride, chlorodimethylphenylsilane, or chlorotriphenylsilane), silyl trifluoromethanesulfonates (e.g., trimethylsilyl trifluoromethanesulfonate, triethylsilyl trifluoromethanesulfonate, triisopropylsilyl trifluoromethanesulfonate, tert-butyldimethylsilyl trifluoromethanesulfonate, dimethylphenylsilyl trifluoromethanesulfonate, or triphenylsilyl trifluoromethanesulfonate), silyl bromides (e.g., bromotrimethylsilane, bromotriethylsilane, bromotripropylsilane, triisopropylsilyl bromide, tert-butyldimethylsilyl bromide, bromodimethylphenylsilane, or bromotriphenylsilane), N,O-bis(trimethylsilyl) acetamide, N,O-bis(trimethylsilyl)trifluoroacetamide, N-methyl-N-(trimethylsilyl)trifluoroacetamide, benzyl halides (e.g., 3,5-dimethoxybenzyl chloride, 3,5-dimethoxybenzyl bromide), dibenzyl carbonate, acid chlorides (e.g., pivaloyl chloride, or 1-adamantanecarbonyl chloride), anhydrides (e.g., di-tert-butyl carbonate), chloroformates (e.g., methyl chloroformate, ethyl chloroformate, benzyl chloroformate, or phenyl chloroformate), alkyl chlorides (e.g., trityl chloride), and alkoxymethyl chlorides (e.g., methoxymethyl chloride);

1.155 Any of Methods 1.150-1.154, wherein the reaction comprises a base;

1.156 Method 1.155, wherein the base is selected from tertiary amines (e.g., triethylamine, N-methylmorpholine, tripropylamine, N,N-diisopropylethylamine, tributylamine, 1,8-diazabicyclo[5.4.0]undec-7-ene, or 1,4-diazabicyclo[2.2.2]octane), aromatic amines (e.g., pyridine, 2,6-lutidine, collidine, imidazole, or 1-methylimidazole), and inorganic bases (e.g., lithium carbonate, sodium carbonate, potassium carbonate, calcium carbonate, potassium phosphate (monobasic, dibasic or tribasic), or sodium phosphate (monobasic, dibasic or tribasic));

1.157 Method 1.156, wherein the base is triethylamine;

1.158 Any of Methods 1.150-1.157, wherein the reaction comprises a catalyst;

1.159 Method 1.158, wherein the catalyst is selected from 4-(dimethylamino)pyridine, 2,6-dimethylpyridine, N-methylimidazole, imidazole, 4-pyrrolidinopyridine, 4-piperidinopyridine, and 9-azajulolidine;

1.160 Method 1.159, wherein the catalyst is 4-(dimethylamino)pyridine;

1.161 Any of Methods 1.150-1.160, wherein the suitable solvent is a nonpolar solvent or polar aprotic solvent;

1.162 Method 1.161, wherein the nonpolar solvent is selected from ethers (e.g., tetrahydrofuran, 2-methyltetrahydrofuran, methyl tert-butyl ether, cyclopentyl methyl ether, or dioxane), hydrocarbon solvents (e.g., toluene, n-hexane, or n-heptane), and halogenated solvents (e.g., dichloromethane, 1,2-dichloroethane, chloroform, or chlorobenzene);

1.163 Method 1.161, wherein the polar aprotic solvent is selected from N,N-dimethylformamide, N,N-dimethylacetamide, N-methyl-2-pyrrolidinone, dimethyl sulfoxide, and nitriles (e.g., acetonitrile);

1.164 Method 1.161, wherein the nonpolar solvent is a halogenated solvent, optionally, wherein the solvent is dichloromethane;

1.165 Any of Methods 1.150-1.161, wherein the temperature of the reaction is from −30 to 40° C., e.g., from −10 to 30° C., or 0° C. to 25° C.;

1.166 Method 1, or any of Methods 1.1-1.165, wherein the method comprises the step of reacting a compound 2-C with a halogenating agent in a suitable solvent for a time and under conditions effective to form a beta-halo ketone compound 2-D, wherein PG is defined as in any of Methods 1.151-1.153, and $R^x$ is defined as in Method 1.139 or 1.140;

1.167 Method 1.166, wherein the substituent X is selected from bromo, chloro and iodo;

1.168 Method 1.167, wherein X is bromo;

1.169 Method 1.166, 1.167 or 1.168 wherein the halogenating agent is selected from N-bromosuccinimide, N-bromophthalimide, bromine, 1,3-dibromo-5,5-dimethylhydantoin, N-bromosaccharin, hypobromous acid, N-chlorophthalimide, N-chlorosuccinimide, N-chlorosaccharin, 1,3-dichloro-5,5-dimethylhydantoin, N-iodosucciminide, N-iodophthalimide, and iodine;

1.170 Method 1.169, wherein the halogenating agent is selected from N-bromosuccinimide, N-bromophthalimide, bromine, 1,3-dibromo-5,5-dimethylhydantoin, N-bromosaccharin, and hypobromous acid;

1.171 Method 1.169, wherein the halogenating agent is N-bromosuccinimide;

1.172 Any of Methods 1.166-1.171, wherein the suitable solvent is a nonpolar solvent;

1.173 Method 1.172, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

1.174 Method 1.172, wherein the nonpolar solvent is a halogenated solvent, optionally wherein the solvent is dichloromethane;

1.175 Any of Methods 1.166-1.174, wherein the temperature of the reaction is from −20 to 30° C., e.g., from −5 to 15° C., or 0° C. to 5° C.;

1.176 Any of Methods 1.166-1.175, wherein the compound 2-C is mixed (e.g., stirred or agitated) in the suitable solvent with the halogenating agent for 0.1 to 3 hours, e.g., 0.2 to 2 hours, or 0.3 to 1 hour, or about 0.5 hours;

1.177 Method 1, or any of Methods 1.1-1.176, wherein the method comprises the step of reacting a compound 2-D with a base in a suitable solvent for a time and under conditions effective to form an alpha, beta-unsaturated ketone compound 2-E, wherein PG is defined as provided in any of Methods 1.151-1.153, and $R^x$ is defined as in Method 1.139 or 1.140, and wherein X is chloro, bromo or iodo;

1.178 Method 1.177, wherein the base is selected from tertiary amines (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, collidine, 1-methylimidazole), and inorganic bases (e.g., alkali metal carbonates such as sodium carbonate, potassium carbonate, and lithium carbonate, alkali metal phosphates such as mono-, di-, or tribasic sodium, potassium or lithium phosphate);

1.179 Method 1.178, wherein the base is selected from triethylamine, N,N-diisopropylethylamine, N-methylmorpholine, and 1,8-diazabicyclo[5.4.0]undec-7-ene;

1.180 Method 1.179, wherein the base is triethylamine;

1.181 Any of Methods 1.177-1.180, wherein the suitable solvent is a nonpolar solvent;

1.182 Method 1.181, wherein the nonpolar solvent is selected from ethers (e.g., tetrahydrofuran, 2-methyltetrahydrofuran, methyl tert-butyl ether, cyclopentyl methyl ether, or dioxane), hydrocarbon solvents (e.g., toluene, n-hexane, or n-heptane), and halogenated solvents (e.g., dichloromethane, 1,2-dichloroethane, chloroform, or chlorobenzene);

1.183 Method 1.182, wherein the nonpolar solvent is a halogenated solvent, optionally wherein the solvent is dichloromethane;

1.184 Any of Methods 1.177-1.183, wherein the temperature of the reaction is from −20 to 30° C., e.g., from −5 to 15° C., or 0° C. to 5° C.;

1.185 Any of Methods 1.166 to 1.184, wherein the conversion of compound 2-C to compound 2-D and the conversion of compound 2-D to compound 2-E takes place consecutively in the same vessel without isolation of compound 2-D;

1.186 Method 1, or any of Methods 1.1-1.185, wherein the method comprises the step of reacting a compound 2-E with a promoter in a suitable solvent for a time and under conditions effective to form an epimerized alpha, beta-unsaturated ketone compound 1-E, wherein PG is defined as provided in any of Methods 1.151-1.153, and $R^x$ is defined as in Method 1.139 or 1.140;

1.187 Method 1.186, wherein the promoter is selected from tertiary amines (e.g., triethylamine, N-methylmorpholine, tripropylamine, N,N-diisopropylethylamine, tributylamine, 1,8-diazabicyclo[5.4.0]undec-7-ene, 1,4-diazabicyclo[2.2.2]octane, or DABCO), aromatic amines (e.g., pyridine, 2,6-lutidine, collidine, or 1-methylimidazole), inorganic bases (e.g., alkali metal carbonates such as sodium carbonate, potassium carbonate, and lithium carbonate, or alkali metal phosphates such as mono-, di-, or tribasic sodium, potassium or lithium phosphate), inorganic halides (e.g., lithium chloride, magnesium bromide, magnesium chloride), and acids (e.g., titanium tetraisopropoxide, benzenesulfonic acid, toluenesulfonic acid, or methanesulfonic acid);

1.188 Method 1.187, wherein the promoter is selected from triethylamine, N,N-diisopropylethylamine, N-methylmorpholine, and 1,8-diazabicyclo[5.4.0]undec-7-ene (DBU);

1.189 Method 1.188, wherein the promoter is DBU;

1.190 Any of Methods 1.186-1.189, wherein the suitable solvent is a nonpolar solvent, polar aprotic solvent or polar protic solvent;

1.191 Method 1.190, wherein the nonpolar solvent is selected from ethers (e.g., tetrahydrofuran, 2-methyltetrahydrofuran, methyl tert-butyl ether, cyclopentyl methyl ether, dioxane), and halogenated solvents (e.g., dichloromethane, 1,2-dichloroethane, chloroform, or chlorobenzene);

1.192 Method 1.190, wherein the polar aprotic solvent is selected from esters (e.g., ethyl acetate, methyl acetate, isopropyl acetate) and nitriles (e.g., acetonitrile);

1.193 Method 1.190, wherein the polar protic solvent is an alcoholic solvent (e.g., methanol, ethanol, propanol, or isopropanol);

1.194 Method 1.190, wherein the nonpolar solvent is a halogenated solvent, optionally wherein the solvent is dichloromethane;

1.195 Any of Methods 1.186-1.194, wherein the temperature of the reaction is from −10 to 50° C., e.g., from 0 to 40° C., or 10° C. to 30° C., or about 25° C.;

1.196 Method 1, or any of Methods 1.1-1.195, wherein the method comprises the step of thiolating a compound 1-E for a time and under conditions effective to form a compound 3-A by reacting the compound 1-E with a thiol and a base in a suitable solvent, wherein PG is defined as provided in Method 1.2, 1.3 or 1.4, and $R^x$ is defined as in Method 1.18 or 1.19;

1.197 Method 1.196, wherein $R^S$ is selected from optionally substituted $C_{1-6}$alkyl (e.g., methyl) and optionally substituted aryl (e.g., phenyl);

1.198 Method 1.197, wherein $R^S$ is $C_{1-6}$alkyl optionally substituted with one or more groups selected from $C_{1-6}$alkoxy, halogen, $C_{1-6}$alkyl, and aryl (e.g., phenyl), optionally wherein $R^S$ is methyl, ethyl or isopropyl;

1.199 Method 1.197, wherein $R^S$ is aryl optionally substituted with one or more groups selected from $C_{1-6}$alkoxy, halogen, $C_{1-6}$alkyl, and aryl (e.g., phenyl), optionally wherein $R^S$ is phenyl or tolyl;

1.200 Method 1.197, wherein $R^S$ is 4-tolyl;

1.201 Any of Methods 1.196-1.200, wherein the thiol is $R^S$—SH (e.g., methanethiol, benzenethiol, or 4-methylbenzenethiol);

1.202 Any of Methods 1.196-1.201, wherein the base is selected from tertiary amines (e.g., triethylamine, N-methylmorpholine, tripropylamine, N,N-diisopropylethylamine, tributylamine, 1,8-diazabicyclo[5.4.0]undec-7-ene, or 1,4-diazabicyclo[2.2.2]octane), and aromatic amines (e.g., pyridine, 2,6-lutidine, collidine, imidazole, or 1-methylimidazole);

1.203 Method 1.202, wherein the base is triethylamine or N,N-diisopropylethylamine;

1.204 Any of Methods 1.196-1.203, wherein the suitable solvent is a nonpolar solvent, or polar aprotic solvent;

1.205 Method 1.204, wherein the nonpolar solvent is selected from ethers (e.g., tetrahydrofuran, 2-methyltetrahydrofuran, methyl tert-butyl ether, cyclopentyl methyl ether, or dioxane), hydrocarbon solvents (e.g., toluene, n-hexane, n-heptane), and halogenated solvents (e.g., dichloromethane, 1,2-dichloroethane, chloroform, or chlorobenzene);

1.206 Method 1.204, wherein the polar aprotic solvent is selected from esters (e.g., ethyl acetate, methyl acetate, or isopropyl acetate) and nitriles (e.g., acetonitrile);

1.207 Method 1.204, wherein the nonpolar solvent is a halogenated solvent, optionally wherein the solvent is dichloromethane;

1.208 Any of Methods 1.196-1.207, wherein the temperature of the reaction is from −20 to 50° C., e.g., from 0 to 30° C., or 10° C. to 20° C., or about 25° C.;

1.209 Method 1, or any of Methods 1.1-1.208, wherein the method comprises the step of reducing unsaturated thio compound 3-A to thio alcohol compound 3-B, wherein PG is defined as provided in Method 1.2, 1.3 or 1.4, $R^x$ is defined as in Method 1.18 or 1.19, and $R^S$ is defined as in any of Methods 1.197-1.200;

1.210 Method 1.209, wherein the reduction is carried out by reacting the compound 3-A with a reducing agent and a Lewis acid catalyst, in a suitable solvent;

1.211 Method 1.210, wherein the reducing agent is selected from a borane agent (e.g., borane, a borane complex [e.g., $BH_3$-THF, $BH_3$-DMS, $BH_3$-CBS], or 9-BBN), a borohydride agent (e.g., sodium borohydride, lithium borohydride, or lithium triethylborohydride), an aluminum hydride agent (e.g., lithium aluminum hydride, diisobutylaluminum hydride, or lithium tri-t-butoxyaluminum hydride), a hydrogen source (e.g., isopropanol) with a transfer hydrogenation agent (e.g., RuCl[(R,R)-Tsdpen](p-cymene), RuCl[(S,S)-Tsdpen](p-cymene), an aluminum alkoxide agent in an alcoholic solvent (e.g., aluminum triisopropoxide in ethanol), and a reductase enzyme (e.g., a ketoreductase);

1.212 Method 1.211, wherein the reducing agent is sodium borohydride;

1.213 Any of Methods 1.209-1.212, wherein the Lewis acid is selected from cerium(III) chloride, magnesium bromide, magnesium chloride, magnesium iodide, calcium chloride, calcium bromide, and calcium iodide;

1.214 Method 1.213, wherein the Lewis acid is cerium (III) chloride, e.g., cerium(III) chloride heptahydrate or anhydrous cerium(III) chloride;

1.215 Any of Methods 1.209-1.214, wherein the suitable solvent is a polar protic solvent or nonpolar solvent;

1.216 Method 1.215, wherein the suitable solvent is a polar protic solvent, such as an alcohol (e.g., methanol, ethanol, propanol, isopropanol, or butanol);

1.217 Method 1.215, wherein the suitable solvent is a nonpolar solvent, such as an ether (e.g., tetrahydrofuran, 2-methyltetrahydrofuran, methyl tert-butyl ether, cyclopentyl methyl ether, dioxane), a hydrocarbon solvent (e.g., toluene, n-hexane, n-heptane), or a halogenated solvent (e.g., dichloromethane, 1,2-dichloroethane, chloroform, chlorobenzene);

1.218 Method 1.215, wherein the solvent is ethanol;

1.219 Any of Methods 1.209-1.218, wherein the temperature of the reaction is from −30 to 30° C., e.g., from −20 to 20° C., or −10 to 10° C.;

1.220 Method 1, or any of Methods 1.1-1.219, wherein the method comprises the step of reacting a compound 3-B with an alkylating agent, and optionally a base, in a suitable solvent for a time and under conditions effective to form an ether compound 3-C, wherein PG is defined as provided in Method 1.2, 1.3 or 1.4, $R^x$ is defined as in Method 1.18 or 1.19, $R^S$ is defined as in any of Methods 1.197-1.200, and wherein $R^S$ is selected from hydrogen, $C_{1-6}$alkyl, —$(CH_2CH_2O)_pR^7$, $C_{1-6}$haloalkyl, or $C_{3-10}$cycloalkyl, wherein said $C_{1-6}$alkyl, $C_{1-6}$haloalkyl, or $C_{3-10}$cycloalkyl, are optionally substituted with 1-5 $R^{10}$ groups ($R^7$ and $R^{10}$ are as defined for the Compound of Formula I);

1.221 Method 1.220, wherein $R^5$ is selected from $C_{1-6}$alkyl and $C_{1-6}$haloalkyl, each optionally substituted with 1-3 groups selected from halogen, oxo, $C_{3-6}$cycloalkyl, and 4-6 membered heterocycloalkyl;

1.222 Method 1.221, wherein $R^5$ is $C_{1-6}$alkyl (e.g., methyl, ethyl, isopropyl, propyl, tert-butyl) optionally substituted with 1-3 halogen (e.g., fluoro);

1.223 Method 1.222, wherein $R^5$ is methyl;

1.224 Any of Methods 1.220-1.223, wherein the alkylating agent is a compound of the formula $R^5$—X, wherein X is selected from Cl, Br, I, OS(O)$_2$OR$^5$, and OSO$_2$-L wherein L is $C_{1-6}$alkyl, optionally substituted aryl, or halo$C_{1-6}$alkyl;

1.225 Method 1.224, wherein the alkylating agent is selected from an alkyl bromide, alkyl chloride, alkyl iodide, alkyl triflate, alkyl tosylate, alkyl mesylate, alkyl nosylate, alkyl benzenesulfonate, and dialkyl sulfate;

1.226 Method 1.224, wherein the alkylating agent is selected from methyl iodide, methyl triflate, methyl tosylate and dimethyl sulfate;

1.227 Any of Methods 1.220-1.226, wherein the reaction further comprises a base selected from inorganic hydrides (e.g., sodium hydride, potassium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide), inorganic hydroxides (e.g., sodium hydroxide, potassium hydroxide, lithium hydroxide), and amide bases (sodium hexamethyldisilazide, lithium hexamethyldisilazide, potassium hexamethyldisilazide, lithium diisopropylamide, sodium diisopropylamide, or potassium diisopropylamide);

1.228 Method 1.227, wherein the base is sodium hydride;

1.229 Any of Methods 1.220-1.228, wherein the suitable solvent is a nonpolar solvent, polar protic solvent, or polar aprotic solvent;

1.230 Method 1.229, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, or n-heptane), and halogenated solvents (e.g., dichloromethane, 1,2-dichloroethane, chloroform, or chlorobenzene);

1.231 Method 1.229, wherein the polar protic solvent is an alcoholic solvent (e.g., tert-butanol, tert-amyl alcohol), optionally in combination with water;

1.232 Method 1.229, wherein the polar aprotic solvent is selected from N,N-dimethylacetamide, N,N-dimethylformamide, N-methyl-2-pyrrolidinone, and dimethyl sulfoxide, optionally in combination with water;

1.233 Method 1.229, wherein the suitable solvent is tetrahydrofuran;

1.234 Any of Methods 1.220-1.233, wherein the temperature of the reaction is from −80 to 50° C., e.g., from −45 to 10° C., or −10° C. to 10° C., or 10 to 20° C.;

1.235 Method 1, or any of Methods 1.1-1.234, wherein the method comprises the step of treating a compound 3-C in a suitable solvent with an S-oxidizing reagent for a time and under conditions effective to form an N-tosylsulfinimidoyl compound 3-D, wherein $R^S$ is defined as in any of Methods 1.197-1.200, wherein PG is defined as in Method 1.2, 1.3 or 1.4, and $R^x$ is defined as in Method 1.18 or 1.19, and wherein $R^5$ is defined as in any of Methods 1.220-1.223;

1.236 Method 1.235, wherein $R^5$ is $C_{1-6}$alkyl (e.g., methyl, ethyl, isopropyl, propyl, tert-butyl) optionally substituted with 1-3 halogen (e.g., fluoro);

1.237 Method 1.236, wherein $R^5$ is methyl, ethyl, or isopropyl, optionally, wherein $R^5$ is methyl;

1.238 Any of Methods 1.235-1.237, wherein the S-oxidizing agent is selected from N-chloro-4-methylbenzenesulfonamide, or a salt thereof, N-chlorobenzenesulfonamide, or a salt thereof, (tosylimido)iodobenzene, and p-tosylamide/phenyliodine diacetate;

1.239 Method 1.238, wherein the agent is sodium N-chloro-4-methylbenzenesulfonamide (Chloramine-T);

1.240 Any of Methods 1.235-1.239, wherein the suitable solvent is a nonpolar solvent, polar protic solvent, or polar aprotic solvent;

1.241 Method 1.240, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, or n-heptane), and halogenated solvents (e.g., dichloromethane, 1,2-dichloroethane, chloroform, or chlorobenzene);

1.242 Method 1.240, wherein the polar protic solvent is an alcoholic solvent (e.g., methanol, ethanol, isopropanol, n-butanol, tert-butanol, or tert-amyl alcohol);

1.243 Method 1.240, wherein the polar aprotic solvent is selected from N,N-dimethylacetamide, N,N-dimethylformamide, N-methyl-2-pyrrolidinone, dimethyl sulfoxide, and a nitrile (e.g., acetonitrile);

1.244 Method 1.240, wherein the suitable solvent is acetonitrile;

1.245 Any of Methods 1.235-1.244, wherein the temperature of the reaction is from 0 to 50° C., e.g., from 10 to 30° C., or about 25° C.;

1.246 Method 1, or any of Methods 1.1-1.245, wherein the method comprises the step of thermolyzing a compound 3-D in a suitable solvent to form allylic ether compound 1-G, wherein PG is defined as provided in Method 1.2, 1.3 or 1.4, and $R^x$ is defined as in Method 1.18 or 1.19, and wherein $R^5$ is defined as in any of Methods 1.220-1.223;

1.247 Method 1.246, wherein $R^5$ is $C_{1-6}$alkyl (e.g., methyl, ethyl, isopropyl, propyl, or tert-butyl) optionally substituted with 1-3 halogen (e.g., fluoro);

1.248 Method 1.247, wherein $R^5$ is methyl, ethyl, or isopropyl, optionally, wherein $R^5$ is methyl;

1.249 Any of Methods 1.246-1.248, wherein heat is applied in the absence of any chemical reagent;

1.250 Any of Methods 1.246-1.249, wherein the suitable solvent is a nonpolar solvent, polar protic solvent, or polar aprotic solvent, optionally wherein the solvent has a boiling point of at least 60° C.;

1.251 Method 1.250, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-heptane), and halogenated solvents (e.g., 1,2-dichloroethane, chloroform, chlorobenzene);

1.252 Method 1.250, wherein the polar protic solvent is an alcoholic solvent (e.g., methanol, ethanol, isopropanol, n-butanol, tert-butanol, tert-amyl alcohol, or any mixture thereof);

1.253 Method 1.250, wherein the polar aprotic solvent is selected from N,N-dimethylacetamide, N,N-dimethylformamide, N-methyl-2-pyrrolidinone, dimethyl sulfoxide, nitriles (e.g., acetonitrile), and esters (e.g., ethyl acetate, methyl acetate, or isopropyl acetate);

1.254 Method 1.250, wherein the suitable solvent is isopropyl acetate;

1.255 Any of Methods 1.246-1.254, wherein the temperature of the reaction is from 70 to 150° C., e.g., from 80 to 100° C., or about 90° C.;

1.256 Method 1, or any of Methods 1.255, wherein the Method produces a compound according to any one or more of Compounds 1-B, 1-C, 1-D, 1-E, 1-F, 1-G, 1-H, 1-I, 1-J, or 1-K;

1.257 Method 1.256, wherein in one or more of said compounds, R' is methyl, $R^x$ is H, X is Cl or Br (e.g., Br), PG is trialkylsilyl or dialkylaryl silyl (e.g., TBDPS), $R^z$ is $C_{1-3}$ alkyl (e.g., methyl), $R^5$ is $C_{1-3}$ alkyl (e.g., methyl), and/or $R^6$ is halogen (e.g., chloro);

1.258 Method 1, or any of Methods 1.1-1.257, wherein the Method produces a compound according to any one or more of Compounds 2-B, 2-C, 2-D, or 2-E;

1.259 Method 1.258, wherein in one or more of said compounds, $R^x$ is H, PG is trialkylsilyl or dialkylaryl silyl (e.g., TBDPS), and/or X is Cl or Br (e.g., Br);

1.260 Method 1, or any of Methods 1.1-1.259, wherein the Method produces a compound according to any one or more of Compounds, 3-A, 3-B, 3-C, or 3-D;

1.261 Method 1.260, wherein in one or more of said compounds, $R^x$ is H, PG is trialkylsilyl or dialkylaryl silyl (e.g., TBDPS), $R^S$ is aryl (e.g., 4-tolyl), and/or $R^5$ is $C_{1-3}$ alkyl (e.g., methyl);

1.262 Method 1, or any of Methods 1.1-1.261, wherein the Method produces a compound according to any one or more of Compounds 9-A, 9-B, 9-C, 9-D, 9-E;

1.263 Method 1.262, wherein one or more of said compounds 9-A, 9-B, 9-C, 9-D, or 9-E are made according to any one or more of Method 4 or Method 4.1, et seq., or Method 5 or Method 5.1, et seq.;

1.264 Method 1.262 or 1.263, wherein in one or more of said compounds, $R^x$ is H, $R^y$ is H, $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), and/or $R^{12}$ is H, or —C(O)—$R^1$, wherein $R^1$ is selected from optionally substituted $C_{1-6}$ alkyl (e.g., methyl), optionally substituted $C_{1-6}$alkoxy (e.g., (S)-1-phenylethoxy), or optionally substituted 5-10 membered heteroaryl (e.g., 1-methyl-3-methoxy-1H-pyrazol-4-yl);

1.265 Method 1.264, wherein in one or more of said compounds, $R^x$ is H, $R^y$ is H, $R^2$ and $R^3$ are independently H or methyl, $R^4$ is H, $R^5$ is methyl, and $R^6$ is chloro;

1.266 Method 1.265, wherein in one or more of said compounds $R^2$ and $R^3$ are H, or $R^2$ and $R^3$ 1.267 are methyl, or $R^2$ is H and $R^3$ is methyl;

1.268 Method 1.266, wherein in one or more of said compounds $R^2$ is H and $R^3$ is methyl;

1.269 Any of Methods 1.262-1.267, wherein in compound 9-C, $R^{12}$ is —C(O)—$R^1$, and $R^1$ is selected from $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, 5-10 membered heteroaryl, and —NR$^8$R$^9$, wherein said $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$ cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —OR$^a$, and —NR$^a$R$^b$; wherein R$^a$ and R$^b$ is independently hydrogen or $C_{1-6}$alkyl;

1.270 Method 1.268, wherein in compound 9-C, $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$ cycloalkyl, $C_{1-6}$haloalkyl, $C_{1-6}$alkoxy and halogen;

1.271 Method 1.269, wherein in compound 9-C, $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

1.272 Method 1.269, wherein in compound 9-C, $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy), for example $R^1$ is 3-methoxy-1-methyl-1H-pyrazolyl;

1.273 Method 1, or any of Methods 1.1-1.271, wherein the Method produces a compound according to Compound I;

1.274 Method 1.272, wherein the Compound I is a compound I(a);

1.275 Method 1.272 or 1.273, wherein the Compound I or I(a) is made according to any one or more of Method 4 or Method 4.1, et seq., or Method 5 or Method 5.1, et seq.;

1.276 Any of Methods 1.272-1.274, wherein in Compound I or I(a), $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), and/or $R^{12}$ is —C(O)—$R^1$, and $R^1$ is selected from $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, 5-10 membered heteroaryl, and —NR$^8$R$^9$, wherein said $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —OR$^a$, and —NR$^a$R$^b$; wherein R$^a$ and R$^b$ is independently hydrogen or $C_{1-6}$alkyl;

1.277 Method 1.275, wherein in Compound I or I(a), $R^2$ and $R^3$ are independently H or methyl, $R^4$ is H, $R^5$ is methyl, and $R^6$ is chloro;

1.278 Method 1.276, wherein in Compound I or I(a), $R^2$ and $R^3$ are H, or $R^2$ and $R^3$ are methyl, or $R^2$ is H and $R^3$ is methyl;

1.279 Method 1.277, wherein in Compound I or I(a), $R^2$ is H and $R^3$ is methyl;

1.280 Any of Methods 1.275-1.278, wherein in Compound I or I(a), $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, $C_{1-6}$alkoxy and halogen;

1.281 Method 1.279, wherein in Compound I or I(a), $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

1.282 Method 1.280, wherein in Compound I or I(a), $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy), for example $R^1$ is 3-methoxy-1-methyl-1H-pyrazolyl;

1.283 Any of Methods 1.262-1.281, wherein in one or more of compound 9-E, Compound I or compound I(a), is a double bond;

1.284 Method 1, or any of Methods 1.1-1.282, wherein the Method produces Compound 1; 1.285 Method 1, or any of Methods 1.1-1.283, wherein the method further comprises any steps described in any of Method 2, et seq., Method 3, et seq., Method 4, et seq., and Method 5, et seq.

In a third aspect, the present disclosure provides a method (Method 2) of making a compound selected from one or more of Compounds 4-B, 4-C, 4-D, 4-E, 5-A, 5-B, 5-C, 5-D, 5-E, 5-E', 5-F, 5-G, 5-G', 5-H, 5-I, 1-J, 1-K, 9-A, 9-B, 9-C, 9-D, 9-E, and Compound I or I(a), as herein described, wherein the method comprises the step of reacting a precursor compound with one or more reagents in a suitable solvent for a time and under conditions effective to form the product compound. Method 2 generally pertains to formation of the tetracyclic moiety (TC), including advanced intermediates 5-F, and 5-I, as well as the evolution of those intermediates to Compound 1. Without being limited in the order or combination of steps employed, the potential embodiments of Method 2 may include any steps shown in Schemes 4 and 5.

In particular embodiments, the present disclosure provides Method 2 as follows:

2.1 Method 2, wherein the method comprises the step of reacting a compound 4-A (6-hydroxy-3,4-dihydronaphthalen-1(2H)-one) with a suitable triflating reagent in a suitable solvent, with a suitable base, for a time and under conditions effective to yield a compound 4-B;

2.2 Method 2.1, wherein the triflating reagent is selected from trifluoromethanesulfonyl anhydride, trifluoromethanesulfonyl chloride, trifluoromethanesulfonyl fluoride, trifluoromethanesulfonic acid, N-trifluoromethanesulfonyl imidazole, and N-phenyl trifluoromethanesulfonimide;

2.3 Method 2.1 or 2.2, wherein the base is selected from tertiary amines (e.g., N-methylmorpholine, tri-n-propylamine, N,N-diisopropylethylamine, triethylamine, tri-n-butylamine, 1,8-diazabicyclo[5.4.0]undec-7-ene, 1,4-diazabicyclo[2.2.2]octane), aromatic amines (e.g., pyridine, 2,6-lutidine, collidine), and inorganic bases (e.g., lithium acetate, potassium acetate, sodium bicarbonate, sodium carbonate, sodium phosphate (monobasic, dibasic or tribasic), potassium bicarbonate, potassium carbonate, potassium phosphate (monobasic, dibasic or tribasic), potassium fluoride, lithium carbonate, cesium carbonate);

Scheme 4

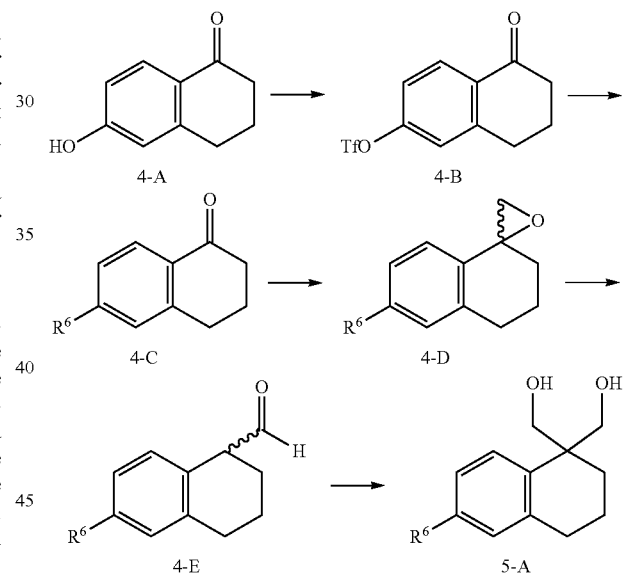

Scheme 5

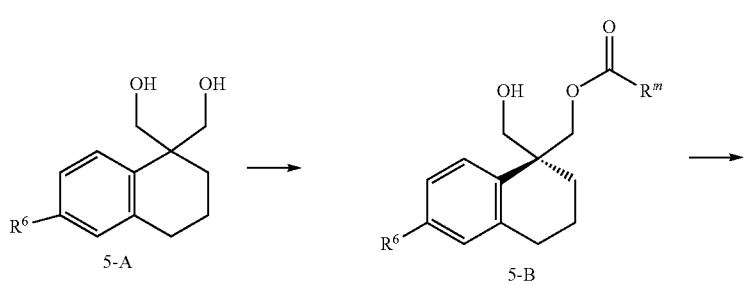

-continued

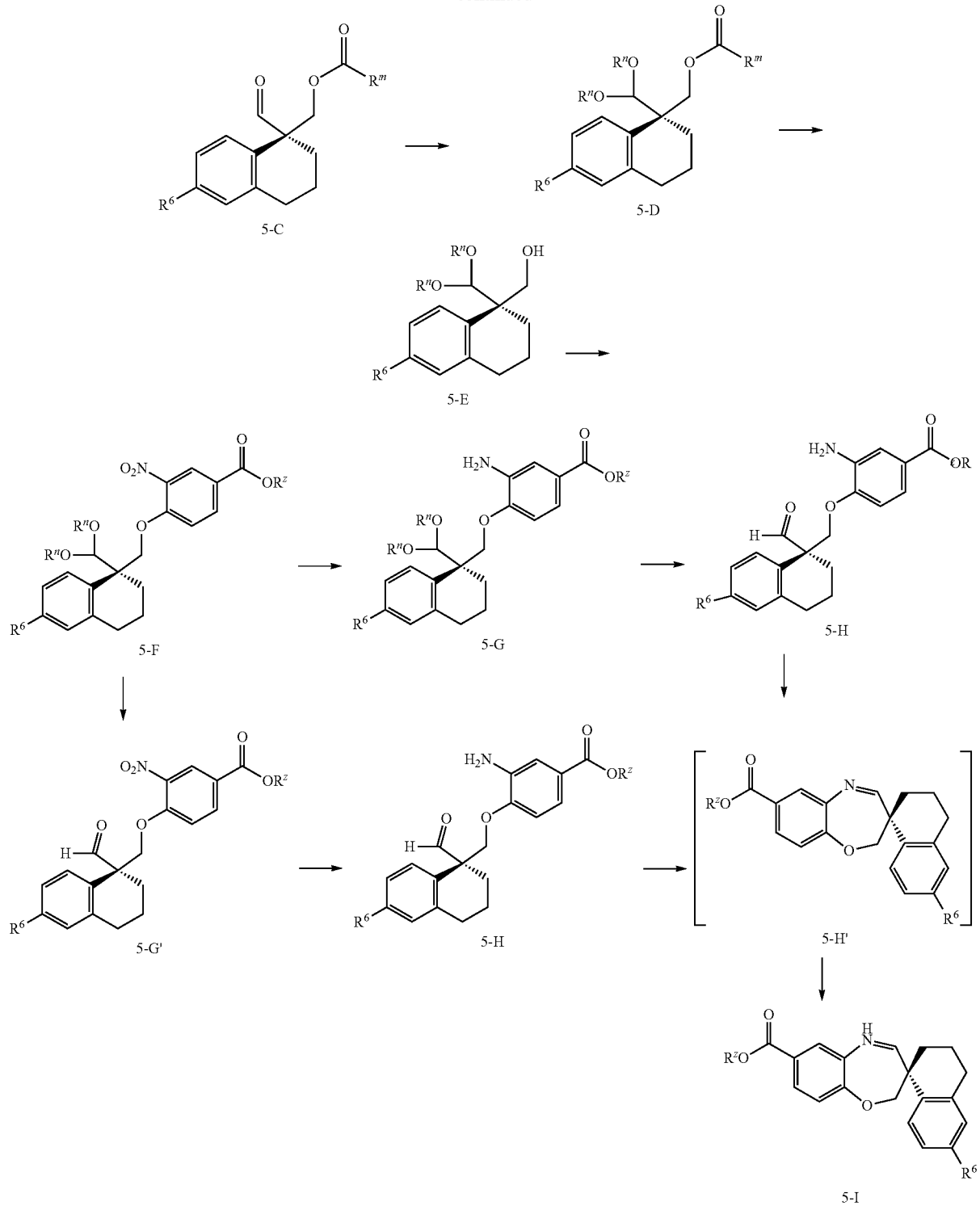

2.4 Any of Methods 2.1-2.3, wherein the reagent is trifluoromethanesulfonyl anhydride and the base is pyridine;

2.5 Any of Methods 2.1-2.4, wherein the suitable solvent is a nonpolar solvent, or polar aprotic solvent;

2.6 Method 2.5, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.7 Method 2.5, wherein the polar aprotic solvent is selected from nitriles (e.g., acetonitrile), and esters (e.g., ethyl acetate, methyl acetate, isopropyl acetate);

2.8 Method 2.5, wherein the nonpolar solvent is dichloromethane;

2.9 Any of Methods 2.1-2.8, wherein the temperature of the reaction is from −80 to 40° C., e.g., from −30 to 20° C., or −10° C. to 10° C., or about 0° C.;

2.10 Method 2, or any of Methods 2.1-2.9, wherein the methods comprises the step of reacting a compound 4-B with a halide source for a time and under conditions effective to form a compound 4-C, wherein $R^6$ is fluoro, chloro, bromo or iodo;

2.11 Method 2.10, wherein $R^6$ is selected from chloro and bromo (e.g., wherein $R^6$ is chloro);

2.12 Method 2.10 or 2.11, wherein the halide source is selected from chloride salts (e.g., lithium chloride, potassium chloride, cesium chloride, tetrabutylammonium chloride), triphenylphosphine dichloride, copper (II) chloride, copper(I) chloride, phosphorus oxychloride, thionyl chloride, sulfuryl chloride, cyanuric chloride, methanesulfonyl chloride, phosgene, triphosgene, bromide salts (e.g., lithium bromide, potassium bromide, cesium bromide, tetrabutylammonium bromide), triphenylphosphine dibromide, copper(II) bromide, copper(I) bromide, phosphorus tribromide, phosphorus oxybromide, thionyl bromide, sulfuryl bromide, iodide salts (e.g., potassium iodide, cesium iodide, tetrabutylammonium iodide), copper(II) iodide, copper (I) iodide, fluoride salts (e.g., lithium fluoride, potassium fluoride, cesium fluoride, tetrabutylammonium fluoride), copper(II) fluoride, and copper(I) fluoride;

2.13 Method 2.12, wherein the halide source is a chloride salt, e.g., lithium chloride;

2.14 Any of Methods 2.10-2.13, wherein the suitable solvent is a nonpolar solvent, or polar aprotic solvent;

2.15 Method 2.14, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., 1,2-dichloroethane, chloroform, chlorobenzene);

2.16 Method 2.14, wherein the polar aprotic solvent is selected from N-methyl-2-pyrrolidinone, N,N-dimethylacetamide, N,N-dimethylformamide, dimethylsulfoxide, nitriles (e.g., acetonitrile), and esters (e.g., ethyl acetate, methyl acetate, isopropyl acetate);

2.17 Method 2.14, wherein the polar aprotic solvent is N-methyl-2-pyrrolidinone;

2.18 Any of Methods 2.10-2.17, wherein the temperature of the reaction is from 50 to 250° C., e.g., from 100 to 220° C., or 130° C. to 150° C., or about 140° C.;

2.19 Method 2, or any of Methods 2.1-2.18, wherein the methods comprises the step of converting a compound 4-C to a compound 4-D, wherein $R^6$ is defined as provided in Method 2.10 or 2.11;

2.20 Method 2.19, wherein $R^6$ is chloro;

2.21 Method 2.19 or 2.20, wherein the reaction comprises treating the compound 4-C with a trimethylsulfonium salt and a base in a polar aprotic solvent;

2.22 Method 2.21, wherein the trimethylsulfonium salt is trimethylsulfonium chloride, trimethylsulfonium bromide, trimethylsulfonium iodide, trimethylsulfonium tetrafluoroborate or trimethylsulfonium methyl sulfate;

2.23 Method 2.21 or 2.22, wherein the base is an inorganic base (e.g., sodium hydroxide, potassium hydroxide or lithium hydroxide);

2.24 Any of Methods 2.21-2.23, wherein the polar aprotic solvent is selected from N-methyl-2-pyrrolidinone, N,N-dimethylacetamide, N,N-dimethylformamide, dimethylsulfoxide, and nitriles (e.g., acetonitrile);

2.25 Any of Methods 2.21-2.24, wherein the temperature of the reaction is from 0 to 50° C., e.g., from 10 to 40° C., or 20° C. to 30° C.;

2.26 Any of Methods 2.19-2.25, wherein the stereoisomers of the compound 4-D are not separated prior to the next step of the method;

2.27 Method 2, or any of Methods 2.1-2.26, wherein the method comprises the step of rearranging a compound 4-D for a time and under conditions effective to form a compound 4-E, wherein $R^6$ is defined as provided in Method 2.10 or 2.11;

2.28 Method 2.27, wherein $R^6$ is chloro;

2.29 Method 2.27 or 2.28, wherein the reaction comprises treating the compound 4-D with a Lewis acid in a nonpolar solvent;

2.30 Method 2.29, wherein the Lewis acid is selected from boron trifluoride, boron trichloride reagent, boron tribromide, magnesium dibromide, indium chloride, bismuth triflate, and copper triflate;

2.31 Method 2.30, wherein the boron trifluoride is boron trifluoride diethyl etherate, boron trifluoride dimethyl sulfide, or boron trifluoride tetrahydrofuran complex;

2.32 Any of Methods 2.29-2.31, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.33 Method 2.32, wherein the nonpolar solvent is tetrahydrofuran;

2.34 Any of Methods 2.27-2.33, wherein the temperature of the reaction is from −10° C. to 50° C., e.g., from 0 to 30° C., or 0° C. to 10° C.;

2.35 Any of Methods 2.27-2.34, wherein the stereoisomers of the compound 4-E are not separated prior to the next step of the method;

2.36 Method 2, or any of Methods 2.1-2.35, wherein the method comprises the step of converting a compound 4-E to a compound 5-A, wherein $R^6$ is defined as provided in Method 2.10 or 2.11;

2.37 Method 2.36, wherein $R^6$ is chloro;

2.38 Method 2.35 or 2.36, wherein the reaction comprises treating the compound 4-E with formaldehyde and a base in a polar protic solvent;

2.39 Method 2.38, wherein the formaldehyde is provided as an aqueous solution;

2.40 Method 2.38 or 2.39, wherein the base is a hydroxide base (e.g., sodium, potassium, lithium, magnesium, barium, calcium, zinc, or aluminum hydroxide);

2.41 Any of Methods 2.38-2.40, wherein the solvent is selected from methanol, ethanol, propanol, isopropanol, t-butyl alcohol, t-amyl alcohol, ethylene glycol, diethylene glycol, triethylene glycol, and water, or a combination thereof;

2.42 Method 2.41, wherein the solvent further comprises one or more of tetrahydrofuran, 2-methyltetrahydrofuran, dioxane, methyl tert-butyl ether, cyclopentyl methyl ether, and dioxane;

2.43 Any of Methods 2.38-2.42, wherein the reaction comprises aqueous formaldehyde, aqueous sodium hydroxide or potassium hydroxide, and diethylene glycol solvent;

2.44 Any of Methods 2.36-2.43, wherein the temperature of the reaction is from 0° C. to 90° C., e.g., from 5 to 50° C., or 10° C. to 40° C.;

2.45 Method 2, or any of Methods 2.1-2.44, wherein the methods comprises the step of acylating a compound 5-A with an acylating agent in a suitable solvent for a time and under conditions effective to form a compound 5-B, wherein $R^6$ is defined as provided in Method 2.10 or 2.11;

2.46 Method 2.45, wherein $R^6$ is chloro;

2.47 Method 2.45 or 2.46, wherein $R^m$ is selected from H, $C_{1-6}$alkyl (e.g., methyl, ethyl, propyl, isopropyl, n-butyl, isobutyl), halo$C_{1-6}$alkyl (e.g., trifluoromethyl, trichloromethyl), carboxy$C_{1-6}$ alkyl (e.g., 3-carboxypropyl), optionally substituted aryl (e.g., phenyl, 4-halophenyl), or optionally substituted heteroaryl (e.g., pyridyl, such as 2-pyridyl);

2.48 Method 2.47, wherein $R^m$ is $C_{1-6}$alkyl, optionally wherein $R^m$ is methyl;

2.49 Any of Methods 2.45-2.48, wherein the acylation is asymmetric, e.g., the acylation produces a product of greater than 50% e.e. before any purification (e.g., greater than 75% e.e., or greater than 85% e.e., or greater than 90% e.e., or greater than 95% e.e.);

2.50 Any of Methods 2.45-2.49, wherein the acylation is enzymatic and the acylating agent is a combination of an enzyme and an acyl donor;

2.51 Method 2.50, wherein the acyl donor is an ester of the formula $R^m$—C(=O)—O—Z or an anhydride of the formula $R^m$—C(=O)—O—C(=O)—$R^m$, wherein Z is selected from $C_{1-6}$alkyl (e.g., methyl, ethyl, isopropyl), $C_{2-6}$alkenyl (e.g., vinyl, allyl, methoxyvinyl, isopropenyl), and halo$C_{1-6}$alkyl (e.g., trifluoromethyl, 2,2,2-trichloroethyl);

2.52 Method 2.50, wherein the acyl donor is selected from vinyl acetate, ethyl acetate, isopropyl acetate, acetic anhydride, 2,2,2-trifluoroethyl acetate, 2,2,2-trichloroethyl acetate, methoxyvinyl acetate, isopropenyl acetate, vinyl propionate, vinyl valerate, vinyl isobutyrate, vinyl trifluoroacetate, vinyl trichloroacetate, vinyl benzoate, vinyl 4-bromoacetate, vinyl picolinate, glutaric anhydride, and vinyl formate;

2.53 Any of Methods 2.50-2.52, wherein the enzyme is a lipase, e.g., a bacterial or fungal lipase, such as from *Candida* species (e.g., Lipozyme TL IM or Novozym 435);

2.54 Any of Methods 2.45-2.53, wherein the suitable solvent is a nonpolar solvent, or polar aprotic solvent;

2.55 Method 2.54, wherein the nonpolar solvent is selected from ethers (e.g., tetrahydrofuran, 2-methyltetrahydrofuran, methyl tert-butyl ether, cyclopentyl methyl ether, dioxane), and hydrocarbon solvents (e.g., toluene, n-hexane, n-heptane);

2.56 Method 2.54, wherein the polar aprotic solvent is selected from N-methyl-2-pyrrolidinone, N,N-dimethylacetamide, N,N-dimethylformamide, dimethylsulfoxide, nitriles (e.g., acetonitrile), and esters (e.g., ethyl acetate, methyl acetate, isopropyl acetate);

2.57 Method 2.54, wherein the polar aprotic solvent is ethyl acetate;

2.58 Any of Methods 2.45-2.57, wherein the temperature of the reaction is from −10° C. to 110° C., e.g., from 0 to 80° C., or 10° C. to 40° C.; or from 20° C. to 30° C.;

2.59 Method 2, or any of Methods 2.1-2.58, wherein the method comprises the step of treating the compound 5-B in a suitable solvent with an oxidizing agent for a time and under conditions effective to form the aldehyde compound 5-C, wherein $R^6$ is defined as provided in Method 2.10 or 2.11, and $R^m$ is defined as in Method 2.47 or 2.48;

2.60 Method 2.59 wherein $R^6$ is chloro and $R^m$ is methyl;

2.61 Method 2.59 or 2.60, wherein the reaction further comprises an additive, a catalyst and/or a base;

2.62 Any of Methods 2.59-2.61, wherein the oxidizing agent is selected from sodium hypochlorite, sulfur trioxide-pyridine, dimethyl sulfoxide with an activating agent (e.g., oxalyl chloride), tetrapropylammonium perruthenate (TPAP)/N-methyl morpholine oxide, Dess-Martin Periodinane, pyridinium chlorochromate, N-chlorosuccinimide/dimethyl sulfide, iodosylbenzene, chromium trioxide, 2-iodoxybenzoic acid, bis (trifluoroacetoxy)iodobenzene, diacetoxyiodobenzene (DAIB), and manganese dioxide;

2.63 Method 2.62, wherein the DMSO activating agent is selected from oxalyl chloride, trifluoroacetic anhydride, cyanuric chloride, N,N'-dicyclohexylcarbodiimide, N,N'-diisopropylcarbodiimide, N-chlorosuccinimide, benzoic anhydride, methanesulfonic anhydride, tosic anhydride, triflic anhydride, methyl chloroglyoxylate, thionyl chloride, diphosgene, triphosgene, methanesulfonyl chloride, tosyl chloride, benzenesulfonyl chloride, trichloroacetonitrile, 2-chloro-1,2-dimethylimidazolinium chloride, polyphosphoric acid, phosphorus trichloride, phosphorus pentoxide, triphenylphosphine dichloride, triphenylphosphine dibromide, phosphorus oxychloride, acetyl chloride, benzoyl chloride, acetyl bromide, phenyl dichlorophosphate, diphenyl chlorophosphate, diethyl chlorophosphate, and ethoxyacetylene;

2.64 Any of Methods 2.61-2.63, wherein the reaction further comprises a catalyst selected from TEMPO ((2,2,6,6-tetramethylpiperidin-1-yl)oxyl), 4-hydroxy-TEMPO, polymer-supported TEMPO, 2-azaadamantane N-oxyl, 9-azabicyclo[3.3.1]nonane N-oxyl, and 9-azanoradamantane N-oxyl;

2.65 Any of Methods 2.61-2.64, wherein the reaction further comprises an additive selected from sodium bromide, lithium bromide and potassium bromide;

2.66 Any of Methods 2.61-2.65, wherein the reaction further comprises a base selected from tertiary amines (e.g., N,N-diisopropylethylamine, N-methylmorpholine, tri-n-propylamine, triethylamine, tri-n-butylamine, 1,8-diazabicyclo[5.4.0]undec-7-ene, 1,4-diazabicyclo[2.2.2]octane), aromatic amines (e.g., pyridine, 2,6-lutidine, collidine), inorganic bases (e.g., sodium bicarbonate, sodium carbonate, sodium phosphate (monobasic, dibasic or tribasic), sodium acetate, potassium bicarbonate, potassium carbonate, potassium phosphate (monobasic, dibasic or tribasic), potassium acetate, potassium fluoride, lithium carbonate, lithium acetate, cesium carbonate), and hydroxide bases (e.g., sodium hydroxide, lithium hydroxide, potassium hydroxide, ammonium hydroxide);

2.67 Any of Methods 2.59-2.66, wherein the oxidizing agent is sulfur trioxide-pyridine;

2.68 Method 2.67, wherein the base is N,N-diisopropylethylamine;

2.69 Any of Methods 2.59-2.68, wherein the suitable solvent is water, a nonpolar solvent, and/or a polar aprotic solvent;

2.70 Method 2.69, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.71 Method 2.69, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), nitriles (e.g., acetonitrile), and ketones (e.g., acetone, methyl ethyl ketone, methyl isobutyl ketone);

2.72 Method 2.69, wherein the suitable solvent is a mixture of ethyl acetate and dimethylsulfoxide;

2.73 Any of Methods 2.59-2.72, wherein the temperature of the reaction is from −80 to 50° C., e.g., from −40 to 40° C., or −10° C. to 10° C.;

2.74 Method 2, or any of Methods 2.1-2.73, wherein the method comprises the step of treating a compound 5-C in a suitable solvent with a protecting agent for a time and under conditions effective to form the acetal compound 5-D, wherein $R^6$ is defined as provided in Method 2.10 or 2.11, and $R'''$ is defined as in Method 2.47 or 2.48;

2.75 Method 2.74 wherein $R^6$ is chloro and $R'''$ is methyl;

2.76 Method 2.74 or 2.75, wherein each $R''$ is independently $C_{1-6}$alkyl (e.g., methyl, ethyl or isopropyl), or wherein the two $R''$ moieties join together to form a $C_{2-10}$ alkyl or $C_{2-10}$ alkenyl bridge (i.e., a cyclic acetal), wherein said bridge is optionally substituted by one to four $C_{1-6}$ alkyl, halogen or aryl; or wherein the two $R''$ moieties join together to form an optionally substituted 1,2-hydroxyaryl bridge (e.g., a catechol bridge);

2.77 Method 2.76, wherein each $R''$ is independently $C_{1-6}$alkyl, optionally wherein each $R''$ is methyl;

2.78 Method 2.76, wherein the two $R''$ moieties join together to form a bridge selected from —CH$_2$CH$_2$—, —CH(CH$_3$)CH(CH$_3$)—, —CH$_2$CH(CH$_3$)—, —CH$_2$CH(Ph)-, —C(CH$_3$)$_2$C(CH$_3$)$_2$—, —CH$_2$CH$_2$CH$_2$—, —CH$_2$CBr$_2$CH$_2$—, —CH$_2$(C═CH)CH$_2$—, —CH$_2$CH(Ph)CH$_2$—, —CH(CH$_3$)CH$_2$CH(CH$_3$)—, —CH$_2$CH(CH$_3$)CH$_2$—, —CH$_2$C(CH$_3$)$_2$CH$_2$—, —CH$_2$C(CH$_2$CH$_3$)$_2$CH$_2$—, —CH$_2$CH$_2$CH$_2$—, —CH$_2$CH$_2$CH$_2$CH$_2$—, —CH(C$_6$H$_5$)CH(C$_6$H$_5$), —CH$_2$CH(C$_6$H$_5$)CH$_2$—, and -(o-C$_6$H$_4$)—;

2.79 Method 2.78, wherein the two $R''$ moieties join together to form a bridge selected from —CH$_2$CH$_2$—, —C(CH$_3$)$_2$C(CH$_3$)$_2$—, —CH$_2$CH$_2$CH$_2$—, and CH$_2$C(CH$_3$)$_2$CH$_2$—, —CH(CH$_3$)CH(CH$_3$)—, —CH(CH$_3$)CH$_2$CH(CH$_3$)—, —CH$_2$CH(CH$_3$)CH$_2$—, —CH$_2$C(CH$_2$CH$_3$)$_2$CH$_2$—, —CH(C$_6$H$_5$)CH(C$_6$H$_5$), and —CH$_2$CH(C$_6$H$_5$)CH$_2$—;

2.80 Method 2.76, wherein each $R''$ is the same $C_{1-6}$alkyl moiety (e.g., methyl, ethyl or isopropyl), and the protecting agent is a $C_{1-6}$ alcohol or a tri($C_{1-6}$alkyl) orthoformate, e.g., wherein each $R''$ is methyl and the protecting agent is methanol or trimethyl orthoformate;

2.81 Method 2.76, wherein the two $R''$ moieties form a $C_{2-10}$alkyl or $C_{2-10}$ alkenyl bridge, and the protecting agent is a $C_{2-10}$alkyl-diol or $C_{2-10}$ alkenyl-diol (e.g., ethylene glycol, propylene glycol);

2.82 Method 2.81, wherein the protecting agent is selected from trimethylorthoformate, trimethylorthoacetate, triethylorthoacetate, triethylorthoformate, alcohols (e.g., MeOH) or diols (e.g., ethylene glycol, pinacol, propylene glycol, butanediol, 2,2-dimethyl-1,3-propanediol, catechol, HOCH$_2$CH$_2$OH, HOCH(CH$_3$)CH(CH$_3$)OH, HOCH$_2$CH(CH$_3$)OH, HOCH$_2$CH(Ph) OH, HOC(CH$_3$)$_2$C(CH$_3$)$_2$OH, HOCH$_2$CH$_2$CH$_2$OH, HOCH$_2$CBr$_2$CH$_2$OH, HOCH$_2$(C═CH)CH$_2$OH, HOCH$_2$CH(Ph)CH$_2$OH, HOCH(CH$_3$)CH$_2$CH(CH$_3$) OH, HOCH$_2$CH(CH$_3$)CH$_2$OH, HOCH$_2$C(CH$_3$)$_2$ CH$_2$OH, HOCH$_2$C(CH$_2$CH$_3$)$_2$CH$_2$OH, HOCH$_2$CH$_2$CH$_2$CH$_2$OH, HOCH$_2$CH$_2$CH$_2$CH$_2$CH$_2$OH));

2.83 Any of Methods 2.74-2.82, wherein the reaction further comprises an acid, e.g., in a catalytic amount (e.g., from 0.001 to 0.10 equivalents, or 0.01-0.05 equivalents);

2.84 Method 2.83, wherein the acid is selected from p-toluenesulfonic acid, methanesulfonic acid, trifluoromethanesulfonic acid, benzenesulfonic acid, camphorsulfonic acid, pyridinium p-toluenesulfonate, sulfuric acid, hydrochloric acid, hydrobromic acid, trifluoroacetic acid, trichloroacetic acid, phosphoric acid, oxalic acid, fumaric acid, phthalic acid, and formic acid; or wherein the acid is an immobilized acidic resin (e.g., Amberlyst resin);

2.85 Any of Methods 2.74 to 2.84, wherein each $R''$ is methyl, the protecting agent is trimethyl orthoformate and the acid catalyst is p-toluenesulfonic acid;

2.86 Any of Methods 2.74 to 2.85, wherein the suitable solvent is a nonpolar solvent, polar protic solvent, or polar aprotic solvent;

2.87 Method 2.86, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.88 Method 2.86, wherein the polar protic solvent is selected from alcohols (e.g., methanol, ethanol, propanol, isopropanol) and diols (e.g., ethylene glycol, propylene glycol), or combinations therefore, optionally wherein the solvent alcohol is the same as the protecting agent;

2.89 Method 2.86, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), and nitriles (e.g., acetonitrile);

2.90 Method 2.86, wherein the suitable solvent is methanol;

2.91 Any of Methods 2.74-2.87, wherein the reaction comprises refluxing in a hydrocarbon solvent (e.g., toluene) with azeotropic removal of water;

2.92 Any of Methods 2.74-2.91, wherein the temperature of the reaction is from 0 to 150° C., e.g., from 25 to 120° C., 0 to 60° C., or 35° C. to 55° C.;

2.93 Method 2, or any of Methods 2.1-2.92, wherein the method comprises the step of hydrolyzing the compound 5-D in water with a base, optionally with a suitable co-solvent, for a time and under conditions effective to form the acetal compound 5-E, wherein $R^6$ is defined as provided in Method 2.10 or 2.11, $R'''$ is defined as in Method 2.47 or 2.48, and $R''$ is defined as in any of Methods 2.76-2.79;

2.94 Method 2.93 wherein $R^6$ is chloro, $R'''$ is methyl, and $R''$ are each methyl;

2.95 Method 2.93 or 2.94, wherein the base is an inorganic base, e.g., a hydroxide, bicarbonate or carbonate base;

2.96 Method 2.95, wherein the base is selected from lithium hydroxide, sodium hydroxide, potassium hydroxide, calcium hydroxide, ammonium hydroxide, tetraethylammonium hydroxide, tetrabutylammonium hydroxide, sodium carbonate, potassium carbonate, cesium carbonate, sodium bicarbonate, potassium bicarbonate and cesium bicarbonate; In one embodiment, the base is potassium carbonate;

2.97 Any of Methods 2.93-2.96, wherein the suitable co-solvent is selected from a nonpolar solvent, polar protic solvent, polar aprotic solvent, or combination thereof;

2.98 Method 2.97, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.99 Method 2.98, wherein the polar protic solvent is an alcohol (e.g., methanol, ethanol, propanol, isopropanol);

2.100 Method 2.98, wherein the polar aprotic solvent is selected from N-methyl-2-pyrrolidinone, N,N-dimethylacetamide, N,N-dimethylformamide, dimethylsulfoxide, and nitriles (e.g., acetonitrile);

2.101 Method 2.97, wherein the suitable solvent is a combination of tetrahydrofuran and water;

2.102 Any of Methods 2.93-2.101, wherein the reaction further comprises a phase-transfer catalyst such as a quaternary ammonium halide salt (e.g., a chloride or bromide salt of tetrabutylammonium, tetraethylammonium, benzyltriethylammonium, methyltricaprylammonium, methyltributylammonium or methyltrioctylammonium);

2.103 Any of Methods 2.93-2.102, wherein the temperature of the reaction is from −10 to 70° C., e.g., from 10 to 30° C., or 20° C. to 30° C.;

2.104 Any of Methods 2.74-2.103, wherein the compound 5-C is converted in two steps to the compound 5-E without isolation or purification of the intermediate compound 5-D;

2.105 Method 2, or any of Methods 2.1-2.104, wherein the method comprises the step of treating the compound 5-E in a suitable solvent with a transacetalization agent for a time and under conditions effective to form the acetal compound 5-E', wherein $R^6$ is defined as provided in Method 2.10 or 2.11, and wherein each $R''$ of the compound 5-E is independently $C_{1-6}$alkyl (e.g., methyl, ethyl or isopropyl), and wherein both $R''$ of the compound 5-E' are not the same as the $R''$ of the compound 5-E;

2.106 Method 2.105 wherein $R^6$ is chloro;

2.107 Method 2.105 or 2.106, wherein both $R''$ of the compound 5-E are methyl;

2.108 Any of Methods 2.105-2.107, wherein each $R''$ of the compound 5-E' is independently $C_{2-6}$alkyl (e.g., ethyl or isopropyl), or wherein the two $R''$ moieties of compound 5-E' join together to form a $C_{2-10}$ alkyl or $C_{2-10}$ alkenyl bridge (i.e., a cyclic acetal), wherein said bridge is optionally substituted by 1-4 halogen or aryl; or wherein the two $R''$ moieties join together to form an optionally substituted 1,2-hydroxyaryl bridge (e.g., a catechol bridge);

2.109 Method 2.108, wherein each $R''$ of compound 5-E' is independently $C_{2-6}$alkyl, optionally wherein each $R''$ is ethyl;

2.110 Method 2.108, wherein the two $R''$ moieties of compound 5-E' join together to form a bridge selected from —$CH_2CH_2$—, —$CH(CH_3)CH(CH_3)$—, —$CH_2CH(CH_3)$—, —$CH_2CH(Ph)$-, —$C(CH_3)_2C(CH_3)_2$—, —$CH_2CH_2CH_2$—, —$CH_2CBr_2CH_2$—, —$CH_2(C=CH)CH_2$—, —$CH_2CH(Ph)CH_2$—, —$CH(CH_3)CH_2CH(CH_3)$—, —$CH_2CH(CH_3)CH_2$—, —$CH_2C(CH_3)_2CH_2$—, —$CH_2C(CH_2CH_3)_2CH_2$—, —$CH_2CH_2CH_2CH_2$—, —$CH_2CH_2CH_2CH_2CH_2$—, —$CH(C_6H_5)CH(C_6H_5)$, —$CH_2CH(C_6H_5)CH_2$—, and -(o-$C_6H_4$)—;

2.111 Method 2.110, wherein the two $R''$ moieties of compound 5-E' join together to form a bridge selected from —$CH_2CH_2$—, —$C(CH_3)_2C(CH_3)_2$—, —$CH_2CH_2CH_2$—, and $CH_2C(CH_3)_2CH_2$—, —$CH(CH_3)CH(CH_3)$—, —$CH(CH_3)$ $CH_2CH(CH_3)$—, —$CH_2CH(CH_3)CH_2$—, —$CH_2C(CH_2CH_3)_2CH_2$—, —$CH(C_6H_5)CH(C_6H_5)$, and —$CH_2CH(C_6H_5)CH_2$—;

2.112 Method 2.108, wherein each $R''$ of compound 5-E' is the same $C_{2-6}$alkyl moiety (e.g., ethyl or isopropyl), and the transacetalization agent is a $C_{2-6}$ alcohol, e.g., wherein each $R''$ is ethyl and the agent is ethanol;

2.113 Method 2.108, wherein the two $R''$ moieties of compound 5-E' form a $C_{2-10}$alkyl or $C_{2-10}$ alkenyl bridge, and the transacetalization agent is a $C_{2-10}$alkyldiol or $C_{2-10}$ alkenyl-diol (e.g., ethylene glycol, propylene glycol);

2.114 Method 2.113, wherein the transacetalization agent is selected from alcohols (e.g. ethanol and propanol), or diols (e.g., ethylene glycol, 2,3-butanediol, pinacol, propylene glycol, 2,4-pentanediol, 2-methyl-1,3-propanediol, 2,2-dimethyl-1,3-propanediol, 2,2-diethyl-1,3-propanediol, 2-phenyl-1,3-propanediol, meso-1,2-diphenyl-1,2-ethanediol, and catechol);

2.115 Any of Methods 2.105-2.114, wherein the reaction further comprises a Lewis acid (e.g., boron trifluoride, titanium isopropoxide) or a Bronstead acid (e.g., p-toluenesulfonic acid);

2.116 Method 2.115, wherein the Lewis acid is selected from boron trifluoride, boron trichloride, boron tribromide, magnesium dibromide, indium chloride, aluminum chloride, tin(IV) chloride, zinc chloride, bismuth triflate, copper triflate, titanium (IV) chloride, and titanium(IV) alkoxide (e.g., titanium(IV) methoxide, titanium(IV) ethoxide, titanium(IV) propoxide, titanium(IV) isopropoxide, or titanium(IV) butoxide);

2.117 Method 2.116, wherein the boron trifluoride is boron trifluoride diethyl etherate, boron trifluoride dimethyl sulfide, or boron trifluoride tetrahydrofuran complex;

2.118 Method 2.115, wherein the Bronsted acid is selected from p-toluenesulfonic acid, methanesulfonic acid, trifluoromethanesulfonic acid, benzenesulfonic acid, camphorsulfonic acid, pyridiniump-toluenesulfonate, sulfuric acid, hydrochloric acid, hydrobromic acid, trifluoroacetic acid, trichloroacetic acid, phosphoric acid, oxalic acid, fumaric acid, phthalic acid, and formic acid; or wherein the acid is an immobilized acidic resin (e.g., Amberlyst resin); in one embodiment, the acid is boron trifluoride diethyl etherate ($BF_3.OEt_2$);

2.119 Any of Methods 2.105 to 2.118, wherein the suitable solvent is a nonpolar solvent, polar protic solvent, or polar aprotic solvent, optionally a nonpolar solvent or polar aprotic solvent combined with a minor volume of polar protic solvent (e.g., less than 10% v/v);

2.120 Method 2.119, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.121 Method 2.119, wherein the polar protic solvent is selected from alcohols (e.g., ethanol, propanol, isopropanol) and diols (e.g., ethylene glycol, propylene glycol), or combinations therefore, optionally wherein the solvent alcohol is the same as the transacetalization agent;

2.122 Method 2.119, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), and nitriles (e.g., acetonitrile);

2.123 Method 2.119, wherein the suitable solvent is 2-methyltetrahydrofuran;

2.124 Any of Methods 2.105-2.120, wherein the reaction comprises refluxing in a hydrocarbon solvent (e.g., toluene) with azeotropic removal of water;

2.125 Any of Methods 2.105-2.124, wherein the temperature of the reaction is from 0 to 100° C., e.g., from 25 to 120° C., or 50° C. to 100° C., or 70° C. to 80° C.;

2.126 Method 2, or any of Methods 2.1-2.125, wherein the method comprises the step of treating a compound 5-E or 5-E' in a suitable solvent with a 4-fluoro-3-nitrobenzoic acid or ester, for a time and under conditions effective to form an ether adduct compound 5-F, wherein $R^6$ is defined as provided in Method 2.10 or 2.11, and wherein each $R''$ is defined as provided in any of Methods 2.76-2.79 or 2.108-2.111; 2.127 Method 2.126, wherein $R^6$ is chloro;

2.128 Method 2.126 or 2.127, wherein both $R''$ moieties of the compound 5-E or 5-E' are methyl or ethyl, or the two $R''$ moieties of the compound 5-E or 5-E' join together to form a bridge selected from —$CH_2CH_2$—, —$C(CH_3)_2C(CH_3)_2$—, —$CH_2CH_2CH_2$—, and $CH_2C(CH_3)_2CH_2$—;

2.129 Any of Methods 2.126-2.128, wherein $R^z$ is H, or optionally substituted $C_{1-6}$alkyl;

2.130 Method 2.129, wherein $R^z$ is selected from H, unsubstituted $C_{1-6}$alkyl (e.g., methyl), $C_{1-6}$ alkoxy substituted $C_{1-6}$alkyl (e.g., methoxyethyl, methoxymethyl), $C_{1-6}$alkoxy substituted $C_{1-6}$ alkoxy substituted $C_{1-6}$alkyl (e.g., methoxyethoxyethyl, methoxyethoxymethyl), 5-6 membered heterocycloalkyl substituted $C_{1-6}$alkyl (e.g., 2-N-(morpholino)ethyl, 2-tetrahydropyranyl), aryloxy substituted $C_{1-6}$alkyl (e.g., benzyloxymethyl), halogen substituted $C_{1-6}$alkyl (e.g., 2,2,2-trichloroethyl), trialkylsilyl substituted $C_{1-6}$alkyl (e.g., 2-(trimethylsilyl)ethyl, triisopropylsilylmethyl), trialkylsilyl substituted $C_{1-6}$alkoxy substituted $C_{1-6}$alkyl (e.g., 2-(trimethylsilyl)ethoxymethyl), and aryl substituted $C_{1-6}$alkyl (e.g., benzyl, 4-methylbenzyl, 4-nitrobenzyl);

2.131 Method 2.130, wherein $R^z$ is H or unsubstituted $C_{1-6}$alkyl (e.g., methyl, ethyl, propyl, isopropyl, n-butyl, s-butyl, isobutyl or tert-butyl);

2.132 Any of Methods 2.126-2.131, wherein the compound 5-E or 5-E' is dissolved or suspended in the suitable solvent and treated with a strong base, and optionally with a promoter (e.g., sodium iodide, tetrabutylammonium iodide);

2.133 Method 2.132, wherein the base is selected from inorganic hydrides (e.g., sodium hydride, potassium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide), inorganic hydroxides (e.g., sodium hydroxide, potassium hydroxide, lithium hydroxide), amide bases (sodium hexamethyldisilazide, lithium hexamethyldisilazide, potassium hexamethyldisilazide, lithium diisopropylamide, sodium diisopropylamide, potassium diisopropylamide), and inorganic bases (e.g., lithium carbonate, sodium carbonate, potassium carbonate, cesium carbonate, potassium phosphate (mono-, di- or tri-basic), sodium phosphate (mono-, di- or tri-basic));

2.134 Method 2.133, wherein the base is selected from sodium methoxide, sodium ethoxide, sodium t-butoxide, potassium methoxide, potassium ethoxide, potassium t-butoxide, lithium t-butoxide, sodium hexamethyldisilazide, lithium hexamethyldisilazide, potassium hexamethyldisilazide, lithium diisopropylamide, sodium diisopropylamide, and potassium diisopropylamide; optionally wherein the base is potassium t-butoxide;

2.135 Method 2.132, 2.133 or 2.134, wherein the 4-fluoro-3-nitrobenzoic acid or ester is added to the reaction about 1 to 60 minutes after addition of the base, e.g., about 1 to 30 minutes after, or 1 to 20 minutes after, or 1 to 15 minutes after, or 1 to 10 minutes after, or 1 to 5 minutes after;

2.136 Any of Methods 2.126-2.135, wherein the 4-fluoro-3-nitrobenzoic acid or ester has the formula 4-F-3-$NO_2$—$C_6H_4$—$COOR^z$;

2.137 Any of Methods 2.126-2.136, wherein the suitable solvent is a nonpolar solvent;

2.138 Method 2.137, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.139 Method 2.138, wherein the nonpolar solvent is tetrahydrofuran;

2.140 Any of Methods 2.126-2.139, wherein the temperature of the reaction is from −80 to 100° C., e.g., from −45 to 10° C., or −30° C. to 10° C., or −10° C. to 5° C., or about 0° C., or −10° C. to 50° C., or −10° C. to 30° C., or 10° C. to 30° C., or 30° C. to 80° C.;

2.141 Method 2, or any of Methods 2.1-2.140, wherein the method comprises the step of treating a nitro compound 5-F or 5-G' in a suitable solvent with a reducing agent for a time and under conditions effective to yield an aniline compound 5-G or 5-H, respectively, wherein $R^6$ is defined as provided in Method 2.10 or 2.11, wherein each $R''$ is defined as provided in any of Methods 2.76-2.79 or 2.108-2.111, and wherein $R^z$ is defined as in any of Methods 2.129 to 2.131;

2.142 Method 2.141 wherein $R^6$ is chloro;

2.143 Method 2.141 or 2.142, wherein both $R''$ moieties of the compound 5-F or 5-G' are methyl or ethyl, or the two $R''$ moieties of the compound 5-F or 5-G' join together to form a bridge selected from —$CH_2CH_2$—, —$C(CH_3)_2C(CH_3)_2$—, —$CH_2CH_2CH_2$—, and $CH_2C(CH_3)_2CH_2$—;

2.144 Any of Methods 2.141-2.143, wherein $R^z$ is unsubstituted $C_{1-6}$alkyl (e.g., methyl, ethyl, propyl, isopropyl, n-butyl, s-butyl, isobutyl or tert-butyl);

2.145 Any of Methods 2.141-2.144, wherein the reducing agent is selected from zinc, tin or iron, in an acid (e.g., in formic acid or acetic acid or HCl in the suitable solvent);

2.146 Any of Methods 2.141-2.144, wherein the reducing agent is a hydrogenation agent (e.g., hydrogen in combination with a heterogenous catalyst (e.g., a transition metal catalyst) or a homogeneous catalyst (e.g., a soluble transition metal complex), or a phase transfer hydrogenation system);

2.147 Method 2.146, wherein the hydrogenation agent is hydrogen gas in combination with a palladium, platinum, rhodium, iridium, ruthenium, or nickel catalyst (e.g., Pd, Pd/C, Pd(OAc)$_2$, Pt/C, PtO$_2$, Ru/C, Raney Nickel, Ru complexes, Rh complexes, PtO$_2$, Pt complexes, Pd complexes, Ir complexes), or ammonium formate in combination with a palladium or platinum catalyst (e.g., Pd, Pd/C, Pt/C, PtO$_2$);

2.148 Method 2.147, wherein the hydrogenation agent is hydrogen gas in combination with a Pd, Pd/C, Pd(OAc)$_2$, Pt/C or PtO$_2$ catalyst, optionally at 1-5 bar pressure (e.g., 1-2 bar);

2.149 Method 2.145, wherein the reducing agent is iron in acetic acid;

2.150 Any of Methods 2.141 to 2.149, wherein the suitable solvent is a nonpolar solvent, polar protic solvent, or polar aprotic solvent;

2.151 Method 2.150, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.152 Method 2.150, wherein the polar protic solvent is an alcohol (e.g., methanol, ethanol, propanol, isopropanol) or acid (e.g., formic acid, acetic acid);

2.153 Method 2.150, wherein the polar aprotic solvent is selected from esters (e.g., ethyl acetate, methyl acetate, isopropyl acetate), and nitriles (e.g., acetonitrile);

2.154 Method 2.150, wherein the suitable solvent is ethyl acetate or isopropyl acetate or acetic acid;

2.155 Any of Methods 2.141-2.154, wherein the temperature of the reaction is from 0 to 100° C., e.g., from 20 to 50° C., or 20° C. to 30° C., or from 50 to 80° C.;

2.156 Method 2, or any of Methods 2.1-2.155, wherein the method comprises the step of treating an acetal compound 5-F or 5-G in a suitable solvent with a deprotection agent for a time and under conditions effective to yield an aldehyde compound 5-G' or 5-H, respectively, wherein $R^6$ is defined as provided in Method 2.10 or 2.11, wherein each $R''$ is defined as provided in any of Methods 2.76-2.79 or 2.108-2.111, and wherein $R^z$ is defined as in any of Methods 2.129 to 2.131;

2.157 Method 2.156 wherein $R^6$ is chloro;

2.158 Method 2.156 or 2.157, wherein both $R''$ are methyl or ethyl, or the two $R''$ moieties join together to form a bridge selected from —CH$_2$CH$_2$—, —C(CH$_3$)$_2$C(CH$_3$)$_2$—, —CH$_2$CH$_2$CH$_2$—, and CH$_2$C(CH$_3$)$_2$CH$_2$—;

2.159 Any of Methods 2.156-2.158, wherein $R^z$ is unsubstituted C$_{1-6}$alkyl (e.g., methyl, ethyl, propyl, isopropyl, n-butyl, s-butyl, isobutyl or tert-butyl);

2.160 Any of Methods 2.156-2.159, wherein the deprotection agent comprises an acid;

2.161 Method 2.160, wherein the acid is selected from HCl (e.g., aqueous HCl or HCl/methanol, HCl/isopropanol, or HCl/dioxane), HBr (e.g., aqueous HBr or HBr/acetic acid), sulfuric acid, phosphoric acid, p-toluenesulfonic acid, pyridinium tosylate, trifluoroacetic acid, methanesulfonic acid, trichloroacetic acid, Lewis acids (e.g., erbium triflate), and acidic resin (e.g., Amberlyst);

2.162 Method 2.161, wherein the acid is selected from HCl (e.g., HCl/dioxane), p-toluenesulfonic acid, methanesulfonic acid, and acidic resin (e.g., Amberlyst);

2.163 Any of Methods 2.156 to 2.162, wherein the suitable solvent is a nonpolar solvent, polar protic solvent, polar aprotic solvent, or a combination thereof, 2.164 Method 2.163, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.165 Method 2.163, wherein the polar protic solvent is water and/or an alcohol (e.g., methanol, ethanol, propanol, isopropanol) or acid (e.g., formic acid, acetic acid);

2.166 Method 2.163, wherein the polar aprotic solvent is selected from ketones (e.g., acetone, methyl ethyl ketone, methyl isobutyl ketone), esters (e.g., ethyl acetate, methyl acetate, isopropyl acetate), and nitriles (e.g., acetonitrile);

2.167 Method 2.163, wherein the suitable solvent is acetone or dioxane;

2.168 Any of Methods 2.156-2.167, wherein the temperature of the reaction is from 0 to 100° C., e.g., from 20 to 50° C., or 20° C. to 30° C.;

2.169 Any of Methods 2.141-2.168, as appropriate, where the intended product compound 5-H undergoes spontaneous condensation to form intermediate imine 5-H' either partly or completely, and the mixture of 5-H and 5-H' is carried forward to the next step, or the product isolated is 5-H' which is used in the next step;

2.170 Method 2, or any of Methods 2.1-2.169, wherein the method comprises the step of treating the aniline/acetal compound 5-H (and/or 5-H') in a suitable solvent with a reducing agent for a time and under conditions effective to yield the secondary amine compound 5-I, wherein $R^6$ is defined as provided in Method 2.10 or 2.11, and wherein $R^z$ is defined as in any of Methods 2.129 to 2.131; 2.171 Method 2.170 wherein $R^6$ is chloro;

2.172 Method 2.170 or 2.171, wherein $R^z$ is unsubstituted C$_{1-6}$alkyl (e.g., methyl, ethyl, propyl, isopropyl, n-butyl, s-butyl, isobutyl or tert-butyl);

2.173 Any of Methods 2.170-2.172, wherein the reducing agent is selected from a hydride reducing agent, a silane reducing agent, and zinc in acid (e.g., zinc in acetic acid);

2.174 Method 2.173, wherein the reducing agent is a hydride reducing agent;

2.175 Method 2.174, wherein the hydride reducing agent is selected from sodium borohydride, lithium borohydride, sodium cyanoborohydride, zinc borohydride, sodium triacetoxyborohydride, and tetramethylammonium triacetoxyborohydride;

2.176 Method 2.175, wherein the hydride reducing agent is sodium triacetoxyborohydride or sodium cyanoborohydride;

2.177 Any of Methods 2.174-2.176, wherein the hydride reducing agent is combined with a reagent to modulate the hydride reducing activity (e.g., titanium isopropoxide, magnesium perchlorate, or zinc chloride); 2.178 Method 2.173, wherein the silane reducing agent is triethylsilane;

2.179 Any of Methods 2.173 to 2.178, wherein the reaction further comprises an acid (e.g., selected from acetic acid, trifluoracetic acid, citric acid, pivalic acid, p-toluenesulfonic acid, methanesulfonic acid, and hydrochloric acid);

2.180 Any of Methods 2.170-2.179, wherein the suitable solvent is a nonpolar solvent, or polar aprotic solvent;

2.181 Method 2.180, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

2.182 Method 2.180, wherein the polar aprotic solvent is selected from N,N-dimethylacetamide, N,N-dimethylformamide, N-methyl-2-pyrrolidinone, and dimethyl sulfoxide;

2.183 Method 2.180, wherein the suitable solvent is dichloromethane or dichloroethane;

2.184 Any of Methods 2.170-2.183, wherein the temperature of the reaction is from −30 to 80° C., e.g., from 0 to 50° C., or 20 to 30° C., or about 20° C.;

2.185 Method 2, or any of Methods 2.1-2.184, wherein the Method produces a compound according to any one or more of Compounds 4-B, 4-C, 4-D, and 4-E;

2.186 Method 2.185, wherein in any one or more of said compounds, $R^6$ is halogen (e.g., chloro);

2.187 Method 2, or any of Methods 2.1-2.186, wherein the Method produces a compound according to any one or more of Compounds 5-A, 5-B, 5-C, 5-D, 5-E, 5-E', 5-F, 5-G, 5-G', 5-H and 5-I;

2.188 Method 2.187, wherein in one or more of said compounds, $R^m$ is $C_{1-3}$ alkyl (e.g., methyl), both $R^n$ are methyl or ethyl, or the two $R^n$ moieties join together to form a bridge selected from —$CH_2CH_2$—, —$C(CH_3)_2C(CH_3)_2$—, —$CH_2CH_2CH_2$—, and $CH_2C(CH_3)_2CH_2$—, $R^z$ is $C_{1-3}$ alkyl (e.g., methyl), and/or $R^6$ is halogen (e.g., chloro);

2.189 Method 2, or any of Methods 2.1-2.188, wherein the Method produces a compound according to any one or more of Compounds 1-J or 1-K;

2.190 Method 2.189, wherein in one or more of said compounds, $R^x$ is H, $R^z$ is H or $C_{1-3}$ alkyl (e.g., methyl), $R^5$ is $C_{1-3}$ alkyl (e.g., methyl), and/or $R^6$ is halogen (e.g., chloro);

2.191 Method 2, or any of Methods 2.1-2.190, wherein the Method produces a compound according to any one or more of Compounds 9-A, 9-B, 9-C, 9-D, or 9-E;

2.192 Method 2.191, wherein one or more of said compounds 9-A, 9-B, 9-C, 9-D, or 9-E are made according to any one or more of Method 4 or Method 4.1, et seq., or Method 5 or Method 5.1, et seq.;

2.193 Method 2.191 or 2.192, wherein in one or more of said compounds, $R^x$ is H, $R^y$ is H, $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), and/or $R^{12}$ is H, or —C(O)—$R^1$, wherein $R^1$ is selected from optionally substituted $C_{1-6}$ alkyl (e.g., methyl), optionally substituted $C_{1-6}$alkoxy (e.g., (S)-1-phenylethoxy), or optionally substituted 5-10 membered heteroaryl (e.g., 1-methyl-3-methoxy-1H-pyrazol-4-yl);

2.194 Method 2.193, wherein in one or more of said compounds, $R^x$ is H, $R^y$ is H, $R^2$ and $R^3$ are independently H or methyl, $R^4$ is H, $R^5$ is methyl, and $R^6$ is chloro;

2.195 Method 2.194, wherein in one or more of said compounds $R^2$ and $R^3$ are H, or $R^2$ and $R^3$ are methyl, or $R^2$ is H and $R^3$ is methyl;

2.196 Method 2.195, wherein in one or more of said compounds $R^2$ is H and $R^3$ is methyl;

2.197 Any of Methods 2.191-2.196, wherein in compound 9-C, $R^{12}$ is —C(O)—$R^1$, and $R^1$ is selected from $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, 5-10 membered heteroaryl, and —$NR^8R^9$, wherein said $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, and —$NR^aR^b$; wherein $R^a$ and $R^b$ is independently hydrogen or $C_{1-6}$alkyl;

2.198 Method 2.197, wherein in compound 9-C, $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$ cycloalkyl, $C_{1-6}$haloalkyl, $C_{1-6}$alkoxy and halogen;

2.199 Method 2.198, wherein in compound 9-C, $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

2.200 Method 2.198, wherein in compound 9-C, $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy), for example $R^1$ is 3-methoxy-1-methyl-1H-pyrazolyl;

2.201 Method 2, or any of Methods 2.1-2.200, wherein the Method produces a compound according to Compound I;

2.202 Method 2.201, wherein the Compound I is a compound I(a);

2.203 Method 2.201 or 2.202, wherein the Compound I or I(a) is made according to any one or more of Method 4 or Method 4.1, et seq., or Method 5 or Method 5.1, et seq.;

2.204 Any of Methods 2.201-2.203, wherein in Compound I or I(a), $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), and/or $R^{12}$ is —C(O)—$R^1$, and $R^1$ is selected from $C_{1-6}$alkyl, $C_{1-6}$haloalkyl, C$_{2-6}$alkynyl, C$_{3-10}$cycloalkyl, C$_{6-10}$aryl, 3-12 membered heterocycloalkyl, 5-10 membered heteroaryl, and —NR$^8$R$^9$, wherein said C$_{1-6}$alkyl, C$_{1-6}$haloalkyl, C$_{2-6}$alkynyl, C$_{3-10}$cycloalkyl, C$_{6-10}$aryl, 3-12 membered heterocycloalkyl, and 5-10 membered heteroaryl are optionally substituted with 1-5 R$^{10}$ groups; wherein each R$^8$ and R$^9$ are independently hydrogen, C$_{1-6}$alkyl, C$_{3-10}$ cycloalkyl, C$_{1-6}$haloalkyl, 3-12 membered heterocycloalkyl, C$_{6-10}$aryl, or 5-10 membered heteroaryl, or R$^8$ and R$^9$ together with the atoms to which they are attached form a 3-12 membered heterocycle, wherein each R$^8$ and R$^9$ are independently hydrogen, C$_{1-6}$alkyl, C$_{3-10}$cycloalkyl, C$_{1-6}$haloalkyl, 3-12 membered heterocycloalkyl, C$_{6-10}$aryl, or 5-10 membered heteroaryl, or R$^8$ and R$^9$ together with the atoms to which they are attached form a 3-12 membered heterocycle, wherein said C$_{1-6}$alkyl, C$_{3-10}$cycloalkyl, C$_{1-6}$haloalkyl, 3-12 membered heterocycloalkyl, C$_{6-10}$aryl, and 5-10 membered heteroaryl are optionally substituted with 1-5 R$^{10}$ groups; wherein each of said R$^{10}$ group is independently selected from C$_{1-6}$alkyl, C$_{3-10}$cycloalkyl, C$_{1-6}$haloalkyl, 3-12 membered heterocycloalkyl, C$_{6-10}$aryl, 5-10 membered heteroaryl, halogen, oxo, —OR$^a$, and —NR$^a$R$^b$; wherein R$^a$ and R$^b$ is independently hydrogen or C$_{1-6}$alkyl;

2.205 Method 2.204, wherein in Compound I or I(a), R$^2$ and R$^3$ are independently H or methyl, R$^4$ is H, R$^5$ is methyl, and R$^6$ is chloro;

2.206 Method 2.205, wherein in Compound I or I(a), R$^2$ and R$^3$ are H, or R$^2$ and R$^3$ are methyl, or R$^2$ is H and R$^3$ is methyl;

2.207 Method 2.206, wherein in Compound I or I(a), R$^2$ is H and R$^3$ is methyl;

2.208 Any of Methods 2.204-2.207, wherein in Compound I or I(a), R$^{12}$ is —C(O)—R$^1$, and R$^1$ is 5-10 membered heteroaryl (e.g., oxazolyl, isoxazolyl, thiazolyl, isothiazolyl, pyrazolyl, imidazolyl), optionally substituted with 1-5 R$^{10}$ groups; wherein each of said R$^{10}$ group is independently selected from C$_{1-6}$alkyl, C$_{3-10}$cycloalkyl, C$_{1-6}$haloalkyl, C$_{1-6}$alkoxy and halogen;

2.209 Method 2.208, wherein in Compound I or I(a), R$^{12}$ is —C(O)—R$^1$, and R$^1$ is pyrazolyl or imidazolyl, optionally substituted with 1-5 R$^{10}$ groups; wherein each of said R$^{10}$ group is independently C$_{1-6}$alkyl (e.g., methyl) or C$_{1-6}$alkoxy (e.g., methoxy);

2.210 Method 2.209, wherein in Compound I or I(a), R$^{12}$ is —C(O)—R$^1$, and R$^1$ is pyrazolyl optionally substituted by 1-3 C$_{1-6}$alkyl (e.g., methyl) or C$_{1-6}$alkoxy (e.g., methoxy), for example R$^1$ is 3-methoxy-1-methyl-1H-pyrazolyl;

2.211 Any of Methods 2.191-2.210, wherein in one or more of compound 9-E, Compound I or compound I(a), is a double bond;

2.212 Method 2, or any of Methods 2.1-2.211, wherein the Method produces Compound 1;

2.213 Method 2, or any of Methods 2.1-2.212, wherein the method further comprises any steps described in any of Method 1, et seq., Method 3, et seq., Method 4, et seq., and Method 5, et seq.

In a fourth aspect, the present disclosure provides a method (Method 3) of making a compound selected from one or more of Compounds 6-B, 6-B', 6-C, 6-D, 6-E, 6-F, 6-G, 6-H, 6-I, 6-J, 6-K, 6-L, 6-L', 7-A, 8-A, 8-B, 9-A, 9-B, 9-C, 9-D, 9-E, and Compound I or I(a), as herein described, wherein the method comprises the step of reacting a precursor compound with one or more reagents in a suitable solvent for a time and under conditions effective to form the product compound. Method 3 generally pertains to formation of the sulfonimidamide moiety (SNO), including advanced intermediates 6-H, 6-L, and 8-B, as well as the evolution of those intermediates to Compound 1. Without being limited in the order or combination of steps employed, the potential embodiments of Method 3 may include any steps shown in Schemes 6, 7 and 8.

Scheme 6

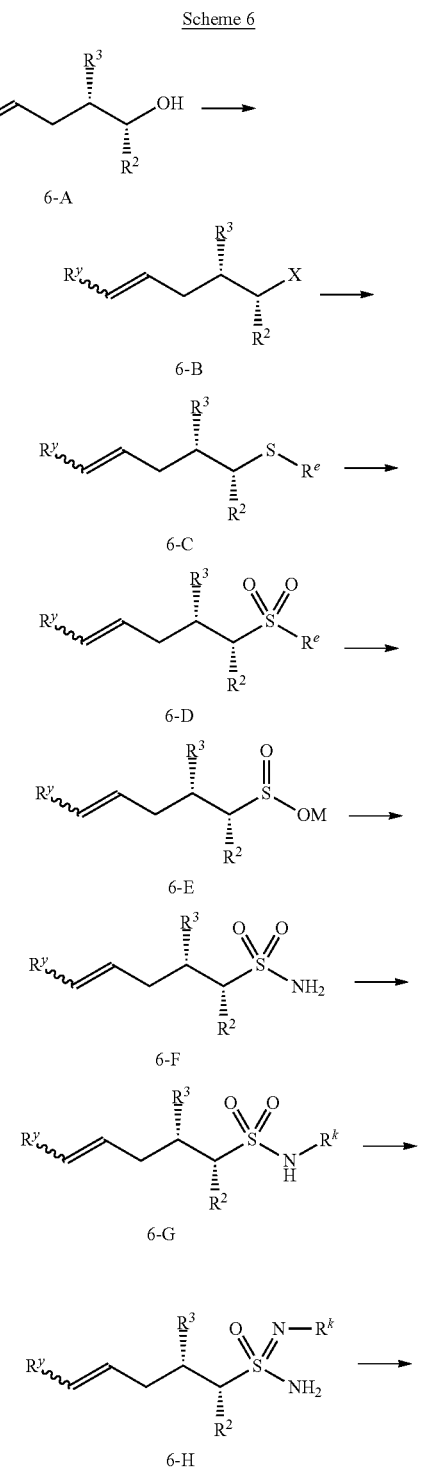

55

-continued

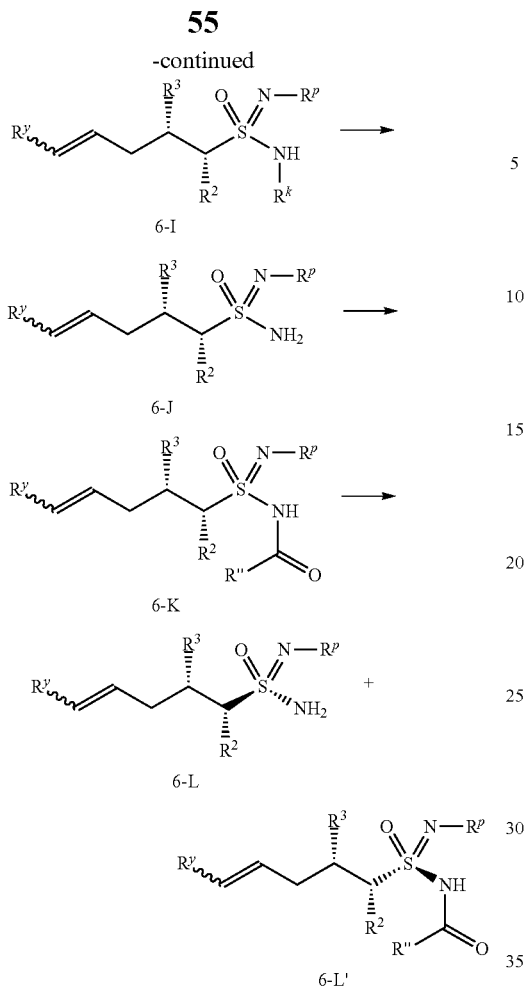

6-I

6-J

6-K

6-L

6-L'

Scheme 7

6-B

6-B'

7-A

6-F

56

-continued

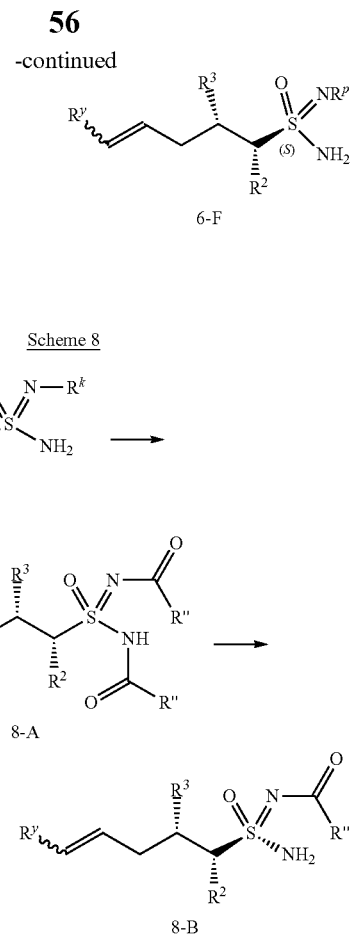

6-F

Scheme 8

6-H

8-A

8-B

In particular embodiments, the present disclosure provides Method 3 as follows:

3.1 Method 3, wherein the method comprises the step of reacting alcohol compound 6-A with an activating agent in a suitable solvent, with a suitable base, for a time and under conditions effective to yield the activated compound 6-B;

3.2 Method 3.1, wherein $R^y$ is selected from H, $C_{1-6}$alkyl (e.g., methyl), and optionally substituted aryl (e.g., phenyl);

3.3 Method 3.2, wherein $R^y$ is H;

3.4 Any of Methods 3.1-3.3, wherein $R^2$ is hydrogen, $C_{1-6}$alkyl, $C_{1-6}$haloalkyl, $C_{3-10}$cycloalkyl, or 3-12 membered heterocycloalkyl, wherein said $C_{1-6}$alkyl, $C_{1-6}$haloalkyl, $C_{3-10}$cycloalkyl, and 3-12 membered heterocycloalkyl are optionally substituted with 1-5 $R^{10}$ groups ($R^{10}$ are as defined for Compound I);

3.5 Method 3.4, wherein $R^2$ is hydrogen or $C_{1-6}$alkyl (e.g., methyl);

3.6 Any of Methods 3.1-3.5, wherein $R^3$ is hydrogen, $C_{1-6}$alkyl, —$OR^7$, $C_{1-6}$haloalkyl, $C_{3-10}$cycloalkyl, 3-12 membered heterocycloalkyl, —C(O)$R^7$, or —CN, wherein said $C_{1-6}$alkyl, $C_{1-6}$haloalkyl, $C_{3-10}$cycloalkyl, and 3-12 membered heterocycloalkyl are optionally substituted with 1-5 $R^{10}$ groups ($R^7$ and $R^{10}$ are as defined for Compound I);

3.7 Method 3.6, wherein $R^3$ is hydrogen, $C_{1-6}$alkyl (e.g., methyl), or —$OR^7$, wherein $R^7$ is $C_{1-6}$alkyl (e.g. methyl);

3.8 Method 3.7, wherein $R^3$ is hydrogen or $C_{1-6}$alkyl (e.g., methyl);

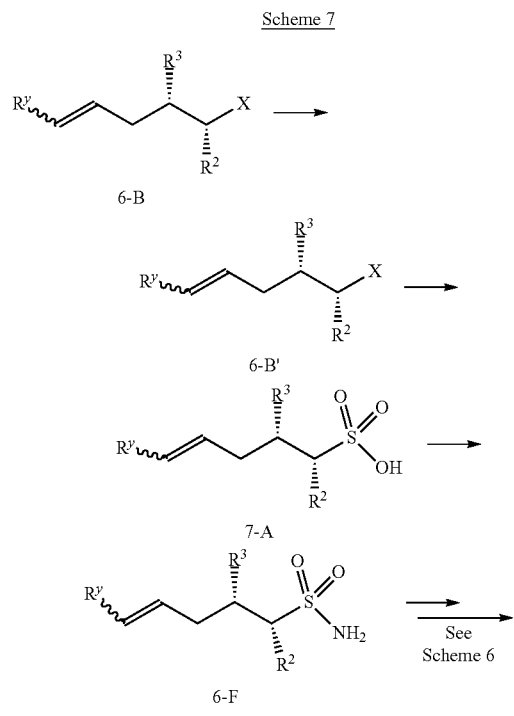

3.9 Any of Methods 3.1-3.9, wherein $R^2$ and $R^3$ are both hydrogens, or wherein $R^2$ is hydrogen and $R^3$ is $C_{1-6}$alkyl (e.g., methyl), or wherein $R^2$ and $R^3$ are both $C_{1-6}$alkyl (e.g., methyl);

3.10 Method 3.9, wherein $R^2$ is hydrogen and $R^3$ is $C_{1-6}$alkyl (e.g., methyl);

3.11 Any of Methods 3.1-3.10, wherein the group X of compound 6-B is selected from a halide (e.g., chloride, bromide, iodide), sulfonate (e.g., 4-toluenesulfonate, mesylate, nosylate, benzenesulfonate, triflate), and oxyphosphonium (e.g., oxytriphenylphosphonium), optionally wherein group X is 4-toluenesulfonate;

3.12 Any of Methods 3.1-3.11, wherein the activating agent is selected from p-toluenesulfonyl chloride, p-toluenesulfonyl fluoride, p-toluenesulfonic anhydride, benzenesulfonyl chloride, p-nitrobenzenesulfonyl chloride, methanesulfonyl chloride, methanesulfonic anhydride, triflic anhydride, N-phenyltriflimide, triphenylphosphine dihalide, triphenylphosphine with tetrahalomethane (e.g. tetrabromomethane), and combinations thereof with metal halide salts (e.g., sodium bromide, potassium iodide);

3.13 Method 3.12, wherein the activating agent is p-toluenesulfonyl chloride;

3.14 Any of Methods 3.1-3.13, wherein the base is selected from tertiary amines (e.g., triethylamine, N-methylmorpholine, N-ethylmorpholine, tri-n-propylamine, N,N-diisopropylethylamine, tri-n-butylamine, 1,8-diazabicyclo[5.4.0]undec-7-ene, 1,4-diazabicyclo[2.2.2]octane), aromatic amines (e.g., pyridine, 2,6-lutidine, collidine, picoline, indole, isoindole, quinoline, isoquinoline), and inorganic bases (e.g., lithium acetate, potassium acetate, sodium bicarbonate, sodium carbonate, sodium phosphate (monobasic, dibasic or tribasic), potassium bicarbonate, potassium carbonate, potassium phosphate (monobasic, dibasic or tribasic), potassium fluoride, lithium carbonate, cesium carbonate);

3.15 Method 3.14, wherein the base is triethylamine;

3.16 Any of Methods 3.1-3.15, wherein the reaction further comprises a catalyst;

3.17 Method 3.16, wherein the catalyst is selected from 4-dimethylaminopyridine, N-methylimidazole, 4-pyrrolidinopyridine, 4-piperidinopyridine, and 9-azajulolidine, optionally wherein the catalyst is 4-dimethylaminopyridine;

3.18 Any of Methods 3.1-3.17, wherein the activation agent is p-toluenesulfonyl chloride, the base is triethylamine and the catalyst is 4-dimethylaminopyridine;

3.19 Any of Methods 3.1-3.18, wherein the suitable solvent is a nonpolar solvent, or polar aprotic solvent;

3.20 Method 3.19, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.21 Method 3.19, wherein the polar aprotic solvent is selected from N,N-dimethylformamide, N,N-dimethylacetamide, N-methyl-2-pyrrolidinone, dimethyl sulfoxide, nitriles (e.g., acetonitrile), and esters (e.g., ethyl acetate, methyl acetate, isopropyl acetate);

3.22 Method 3.19, wherein the nonpolar solvent is dichloromethane;

3.23 Any of Methods 3.1-3.22, wherein the temperature of the reaction is from −20 to 80° C., e.g., from −10 to 30° C., or 0° C. to 20° C.;

3.24 Method 3, or any of 3.1-3.23, wherein the method comprises the step of reacting a compound 6-B with a thiol in a suitable solvent, optionally with a suitable base, for a time and under conditions effective to form a thioether 6-C, wherein $R^y$ is defined as in Method 3.2 or 3.3, and wherein $R^2$ and $R^3$ are as defined in any of Methods 3.4-3.10, and X is as defined in Method 3.11;

3.25 Method 3.24, wherein $R^e$ is selected from optionally substituted 5-10 membered heteroaryl (e.g., optionally substituted pyridyl or pyrimidinyl), —C(=NH)NH($C_{1-6}$ alkyl), —C(=NH)N($C_{1-6}$ alkyl)$_2$, and —C(=NH)NH$_2$;

3.26 Method 3.25, wherein $R^e$ is 5-10 membered heteroaryl, e.g., 6-membered heteroaryl (e.g., 2-pyridyl or 2-pyrimidinyl);

3.27 Any of Methods 3.24-3.26, wherein the thiol is a compound having the formula $R^e$—SH, optionally a salt form thereof (e.g., lithium, sodium or potassium), or a tautomeric equivalent thereof (e.g., a thiourea or thiopyridone);

3.28 Method 3.27, wherein the thiol is selected from 2-mercaptopyrimidine, 2-mercaptopyridine, thiourea, N-methyl thiourea, N,N-dimethylthiourea, each optionally in the form of a salt (e.g., sodium or potassium salt);

3.29 Any of Methods 3.24-3.28, wherein the reaction comprises a base selected from inorganic hydrides (e.g., sodium hydride, potassium hydride, lithium hydride, calcium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide, sodium isopropoxide, potassium isopropoxide, lithium isopropoxide), inorganic hydroxides (e.g., sodium hydroxide, potassium hydroxide, lithium hydroxide), amide bases (sodium hexamethyldisilazide, lithium hexamethyldisilazide, potassium hexamethyldisilazide, lithium diisopropylamide, sodium diisopropylamide, potassium diisopropylamide), tertiary amines (e.g., triethylamine, N-methylmorpholine, N-ethylmorpholine, tri-n-propylamine, N,N-diisopropylethylamine, tri-n-butylamine, 1,8-diazabicyclo[5.4.0]undec-7-ene, 1,4-diazabicyclo[2.2.2]octane), quinoline, isoquinoline), and inorganic bases (e.g., lithium acetate, potassium acetate, sodium bicarbonate, sodium carbonate, sodium phosphate (monobasic, dibasic or tribasic), potassium bicarbonate, potassium carbonate, potassium phosphate (monobasic, dibasic or tribasic));

3.30 Method 3.29, wherein the base is an inorganic hydride (e.g., sodium hydride or potassium hydride) or alkoxide base (e.g., sodium ethoxide or sodium methoxide);

3.31 Any of Methods 3.27-3.29 wherein the thiol is 2-mercaptopyrimidine and the base is sodium ethoxide;

3.32 Any of Methods 3.24-3.31, wherein the suitable solvent is a nonpolar solvent, polar protic solvent, or polar aprotic solvent;

3.33 Method 3.32, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.34 Method 3.32, wherein the polar protic solvent is an alcohol (e.g., methanol, ethanol, propanol, isopropanol);

3.35 Method 3.32, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), and nitriles (e.g., acetonitrile);

3.36 Method 3.32, wherein the suitable solvent is methanol or ethanol, optionally wherein the suitable solvent is ethanol;

3.37 Any of Methods 3.24-3.36, wherein the temperature of the reaction is from 0 to 100° C., e.g., from 20 to 80° C., or 55° C. to 75° C., or about 65° C.;

3.38 Method 3, or any of Methods 3.1-3.37, wherein the method comprises the step of oxidizing a thioether compound 6-C to with an oxidizing agent in a suitable solvent for a time and under conditions effective to form a sulfone compound 6-D, wherein $R^y$ is as defined in Method 3.2 or 3.3, and wherein $R^2$ and $R^3$ are as defined in any of Methods 3.4-3.10, and $R^e$ is as defined in Method 3.25 or 3.26;

3.39 Method 3.38, wherein the oxidizing agent is selected from peroxides (e.g., hydrogen peroxide, sodium peroxide, potassium peroxide), organic peroxides and peroxy compounds (e.g., tert-butyl hydroperoxide, peracetic acid, trifluoroperacetic acid, meta-chloroperoxybenzoic acid, magnesium monoperoxyphthalate), hypochlorite salts (e.g., sodium hypochlorite, potassium hypochlorite, calcium hypochlorite), periodate salts (e.g., sodium periodate, potassium periodate), perborate salts (e.g., sodium perborate), peroxymonosulfate salts (e.g., potassium peroxymonosulfate, Oxone), permanganate salts (e.g., potassium permanganate), tetramethylperruthenate (TPAP), and any combination thereof;

3.40 Method 3.39, wherein the oxidizing agent is a peroxide (e.g., hydrogen peroxide);

3.41 Any of Methods 3.38-3.40, wherein the reaction further comprises a catalyst, e.g., selected from sodium tungstate, tungsten oxytetrachloride, tetrabutylammonium hexapolytungstate, ammonium molybdate, vanadyl acetylacetonate, manganese sulfate, phosphotungstic acid, cerium ammonium nitrate, ruthenium trichloride, methyltrioxorhenium, scandium triflate, iron, and any combination thereof, 3.42 Any of Methods 3.38-3.41 wherein the oxidizing agent is hydrogen peroxide and the catalyst is sodium tungstate;

3.43 Any of Methods 3.38-3.42, wherein the reaction further comprises an acid, e.g., a phosphorus acid, optionally in a catalytic amount (e.g., 0.01-0.1 equivalents);

3.44 Method 3.43, wherein the phosphorus acid is selected from phenylphosphonic acid, methylphosphonic acid, phenylphosphinic acid, methylphosphinic acid, phosphoric acid, polyphosphoric acid (PPA), phosphonic acid, phosphinic acid and combinations thereof;

3.45 Any of Methods 3.38-3.44, wherein the reaction further comprises a phase transfer reagent, e.g., a tetraalkylammonium salt (e.g., a tetraethylammonium or tetrabutylammonium salt), optionally in a catalytic amount (e.g., 0.01-0.1 equivalents);

3.46 Method 3.45, wherein the phase transfer reagent is selected from tetrabutylammonium hydrogen sulfate, tetrabutylammonium sulfate, tetrabutylammonium chloride, tetrabutylammonium bromide, tetrabutylammonium fluoride, and tetrabutylammonium iodide;

3.47 Any of Methods 3.42-3.46, wherein the reaction further comprises phenylphosphonic acid and tetrabutylammonium hydrogen sulfate, each optionally in a catalytic amount (e.g., 0.01-0.1 equivalents);

3.48 Any of Methods 3.38-3.47, wherein the suitable solvent is a nonpolar solvent, polar protic solvent, or polar aprotic solvent;

3.49 Method 3.48, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.50 Method 3.48, wherein the polar protic solvent is an alcohol (e.g., methanol, ethanol, propanol, isopropanol), water, or a combination thereof, 3.51 Method 3.48, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), and nitriles (e.g., acetonitrile);

3.52 Method 3.48, wherein the suitable solvent is toluene;

3.53 Any of Methods 3.38-3.52, wherein the temperature of the reaction is from 0 to 100° C., e.g., from 0 to 60° C., or 10° C. to 30° C.;

3.54 Method 3, or any of Methods 3.1-3.53, wherein the method comprises the step of reacting a compound 6-D with a base in a suitable solvent for a time and under conditions effective to form a compound 6-E, wherein $R^y$ is as defined in Method 3.2 or 3.3, and wherein $R^2$ and $R^3$ are as defined in any of Methods 3.4-3.10, and $R^e$ is as defined in Method 3.25 or 3.26;

3.55 Method 3.54, wherein M is selected from hydrogen and an alkali metal or alkaline earth metal, for example, wherein M is selected from H, Li, Na, K, Mg, and Ca;

3.56 Method 3.54 or 3.55, wherein the base is selected from inorganic hydrides (e.g., sodium hydride, potassium hydride, lithium hydride, calcium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide, sodium isopropoxide, potassium isopropoxide, lithium isopropoxide), inorganic hydroxides (e.g., sodium hydroxide, potassium hydroxide, lithium hydroxide), amide bases (sodium hexamethyldisilazide, lithium hexamethyldisilazide, potassium hexamethyldisilazide, lithium diisopropylamide, sodium diisopropylamide, potassium diisopropylamide), organolithium bases (e.g., methyllithium, ethyllithium, propyllithium, n-butyllithium, s-butyllithium, t-butyllithium), and inorganic carbonates (e.g., sodium carbonate, potassium carbonate, cesium carbonate);

3.57 Method 3.56, wherein the base is selected from inorganic hydrides, alkoxides and inorganic hydroxides;

3.58 Method 3.57, wherein the base is selected from sodium methoxide and potassium methoxide;

3.59 Any of Methods 3.54-3.58, wherein the suitable solvent is a nonpolar solvent, polar protic solvent, or polar aprotic solvent;

3.60 Method 3.59, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.61 Method 3.59, wherein the polar protic solvent is an alcohol (e.g., methanol, ethanol, propanol, isopropanol), or water, or a mixture of the two; optionally wherein the base is the alkoxide corresponding to the alcohol (e.g., a methoxide base and methanol solvent), or the base is a hydroxide base and the solvent is water;

3.62 Method 3.59, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), and nitriles (e.g., acetonitrile);

3.63 Any of Methods 3.58 to 3.61, wherein the base is sodium methoxide or potassium methoxide and the solvent is methanol;

3.64 Any of Methods 3.54-3.63, wherein the temperature of the reaction is from 0 to 100° C., e.g., from 0 to 60° C., or 10° C. to 30° C.;

3.65 Any of Methods 3.54-3.64, wherein the solvents are removed from the reaction and the crude compound 6-E is washed with water and/or with organic solvents, then carried onto the next step without further purification 3.66 Method 3, or any of 3.1-3.65, wherein the method comprises the step of oxidizing a compound 6-E with a suitable oxidizing agent and a base in a suitable solvent to from a sulfonamide compound 6-F, wherein $R^y$ is defined as in Method 3.2 or 3.3, and wherein $R^2$ and $R^3$ are as defined in any of Methods 3.4-3.10, and M is as defined in Method 3.55;

3.67 Method 3.66, wherein the oxidizing agent is hydroxylamine-O-sulfonic acid, or the oxidizing agent is a combination of ammonia with an oxidant selected from iodine, N-chlorosuccinimide, N-bromosuccinimide, tert-butyl hydroperoxide, and m-chloroperoxybenzoic acid;

3.68 Method 3.67, wherein the oxidizing agent is hydroxylamine-O-sulfonic acid;

3.69 Any of Methods 3.66-3.68, wherein the base is selected from alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide, sodium isopropoxide, potassium isopropoxide, lithium isopropoxide), inorganic hydroxides (e.g., sodium hydroxide, potassium hydroxide, lithium hydroxide, tetrabutylammonium hydroxide), inorganic bases (e.g., lithium acetate, sodium acetate, potassium acetate, sodium bicarbonate, sodium carbonate, sodium phosphate (monobasic, dibasic or tribasic), potassium bicarbonate, potassium carbonate, potassium phosphate (monobasic, dibasic or tribasic), lithium carbonate, cesium carbonate), other alkali metal carboxylates (e.g., potassium propionate), and combinations thereof;

3.70 Method 3.69, wherein the base is sodium acetate or potassium acetate;

3.71 Any of Methods 3.66-3.70, wherein the suitable solvent is a nonpolar solvent, polar protic solvent, or polar aprotic solvent;

3.72 Method 3.71, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.73 Method 3.71, wherein the polar protic solvent is an alcohol (e.g., methanol, ethanol, propanol, isopropanol), or water, or a mixture of the two;

3.74 Method 3.71, wherein the polar aprotic solvent is selected from N-methyl-2-pyrrolidinone, N,N-dimethylacetamide, N,N-dimethylformamide, dimethylsulfoxide, esters (e.g., ethyl acetate, methyl acetate, isopropyl acetate), and nitriles (e.g., acetonitrile);

3.75 Method 3.71, wherein the suitable solvent is water;

3.76 Any of Methods 3.66-3.71, wherein the temperature of the reaction is from 0 to 100° C., e.g., from 20 to 80° C., or 35° C. to 55° C., or about 45° C.;

3.77 Method 3, or any of Methods 3.1-3.76, wherein the method comprises the step of reacting a compound 6-F with a protecting agent in a suitable solvent for a time and under conditions effective to form an N-protected compound 6-G, wherein $R^y$ is as defined in Method 3.2 or 3.3, and wherein $R^2$ and $R^3$ are as defined in any of Methods 3.4-3.10;

3.78 Method 3.77, wherein the protecting group $R^k$ is selected from a silyl group, an alkylcarbonyl group (e.g., —C(=O)—$C_{1-6}$alkyl, such as acetyl, isobutyryl, pivaloyl, or —C(=O)—$C_{1-6}$ alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl (aryl), such as 2-phenylethoxycarbonyl or 1-phenylethoxycarbonyl), an aryloxycarbonyl group (e.g., phenoxycarbonyl), a tertiary alkyl group (e.g., t-butyl or trityl), an $C_{1-6}$alkoxy $C_{1-6}$alkyl group (e.g., $C_{1-6}$alkoxymethyl, such as methoxymethyl or ethoxymethyl), a $C_{1-6}$alkylaryl group (e.g., benzyl, 3,5-dimethoxybenzyl, 1-methylbenzyl), a diarylalkyl group (e.g., $C_{1-6}$alkyl(aryl)(aryl), such as diphenylmethyl), an alkylsulfonyl group (e.g., $SO_2C_{1-6}$alkyl, such as methanesulfonyl or isopropylsulfonyl), and an arylsulfonyl group (e.g., $SO_2$-aryl, such as benzenesulfonyl, toluenesulfonyl);

3.79 Method 3.78, wherein $R^k$ is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

3.80 Method 3.79, wherein $R^k$ is selected from tert-butyldimethylsilyl, tert-butyldiphenylsilyl, dimethylphenylsilyl, trimethylsilyl, triethylsilyl and triisopropylsilyl;

3.81 Method 3.80, wherein $R^k$ is tert-butyldimethylsilyl;

3.82 Any of Methods 3.77-3.81, wherein the protecting reagent is selected from silyl chlorides (e.g., chlorotrimethylsilane, chlorotriethylsilane, chlorotripropylsilane, triisopropylsilyl chloride, tert-butyldimethylsilyl chloride, chlorodimethylphenylsilane, chlorotriphenylsilane), silyl trifluoromethanesulfonates (e.g., trimethylsilyl trifluoromethanesulfonate, triethylsilyl trifluoromethanesulfonate, triisopropylsilyl trifluoromethanesulfonate, tert-butyldimethylsilyl trifluoromethanesulfonate, dimethylphenylsilyl trifluoromethanesulfonate, triphenylsilyl trifluoromethanesulfonate), silyl bromides (e.g., bromotrimethylsilane, bromotriethylsilane, bromotripropylsilane, triisopropylsilyl bromide, tert-butyldimethylsilyl bromide, bromodimethylphenylsilane, bromotriphenylsilane), N,O-bis(trimethylsilyl)acetamide, N,O-bis(trimethylsilyl)trifluoroacetamide, N-methyl-N-(trimethylsilyl)trifluoroacetamide, benzyl halides (e.g., 3,5-dimethoxybenzyl chloride, 3,5-dimethoxybenzyl bromide), dibenzyl carbonate, acid chlorides (e.g., pivaloyl chloride, acetyl chloride, benzoyl chloride), anhydrides (e.g., di-tert-butyl carbonate), chloroformates (e.g., methyl chloroformate, ethyl chloroformate, benzyl chloroformate, phenyl chloroformate, 1-phenylethylchloroformate), alkyl halides (e.g., trityl chloride, tert-butyl chloride, benzyl bromide, benzyl chloride, 2-chloro-2-phenylpropane), and alkoxymethyl halides (e.g., methoxymethyl chloride);

3.83 Any of Methods 3.77-3.82, wherein the reaction further comprises a base;

3.84 Method 3.83, wherein the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane), aromatic amines (e.g., pyridine, 2,6-lutidine, picoline, collidine, imidazole, 1-methylimidazole, indole, isoindole, quinoline, isoquinoline, 4-dimethylaminopyridine), inorganic hydrides (e.g., sodium hydride, potassium hydride, lithium hydride), amide bases (sodium hexamethyldisilazide, lithium hexamethyldisilazide, potassium hexamethyldisilazide, lithium diisopropylamide, sodium diisopropylamide, potassium diisopropylamide), organolithium bases (e.g., n-butyllithium, s-butyllithium, t-butyllithium), and inorganic bases (e.g., lithium carbonate, sodium carbonate, potassium carbonate, calcium carbonate, potassium phosphate (monobasic, dibasic or tribasic), sodium phosphate (monobasic, dibasic or tribasic));

3.85 Method 3.84, wherein the protecting agent is tert-butyldimethylsilyl chloride and the base is triethylamine;

3.86 Any of Methods 3.77-3.85, wherein the reaction further comprises a catalyst selected from 4-(dimethylamino)pyridine, 2,6-dimethylpyridine, N-methylimidazole, imidazole, 4-pyrrolidinopyridine, 4-piperidinopyridine, and 9-azajulolidine;

3.87 Any of Methods 3.77-3.86, wherein the suitable solvent is a nonpolar solvent or polar aprotic solvent;

3.88 Method 3.87, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.89 Method 3.87, wherein the polar aprotic solvent is selected from N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

3.90 Method 3.87, wherein the nonpolar solvent is an ether, optionally wherein the solvent is tetrahydrofuran or 2-methyltetrahydrofuran;

3.91 Any of Methods 3.77-3.90, wherein the temperature of the reaction is from −30 to 100° C., e.g., from −10 to 30° C., from 0° C. to 25° C., from 0 to 100° C., e.g., from 20 to 80° C., or 35° C. to 55° C., or about 45° C.;

3.92 Method 3, or any of Methods 3.1-3.91, wherein the method comprises the step of treating a protected sulfonamide 6-G with (1) a chlorinating agent and a base in a suitable solvent, followed by (2) an ammonia source in a suitable solvent, for a time and under conditions effective to form a compound 6-H, wherein $R^y$ is as defined in Method 3.2 or 3.3, wherein $R^2$ and $R^3$ are as defined in any of Methods 3.4-3.10, and wherein $R^k$ is as defined in any of Methods 3.78-3.81;

3.93 Method 3.92, wherein the chlorinating agent is a selected from triphenylphosphine dichloride ($Ph_3PCl_2$) (optionally prepared in situ from triphenylphosphine and oxalyl chloride), phosphorus oxychloride (optionally prepared in situ from phosphorus pentoxide and a chloride salt, e.g., sodium chloride, potassium chloride or tetrabutylammonium chloride), phenyldichlorophosphate, triphenyldichlorophosphorane, phenylphosphonic dichloride, oxalyl chloride, thionyl chloride, sulfuryl chloride, triphenylphosphite dichloride complex $((PhO)_3PCl_2)$ (optionally prepared in situ from chlorine and triphenylphosphite), phosphorus (V) oxychloride, phosphorus trichloride, phosphorus pentachloride, and hydrogen chloride;

3.94 Method 3.93, wherein the chlorinating agent is triphenylphosphine dichloride, optionally wherein the triphenylphosphine dichloride is prepared in situ from triphenylphosphine oxide and oxalyl chloride;

3.95 Any of Methods 3.92-3.94, wherein the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane), and aromatic amines (e.g., pyridine, 2,6-lutidine, picoline, collidine, imidazole, 1-methylimidazole, indole, isoindole, quinoline, isoquinoline, 4-dimethylaminopyridine);

3.96 Method 3.95 wherein the base is N,N-diisopropylethylamine;

3.97 Any of Methods 3.92-3.96, wherein the suitable solvent is a nonpolar solvent or polar aprotic solvent;

3.98 Method 3.97, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.99 Method 3.97, wherein the polar aprotic solvent is selected from N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

3.100 Method 3.97, wherein the nonpolar solvent is dichloromethane;

3.101 Any of Methods 3.92-3.100, wherein the ammonia source is selected from ammonia gas dissolved in any of the solvents provided in Methods 3.97-3.100, aqueous ammonia, inorganic ammonium salts (e.g., ammonium chloride, ammonium bromide, ammonium sulfate, ammonium acetate), ammonia surrogates (e.g., hexamethyldisilazane), amides (e.g., acetamide), and carbamates (e.g., tert-butyl carbamate);

3.102 Method 3.101, wherein the ammonia source is ammonia dissolved in a solvent, optionally wherein the solvent is the same solvent as the reaction solvent from step (1) (e.g., wherein the reaction solvent is dichloromethane and the ammonia source is ammonia gas dissolved in dichloromethane);

3.103 Any of Methods 3.92-3.102, wherein the temperature of the reaction for step (1) and step (2) is independently selected from −40 to 60° C., −25 to 30° C., −20 to 30° C., −20 to 10° C., −10 to 30° C., −10 to 10° C., −20 to 0° C., −10 to 0° C., and 0 to 30° C.;

3.104 Any of Methods 3.92-3.103, wherein step (1) comprises combining the compound 6-G with the base and the suitable solvent at a temperature of −20 to 0° C. followed by addition of the chlorinating agent (or formation of the chlorinating agent in situ), stirring the reaction for a period of time from 0.5 hours to 10 hours (e.g., 1 to 5 hours), followed by step (2) which comprises cooling the reaction to −40 to −10° C., adding the ammonia source and stirring the reaction for a period of time from 0.1 to 5 hours (e.g., 0.1 to 2 hours) at a temperature ranging from −10 to 10° C.;

3.105 Method 3, or any of Methods 3.1-3.104, wherein the method comprises the step of reacting a monoprotected sulfonimidamide compound 6-H with a protecting agent in a suitable solvent for a time and under conditions effective to yield diprotected sulfonimidamide compound 6-I, wherein R is as defined in Method 3.2 or 3.3, wherein $R^2$ and $R^3$ are as defined in any of Methods 3.4-3.10, and wherein $R^k$ is as defined in any of Methods 3.78-3.81, provided that $R^p$ is not the same as $R^k$;

3.106 Method 3.105 wherein $R^k$ is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

3.107 Method 3.106, wherein $R^k$ is selected from tert-butyldimethylsilyl, tert-butyldiphenylsilyl, dimethylphenylsilyl, trimethylsilyl, triethylsilyl and triisopropylsilyl;

3.108 Method 3.107, wherein $R^k$ is tert-butyldimethylsilyl;

3.109 Any of Methods 3.105-3.108, wherein the protecting group $R^p$ is selected from a silyl group, an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), an aryloxycarbonyl group (e.g., phenoxycarbonyl), a tertiary alkyl group (e.g., t-butyl or trityl), an $C_{1-6}$alkoxy $C_{1-6}$alkyl group (e.g., $C_{1-6}$alkoxymethyl, such as methoxymethyl or ethoxymethyl), a $C_{1-6}$alkylaryl group (e.g., benzyl, 3,5-dimethoxybenzyl, 1-methylbenzyl), a diarylalkyl group (e.g., $C_{1-6}$ alkyl(aryl)(aryl), such as diphenylmethyl), an alkylsulfonyl group (e.g., $SO_2C_{1-6}$alkyl, such as methanesulfonyl or isopropylsulfonyl), and an arylsulfonyl group (e.g., $SO_2$-aryl, such as benzenesulfonyl, toluenesulfonyl);

3.110 Method 3.109, wherein $R^p$ is selected from —C(=O)—$C_{1-6}$alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

3.111 Method 3.110, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

3.112 Method 3.111, wherein $R^p$ is 1-phenylethoxycarbonyl, optionally in (R) or (S) form;

3.113 Any of Methods 3.105-3.112, wherein the protecting reagent is selected from silyl chlorides (e.g., chlorotrimethylsilane, chlorotriethylsilane, chlorotripropylsilane, triisopropylsilyl chloride, tert-butyldimethylsilyl chloride, chlorodimethylphenylsilane, chlorotriphenylsilane), silyl trifluoromethanesulfonates (e.g., trimethylsilyl trifluoromethanesulfonate, triethylsilyl trifluoromethanesulfonate, triisopropylsilyl trifluoromethanesulfonate, tert-butyldimethylsilyl trifluoromethanesulfonate, dimethylphenylsilyl trifluoromethanesulfonate, triphenylsilyl trifluoromethanesulfonate), silyl bromides (e.g., bromotrimethylsilane, bromotriethylsilane, bromotripropylsilane, triisopropylsilyl bromide, tert-butyldimethylsilyl bromide, bromodimethylphenylsilane, bromotriphenylsilane), N,O-bis(trimethylsilyl)acetamide, N,O-bis(trimethylsilyl)trifluoroacetamide, N-methyl-N-(trimethylsilyl)trifluoroacetamide, benzyl halides (e.g., 3,5-dimethoxybenzyl chloride, 3,5-dimethoxybenzyl bromide), dibenzyl carbonate, acid chlorides (e.g., pivaloyl chloride, acetyl chloride, benzoyl chloride), anhydrides (e.g., di-tert-butyl carbonate), chloroformates (e.g., methyl chloroformate, ethyl chloroformate, benzyl chloroformate, phenyl chloroformate, 1-phenylethylchloroformate), alkyl halides (e.g., trityl chloride, tert-butyl chloride, benzyl bromide, benzyl chloride, 2-chloro-2-phenylpropane), and alkoxymethyl halides (e.g., methoxymethyl chloride);

3.114 Any of Methods 3.105-3.112, wherein the protecting agent is a $C_{1-6}$alkyl or $C_{1-6}$ alkyl(aryl) 1H-imidazole-1-carboxylate, optionally made in situ by reacting the corresponding $C_{1-6}$alkyl alcohol or $C_{1-6}$alkyl(aryl) alcohol with carbonyldiimidazole (CDI), in a suitable solvent, followed by addition of the compound 6-H;

3.115 Method 3.113 or 3.114, wherein the protecting agent is selected from a symmetrical or unsymmetrical carbonate (e.g., di-tert-butyldicarbonate or 4-nitrophenyl (1-phenylethyl) carbonate), a $C_{1-6}$alkyl or $C_{1-6}$alkyl(aryl) chloroformate (e.g., methyl chloroformate, ethyl chloroformate, benzyl chloroformate, phenyl chloroformate, 1-phenylethylchloroformate) or a $C_{1-6}$alkyl or $C_{1-6}$alkyl(aryl) 1H-imidazole-1-carboxylate;

3.116 Method 3.115, wherein the protecting agent is selected from 1-phenylethyl-1H-imidazole-1-carboxylate (optionally made in situ from 1-phenylethanol and CDI), 4-nitrophenyl-(1-phenylethyl) carbonate, and 1-phenylethyl chloroformate, wherein each of said reagents is optionally in (R) or (S) form;

3.117 Any of Methods 3.105-3.116, wherein the reaction further comprises a base;

3.118 Method 3.117, wherein the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane, aromatic amines (e.g., pyridine, 2,6-lutidine, picoline, collidine, imidazole, 1-methylimidazole, indole, isoindole, quinoline, isoquinoline, 4-dimethylaminopyridine), inorganic hydrides (e.g., sodium hydride, potassium hydride, lithium hydride), amide bases (sodium hexamethyldisilazide, lithium hexamethyldisilazide, potassium hexamethyldisilazide, lithium diisopropylamide, sodium diisopropylamide, potassium diisopropylamide), organolithium bases (e.g., n-butyllithium, s-butyllithium, t-butyllithium), and inorganic bases (e.g., lithium carbonate, sodium carbonate, potassium carbonate, calcium carbonate, potassium phosphate (monobasic, dibasic or tribasic), sodium phosphate (monobasic, dibasic or tribasic));

3.119 Method 3.118, wherein the base is an inorganic hydride (e.g., sodium hydride, potassium hydride, lithium hydride), amide base (sodium hexamethyldisilazide, lithium hexamethyldisilazide, potassium hexamethyldisilazide, lithium diisopropylamide, sodium diisopropylamide, potassium diisopropylamide), or organolithium base (e.g., n-butyllithium, s-butyllithium, t-butyllithium);

3.120 Method 3.119, wherein the protecting agent is (S)-1-phenylethyl 1H-imidazole-1-carboxylate (optionally made in situ from (S)-1-phenylethanol and CDI), and the base is lithium hexamethyldisilazide;

3.121 Any of Methods 3.105-3.120, wherein the reaction further comprises a catalyst selected from 4-(dimethylamino)pyridine, 2,6-dimethylpyridine, N-methylimidazole, imidazole, 4-pyrrolidinopyridine, 4-piperidinopyridine, and 9-azajulolidine;

3.122 Any of Methods 3.105-3.121, wherein the suitable solvent is a nonpolar solvent or polar aprotic solvent;

3.123 Method 3.122, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.124 Method 3.122, wherein the polar aprotic solvent is selected from N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

3.125 Method 3.122, wherein the nonpolar solvent is an ether, optionally, wherein the solvent is tetrahydrofuran or 2-methyltetrahydrofuran;

3.126 Any of Methods 3.105-3.125, wherein the temperature of the reaction is from −30 to 100° C., e.g., from −20 to 60° C., from −20 to 10° C., from 0° C. to 25° C., from 0 to 100° C., e.g., from 20 to 80° C., or 35° C. to 55° C.;

3.127 Method 3, or any of Methods 3.1-3.126, wherein the method comprises the step of reacting a compound 6-I with a deprotecting agent in a suitable solvent for a time and under conditions effective to form a compound 6-J, wherein $R^y$ is as defined in Method 3.2 or 3.3, wherein $R^2$ and $R^3$ are as defined in any of Methods 3.4-3.10, wherein $R^k$ is as defined in any of Methods 3.78-3.81, and wherein $R^p$ is as defined in any of Methods 3.109-3.112, provided that $R^p$ is not the same as $R^k$;

3.128 Method 3.127 wherein $R^k$ is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

3.129 Method 3.128, wherein $R^k$ is selected from tert-butyldimethylsilyl, tert-butyldiphenylsilyl, dimethylphenylsilyl, trimethylsilyl, triethylsilyl and triisopropylsilyl;

3.130 Method 3.129, wherein $R^k$ is tert-butyldimethylsilyl;

3.131 Any of Methods 3.127-3.130, $R^p$ is selected from —C(=O)—$C_{1-6}$alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

3.132 Method 3.131, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

3.133 Method 3.132, wherein $R^p$ is 1-phenylethoxycarbonyl, optionally in (R) or (S) form;

3.134 Method 3.133, wherein $R^k$ is tert-butyldimethylsilyl and $R^p$ is 1-phenylethoxycarbonyl, optionally in (R) or (S) form;

3.135 Any of Methods 3.127-3.134, wherein the deprotection reagent is selected from an inorganic base (e.g., an aqueous solution thereof), an inorganic acid (e.g., an aqueous solution thereof or a solution in an organic solvent), a fluoride agent (e.g., in an organic solvent), a hydrogenation agent (e.g., hydrogen in combination with a heterogenous catalyst (e.g., a transition metal catalyst) or a homogeneous catalyst (e.g., a soluble transition metal complex), or a phase transfer hydrogenation system), optionally further comprising a phase transfer agent;

3.136 Method 3.135, wherein the deprotection reagent is selected from sodium hydroxide, potassium hydroxide, lithium hydroxide, sodium bicarbonate, sodium carbonate, potassium bicarbonate, potassium carbonate, lithium carbonate, sodium phosphate (mono-, di- or tri-basic), potassium phosphate (mono-, di- or tri-basic), hydrochloric acid (e.g., aqueous HCl, HCl in ether, HCl in methanol, HCl in isopropanol), sulfuric acid, acetic acid, trifluoroacetic acid, phosphoric acid, methanesulfonic acid, hydrofluoric acid, hydrogen fluoride pyridine, hydrogen fluoride triethylamine, potassium fluoride, sodium fluoride, lithium fluoride, cesium fluoride, tetramethylammonium fluoride, tetraethylammonium fluoride, tetrabutylammonium fluoride, triethylamine trihydrofluoride, tetrabutylammonium difluorotriphenylsilicate, hydrogen in combination with a catalyst (e.g., Pd, Pd/C, Pt, Ru/C, Raney Nickel, Ru complexes, Rh complexes, $PtO_2$, Pt complexes, Pd complexes, Ir complexes), and ammonium formate in combination with a palladium or platinum catalyst (e.g., Pd, Pd/C, Pt, $PtO_2$);

3.137 Any of Methods 3.127-3.136, wherein $R^k$ is a silyl group, and the deprotection agent is fluoride agent or an inorganic base;

3.138 Method 3.137, wherein $R^k$ is a trialkyl silyl group (e.g., tripropylsilyl, triisopropylsilyl, t-butyldiethylsilyl, t-butyldimethylsilyl), and the deprotection reagent is selected from potassium hydroxide, sodium hydroxide, lithium hydroxide, sodium bicarbonate, sodium carbonate, sodium phosphate monobasic, sodium phosphate dibasic, sodium phosphate tribasic, potassium bicarbonate, potassium carbonate, potassium phosphate monobasic, potassium phosphate dibasic, potassium phosphate tribasic, lithium carbonate, cesium carbonate, sodium fluoride, potassium fluoride, cesium fluoride, triethylamine trihydrofluoride, tetrabutylammonium fluoride, tetrabutylammonium difluorotriphenylsilicate, and tetrabutylammonium difluorotriphenylsilicate;

3.139 Method 3.138, wherein $R^k$ is t-butyldimethylsilyl and the deprotection agent is selected from sodium carbonate, potassium carbonate and cesium carbonate;

3.140 Any of Methods 3.127-3.139, wherein the suitable solvent is a nonpolar solvent, polar protic solvent, or polar aprotic solvent, or a combination thereof;

3.141 Method 3.140, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.142 Method 3.140, wherein the polar protic solvent is an alcoholic solvent (e.g., methanol, ethanol, propanol, isopropanol, tert-butanol, tert-amyl alcohol), optionally in combination with water, or wherein the polar protic solvent is water;

3.143 Method 3.140, wherein the polar aprotic solvent is selected from N,N-dimethylacetamide, N,N-dimethylformamide, N-methyl-2-pyrrolidinone, and dimethyl sulfoxide, esters (e.g., ethyl acetate, methyl acetate, isopropyl acetate), and nitriles (e.g., acetonitrile), optionally in combination with water;

3.144 Method 3.140, wherein the suitable solvent is tetrahydrofuran or 2-methyltetrayhydrofuran, optionally in combination with water;

3.145 Any of Methods 3.127-3.144, wherein the temperature of the reaction is from −15 to 70° C., e.g., from −5 to 40° C., or 0° C. to 30° C., or from 10° C. to 30° C., or from 20° C. to 70° C., 40° C. to 60° C., or about 50° C.;

3.146 Method 3, or any of Methods 3.1-3.145, wherein the method comprises the step of acylating a compound 6-J with an acylating agent and a base for a time and under conditions effective to form a compound 6-K, wherein R is as defined in Method 3.2 or 3.3, wherein $R^2$ and $R^3$ are as defined in any of Methods 3.4-3.10, and wherein $R^p$ is as defined in any of Methods 3.109-3.112;

3.147 Method 3.146, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

3.148 Method 3.147, wherein $R^p$ is 1-phenylethoxycarbonyl, optionally in (R) or (S) form;

3.149 Any of Methods 3.146-3.148, wherein R" is selected from H, $C_{1-6}$alkyl (e.g., methyl, ethyl, propyl, isopropyl, n-butyl, isobutyl), halo$C_{1-6}$alkyl (e.g., trifluoromethyl, trichloromethyl), optionally substituted aryl (e.g., phenyl, 4-bromophenyl), and optionally substituted heteroaryl (e.g., 2-pyridyl);

3.150 Method 3.149, wherein R" is $C_{1-6}$alkyl (e.g., methyl, ethyl, propyl, isopropyl, n-butyl, isobutyl);

3.151 Method 3.150, wherein R" is methyl;

3.152 Any of methods 3.146-3.151, wherein the acylating agent is an acid chloride (e.g., R"—C(=O)—Cl), an acid anhydride (e.g., R"—C(=O)—O—(C=O)—R"), or a combination of a carboxylic acid (e.g., R"—COOH) with an activator or coupling reagent (e.g., oxalyl chloride, thionyl chloride, phosphoryl chloride, 1,1-carbonyldiimidazole, a carbodiimide reagent (e.g., DCC or EDC), or any other peptide coupling reagent (e.g., HATU, T3P, isobutyl chloroformate);

3.153 Method 3.152, wherein R" is $C_{1-6}$alkyl (e.g., methyl), and the acylating agent is an acid chloride (e.g., R"—C(=O)—Cl), or an acid anhydride (e.g., R"—C(=O)—O—(C=O)—R");

3.154 Any of methods 3.146-3.153, wherein the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane), and aromatic amines (e.g., pyridine, 2,6-lutidine, picoline, collidine, imidazole, 1-methylimidazole, indole, isoindole, quinoline, isoquinoline, 4-dimethylaminopyridine);

3.155 Method 3.154 wherein the base is pyridine;

3.156 Any of Methods 3.146-3.155, wherein the reaction further comprises a catalyst, e.g., selected from 4-dimethylaminopyridine, imidazole, N-methylimidazole, triphenylphosphine oxide, 1-hydroxy-7-azabenzotriazole, and N,N-dimethylformamide;

3.157 Any of Methods 3.146-3.156, wherein the suitable solvent is a nonpolar solvent or polar aprotic solvent;

3.158 Method 3.157, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.159 Method 3.157, wherein the polar aprotic solvent is selected from N,N-dimethylformamide, N,N-dimethylacetamide, N-methyl-2-pyrrolidinone, dimethyl sulfoxide, ketones (e.g., acetone, methyl ethyl ketone, methyl isobutyl ketone), esters (e.g., ethyl acetate, methyl acetate, isopropyl acetate), and nitriles (e.g., acetonitrile);

3.160 Method 3.157, wherein the nonpolar solvent is dichloromethane;

3.161 Any of Methods 3.146-3.160, wherein the temperature of the reaction is from −20 to 60° C., e.g., from −5 to 40° C., or 0° C. to 30° C., or from 10° C. to 30° C., or about 25° C.;

3.162 Method 3, or any of Methods 3.1-3.161, wherein the method comprises the step of stereoselectively (e.g., enantioselectively or diastereoselectively) hydrolyzing a compound 6-K in a suitable solvent for a time and under conditions effective to yield a mixture of hydrolyzed stereoisomer 6-L and unreacted stereoisomer 6-L', wherein R is defined as in Method 3.2 or 3.3, wherein $R^2$ and $R^3$ are as defined in any of Methods 3.4-3.10, and wherein $R^p$ is defined as in any of Methods 3.109-3.112;

3.163 Method 3.162, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

3.164 Method 3.163, wherein $R^p$ is 1-phenylethoxycarbonyl, optionally in (R) or (S) form;

3.165 Method 3.164, wherein R" is $C_{1-6}$alkyl (e.g., methyl, ethyl, propyl, isopropyl, n-butyl, isobutyl);

3.166 Method 3.165, wherein R" is methyl;

3.167 Any of Methods 3.162-3.166, wherein the reaction comprises treating the compound 6-K with an enzyme, such as a lipase or protease, e.g., a bacterial or fungal lipase or protease;

3.168 Method 3.167, wherein the lipase or protease is derived from *Candida* species (e.g., *Candida rugosa*), *Pseudomonas* species (e.g., *Pseudomonas stutzeri*), or *Rhizomucor* species (e.g., *Rhizomucor miehei*);

3.169 Any of Methods 3.162-3.168, wherein the reaction further comprises an aqueous buffer, e.g., sodium phosphate buffer or potassium phosphate buffer, optionally having a pH of 5-8 (e.g., about pH 7);

3.170 Any of Methods 3.162-3.169, wherein the suitable solvent is a nonpolar solvent or polar aprotic solvent, water or a combination thereof, 3.171 Method 3.170, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.172 Method 3.170, wherein the polar aprotic solvent is selected from N,N-dimethylformamide, N,N-dimethylacetamide, N-methyl-2-pyrrolidinone, dimethyl sulfoxide, ketones (e.g., acetone, methyl ethyl ketone, methyl isobutyl ketone), and nitriles (e.g., acetonitrile);

3.173 Method 3.170, wherein the nonpolar solvent is methyl isobutyl ketone, in combination with aqueous sodium phosphate buffer (pH about 7);

3.174 Any of Methods 3.162-3.173, wherein the temperature of the reaction is from 0 to 50° C., e.g., from 10 to 40° C., or 10° C. to 30° C., or about 20° C.;

3.175 Any of Methods 3.162-3.174, wherein the compound 6-L and the compound 6-L' are purified and separately isolated;

3.176 Method 3, or any of Methods 3.1-3.175, wherein the method comprises the step of converting a compound 6-B to a compound 6-B' by substituting the group X with a different group X, wherein $R^y$ is as defined in Method 3.2 or 3.3, wherein $R^2$ and $R^3$ are as defined in any of Methods 3.4-3.10, wherein the group X of compound 6-B is a sulfonate (e.g., 4-toluenesulfonate, mesylate, nosylate, benzenesulfonate, triflate);

3.177 Method 3.176, wherein group X of compound 6-B' is a halide (e.g., chloride, bromide or iodide);

3.178 Method 3.177, wherein group X of compound 6-B is 4-toluenesulfonate and group X of compound 6-B' is bromide;

3.179 Method 3.176, 3.177 or 3.178, wherein the method comprises treating the compound 6-B with an inorganic halide salt (e.g., the lithium, sodium, potassium or cesium salt of chloride, bromide or iodide) in a suitable solvent;

3.180 Method 3.179, wherein the inorganic halide is lithium bromide;

3.181 Any of Methods 3.176-3.180, wherein the suitable solvent is a nonpolar solvent, or polar aprotic solvent;

3.182 Method 3.181, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.183 Method 3.181, wherein the polar aprotic solvent is selected from N,N-dimethylformamide, N,N-dimethylacetamide, N-methyl-2-pyrrolidinone, dimethyl sulfoxide, nitriles (e.g., acetonitrile), and esters (e.g., ethyl acetate, methyl acetate, isopropyl acetate);

3.184 Method 3.181, wherein the polar aprotic solvent is N-methyl-2-pyrrolidinone;

3.185 Any of Methods 3.176-3.184, wherein the temperature of the reaction is from 20 to 120° C., e.g., from 20 to 100° C., or 40° C. to 60° C.;

3.186 Method 3, or any of 3.1 to 3.185, wherein the method comprises the step of treating a compound 6-B or 6-B' with a sulfite source for a time and under conditions effective to yield sulfonic acid 7-A, wherein R is as defined in Method 3.2 or 3.3, wherein $R^2$ and $R^3$ are as defined in any of Methods 3.4-3.10, wherein the group X of compound 6-B is selected from halide (e.g., chloride, bromide, iodide), sulfonate (e.g., 4-toluenesulfonate, mesylate, nosylate, benzenesulfonate, triflate), and oxyphosphonium (e.g., oxytriphenylphosphonium), or the group X of compound 6-B' is halide (e.g., bromide, chloride or iodide);

3.187 Method 3.186, wherein the group X of compound 6-B or 6-B' is halide, optionally wherein the halide is bromide or iodide;

3.188 Method 3.186 or 3.187 wherein the sulfite source is an inorganic sulfite or bisulfite salt, e.g., the lithium, sodium, potassium or cesium salt of sulfite or bisulfite;

3.189 Method 3.188 wherein the sulfite source is sodium sulfite;

3.190 Any of Methods 3.186-3.189, wherein the suitable solvent is a nonpolar solvent, polar aprotic solvent, water, or a combination thereof;

3.191 Method 3.190, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.192 Method 3.190, wherein the polar aprotic solvent is selected from N,N-dimethylformamide, N,N-dimethylacetamide, N-methyl-2-pyrrolidinone, dimethyl sulfoxide, nitriles (e.g., acetonitrile), ketones (e.g., acetone, methyl ethyl ketone, methyl isobutyl ketone), and esters (e.g., ethyl acetate, methyl acetate, isopropyl acetate);

3.193 Method 3.190, wherein the solvent is a mixture of acetone and water;

3.194 Any of Methods 3.186-3.193, wherein the temperature of the reaction is from 20 to 120° C., e.g., from 40 to 100° C., or 50° C. to 70° C.;

3.195 Method 3, or any of Methods 3.1-3.194, wherein the method comprises the step of treating a sulfonic acid 7-A with (1) a chlorinating agent and optionally a catalyst in a suitable solvent, followed by (2) an ammonia source in a suitable solvent, for a time and under conditions effective to form a sulfonamide compound 6-F, wherein R is as defined in Method 3.2 or 3.3, wherein $R^2$ and $R^3$ are as defined in any of Methods 3.4-3.10;

3.196 Method 3.195, wherein the chlorinating agent is selected from oxalyl chloride, thionyl chloride, sulfuryl chloride, phosphorus (V) oxychloride, phosphorus trichloride, and phosphorus pentachloride;

3.197 Method 3.196, wherein the chlorinating agent is oxalyl chloride;

3.198 Any of Methods 3.195-3.197, wherein the reaction step (1) further comprises a catalyst, e.g., 4-dimethylaminopyridine or N,N-dimethylformamide;

3.199 Any of Methods 3.195-3.198, wherein the suitable solvent is a nonpolar solvent or polar aprotic solvent, or wherein the solvent is the neat chlorinating agent (e.g., thionyl chloride);

3.200 Method 3.199, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.201 Method 3.199, wherein the polar aprotic solvent is selected from N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

3.202 Method 3.199, wherein solvent is tetrahydrofuran;

3.203 Any of Methods 3.195-3.302, wherein the ammonia source is selected from ammonia gas dissolved in any of the solvents provided in Methods 3.199-3.202, gaseous ammonia, aqueous ammonia, and ammonia surrogates (e.g., hexamethyldisilazane);

3.204 Method 3.203, wherein the ammonia source is aqueous ammonia;

3.205 Any of Methods 3.195-3.204, wherein the temperature of the reaction for step (1) and step (2) is independently selected from −10 to 100° C., 0 to 50° C., 0 to 30° C., and 20 to 30° C.;

3.206 Any of Methods 3.195-3.205, wherein step (1) comprises combining the compound 7-A with the catalyst and the suitable solvent at a temperature of 0 to 30° C. followed by addition of the chlorinating agent, stirring the reaction for a period of time from 0.1 hours to 2 hours (e.g., 0.5 to 1 hour), followed by step (2) which comprises adding the reaction mixture from step (1) into a reactor containing the ammonia source and stirring the reaction for a period of time from 0.1 to 2 hours (e.g., 0.1 to 0.5 hours) at a temperature ranging from 10 to 30° C.;

3.207 Method 3, or any of Methods 3.1-3.206, wherein the method comprises the step of acylating a compound 6-H with an acylating agent and a base in a suitable solvent for a time and under conditions effective to form the di-acyl compound 8-A, wherein $R^y$ is defined as in Method 3.2 or 3.3, wherein $R^2$ and $R^3$ are as defined in any of Methods 3.4-3.10, and wherein $R^k$ is a silyl group;

3.208 Method 3.207 wherein $R^k$ is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

3.209 Method 3.208, wherein $R^k$ is selected from tert-butyldimethylsilyl, tert-butyldiphenylsilyl, dimethylphenylsilyl, trimethylsilyl, triethylsilyl and triisopropylsilyl;

3.210 Method 3.209, wherein $R^k$ is tert-butyldimethylsilyl;

3.211 Any of Methods 3.207-3.210, wherein R" is selected from H, $C_{1-6}$alkyl (e.g., methyl, ethyl, propyl, isopropyl, n-butyl, isobutyl), halo$C_{1-6}$alkyl (e.g., trifluoromethyl, trichloromethyl), optionally substituted aryl (e.g., phenyl, 4-bromophenyl), and optionally substituted heteroaryl (e.g., 2-pyridyl), 3.212 Method 3.211, wherein R" is $C_{1-6}$alkyl (e.g., methyl, ethyl, propyl, isopropyl, n-butyl, isobutyl);

3.213 Method 3.212, wherein R" is methyl;

3.214 Any of methods 3.207-3.213, wherein the acylating agent is an acid chloride (e.g., R"—C(=O)—Cl), an acid anhydride (e.g., R"—C(=O)—O—(C=O)—R"), or a combination of a carboxylic acid (e.g., R"—COOH) with an activator or coupling reagent (e.g., oxalyl chloride, thionyl chloride, phosphoryl chloride, 1,1-carbonyldiimidazole, a carbodiimide reagent (e.g., DCC or EDC), or any other peptide coupling reagent (e.g., HATU, T3P, isobutyl chloroformate);

3.215 Method 3.214, wherein R" is $C_{1-6}$alkyl (e.g., methyl), and the acylating agent is an acid chloride (e.g., R"—C(=O)—Cl), an acid anhydride (e.g., R"—C(=O)—O—(C=O)—R");

3.216 Method 3.215, wherein R" is methyl and the acylating agent is acetyl chloride;

3.217 Any of methods 3.207-3.216, wherein the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane), aromatic amines (e.g., pyridine, pyrimidine, pyridazine, pyrazine, 2,6-lutidine, picoline, collidine, imidazole, 1-methylimidazole, indole, isoindole, quinoline, isoquinoline, 4-dimethylaminopyridine), amide bases (e.g., sodium hexamethyldisilazide, lithium hexamethyldisilazide, potassium hexamethyldisilazide, lithium diisopropylamide, sodium diisopropylamide, potassium diisopropylamide), and alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide, sodium isopropoxide, potassium isopropoxide, lithium isopropoxide);

3.218 Method 3.217 wherein the base is an aromatic amine selected from pyridine, pyrimidine, pyridazine, and pyrazine;

3.219 Any of Methods 3.207-3.218, wherein the reaction further comprises a catalyst, e.g., selected from 4-dimethylaminopyridine, imidazole, N-methylimidazole, triphenylphosphine oxide, 1-hydroxy-7-azabenzotriazole, and N,N-dimethylformamide;

3.220 Any of Methods 3.207-3.219, wherein the suitable solvent is a nonpolar solvent or polar aprotic solvent;

3.221 Method 3.220, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.222 Method 3.220, wherein the polar aprotic solvent is selected from N,N-dimethylformamide, N,N-dimethylacetamide, N-methyl-2-pyrrolidinone, dimethyl sulfoxide, ketones (e.g., acetone, methyl ethyl ketone, methyl isobutyl ketone), esters (e.g., ethyl acetate, methyl acetate, isopropyl acetate), and nitriles (e.g., acetonitrile);

3.223 Method 3.220, wherein the solvent is acetonitrile;

3.224 Any of Methods 3.207-3.223, wherein the temperature of the reaction is from −20 to 50° C., e.g., from −5 to 40° C., or 0° C. to 30° C., or from 10° C. to 30° C., or about 20° C.;

3.225 Method 3, or any of Methods 3.1-3.224, wherein the method comprises the step of stereoselectively (e.g., enantioselectively or diastereoselectively) hydrolyzing a compound 8-A in a suitable solvent for a time and under conditions effective to yield a hydrolyzed stereoisomer 8-B, wherein R is defined as in Method 3.2 or 3.3, wherein $R^2$ and $R^3$ are as defined in any of Methods 3.4-3.10, and wherein R" is as defined in any of Methods 3.211-3.213;

3.226 Method 3.225, wherein R" is $C_{1-6}$alkyl (e.g., methyl, ethyl, propyl, isopropyl, n-butyl, isobutyl);

3.227 Method 3.226, wherein R" is methyl;

3.228 Any of Methods 3.225-3.227, wherein the reaction comprises treating the compound 8-B with an enzyme, such as a lipase or protease, e.g., a bacterial or fungal lipase or protease;

3.229 Method 3.228, wherein the lipase or protease is derived from *Carica* species (e.g., *Carica papaya*);

3.230 Any of Methods 3.225-3.229, wherein the reaction further comprises an aqueous buffer, e.g., sodium phosphate buffer or potassium phosphate buffer, optionally having a pH of 5-8 (e.g., about pH 7);

3.231 Any of Methods 3.225-3.230, wherein the suitable solvent is a nonpolar solvent or polar aprotic solvent, water or a combination thereof, 3.232 Method 3.231, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

3.233 Method 3.231, wherein the polar aprotic solvent is selected from N,N-dimethylformamide, N,N-dimethylacetamide, N-methyl-2-pyrrolidinone, dimethyl sulfoxide, ketones (e.g., acetone, methyl ethyl ketone, methyl isobutyl ketone), and nitriles (e.g., acetonitrile);

3.234 Method 3.231, wherein the nonpolar solvent is methyl isobutyl ketone, in combination with aqueous sodium phosphate buffer (pH about 7);

3.235 Any of Methods 3.225-3.234, wherein the temperature of the reaction is from 0 to 50° C., e.g., from 10 to 40° C., or 20° C. to 40° C., or about 30° C.;

3.236 Method 3, or any of Methods 3.1-3.235, wherein the Method produces a compound according to any one or more of Compounds 6-B, 6-B', 6-C, 6-D, 6-E, 6-F, 6-G, 6-H, 6-I, 6-J, 6-K, 6-L, 6-L', 7-A, 8-A, and 8-B;

3.237 Method 3.236 wherein in any one or more of said compounds, $R^y$ is H, $R^2$ is H or $C_{1-3}$ alkyl (e.g., methyl), $R^3$ is H or $C_{1-3}$alkyl (e.g., methyl), X is 4-toluenesulfonyl or bromo, $R^e$ is 2-pyrimidyl, M is Na, $R^k$ is trialkylsilyl (e.g., tert-butyldimethylsilyl), $R^p$ is —C(=O)—O—$C_{1-6}$ alkyl(aryl) (e.g., 1-phenylethoxycarbonyl, optionally in (R) or (S) form), and R" is $C_{1-3}$alkyl (e.g., methyl);

3.238 Method 3.237, wherein in one or more of said compounds $R^2$ and $R^3$ are H, or $R^2$ and $R^3$ are methyl, or $R^2$ is H and $R^3$ is methyl;

3.239 Method 3.238, wherein in one or more of said compounds $R^2$ is H and $R^3$ is methyl;

3.240 Method 3, or any of Methods 3.1-3.239, wherein the Method produces a compound according to any one or more of Compounds 9-A, 9-B, 9-C, 9-D, or 9-E;

3.241 Method 3.240, wherein one or more of said compounds 9-A, 9-B, 9-C, 9-D, or 9-E are made according to any one or more of Method 4 or Method 4.1, et seq., or Method 5 or Method 5.1, et seq.;

3.242 Method 3.240 or 3.241, wherein in one or more of said compounds, $R^x$ is H, $R^y$ is H, $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), and/or $R^{12}$ is H, or —C(O)—$R^1$, wherein $R^1$ is selected from optionally substituted $C_{1-6}$ alkyl (e.g., methyl), optionally substituted $C_{1-6}$alkoxy (e.g., (S)-1-phenylethoxy), or optionally substituted 5-10 membered heteroaryl (e.g., 1-methyl-3-methoxy-1H-pyrazol-4-yl);

3.243 Method 3.242, wherein in one or more of said compounds, $R^x$ is H, $R^y$ is H, $R^2$ and $R^3$ are independently H or methyl, $R^4$ is H, $R^5$ is methyl, and $R^6$ is chloro;

3.244 Method 3.243, wherein in one or more of said compounds $R^2$ and $R^3$ are H, or $R^2$ and $R^3$ are methyl, or $R^2$ is H and $R^3$ is methyl;

3.245 Method 3.244, wherein in one or more of said compounds $R^2$ is H and $R^3$ is methyl;

3.246 Any of Methods 3.240-3.245, wherein in compound 9-C, $R^{12}$ is —C(O)—$R^1$, and $R^1$ is selected from $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, 5-10 membered heteroaryl, and —$NR^8R^9$, wherein said $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, and —$NR^aR^b$; wherein $R^a$ and $R^b$ is independently hydrogen or $C_{1-6}$alkyl;

3.247 Method 3.246, wherein in compound 9-C, $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$ cycloalkyl, $C_{1-6}$haloalkyl, $C_{1-6}$alkoxy and halogen;

3.248 Method 3.247, wherein in compound 9-C, $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

3.249 Method 3.247, wherein in compound 9-C, $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy), for example $R^1$ is 3-methoxy-1-methyl-1H-pyrazolyl;

3.250 Method 3, or any of Methods 3.1-3.249, wherein the Method produces a compound according to Compound I;
3.251 Method 3.250, wherein the Compound I is a compound I(a);
3.252 Method 3.251 or 3.251, wherein the Compound I or I(a) is made according to any one or more of Method 4 or Method 4.1, et seq., or Method 5 or Method 5.1, et seq.;
3.253 Any of Methods 3.250-3.252, wherein in Compound I or I(a), $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), and/or $R^{12}$ is —C(O)—$R^1$, and $R^1$ is selected from $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, 5-10 membered heteroaryl, and —$NR^8R^9$, wherein said $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, and —$NR^aR^b$; wherein $R^a$ and $R^b$ is independently hydrogen or $C_{1-6}$alkyl;
3.254 Method 3.253, wherein in Compound I or I(a), $R^2$ and $R^3$ are independently H or methyl, $R^4$ is H, $R^5$ is methyl, and $R^6$ is chloro;
3.255 Method 3.254, wherein in Compound I or I(a), $R^2$ and $R^3$ are H, or $R^2$ and $R^3$ are methyl, or $R^2$ is H and $R^3$ is methyl;
3.256 Method 3.255, wherein in Compound I or I(a), $R^2$ is H and $R^3$ is methyl;
3.257 Any of Methods 3.253-3.256, wherein in Compound I or I(a), $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, $C_{1-6}$alkoxy and halogen;
3.258 Method 3.257, wherein in Compound I or I(a), $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);
3.259 Method 3.258, wherein in Compound I or I(a), $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy), for example $R^1$ is 3-methoxy-1-methyl-1H-pyrazolyl;
3.260 Any of Methods 3.240-3.259, wherein in one or more of compound 9-E, Compound I or compound I(a), === is a double bond;
3.261 Method 3, or any of Methods 3.1-3.260, wherein the Method produces Compound 1; 3.262 Method 3, or any of Methods 3.1-3.261, wherein the method further comprises any steps described in any of Method 1, et seq., Method 2, et seq., Method 4, et seq., and Method 5, et seq.

In a fifth aspect, the present disclosure provides a method (Method 4) of making a compound selected from one or more of Compounds 9-A, 9-B, 9-C, 9-D, 9-E, and Compound I or I(a), as herein described, wherein the method comprises the step of reacting a precursor compound with one or more reagents in a suitable solvent for a time and under conditions effective to form the product compound. Method 4 generally pertains to formation of the SNO-CB-TC cyclic fragment (including the ring closing metathesis step) and attachment of the side chain fragment (SC), including advanced intermediates 9-B, 9-C, and 9-E, as well as the evolution of those intermediates to Compound 1. Without being limited in the order or combination of steps employed, the potential embodiments of Method 4 may include any steps shown in Scheme 9.

Scheme 9

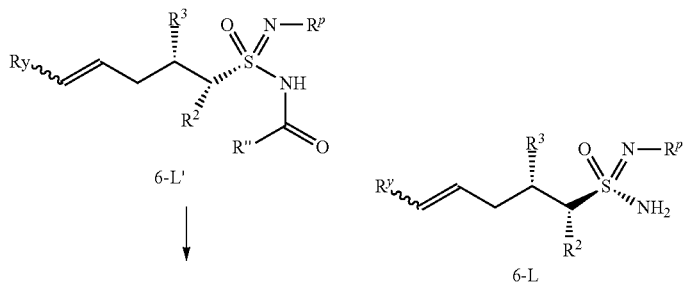

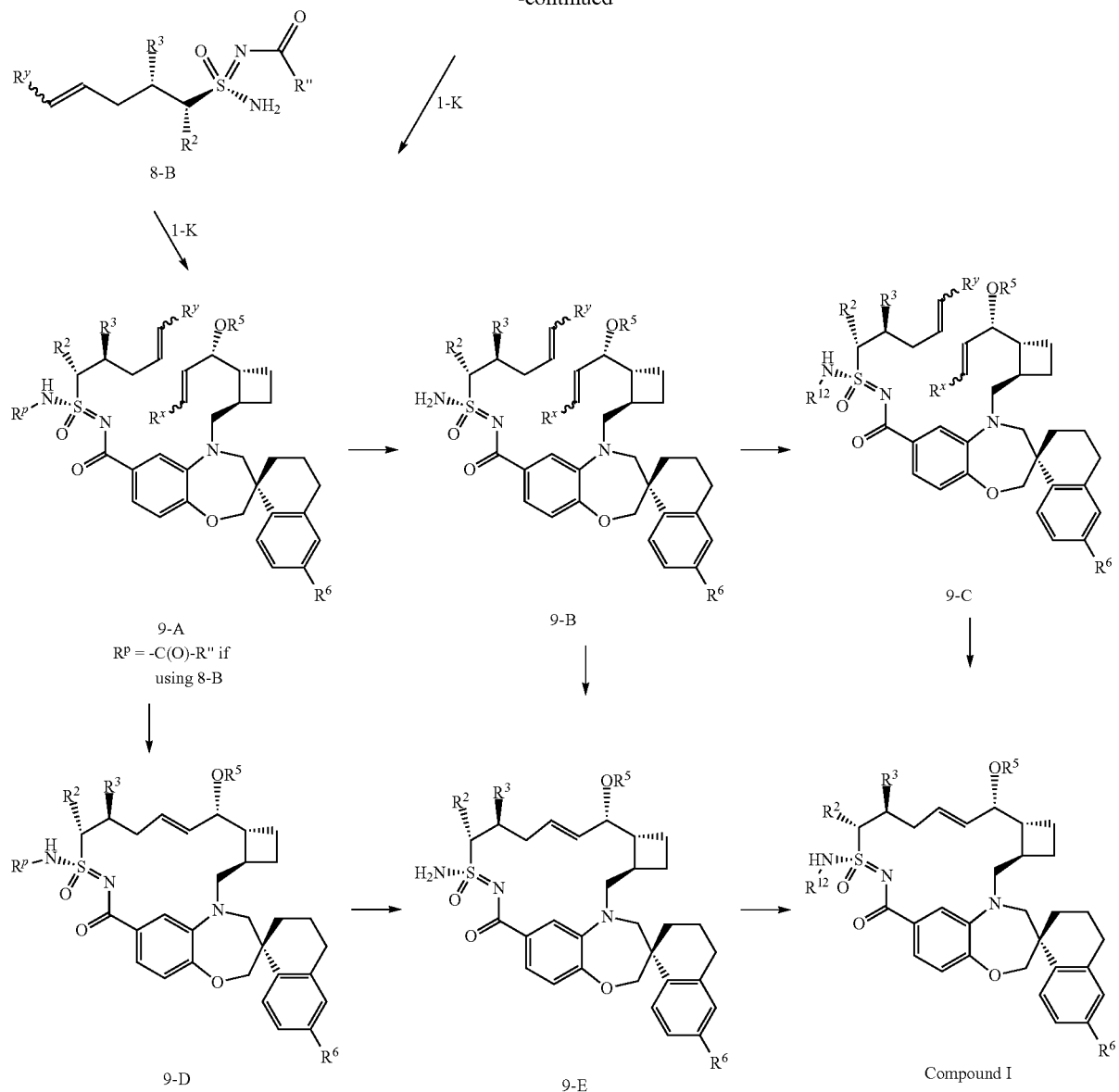

In particular embodiments, the present disclosure provides Method 4 as follows:

4.1 Method 4, wherein the method comprises the step of deprotecting a compound 6-L' with a deprotection agent in a suitable solvent for a time and under conditions effective to yield the inverted stereoisomer 8-B, wherein $R^y$ is as defined in Method 3.2 or 3.3, wherein $R^2$ and $R^3$ are as defined in any of Methods 3.4-3.10, and wherein $R^p$ is as defined in any of Methods 3.109-3.112, and wherein R" is as defined in any of Methods 3.211-3.213;

4.2 Method 4.1, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

4.3 Method 4.2, wherein $R^p$ is 1-phenylethoxycarbonyl, optionally in (R) or (S) form; 4.4 Any of Methods 4.1-4.3, wherein R" is $C_{1-6}$alkyl (e.g., methyl, ethyl, propyl, isopropyl, n-butyl, isobutyl);

4.5 Method 4.4, wherein R" is methyl;

4.6 Any of Methods 4.1-4.5, wherein the deprotection reagent is selected from an inorganic base (e.g., sodium hydroxide, potassium hydroxide, lithium hydroxide, sodium bicarbonate, sodium carbonate, potassium bicarbonate, potassium carbonate, lithium carbonate, sodium phosphate (mono-, di- or tri-basic), potassium phosphate (mono-, di- or tri-basic), optionally as an aqueous solution thereof), an inorganic acid (e.g., an aqueous solution thereof or a solution in an organic solvent), a fluoride agent (e.g., hydrofluoric acid, hydrogen fluoride pyridine, hydrogen fluoride triethylamine, potassium fluoride, sodium fluoride, lithium fluoride, cesium fluoride, tetramethylammonium fluoride, tetraethylammonium fluoride, tetrabutylammonium fluoride, triethylamine trihydrofluoride, tetrabutylammonium difluorotriphenylsilicate, optionally in an organic solvent), a hydrogenation agent (e.g., hydrogen in combination with a heterogenous catalyst (e.g., a transition metal catalyst) or a homogeneous catalyst (e.g., a soluble transition metal complex), such as Pd, Pd/C, Pt, Ru/C, Raney Nickel, Ru complexes, Rh complexes, PtO$_2$, Pt complexes, Pd complexes, Ir complexes, or a phase transfer hydrogenation system, such as ammonium formate in combination with a palladium or platinum catalyst (e.g., Pd, Pd/C, Pt, PtO$_2$)), optionally further comprising a phase transfer agent, or an enzyme;

4.7 Method 4.6, wherein the deprotection agent is an acid, e.g., selected from trifluoroacetic acid, methanesulfonic acid, trifluoromethanesulfonic acid, benzenesulfonic acid, camphorsulfonic acid, pyridiniump-toluenesulfonate, sulfuric acid, hydrochloric acid (e.g., aqueous HCl, HCl in ether, HCl in methanol, HCl in isopropanol), hydrobromic acid, acetic acid, formic acid, phosphoric acid, and oxalic acid, optionally wherein the acid is trifluoroacetic acid;

4.8 Any of Methods 4.1-4.7, wherein the suitable solvent is a nonpolar solvent or polar aprotic solvent;

4.9 Method 4.8, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

4.10 Method 4.8, wherein the polar aprotic solvent is selected from N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

4.11 Method 4.8, wherein the solvent is dichloromethane;

4.12 Any of Methods 4.1-4.11, wherein the temperature of the reaction is from −50 to 50° C., e.g., from 0 to 40° C., or 10° C. to 30° C., or about 20° C.;

4.13 Method 4, or any of 4.1-4.12, wherein the method comprises the step of condensing a sulfonimidamide compound 8-B or a sulfonimidamide compound 6-L with carboxylic acid 1-K using an acid activator, a base, and optionally a promoter, in a suitable solvent for a time and under conditions effective to form the N-acyl sulfonimidamide compound 9-A, wherein R is defined as in Method 3.2 or 3.3, wherein $R^2$ and $R^3$ are as defined in any of Methods 3.4-3.10, and wherein $R^p$ of compound 6-L is defined as in any of Methods 3.109-3.112, wherein R'' of compound 8-B is as defined in any of Methods 3.211-3.213, wherein $R^x$ is defined as in Method 1.18 or 1.19, wherein $R^5$ is defined as in any of Methods 1.75-1.78, and wherein $R^6$ is hydrogen or halogen;

4.14 Method 4.13, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

4.15 Method 4.14, wherein $R^p$ is 1-phenylethoxycarbonyl, optionally in (R) or (S) form;

4.16 Any of Methods 4.13-4.15, wherein R'' is $C_{1-6}$alkyl (e.g., methyl, ethyl, propyl, isopropyl, n-butyl, isobutyl);

4.17 Method 4.16, wherein R'' is methyl;

4.18 Any of Methods 4.13-4.17, wherein the acid activator is selected from N-(3-dimethylaminopropyl)-N'-ethylcarbodiimide hydrochloride (EDC-HCl), carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methyl-morpholinium chloride (DMTMM), thionyl chloride, oxalyl chloride, (chloromethylene)-dimethyliminium chloride, isobutyl chloroformate, N,N,N,N'N'-tetramethylchloroformamidinium hexafluorophosphate (TCFH), N,N'-diisopropylcarbodiimide, N,N'-dicyclohexylcarbodiimide, diphenyl chlorophosphate, 2,4,6-trichlorobenzoyl chloride, 2-chloro-4,6-dimethoxy-1,3,5-triazine (CDMT), (PhO)$_2$POCl, oxalyl chloride ((COCl)$_2$), and thionyl chloride (SOCl$_2$);

4.19 Method 4.18, wherein the acid activator is N-(3-dimethylaminopropyl)-N'-ethylcarbodiimide hydrochloride (EDC HCl);

4.20 Any of Methods 4.13-4.19, wherein the base is selected from tertiary amines (e.g., N-methylmorpholine, triethyl amine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, collidine, imidazole, 1-methylimidazole), inorganic bases (e.g., lithium carbonate, sodium carbonate, potassium carbonate, calcium carbonate and bicarbonate derivatives, mono, di and tri basic potassium and sodium phosphate;

4.21 Method 4.20, wherein the base is imidazole; or in one embodiment, the base is 1-methylimidazole;

4.22 Any of Methods 4.13-4.21, wherein the reaction comprises a promoter selected from 4-dimethylaminopyridine (DMAP), N-methylimidazole, 1-hydroxy-7-azabenzotriazole (HOAt), and 1-hydroxybenzotriazole (HOBt);

4.23 Any of Methods 4.13-4.22, wherein the acid activator is EDC-HCl, the base is 1-methylimidazole and the promoter is DMAP;

4.24 Any of Methods 4.13-4.23, wherein the suitable solvent is a nonpolar solvent or polar aprotic solvent, or a combination with water thereof, 4.25 Method 4.24, wherein the solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

4.26 Method 4.24, wherein the solvent is selected from ethers (e.g., tetrahydrofuran, 2-methyltetrahydrofuran, methyl tert-butyl ether, cyclopentyl methyl ether), esters (e.g, ethyl acetate, isopropyl acetate), polar aprotic solvents (e.g., N,N-dimethylacetamide, N-methyl-2-pyrrolidinone, dimethyl sulfoxide, N-Methyl-2-pyrrolidone (NMP)), nitriles (e.g., acetonitrile), hydrocarbon solvents (e.g., toluene), ketones (acetone, 2-butanone, 4-methyl-2-pentanone), alcohols (2-propanol); halogenated solvents (e.g., dichloromethane, 1,2-dichloroethane, chloroform, chlorobenzene), N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

4.27 Method 4.24, wherein the solvent is N,N-dimethylformamide. In one embodiment, the solvent is acetonitrile;

4.28 Any of Methods 4.13-4.27, wherein the temperature of the reaction is from −50 to 50° C., e.g., from 0 to 40° C., or 10° C. to 30° C., or 0° C. to 80° C., or about 20° C.;

4.29 Method 4, or any of Methods 4.1-4.28, wherein the method comprises the step of deprotecting a compound 9-A for a time and under conditions effective to form a compound 9-B, or of deprotecting a compound 9-D for a time and under conditions effective to form a compound 9-E, using a deprotection agent in a suitable solvent, wherein R is defined as in Method 3.2 or 3.3, wherein $R^2$ and $R^3$ are as defined in any of Methods 3.4-3.10, and wherein $R^p$ is as defined either as in any of Methods 3.109-3.112 or as —C(=O)—R", wherein R" is as defined in any of Methods 3.211-3.213, wherein $R^x$ is defined as in Method 1.18 or 1.19, wherein $R^5$ is defined as in any of Methods 1.75-1.78, and wherein $R^6$ is hydrogen or halogen;

4.30 Method 4.29, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

4.31 Method 4.30, wherein $R^p$ is 1-phenylethoxycarbonyl, optionally in (R) or (S) form;

4.32 Any of Methods 4.31, wherein $R^p$ is —C(=O)—R", and R" is $C_{1-6}$alkyl (e.g., methyl, ethyl, propyl, isopropyl, n-butyl, isobutyl);

4.33 Method 4.32, wherein R" is methyl;

4.34 Any of Methods 4.29-4.33, wherein the deprotection reagent is selected from an inorganic base (e.g., an aqueous solution thereof), an inorganic acid (e.g., an aqueous solution thereof or a solution in an organic solvent), a fluoride agent (e.g., in an organic solvent), a hydrogenation agent (e.g., hydrogen in combination with a heterogenous catalyst (e.g., a transition metal catalyst) or a homogeneous catalyst (e.g., a soluble transition metal complex), or a phase transfer hydrogenation system), optionally further comprising a phase transfer agent, or an enzyme;

4.35 Method 4.34, wherein the deprotection reagent is selected from sodium hydroxide, potassium hydroxide, lithium hydroxide, sodium methoxide, potassium methoxide, sodium ethoxide, potassium ethoxide, sodium isopropoxide, potassium isopropoxide, sodium bicarbonate, sodium carbonate, potassium bicarbonate, potassium carbonate, lithium carbonate, sodium phosphate (mono-, di- or tri-basic), potassium phosphate (mono-, di- or tri-basic), methanesulfonic acid, trifluoromethanesulfonic acid, benzenesulfonic acid, p-touenesulfonic acid, camphorsulfonic acid, pyridiniumptoluenesulfonate, sulfuric acid, hydrochloric acid, hydrobromic acid, acetic acid, formic acid, phosphoric acid, oxalic acid, citric acid, hydrochloric acid (e.g., aqueous HCl, HCl in ether, HCl in methanol, HCl in isopropanol), methanesulfonic acid, hydrofluoric acid, hydrogen fluoride pyridine, hydrogen fluoride triethylamine, potassium fluoride, sodium fluoride, lithium fluoride, cesium fluoride, tetramethylammonium fluoride, tetraethylammonium fluoride, tetrabutylammonium fluoride, triethylamine trihydrofluoride, tetrabutylammonium difluorotriphenylsilicate, hydrogen in combination with a catalyst (e.g., Pd, Pd/C, Pt, Ru/C, Raney Nickel, Ru complexes, Rh complexes, $PtO_2$, Pt complexes, Pd complexes, Ir complexes), and ammonium formate in combination with a palladium or platinum catalyst (e.g., Pd, Pd/C, Pt, $PtO_2$); in one embodiment, the deprotection reagent is sodium isopropoxide; in one embodiment, the deprotection reagents is trifluoroacetic acid;

4.36 Method 4.34, wherein the deprotection agent is an enzyme, such as a lipase or protease, e.g., a bacterial or fungal lipase or protease;

4.37 Method 4.36, wherein the lipase or protease is derived from *Candida* species (e.g., *Candida rugosa*), *Pseudomonas* species (e.g., *Pseudomonas stutzeri*), or *Rhizomucor* species (e.g., *Rhizomucor miehei*);

4.38 Method 4.37 wherein the enzyme is lipase from *Pseudomonas stutzeri;*

4.39 Method 4.36-4.38, wherein the reaction further comprises an aqueous buffer, e.g., sodium phosphate buffer or potassium phosphate buffer, optionally having a pH of 5-8 (e.g., about pH 7);

4.40 Any of Methods 4.29-4.39, wherein the suitable solvent is a nonpolar solvent, polar aprotic solvent, polar protic solvent, water or a combination thereof;

4.41 Method 4.40, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene); in one embodiment, the nonpolar solvent is toluenene;

4.42 Method 4.40, wherein the polar aprotic solvent is selected from N,N-dimethylformamide, N,N-dimethylacetamide, N-methyl-2-pyrrolidinone, dimethyl sulfoxide, ketones (e.g., acetone, methyl ethyl ketone, methyl isobutyl ketone), and nitriles (e.g., acetonitrile);

4.43 Method 4.40, wherein the polar protic solvent is selected from alcohols (e.g., methanol, ethanol, propanol, isopropanol, butanol) and water, or a combination thereof, 4.44 Method 4.40, wherein the nonpolar solvent is methyl tert-butyl ether, in combination with aqueous sodium phosphate buffer (pH about 7). In one embodiment, the solvent is a combination of tetrahydrofuran (THF) and 2-propanol (IPA);

4.45 Any of Methods 4.29-4.44, wherein the temperature of the reaction is from 0 to 100° C., e.g., from 10 to 80° C., or 20° C. to 60° C., or 20° C. to 40° C., or 40° C. to 80° C., or 60° C. to 80° C., or about 30° C.; in one embodiment, the temperature of the reaction is from 10-30° C. In one embodiment, the temperature of the reaction is from 60-80° C.;

4.46 Method 4, or any of 4.1-4.45, wherein the method comprises the step of acylating a compound 9-B for a time and under conditions effective to form a compound 9-C, or acylating a compound 9-E for a time and under conditions effective to form a Compound I, the step comprising treating the starting material compound with a suitable acylating agent and a base, in a suitable solvent, wherein $R^y$ is as defined in Method 3.2 or 3.3, wherein $R^2$ and $R^3$ are as defined in any of Methods 3.4-3.10, wherein $R^x$ is defined as in Method 1.18 or 1.19, wherein $R^5$ is defined as in any of Methods 1.75-1.78, and wherein $R^6$ is hydrogen or halogen;

4.47 Method 4.46, wherein $R^{12}$ is as defined in Compound I or I(a);

4.48 Method 4.46, $R^{12}$ is —C(O)—$R^1$, and $R^1$ is selected from $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, 5-10 membered heteroaryl, and —$NR^8R^9$, wherein said $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, and —$NR^aR^b$; wherein $R^a$ and $R^b$ is independently hydrogen or $C_{1-6}$alkyl;

4.49 Method 4.48, wherein $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, $C_{1-6}$alkoxy and halogen;

4.50 Method 4.49, wherein $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

4.51 Method 4.50, wherein $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy);

4.52 Method 4.51, wherein $R^{12}$ is —C(O)—$R^1$, and $R^1$ is 3-methoxy-1-methyl-1H-pyrazolyl;

4.53 Any of Methods 4.46-4.52, wherein $R^{12}$ is —C(O)—$R^1$, and $R^1$ is any optionally substituted $C_{1-6}$alkyl, $C_{1-6}$haloalkyl, $C_{2-6}$alkenyl, $C_{2-6}$alkynyl, $C_{3-10}$ cycloalkyl, $C_{6-10}$aryl, 3-12 membered heterocycloalkyl, or 5-10 membered heteroaryl, and the acylating agent is an acid chloride (e.g., $R^1$—C(=O)—Cl), an acid anhydride (e.g., $R^1$—C(=O)—O—(C=O)—$R^1$), or a combination of a carboxylic acid (e.g., $R^1$—COOH) with an activator or coupling reagent (e.g., oxalyl chloride, thionyl chloride, phosphoryl chloride, 1,1-carbonyldiimidazole, a carbodiimide reagent (e.g., DCC or EDC), or any other peptide coupling reagent (e.g., HATU, T3P, isobutyl chloroformate);

4.54 Method 4.53, wherein the activating agent is selected from N-(3-dimethylaminopropyl)-N'-ethylcarbodiimide hydrochloride (EDC HCl), carbonyldiimidazole (CDI), propylphosphonic anhydride (T3P), 1-[bis(dimethylamino)methylene]-1H-1,2,3-triazolo[4,5-b]pyridinium 3-oxide hexafluoropbosphate (HATU), 4-(4,6-dimethoxy-1,3,5-triazin-2-yl)-4-methyl-morpholinium chloride (DMTMM), thionyl chloride, oxalyl chloride, (chloromethylene)-dimethyliminium chloride, isobutyl chloroformate, N,N,N,N'N'-tetramethylchloroformamidinium hexafluorophosphate (TCFH), N,N'-diisopropylcarbodiimide, N,N'-dicyclohexylcarbodiimide, diphenyl chlorophosphate, 2,4,6-trichlorobenzoyl chloride, and 2-chloro-4,6-dimethoxy-1,3,5-triazine (CDMT);

4.55 Method 4.54, wherein the activating agent is N-(3-dimethylaminopropyl)-N'-ethylcarbodiimide hydrochloride (EDC HCl);

4.56 Any of Methods 4.46-4.52, wherein $R^{12}$ is —C(O)—$R^1$, and $R^1$ is any optionally substituted —$OR^7$, and the acylating agent is a chloroformate (e.g., $R^7$—O—C(=O)—$C_1$), or a carbonate (e.g., $R^7$—O—C(=O)—O—$R^7$).

4.57 Any of Methods 4.46-4.52, wherein $R^{12}$ is —C(O)—$R^1$, and $R^1$ is any optionally substituted —$NR^8R^9$, and the acylating agent is an isocyanate (e.g., $R^8R^9$—N—C(=O));

4.58 Any of Methods 4.46-4.57, wherein the base is selected from tertiary amines (e.g N-methylmorpholine, triethyl amine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, picoline, collidine, imidazole, 1-methylimidazole, indole, isoindole, quinoline, isoquinoline, 4-dimethylaminopyridine), inorganic bases (e.g., lithium carbonate, sodium carbonate, potassium carbonate, calcium carbonate, potassium phosphate (monobasic, dibasic or tribasic), sodium phosphate (monobasic, dibasic or tribasic)), amide bases (e.g., sodium hexamethyldisilazide, lithium hexamethyldisilazide, potassium hexamethyldisilazide, lithium diisopropylamide, sodium diisopropylamide, potassium diisopropylamide), and alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide, sodium isopropoxide, potassium isopropoxide, and lithium isopropoxide). In one embodiment, the base is 1-methylimidazole;

4.59 Any of Methods 4.46-4.58, wherein the reaction further comprises a catalyst/promoter, e.g., selected from 4-dimethylaminopyridine, imidazole, N-methylimidazole, triphenylphosphine oxide, 1-hydroxy-7-azabenzotriazole, N,N-dimethylformamide, N,N-dimethylacetamide, and dichloromethylene-dimethyliminium chloride; in one embodiment, the catalyst/promoter is 4-dimethylaminopyridine;

4.60 Any of Methods 4.46-4.59, wherein the suitable solvent is a nonpolar solvent or polar aprotic solvent, optionally further comprising water;

4.61 Method 4.60, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, and chlorobenzene);

4.62 Method 4.60, wherein the solvent is selected from esters (e.g., ethyl acetate, isopropyl acetate), carbonates (e.g., dimethyl carbonate), ethers (e.g., tetrahydrofuran, 2-methyltetrahydrofuran, methyl tert-butyl ether, cyclopentyl methyl ether), chlorinated solvents (e.g., dichloromethane, 1,2-dichloroethane, chloroform), hydrocarbon solvents (e.g., toluene), polar aprotic solvents (e.g., N,N-dimethylformamide, N,N-dimethylacetamide, dimethylsulfoxide, N-methyl-2-pyrrolidone), and nitriles (e.g., propionitrile);

4.63 Method 4.60, wherein the solvent is acetonitrile;

4.64 Any of Methods 4.46-4.63, wherein the temperature of the reaction is from −20 to 60° C., e.g., from −5 to 40° C., or 0° C. to 30° C., or from 10° C. to 30° C., or about 20° C.;

4.65 Method 4, or any of Methods 4.1-4.64, wherein the reaction comprises the step of performing a ring-closing metathesis on a compound 9-A for a time and under conditions effective to form a compound 9-D, or on a compound 9-B for a time and under conditions effective to form a compound 9-E, or on a compound 9-C for a time and under conditions effective to form a Compound I, using a suitable catalyst in a suitable solvent, wherein R is as defined in Method 3.2 or 3.3, wherein $R^2$ and $R^3$ are as defined in any of Methods 3.4-3.10, wherein $R^x$ is defined as in Method 1.18 or 1.19, wherein $R^5$ is defined as in any of Methods 1.75-1.78, wherein $R^6$ is hydrogen or halogen, and wherein   is a double bond;

4.66 Method 4.65, wherein $R^x$ and $R^y$ are both hydrogen;

4.67 Method 4.65 or 4.66, wherein $R^{12}$ is as defined in Compound I or I(a);

4.68 Method 4.67, $R^{12}$ is —C(O)—$R^1$, and $R^1$ is selected from $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, 5-10 membered heteroaryl, and —$NR^8R^9$, wherein said $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$ cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^8$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, and —$NR^aR^b$; wherein $R^a$ and $R^b$ is independently hydrogen or $C_{1-6}$alkyl;

4.69 Method 4.68, wherein $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, $C_{1-6}$alkoxy and halogen;

4.70 Method 4.69, wherein $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

4.71 Method 4.70, $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy);

4.72 Method 4.71, wherein $R^{12}$ is —C(O)—$R^1$, and $R^1$ is 3-methoxy-1-methyl-1H-pyrazolyl;

4.73 Any of Methods 4.65-4.72, wherein the catalyst is a ruthenium catalyst or a molybdenum catalyst;

4.74 Method 4.73, wherein the catalyst is selected from dichloro[1,3-bis(2,4,6-trimethylphenyl)-2-imidazolidinylidene](2-isopropoxyphenylmethylene) ruthenium(II), dichloro(benzylidene)bis(tricyclohexylphosphine) ruthenium(II), dichloro[1,3-bis(2,4,6-trimethylphenyl)-2-imidazolidinylidene] (benzylidene) (tricyclohexylphosphine) ruthenium(II), dichloro(o-isopropoxyphenylmethylene)(tricyclohexylphosphine) ruthenium(II), dichloro[1,3-bis(2,4,6-trimethylphenyl)-2-imidazolidinylidene](2-isopropoxyphenylmethylene) ruthenium(II), dichloro[1,3-bis(2-methylphenyl)-2-imidazolidinylidene] (benzylidene) (tricyclohexylphosphine)ruthenium(II), dichloro[1,3-bis(2,4,6-trimethylphenyl)-2-imidazolidinylidene][3-(2-pyridinyl)propylidene]ruthenium(II), [1,3-dimesityl-2-imidazolidinylidene]dichloro(phenylmethylene) bis(3-bromopyridine)ruthenium(II), dichloro[1,3-bis(2,4,6-trimethylphenyl)-2-imidazolidinylidene](3-methyl-2-butenylidene) (tricyclohexylphosphine) ruthenium(II), dichloro[1,3-bis(2-methylphenyl)-2-imidazolidinylidene](2-isopropoxyphenylmethylene) ruthenium(II), [1,3-dimesityl-2-imidazolidinylidene] dichloro[3-(2-pyridinyl)propylidene]-ruthenium(II), (1,3-dimesitylimidazolidin-2-ylidene)dichloro(2-isopropoxy-5-nitrobenzylidene) ruthenium(II), tricyclohexylphosphine[4,5-dimethyl-1,3-bis(2,4,6-trimethylphenyl) imidazol-2-ylidene][2-thienylmethylene] ruthenium(II) dichloride, tricyclohexylphosphine[1,3-bis(2,4,6-trimethylphenyl)imidazol-2-ylidene][2-thienylmethylene]ruthenium(II) dichloride, tricyclohexylphosphine[2,4-dihydro-2,4,5-triphenyl-3H-1,2,4-triazol-3-ylidene][2-thienylmethylene]ruthenium(II) dichloride, tricyclohexylphosphine[1,3-bis(2,4,6-trimethylphenyl)imidazol-2-ylidene][3-phenyl-1H-inden-1-ylidene]ruthenium(II) dichloride, dichloro[1,3-bis(2,4,6-trimethylphenyl)-2-imidazolidinylidene](2-isopropoxyphenylmethylene)ruthenium(II), and bis(tricyclohexylphosphine)-3-phenyl-1H-inden-1-ylideneruthenium(II) dichloride;

4.75 Method 4.73, wherein the catalyst is selected from 2,6-diisopropyl-phenylimido-neophylidene[(S)-(−)-BIPHEN]molybdenum(VI), dichlorobis[(2,6-diisopropylphenyl)imido](1,2-dimethoxyethane)molybdenum (VI), and (T-4)-chloro(2,2-dimethylpropylidene)[2,2'',4,4',6,6'-hexakis(1-methylethyl)[1,1':3',1-terphenyl]-2'-olato][2-methyl-2-propanaminoato(2-)] molybdenum(VI);

4.76 Method 4.73, wherein the suitable catalyst is the Hoveyda-Grubbs II catalyst (dichloro[1,3-bis(2,4,6-trimethylphenyl)-2-imidazolidinylidene](2-isopropoxyphenylmethylene)ruthenium(II));

4.77 Any of Methods 4.65-4.76, wherein the solvent is a nonpolar solvent or polar aprotic solvent;

4.78 Method 4.77, wherein the solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene); in one embodiment, the solvent is toluene;

4.79 Method 4.77, wherein the polar aprotic solvent is selected from esters (e.g., ethyl acetate, methyl acetate, isopropyl acetate), ketones (e.g., acetone, methyl ethyl ketone, methyl isobutyl ketone, 2-pentanone), and carbonates (e.g., dimethyl carbonate, diethyl carbonate, diisopropyl carbonate);

4.80 Any of Methods 4.65-4.79, wherein the temperature of the reaction is from 0 to 150° C., e.g., from 20 to 90° C., or 40° C. to 90° C., or 20° C. to 60° C., or 40° C. to 80° C., or about 80° C.; in one embodiment, the temperature of the reaction is from 70° C. to 90° C.;

4.81 Method 4, or any of Methods 4.1-4.80, wherein the method further comprises a step of reducing the double bond of a compound 9-D, 9-E, I or I(a), wherein === is a double bond, for a time and under conditions effective to form a compound 9-D, 9-E, I or I(a), respectively, wherein === is a double bond, the step comprising treating said compound with hydrogen gas over a suitable catalyst (e.g., Pd/C, Pt, PtO2, Raney nickel, nickel boride, RhCl(Ph3P)3), in a suitable solvent (e.g., acetone, ethyl acetate, isopropyl acetate, tetrahydrofuran, toluene);

4.82 Method 4, or any of Methods 4.1-4.81, wherein the Method produces a compound according to one or more of Compounds 8-B, 9-A, 9-B, 9-C, 9-D, 9-E or Compound I or I(a);

4.83 Method 4.82, wherein in any one or more of said compounds, $R^x$ is H, $R^y$ is H, $R^2$ and $R^3$ are independently H or $C_{1-6}$alkyl (e.g., methyl), $R^4$ is H, $R^5$ is $C_{1-3}$ alkyl (e.g., methyl), $R^6$ is halogen (e.g., chloro), $R^p$ is —C(=O)—O—$C_{1-6}$alkyl(aryl) (e.g., 1-phenylethoxycarbonyl, optionally in (R) or (S) form), R" is $C_{1-3}$alkyl (e.g., methyl), and/or $R^{12}$ is H, or —C(O)—$R^1$, wherein $R^1$ is selected from optionally substituted $C_{1-6}$ alkyl (e.g., methyl), optionally substituted $C_{1-6}$alkoxy (e.g., (S)-1-phenylethoxy), or optionally substituted 5-10 membered heteroaryl (e.g., 1-methyl-3-methoxy-1H-pyrazol-4-yl);

4.84 Method 4.83, wherein in one or more of said compounds $R^2$ and $R^3$ are H, or $R^2$ and $R^3$ are methyl, or $R^2$ is H and $R^3$ is methyl;

4.85 Method 4.84, wherein in one or more of said compounds $R^2$ is H and $R^3$ is methyl;

4.86 Any of Methods 4.82-4.85, wherein in one or more of compound 9-C, Compound I and Compound I(a), $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, $C_{1-6}$alkoxy and halogen;

4.87 Method 4.86, wherein $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

4.88 Method 4.87, wherein $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy), for example $R^1$ is 3-methoxy-1-methyl-1H-pyrazolyl;

4.89 Any of Methods 4.82-4.88, wherein in one or more of compound 9-D, 9-E, Compound I or compound I(a), === is a double bond;

4.90 Method 4, or any of Methods 4.1-4.89, wherein the product of the method is the Compound 1;

4.91 Method 4, or any of Methods 4.1-4.90, wherein the method further comprises any steps described in any of Method 1, et seq., Method 2, et seq., Method 3, et seq., and Method 5, et seq.

In a sixth aspect, the present disclosure provides a method (Method 5) of making a compound selected from one or more of Compounds 5-F, 5-F', 10-A, 10-B, 10-C, 10-C', 10-D, 10-E, 9-A, and 9-D, as herein described, wherein the method comprises the step of reacting a precursor compound with one or more reagents in a suitable solvent for a time and under conditions effective to form the product compound. Method 5 generally pertains to alternative routes for formation of the SNO-CB-TC cyclic fragment (including the ring closing metathesis step) and attachment of the side chain fragment, including advanced intermediates 10-C, 10-C', and 10-E, as well as the evolution of those intermediates to Compound 1. Without being limited in the order or combination of steps employed, the potential embodiments of Method 5 may include any steps shown in Scheme 10.

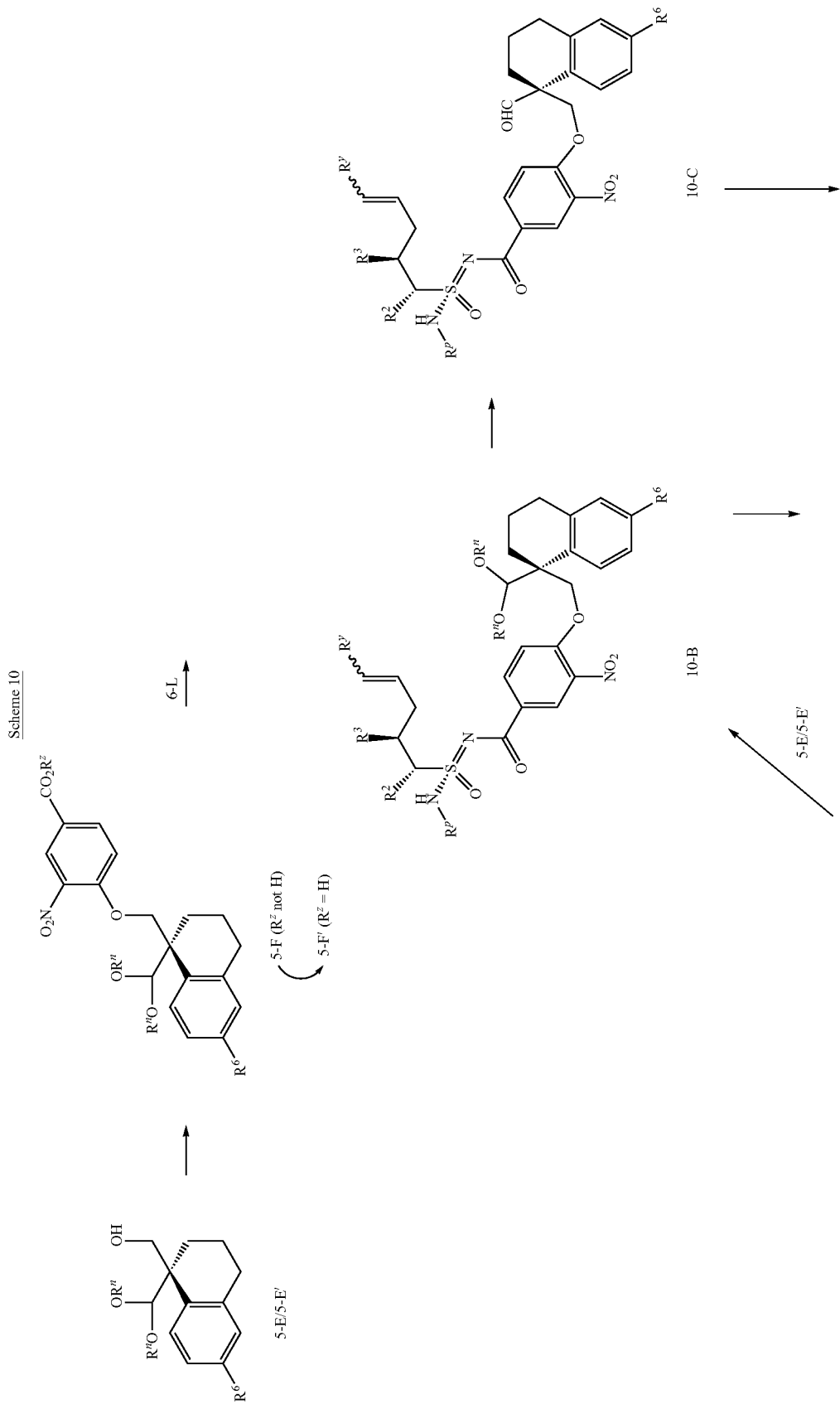

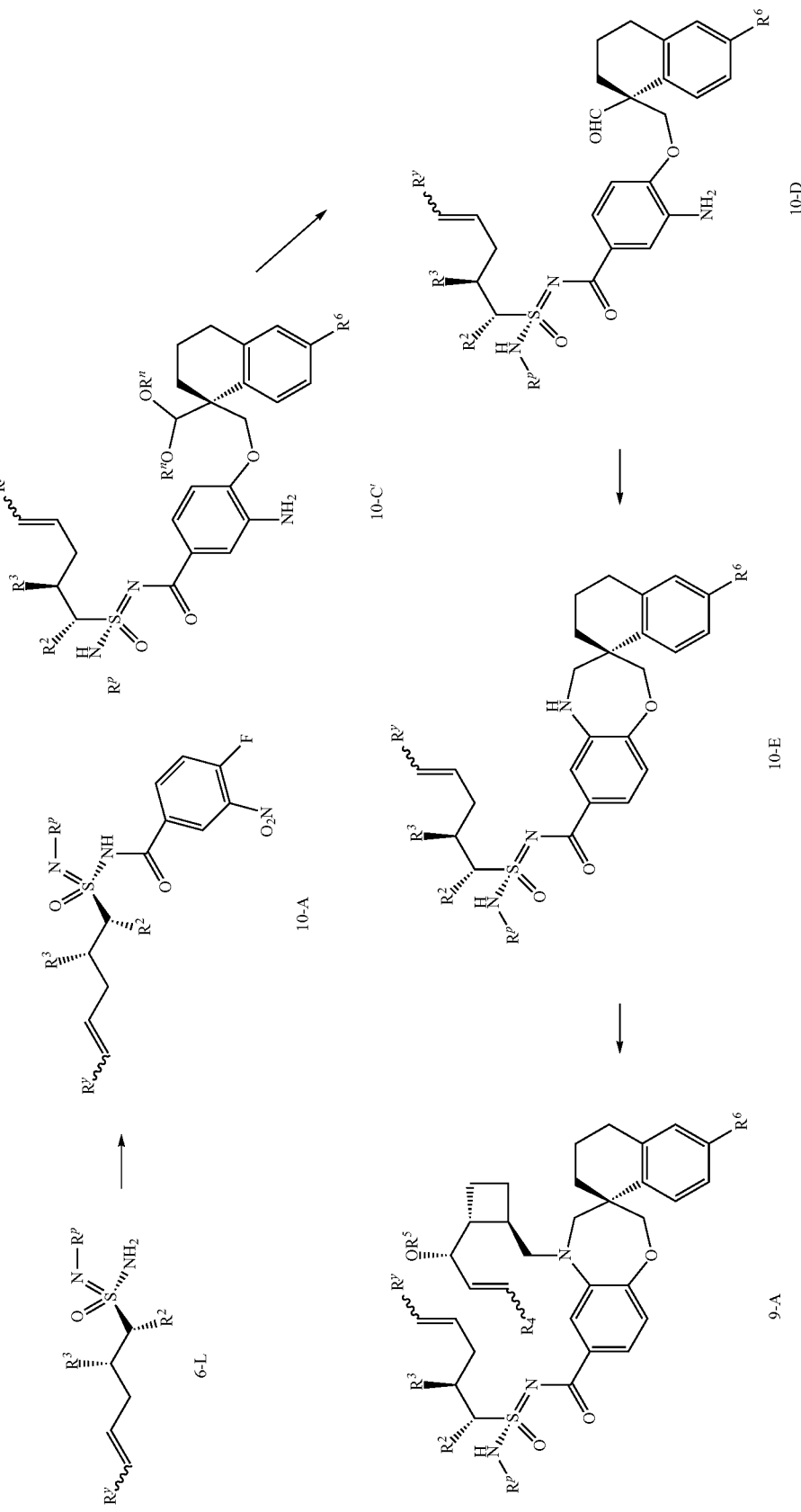

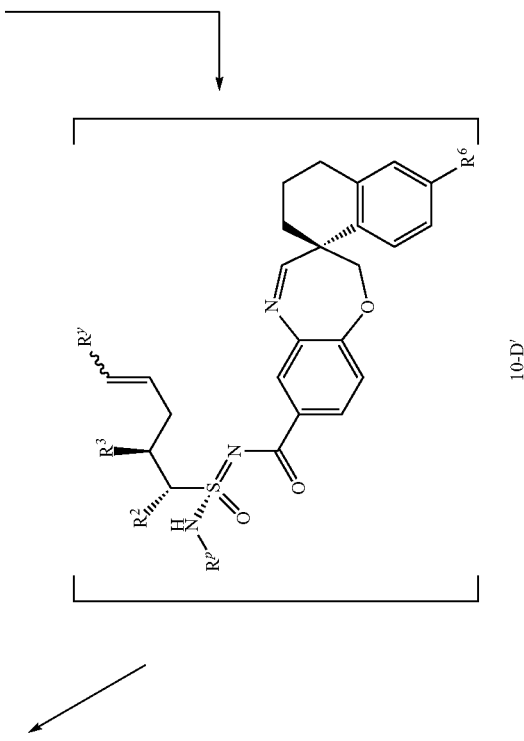
10-D'

In particular embodiments, the present disclosure provides Method 5 as follows.

5.1 Method 5, wherein the method comprises any of the steps described in any of Method 1, et seq., Method 2, et seq., Method 3, et seq., and Method 4, et seq.;

5.2 Method 5 or 5.1, wherein the method comprises the step of (1) reacting a compound 5-E or 5-E' with a 4-fluoro-3-nitrobenzoic acid or ester for a time and under conditions effective to form a compound 5-F, as described in any of Methods 2.126-2.2.140, wherein $R^6$, $R''$ and $R^z$ are defined as in any of Methods 2.126-2.131, and optionally (2) hydrolyzing a compound 5-F wherein $R^z$ is not H to the corresponding compound 5-F' wherein $R^z$ is H by treating with compound 5-F as provided in any of Methods 1.134-1.138, for a time and under conditions effective to form the compound 5-F'; in one embodiment, $R''$ is each independently $CH_3$, or wherein the two $R''$ moieties join together to form a bridge selected from —$CH_2CH_2$—, —$CH(CH_3)CH(CH_3)$—, —$CH_2CH(CH_3)$—, —$CH_2CH(Ph)$-, —$C(CH_3)_2C(CH_3)_2$—, —$CH_2CH_2CH_2$—, —$CH_2CBr_2CH_2$—, —$CH_2(C\!\!=\!\!CH)CH_2$—, —$CH_2CH(Ph)CH_2$—, —$CH(CH_3)CH(CH_3)$—, —$CH_2CH(CH_3)CH_2$—, —$CH_2C(CH_3)_2CH_2$—, —$CH_2C(CH_2CH_3)_2CH_2$—, —$CH_2CH_2CH_2CH_2$—, —$CH_2CH_2CH_2CH_2CH_2$—, —$CH(C_6H_5)CH(C_6H_5)$, —$CH_2CH(C_6H_5)CH_2$—, and -(o-$C_6H_4$)—;

5.3 Method 5.2, wherein $R^z$ of compound 5-F is unsubstituted $C_{1-6}$alkyl (e.g., methyl, ethyl, propyl, isopropyl, n-butyl, s-butyl, isobutyl or tert-butyl);

5.4 Method 5.3, wherein $R^z$ of compound 5-F or 5-F' is H;

5.5 Method 5, or any of Methods 5.1 or 5.2, wherein the method comprises the step of acylating a compound 6-L with 4-fluoro-3-nitrobenzoic acid for a time and under conditions effective to form a compound 10-A, or acylating a compound 6-L with a benzoic acid compound 5-F/5-F' for a time and under conditions effective to form a compound 10-B, using an acid activator and a base in a suitable solvent, wherein $R^6$ is defined as provided in Method 2.10 or 2.11, wherein each $R''$ is defined as provided in any of Methods 2.76-2.79 or 2.108-2.111, wherein $R^z$ of compound 5-F or 5-F' is H, wherein $R^y$ is as defined in Method 3.2 or 3.3, wherein $R^2$ and $R^3$ are as defined in any of Methods 3.4-3.10, and wherein $R^p$ is as defined in any of Methods 3.109-3.112;

5.6 Method 5.5, wherein $R^6$ is chloro;

5.7 Method 5.5 or 5.6 wherein both $R''$ are methyl or ethyl, or the two $R''$ moieties join together to form a bridge selected from —$CH_2CH_2$—, —$C(CH_3)_2C(CH_3)_2$—, —$CH_2CH_2CH_2$—, and $CH_2C(CH_3)_2CH_2$—, —$CH(CH_3)CH(CH_3)$—, —$CH(CH_3)CH_2CH(CH_3)$—, —$CH_2CH(CH_3)CH_2$—, —$CH_2C(CH_2CH_3)_2CH_2$—, —$CH(C_6H_5)CH(C_6H_5)$, and —$CH_2CH(C_6H_5)CH_2$—;

5.8 Any of Methods 5.5-5.7, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

5.9 Method 5.8, wherein $R^p$ is 1-phenylethoxycarbonyl, optionally in (R) or (S) form;

5.10 Any of Methods 5.5-5.9, wherein the acid activator is selected from N-(3-dimethylaminopropyl)-N'-ethylcarbodiimide hydrochloride (EDC HCl), (PhO)$_2$POCl, carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methyl-morpholinium chloride (DMTMM), thionyl chloride, oxalyl chloride, and sulfuryl chloride;

5.11 Method 5.10, wherein the acid activator is N-(3-dimethylaminopropyl)-N'-ethylcarbodiimide hydrochloride (EDC HCl);

5.12 Any of Methods 5.5-5.11, wherein the base is selected from tertiary amines (e.g., trimethylamine, triethylamine, N-methylmorpholine, N-ethylmorpholine, tripropylamine, N,N-diisopropylethylamine, tributylamine, 1,8-diazabicyclo[5.4.0]undec-7-ene, 1,4-diazabicyclo[2.2.2]octane), aromatic amines (e.g., pyridine, 2,6-lutidine, picoline, collidine, imidazole, 1-methylimidazole, indole, isoindole, quinoline, isoquinoline, 4-dimethylaminopyridine), and inorganic bases (e.g., lithium carbonate, sodium carbonate, potassium carbonate, calcium carbonate, potassium phosphate (monobasic, dibasic or tribasic), sodium phosphate (monobasic, dibasic or tribasic));

5.13 Method 5.12, wherein the base is imidazole or 1-methylimidazole;

5.14 Any of Methods 5.5-5.13, wherein the reaction further comprises a promoter selected from 4-dimethylaminopyridine (DMAP), N-methylimidazole, 1-hydroxy-7-azabenzotriazole (HOAt), and 1-hydroxybenzotriazole (HOBt);

5.15 Any of Methods 5.5-5.14, wherein the acid activator is EDC-HCl, the base is 1-methylimidazole and the promoter is DMAP;

5.16 Any of Methods 5.5-5.15, wherein the suitable solvent is a nonpolar solvent or polar aprotic solvent;

5.17 Method 5.16, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

5.18 Method 5.16, wherein the polar aprotic solvent is selected from N,N-dimethylformamide, N,N-dimethylacetamide, N-methyl-2-pyrrolidinone, dimethyl sulfoxide, esters (e.g., ethyl acetate, methyl acetate, isopropyl acetate), and nitriles (e.g., acetonitrile);

5.19 Method 5.16, wherein the solvent is acetonitrile;

5.20 Any of Methods 5.5-5.19, wherein the temperature of the reaction is from −50 to 50° C., e.g., from 0 to 40° C., or 10° C. to 30° C., or about 20° C.;

5.21 Method 5, or any of Methods 5.1-5.20, wherein the method comprises the step of treating a fluorophenyl compound 10-A in a suitable solvent with an alcohol compound 5-E or 5-E', for a time and under conditions effective to form the ether adduct compound 10-B, wherein $R^6$ is defined as provided in Method 2.10 or 2.11, wherein each $R''$ is defined as provided in any of Methods 2.76-2.79 or 2.108-2.111, wherein R is defined as in Method 3.2 or 3.3, wherein $R^2$ and $R^3$ are as defined in any of Methods 3.4-3.10, and wherein $R^p$ is as defined in any of Methods 3.109-3.112;

5.22 Method 5.21, wherein $R^6$ is chloro;

5.23 Method 5.21 or 5.22, wherein both $R''$ of the compound 5-E are methyl or ethyl, or the two $R''$ moieties of the compound 5-E or 5-E' join together to form a bridge selected from —$CH_2CH_2$—, —$C(CH_3)_2C(CH_3)_2$—, —$CH_2CH_2CH_2$—, and $CH_2C(CH_3)_2CH_2$—;

5.24 Any of Methods 5.21-5.23, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

5.25 Method 5.24, wherein $R^p$ is 1-phenylethoxycarbonyl, optionally in (R) or (S) form;

5.26 Any of Methods 5.21-5.25, wherein the compound 5-E or 5-E' is dissolved or suspended in the suitable solvent and treated with a strong base, and optionally with a promoter (e.g., sodium iodide, tetrabutylammonium iodide);

5.27 Method 5.26, wherein the base is selected from inorganic hydrides (e.g., sodium hydride, potassium hydride), alkoxides (e.g., sodium methoxide, sodium ethoxide, sodium t-butoxide, potassium methoxide, potassium ethoxide, potassium t-butoxide, lithium t-butoxide, potassium t-pentoxide, sodium t-pentoxide, lithium t-pentoxide), inorganic hydroxides (e.g., sodium hydroxide, potassium hydroxide, lithium hydroxide), amide bases (sodium hexamethyldisilazide, lithium hexamethyldisilazide, potassium hexamethyldisilazide, lithium diisopropylamide, sodium diisopropylamide, potassium diisopropylamide), and inorganic bases (e.g., lithium carbonate, sodium carbonate, potassium carbonate, cesium carbonate, potassium phosphate (mono-, di- or tri-basic), sodium phosphate (mono-, di- or tri-basic));

5.28 Method 5.27, wherein the base is selected from sodium methoxide, sodium ethoxide, sodium t-butoxide, potassium methoxide, potassium ethoxide, potassium t-butoxide, lithium t-butoxide, sodium hexamethyldisilazide, lithium hexamethyldisilazide, potassium hexamethyldisilazide, lithium diisopropylamide, sodium diisopropylamide, and potassium diisopropylamide; optionally wherein the base is potassium t-butoxide;

5.29 Any of Methods 5.21-5.28, wherein the compound 10-A is added to the reaction about 1 to 60 minutes after addition of the base, e.g., about 1 to 30 minutes after, or 1 to 20 minutes after, or 1 to 15 minutes after, or 1 to 10 minutes after, or 1 to 5 minutes after;

5.30 Any of Methods 5.21-5.29, wherein the suitable solvent is a nonpolar solvent;

5.31 Method 5.30, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

5.32 Method 5.30, wherein the nonpolar solvent is tetrahydrofuran;

5.33 Any of Methods 5.21-5.32, wherein the temperature of the reaction is from −80 to 100° C., e.g., from −45 to 10° C., or −30° C. to 10° C., or −10° C. to 5° C., or about 0° C., or −10° C. to 50° C., or −10° C. to 30° C., or 10° C. to 30° C., or 30° C. to 80° C.;

5.34 Method 5, or any of 5.1-5.33, wherein the method comprises the step of treating the acetal compound 10-B or 10-C' with a deprotecting agent in a suitable solvent for a time and under conditions effective to form an aldehyde compound 10-C or 10-D, respectively, wherein $R^6$ is defined as in Method 2.10 or 2.11, wherein each $R''$ is defined as provided in any of Methods 2.76-2.79 or 2.108-2.111, wherein $R^y$ is as defined in Method 3.2 or 3.3, wherein $R^2$ and $R^3$ are as defined in any of Methods 3.4-3.10, and wherein $R^p$ is as defined in any of Methods 3.109-3.112;

5.35 Method 5.34, wherein $R^6$ is chloro;

5.36 Method 5.34 or 5.35, wherein both $R''$ of the compound 5-E are methyl or ethyl, or the two $R''$ moieties of the compound 5-E or 5-E' join together to form a bridge selected from —CH$_2$CH$_2$—, —C(CH$_3$)$_2$C(CH$_3$)$_2$—, —CH$_2$CH$_2$CH$_2$—, and CH$_2$C(CH$_3$)$_2$CH$_2$—;

5.37 Any of Methods 5.34-5.36, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

5.38 Method 5.37, wherein $R^p$ is 1-phenylethoxycarbonyl, optionally in (R) or (S) form;

5.39 Any of Methods 5.34-5.38, wherein the acid is selected from HCl (e.g., aqueous HCl or HCl/methanol, HCl/isopropanol, or HCl/dioxane), HBr (e.g., aqueous HBr or HBr/acetic acid), sulfuric acid, phosphoric acid, p-toluenesulfonic acid, pyridinium tosylate, trifluoroacetic acid, methanesulfonic acid, trichloroacetic acid, Lewis acids (e.g., erbium triflate), and acidic resin (e.g., Amberlyst);

5.40 Method 5.39, wherein the acid is methanesulfonic acid;

5.41 Any of Methods 5.34-5.40, wherein the suitable solvent is a nonpolar solvent, polar protic solvent, polar aprotic solvent, or a combination thereof, 5.42 Method 5.41, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

5.43 Method 5.41, wherein the polar protic solvent is water and/or an alcohol (e.g., methanol, ethanol, propanol, isopropanol) or acid (e.g., formic acid, acetic acid);

5.44 Method 5.41, wherein the polar aprotic solvent is selected from ketones (e.g., acetone, methyl ethyl ketone, methyl isobutyl ketone), esters (e.g., ethyl acetate, methyl acetate, isopropyl acetate), and nitriles (e.g., acetonitrile);

5.45 Method 5.41, wherein the suitable solvent is tetrahydrofuran and water;

5.46 Any of Methods 5.34-5.45, wherein the temperature of the reaction is from 0 to 100° C., e.g., from 20 to 50° C., or 20° C. to 30° C., or from 60 to 70° C.;

5.47 Any of Methods 5.34-5.46, wherein the method results in the cleavage of the $R^p$ protecting group, such that in the product compound 10-C or 10-D of the reaction $R^p$ is hydrogen;

5.48 Method 5, or any of 5.1-5.47, wherein the method comprises the step of reducing a nitro/aldehyde compound 10-C to a aniline/aldehyde compound 10-D, or of reducing nitro/acetal 10-B to aniline/acetal 10-C', wherein $R^6$ is defined as provided in Method 2.10 or 2.11, wherein each $R''$ is defined as provided in any of Methods 2.76-2.79 or 2.108-2.111, wherein $R^y$ is defined as in Method 3.2 or 3.3, wherein $R^2$ and $R^3$ are as defined in any of Methods 3.4-3.10, and wherein $R^p$ is as defined in any of Methods 3.109-3.112 or $R^p$ is hydrogen; and wherein each $R''$ is defined as provided in any of Methods 2.76-2.79 or 2.108-2.111;

5.49 Method 5.48, wherein $R^6$ is chloro;

5.50 Method 5.48 or 5.49, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

5.51 Method 5.50, wherein $R^p$ is 1-phenylethoxycarbonyl, optionally in (R) or (S) form;

5.52 Method 5.48 or 5.49, wherein $R^p$ is hydrogen;

5.53 Any of Methods 5.48-5.52, wherein the reducing agent is selected from zinc, tin or iron in an acid (e.g., in formic acid or acetic acid or HCl in the suitable solvent, or ammonium chloride);

5.54 Method 5.53, wherein the reducing agent is iron (e.g., powder) in acetic acid;

5.55 Any of Methods 5.48-5.52, wherein the reducing agent is a hydrogenation agent (e.g., hydrogen in combination with a heterogenous catalyst (e.g., a transition metal catalyst) or a homogeneous catalyst (e.g., a soluble transition metal complex), or a phase transfer hydrogenation system);

5.56 Method 5.55, wherein the hydrogenation agent is hydrogen gas in combination with a palladium, platinum, rhodium, iridium, ruthenium, or nickel catalyst (e.g., Pd, Pd/C, Pd(OAc)$_2$, Pt/C, PtO$_2$, Ru/C, Raney Nickel, Ru complexes, Rh complexes, PtO$_2$, Pt complexes, Pd complexes, Ir complexes), or ammonium formate in combination with a palladium or platinum catalyst (e.g., Pd, Pd/C, Pt/C, PtO$_2$);

5.57 Method 5.56, wherein the hydrogenation agent is hydrogen gas in combination with a Pd, Pd/C, Pd(OAc)$_2$, Pt/C or PtO$_2$ catalyst, optionally at 1-5 bar pressure (e.g., 1-2 bar);

5.58 Any of Methods 5.48-5.57, wherein the suitable solvent is a nonpolar solvent, polar protic solvent, or polar aprotic solvent;

5.59 Method 5.58, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

5.60 Method 5.58, wherein the polar protic solvent is an alcohol (e.g., methanol, ethanol, propanol, isopropanol) or acid (e.g., formic acid, acetic acid) or an aqueous acid (e.g., aqueous HCl);

5.61 Method 5.58, wherein the polar aprotic solvent is selected from esters (e.g., ethyl acetate, methyl acetate, isopropyl acetate), and nitriles (e.g., acetonitrile);

5.62 Method 5.58, wherein the suitable solvent is acetic acid;

5.63 Any of Methods 5.48-5.62, wherein the temperature of the reaction is from 0 to 100° C., e.g., from 20 to 50° C., or 20° C. to 30° C., or from 50 to 90° C., or from 65 to 85° C.;

5.64 Any of Methods 5.34-5.63, where the intended product compound 10-D of the step undergoes spontaneous condensation to form intermediate imine 10-D' either partly or completely, and the mixture of 10-D and 10-D' is carried forward to the next step, or the product isolated is 10-D' which is used in the next step;

5.65 Method 5 or any of 5.1-5.64, wherein the method comprises the step of treating the aniline/acetal compound 10-D (and/or 10-D') in a suitable solvent with a reducing agent for a time and under conditions effective to yield the secondary amine compound 10-E, wherein $R^6$ is defined as provided in Method 2.10 or 2.11, wherein $R^y$ is as defined in Method 3.2 or 3.3, wherein $R^2$ and $R^3$ are as defined in any of Methods 3.4-3.10, and wherein $R^p$ is as defined in any of Methods 3.109-3.112 or $R^p$ is hydrogen;

5.66 Method 5.65, wherein $R^6$ is chloro;

5.67 Method 5.65 or 5.66, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

5.68 Method 5.67, wherein $R^p$ is 1-phenylethoxycarbonyl, optionally in (R) or (S) form;

5.69 Method 5.65 or 5.66, wherein $R^p$ is hydrogen;

5.70 Any of Methods 5.65-5.69, wherein the reducing agent is selected from a hydride reducing agent, a silane reducing agent, hydrogenation, iron powder (Fe) in combination, sodium triacetoxyborohydride (NaBH(OAc)$_3$), tin or zinc in combination with acids (e.g. hydrochloric acid, acetic acid, ammonium chloride), transition metal (e.g. Pd, Pt or Rh) in combination with H$_2$ or a formate salt, poisoned heterogeneous catalysts (e.g. Pt/S/C), silanes (triisopropylsilane, triphenylsilane, diethylsilane, etc.), sodium borohydride, sodium borohydride/acetic acid, sodium cyanoborohydride, titanium isopropoxide/sodium cyanoborohydride, zinc/acetic acid, sodium borohydride/magnesium perchlorate, zinc borohydride/zinc chloride, tetramethylammonium triacetoxyborohydride; in one embodiment, the reducing agent is iron powder (Fe) in combination with sodium triacetoxyborohydride (NaBH(OAc)$_3$);

5.71 Method 5.70, wherein the reducing agent is a hydride reducing agent;

5.72 Method 5.71, wherein the hydride reducing agent is selected from sodium borohydride, lithium borohydride, sodium cyanoborohydride, zinc borohydride, sodium triacetoxyborohydride, and tetramethylammonium triacetoxyborohydride;

5.73 Method 5.72, wherein the hydride reducing agent is sodium triacetoxyborohydride or sodium cyanoborohydride;

5.74 Any of Methods 5.71-5.73, wherein the hydride reducing agent is combined with a reagent to modulate the hydride reducing activity (e.g., titanium isopropoxide, titanium ethoxide, borate salts, magnesium perchlorate, or zinc chloride);

5.75 Method 5.70, wherein the silane reducing agent is triethylsilane;

5.76 Any of Methods 5.70-5.75, wherein the reaction further comprises an acid (e.g., selected from formic acid, acetic acid, trifluoracetic acid, citric acid, pivalic acid, p-toluenesulfonic acid, methanesulfonic acid, and hydrochloric acid);

5.77 Any of Methods 5.65-5.76, wherein the suitable solvent is a nonpolar solvent, a polar protic solvent, or polar aprotic solvent;

5.78 Method 5.77, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

5.79 Method 5.77, wherein the polar protic solvent is selected from alcohols (e.g., methanol, ethanol, propanol, isopropanol) and acids (e.g., acetic acid, formic acid, trifluoracetic acid);

5.80 Method 5.77, wherein the polar aprotic solvent is selected from N,N-dimethylacetamide, N,N-dimethylformamide, N-methyl-2-pyrrolidinone, dimethyl sulfoxide, esters (e.g., methyl acetate, ethyl acetate, isopropyl acetate), and nitriles (e.g., acetonitrile);

5.81 Method 5.77, wherein the suitable solvent is acetic acid;

5.82 Any of Methods 5.65-5.81, wherein the temperature of the reaction is from −30 to 100° C., e.g., from 0 to 80° C., or 20 to 30° C., 20 to 50° C., from 50 to 90° C., or 60 to 80° C.;

5.83 Method 5, or any of Methods 5.1-5.82, wherein the method comprises the step of treating the compound 10-E in a suitable solvent with a reducing agent and the compound 1-I, for a time and under conditions effective to form a tertiary amine compound 9-A, wherein $R^6$ is defined as provided in Method 2.10 or 2.11, wherein $R^y$ is as defined in Method 3.2 or 3.3, wherein $R^2$ and $R^3$ are as defined in any of Methods 3.4-3.10, wherein $R^p$ is as defined in any of Methods 3.109-3.112 or $R^p$ is hydrogen, wherein $R^x$ is defined as in Method 1.18 or 1.19, and wherein $R^5$ is defined as in any of Methods 1.75-1.78;

5.84 Method 5.83, wherein $R^6$ is chloro;

5.85 Method 5.83 or 5.84, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

5.86 Method 5.85, wherein $R^p$ is 1-phenylethoxycarbonyl, optionally in (R) or (S) form;

5.87 Method 5.83 or 5.84, wherein $R^p$ is hydrogen;

5.88 Any of Methods 5.83-5.87, wherein the reducing agent is selected from a hydride reducing agent, a silane reducing agent, or hydrogenation;

5.89 Method 5.88, wherein the reducing agent is a hydride reducing agent;

5.90 Method 5.89, wherein the hydride reducing agent is selected from sodium borohydride, lithium borohydride, sodium cyanoborohydride, zinc borohydride, sodium triacetoxyborohydride, and tetramethylammonium triacetoxyborohydride;

5.91 Method 5.90, wherein the hydride reducing agent is sodium triacetoxyborohydride or sodium cyanoborohydride;

5.92 Any of Methods 5.89-5.91, wherein the hydride reducing agent is combined with a reagent to modulate the hydride reducing activity (e.g., titanium isopropoxide, titanium ethoxide, borate salts, magnesium perchlorate, or zinc chloride);

5.93 Method 5.88, wherein the silane reducing agent is triethylsilane;

5.94 Any of Methods 5.83-5.93, wherein the reaction further comprises an acid (e.g., selected from acetic acid, trifluoroacetic acid, citric acid, pivalic acid, p-toluenesulfonic acid, methanesulfonic acid, and hydrochloric acid);

5.95 Any of Methods 5.83-5.94, wherein the suitable solvent is a nonpolar solvent, a polar protic solvent, or polar aprotic solvent;

5.96 Method 5.95, wherein the nonpolar solvent is selected from ethers (e.g., tetrahydrofuran, 2-methyltetrahydrofuran, methyl tert-butyl ether, cyclopentyl methyl ether, dioxane), hydrocarbon solvents (e.g., toluene, n-hexane, n-heptane), and halogenated solvents (e.g., dichloromethane, 1,2-dichloroethane, chloroform, chlorobenzene);

5.97 Method 5.95, wherein the polar protic solvent is selected from alcohols (e.g., methanol, ethanol, propanol, isopropanol) and acids (e.g., acetic acid, formic acid, trifluoracetic acid);

5.98 Method 5.95, wherein the polar aprotic solvent is selected from N,N-dimethylacetamide, N,N-dimethylformamide, N-methyl-2-pyrrolidinone, dimethyl sulfoxide, esters (e.g., methyl acetate, ethyl acetate, isopropyl acetate), and nitriles (e.g., acetonitrile);

5.99 Method 5.95, wherein the suitable solvent is dichloromethane;

5.100 Any of Methods 5.83-5.95, wherein the temperature of the reaction is from −30 to 80° C., e.g., from 0 to 80° C., or 10 to 30° C.;

5.101 Method 5, or any of Methods 5.1-5.100, wherein the Method produces a compound according to one or more of Compounds 10-A, 10-B, 10-C, 10-C', 10-D, 10-E, or 9-A;

5.102 Method 5, or any of 5.1-5.101, wherein the product compounds 9-A is further elaborated to Compound I, Compound I(a) or Compound 1, as provided by any steps described in Method 4.

In a further aspect the present disclosure provides each of the compounds 1-A, 1-B, 1-C, 1-D, 1-E, 1-F, 1-G, 1-H, 1-I, 2-A, 2-B, 2-C, 2-D, 2-E, 3-A, 3-B, 3-C, 3-D, 4-A, 4-B, 4-C, 5-A, 5-B, 5-C, 5-D, 5-E, 5-E', 5-F, 5-G, 5-G', 5-H, 5-I, 6-A, 6-B, 6-B', 6-C, 6-D, 6-E, 6-F, 6-G, 6-H, 6-I, 6-J, 6-K, 6-L, 6-L', 7-A, 8-A, 8-B, 9-A, 9-B, 9-C, 9-D, 9-E, 10-A, 10-B, 10-C, 10-C', 10-D, or 10-E, in each of their disclosed embodiments for all purposes, as well as for use in a method of manufacturing Compound I, Compound I(a) or Compound 1, as well as for use in a method of manufacturing any other compound disclosed herein. In particular embodiments, the present disclosure provides:

6.1 Compound 9-A, wherein $R^x$ and $R^y$ are each independently H, $C_{1-6}$alkyl, or $C_{6-10}$aryl, wherein the alkyl is optionally substituted with $C_{6-10}$aryl, $R^2$ and $R^3$ are independently H or $C_{1-6}$ alkyl (e.g., methyl), $R^5$ is $C_{1-6}$ alkyl (e.g., methyl), $R^6$ is halogen (e.g., chloro), and $R^p$ is selected from an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.2 Compound 9-A, as provided in Formula 6.1, wherein $R^p$ is selected from C(=O)—$C_{1-6}$alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.3 Compound 9-A, as provided in Formula 6.2, wherein $R^p$ is —C(=O)—O—$C_{1-6}$alkyl(aryl);

6.4 Compound 9-A, as provided in Formula 6.3, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.5 Compound 9-A, as provided in Formula 6.4 wherein $R^p$ is 1-phenylethoxycarbonyl, optionally in (R) or (S) form;

6.6 Compound 9-A, as provided in Formula 6.5, wherein $R^p$ is 1-phenylethoxycarbonyl, in (S) form;

6.7 Compound 9-A, as provided in any of Formulas 6.1-6.6, wherein $R^x$ and $R^y$ are each H;

6.8 Compound 9-A, as provided in any of Formulas 6.1-6.7, wherein $R^2$ is H and $R^3$ is methyl;

6.9 Compound 9-A, as provided in any of Formulas 6.1-6.8, wherein $R^5$ is methyl;

6.10 Compound 9-A, as provided in any of Formulas 6.1-6.9, wherein $R^6$ is chloro;

6.11 Compound 9-B, wherein $R^x$ and $R^y$ are each independently H, $C_{1-6}$alkyl, or $C_{6-10}$aryl, wherein the alkyl is optionally substituted with $C_{6-10}$aryl, $R^2$ and $R^3$ are independently H or $C_{1-6}$ alkyl (e.g., methyl), $R^4$ is H, $R^5$ is $C_{1-6}$ alkyl (e.g., methyl), and $R^6$ is halogen (e.g., chloro);

6.12 Compound 9-B as provided in Formula 6.11, wherein $R^x$ and $R^y$ are each H;

6.13 Compound 9-B, as provided in Formulas 6.11 or 6.12, wherein $R^2$ is H and $R^3$ is methyl;

6.14 Compound 9-B, as provided in any of Formulas 6.11-6.13, wherein $R^5$ is methyl;

6.15 Compound 9-B, as provided in any of Formulas 6.11-6.14, wherein $R^6$ is chloro;

6.16 Compound 9-C, wherein $R^x$ and $R^y$ are each independently H, $C_{1-6}$alkyl, or $C_{6-10}$aryl, wherein the alkyl is optionally substituted with $C_{6-10}$aryl, $R^2$ and $R^3$ are independently H or $C_{1-6}$ alkyl (e.g., methyl), $R^4$ is H, $R^5$ is $C_{1-6}$ alkyl (e.g., methyl), $R^6$ is halogen (e.g., chloro), and $R^{12}$ is —C(O)—$R^1$, and $R^1$ is selected from $C_{1-6}$alkyl, $C_{1-6}$haloalkyl, $C_{2-6}$alkynyl, $C_{3-10}$cycloalkyl, $C_{6-10}$aryl, 3-12 membered heterocycloalkyl, 5-10 membered heteroaryl, and —$NR^8R^9$, wherein said $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, and 5-10 membered heteroaryl are optionally substituted with 1-5 $R^{10}$ groups; wherein each $R^8$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein each $R^1$ and $R^9$ are independently hydrogen, $C_{1-6}$alkyl, $C_{3-10}$cycloalkyl, $C_{1-6}$haloalkyl, 3-12 membered heterocycloalkyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$haloalkyl, 3-12 membered heterocycloalkyl, $C_{6-10}$aryl, and 5-10 membered heteroaryl are optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, 3-12 membered heterocycloalkyl, $C_{6-10}$aryl, 5-10 membered heteroaryl, halogen, oxo, —$OR^a$, and —$NR^aR^b$; wherein $R^a$ and $R^b$ is independently hydrogen or $C_{1-6}$alkyl;

6.17 Compound 9-C, as provided in Formula 6.16, wherein $R^{12}$ is —C(O)—$R^1$, and $R^1$ is 5-10 membered heteroaryl (e.g., oxazolyl, isoxazolyl, thiazolyl, isothiazolyl, pyrazolyl, imidazolyl), optionally substituted with 1-5 $R^{10}$ groups; wherein each of said $R^{10}$ group is independently selected from $C_{1-6}$alkyl, $C_{3-10}$cycloalkyl, $C_{1-6}$haloalkyl, $C_{1-6}$alkoxy and halogen;

6.18 Compound 9-C, as provided in Formula 6.17, wherein $R^{12}$ is —C(O)—$R^1$, and $R^1$ is pyrazolyl or imidazolyl, optionally substituted with 1-5 $R^{10}$ groups; wherein each of said $R^{10}$ group is independently $C_{1-6}$alkyl (e.g., methyl) or $C_{1-6}$alkoxy (e.g., methoxy);

6.19 Compound 9-C, as provided in Formula 6.18, wherein $R^{12}$ is —C(O)—$R^1$, and $R^1$ is pyrazolyl optionally substituted by 1-3 $C_{1-6}$alkyl (e.g., methyl) or $C_{1-6}$alkoxy (e.g., methoxy);

6.20 Compound 9-C, as provided in Formula 6.19, wherein $R^{12}$ is —C(O)—$R^1$, and $R^1$ is 3-methoxy-1-methyl-1H-pyrazolyl;

6.21 Compound 9-C as provided in any of Formulas 6.16-6.20, wherein $R^x$ and $R^y$ are each H;

6.22 Compound 9-C, as provided in any of Formulas 6.16-6.21, wherein $R^2$ is H and $R^3$ is methyl;

6.23 Compound 9-C, as provided in any of Formulas 6.16-6.22, wherein $R^5$ is methyl;

6.24 Compound 9-C, as provided in any of Formulas 6.16-6.23, wherein $R^6$ is chloro;

6.25 Compound 9-E, wherein $R^2$ and $R^3$ are independently H or $C_{1-6}$alkyl (e.g., methyl), $R^4$ is H, $R^5$ is $C_{1-6}$ alkyl (e.g., methyl), and $R^6$ is halogen (e.g., chloro);

6.26 Compound 9-E as provided in Formula 6.25, wherein ⸺ is a double bond;

6.27 Compound 9-E, as provided in Formulas 6.25 or 6.26, wherein $R^2$ is H and $R^3$ is methyl;

6.28 Compound 9-E, as provided in any of Formulas 6.25-6.27, wherein $R^5$ is methyl;

6.29 Compound 9-E, as provided in any of Formulas 6.25-6.28, wherein $R^6$ is chloro;

6.30 Compound 10-E, wherein $R^y$ is H or $C_{1-6}$alkyl (e.g., methyl), $R^2$ and $R^3$ are independently H or $C_{1-6}$alkyl (e.g., methyl), $R^6$ is halogen (e.g., chloro), and $R^p$ is selected from an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.31 Compound 10-E, as provided in Formula 6.30, wherein $R^p$ is selected from C(=O)—$C_{1-6}$ alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.32 Compound 10-E, as provided in Formula 6.30 or 6.31, wherein $R^p$ is —C(=O)—O—$C_{1-6}$alkyl(aryl);

6.33 Compound 10-E, as provided in any of Formulas 6.30-6.32, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.34 Compound 10-E, as provided in Formula 6.33 wherein $R^p$ is 1-phenylethoxycarbonyl, optionally in (R) or (S) form;

6.35 Compound 10-E, as provided in Formula 6.34, wherein $R^p$ is 1-phenylethoxycarbonyl, in (S) form;

6.36 Compound 10-E, as provided in any of Formulas 6.30-6.35, wherein $R^y$ is H;

6.37 Compound 10-E, as provided in any of Formulas 6.30-6.36, wherein $R^2$ is H and $R^3$ is methyl;

6.38 Compound 10-E, as provided in any of Formulas 6.30-6.37, wherein $R^6$ is chloro;

6.39 Compound 10-B or 10-C', wherein $R^y$ is H or $C_{1-6}$alkyl (e.g., methyl), $R^2$ and $R^3$ are independently H or $C_{1-6}$alkyl (e.g., methyl), $R^6$ is halogen (e.g., chloro), each R" is independently $C_{1-6}$alkyl (e.g., methyl, ethyl or isopropyl), or wherein the two R" moieties join together to form a $C_{2-10}$ alkyl or $C_{2-10}$ alkenyl bridge (i.e., a cyclic acetal), wherein said bridge is optionally substituted by 1-4 halogen or aryl, or wherein the two R" moieties join together to form an optionally substituted 1,2-hydroxyaryl bridge (e.g., a catechol bridge), and $R^p$ is selected from an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.40 Compound 10-B or 10-C', as provided in Formula 6.39, wherein $R^p$ is selected from C(=O)—$C_{1-6}$alkyl (e.g., acetyl, isobutyryl, pivaloyl), —C(=O)-aryl (e.g. benzoyl), —C(=O)—O—$C_{1-6}$ alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.41 Compound 10-B or 10-C', as provided in Formula 6.39 or 6.40, wherein $R^p$ is —C(=O)—O—$C_{1-6}$alkyl (aryl);

6.42 Compound 10-B or 10-C', as provided in any of Formulas 6.39-6.41, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.43 Compound 10-B or 10-C', as provided in Formula 6.42 wherein $R^p$ is 1-phenylethoxycarbonyl, optionally in (R) or (S) form;

6.44 Compound 10-B or 10-C', as provided in Formula 6.43, wherein $R^p$ is 1-phenylethoxycarbonyl, in (S) form;

6.45 Compound 10-B or 10-C', as provided in any of Formulas 6.39-6.44, wherein $R^y$ is H;

6.46 Compound 10-B or 10-C', as provided in any of Formulas 6.39-6.45, wherein $R^2$ is H and $R^3$ is methyl;

6.47 Compound 10-B or 10-C', as provided in any of Formulas 6.39-6.46, wherein each R" is independently $C_{1-6}$alkyl, optionally wherein each R" is methyl;

6.48 Compound 10-B or 10-C', as provided in Formula 6.47, wherein the two R" moieties join together to form a bridge selected from —$CH_2CH_2$—, —CH($CH_3$)CH ($CH_3$)—, —$CH_2$CH($CH_3$)—, —$CH_2$CH(Ph)-, —C($CH_3$)$_2$C($CH_3$)$_2$—, —$CH_2CH_2CH_2$—, —$CH_2CBr_2CH_2$—, —$CH_2$(C=CH)$CH_2$—, —$CH_2$CH (Ph)$CH_2$—, —CH($CH_3$)$CH_2$CH($CH_3$)—, —$CH_2$CH ($CH_3$)$CH_2$—, —$CH_2$C($CH_3$)$_2$$CH_2$—, —$CH_2$C ($CH_2CH_3$)$_2$$CH_2$—, —$CH_2CH_2CH_2CH_2$—, —$CH_2CH_2CH_2CH_2$—, and -(o-$C_6H_4$)—;

6.49 Compound 10-B or 10-C', as provided in Formula 6.48, wherein the two R" moieties join together to form a bridge selected from —$CH_2CH_2$—, —C($CH_3$)$_2$C ($CH_3$)$_2$—, —$CH_2CH_2CH_2$—, and $CH_2$C($CH_3$)$_2$ $CH_2$—;

6.50 Compound 10-B or 10-C', as provided in any of Formulas 6.39-6.49, wherein $R^6$ is chloro;

6.51 Compound 10-C or 10-D, wherein $R^y$ is H or $C_{1-6}$alkyl (e.g., methyl), $R^2$ and $R^3$ are independently H or $C_{1-6}$alkyl (e.g., methyl), $R^6$ is halogen (e.g., chloro), and $R^p$ is selected from an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.52 Compound 10-C or 10-D, as provided in Formula 6.51, wherein $R^p$ is selected from C(=O)—$C_{1-6}$alkyl (e.g., acetyl, isobutyryl, pivaloyl), —C(=O)-aryl (e.g. benzoyl), —C(=O)—O—$C_{1-6}$ alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.53 Compound 10-C or 10-D, as provided in Formula 6.51 or 6.52, wherein $R^p$ is —C(=O)—O—$C_{1-6}$alkyl (aryl);

6.54 Compound 10-C or 10-D, as provided in any of Formulas 6.51-6.53, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.55 Compound 10-C or 10-D, as provided in Formula 6.54, wherein $R^p$ is 1-phenylethoxycarbonyl, optionally in (R) or (S) form;

6.56 Compound 10-C or 10-D, as provided in Formula 6.55, wherein $R^p$ is 1-phenylethoxycarbonyl, in (S) form;

6.57 Compound 10-C or 10-D, as provided in any of Formulas 6.51-6.56, wherein $R^y$ is H;

6.58 Compound 10-C or 10-D, as provided in any of Formulas 6.51-6.57, wherein $R^2$ is H and $R^3$ is methyl;

6.59 Compound 10-C or 10-D, as provided in any of Formulas 6.51-6.58, wherein $R^6$ is chloro;

6.60 Compound 10-A, wherein $R^y$ is H or $C_{1-6}$alkyl (e.g., methyl), $R^2$ and $R^3$ are independently H or $C_{1-6}$alkyl (e.g., methyl), and $R^p$ is selected from an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.61 Compound 10-A, as provided in Formula 6.60, wherein $R^p$ is selected from C(=O)—$C_{1-6}$ alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.62 Compound 10-A, as provided in Formula 6.61, wherein $R^p$ is —C(=O)—O—$C_{1-6}$alkyl(aryl);

6.63 Compound 10-A, as provided in Formula 6.62, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.64 Compound 10-A, as provided in Formula 6.63, wherein $R^p$ is 1-phenylethoxycarbonyl, optionally in (R) or (S) form;

6.65 Compound 10-A, as provided in Formula 6.64, wherein $R^p$ is 1-phenylethoxycarbonyl, in (S) form;

6.66 Compound 10-A, as provided in any of Formulas 6.60-6.65, wherein $R^y$ is H;

6.67 Compound 10-A, as provided in any of Formulas 6.60-6.66, wherein $R^2$ is H and $R^3$ is methyl;

6.68 Compound 5-F, wherein $R^6$ is halogen (e.g., chloro), each $R''$ is independently $C_{1-6}$alkyl (e.g., methyl, ethyl or isopropyl), or wherein the two $R''$ moieties join together to form a $C_{2-10}$alkyl or $C_{2-10}$ alkenyl bridge (i.e., a cyclic acetal), wherein said bridge is optionally substituted by 1-4 halogen or aryl, or wherein the two $R''$ moieties join together to form an optionally substituted 1,2-hydroxyaryl bridge (e.g., a catechol bridge), and $R^z$ is selected from H, and unsubstituted $C_{1-6}$alkyl (e.g., methyl or ethyl), and $C_{1-6}$alkyl (e.g., methyl or ethyl) substituted by one $C_{1-6}$alkoxy, aryloxy, trialkylsilyl, aryl, or halo$C_{1-6}$alkyl;

6.69 Compound 5-F, as provided in Formula 6.68, wherein each $R''$ is independently $C_{1-6}$alkyl, optionally wherein each $R''$ is methyl;

6.70 Compound 5-F, as provided in Formula 6.69, wherein the two $R''$ moieties join together to form a bridge selected from —$CH_2CH_2$—, —$CH(CH_3)CH(CH_3)$—, —$CH_2CH(CH_3)$—, —$CH_2CH(Ph)$-, —$C(CH_3)_2C(CH_3)_2$—, —$CH_2CH_2CH_2$—, —$CH_2CBr_2CH_2$—, —$CH_2(C=CH)CH_2$—, —$CH_2CH(Ph)CH_2$—, —$CH(CH_3)CH_2CH(CH_3)$—, —$CH_2CH(CH_3)CH_2$—, —$CH_2C(CH_3)_2CH_2$—, —$CH_2C(CH_2CH_3)_2CH_2$—, —$CH_2CH_2CH_2CH_2$—, —$CH_2CH_2CH_2CH_2CH_2$—, and -(o-$C_6H_4$)—;

6.71 Compound 5-F, as provided in Formula 6.70, wherein the two $R''$ moieties join together to form a bridge selected from —$CH_2CH_2$—, —$C(CH_3)_2C(CH_3)_2$—, —$CH_2CH_2CH_2$—, and $CH_2C(CH_3)_2CH_2$—;

6.72 Compound 5-F, as provided in any of Formulas 6.68-6.71, wherein $R^z$ is H;

6.73 Compound 5-F, as provided in any of Formulas 6.68-6.72, wherein $R^z$ is unsubstituted $C_{1-6}$alkyl (e.g., methyl or ethyl);

6.74 Compound 5-F, as provided in any of Formulas 6.68-6.73, wherein $R^6$ is chloro;

6.75 Compound 5-E, wherein $R^6$ is halogen (e.g., chloro), and the two $R''$ moieties join together to form a $C_{2-10}$ alkyl or $C_{2-10}$ alkenyl bridge (i.e., a cyclic acetal), wherein said bridge is optionally substituted by 1-4 halogen or aryl, or wherein the two $R''$ moieties join together to form an optionally substituted 1,2-hydroxyaryl bridge (e.g., a catechol bridge);

6.76 Compound 5-E, as provided in Formula 6.75, wherein the two $R''$ moieties join together to form a bridge selected from —$CH_2CH_2$—, —$CH(CH_3)CH(CH_3)$—, —$CH_2CH(CH_3)$—, —$CH_2CH(Ph)$-, —$C(CH_3)_2C(CH_3)_2$—, —$CH_2CH_2CH_2$—, —$CH_2CBr_2CH_2$—, —$CH_2(C=CH)CH_2$—, —$CH_2CH(Ph)CH_2$—, —$CH(CH_3)CH_2CH(CH_3)$—, —$CH_2CH(CH_3)CH_2$—, —$CH_2C(CH_3)_2CH_2$—, —$CH_2C(CH_2CH_3)_2CH_2$—, —$CH_2CH_2CH_2CH_2$—, —$CH_2CH_2CH_2CH_2CH_2$—, and -(o-$C_6H_4$)—;

6.77 Compound 5-E, as provided in Formula 6.76, wherein the two $R''$ moieties join together to form a bridge selected from —$CH_2CH_2$—, —$C(CH_3)_2C(CH_3)_2$—, —$CH_2CH_2CH_2$—, and $CH_2C(CH_3)_2CH_2$—;

6.78 Compound 5-E, as provided in any of Formulas 6.75-6.77, wherein $R^6$ is chloro;

6.79 Compound 8-A or 8-B, wherein $R^y$ is H or $C_{1-6}$alkyl (e.g., methyl), $R^2$ and $R^3$ are independently H or $C_{1-6}$alkyl (e.g., methyl), $R^6$ is halogen (e.g., chloro), and $R''$ is $C_{1-6}$alkyl (e.g., methyl, ethyl, propyl, isopropyl, n-butyl, isobutyl);

6.80 Compound 8-A or 8-B, as provided in Formula 6.79, wherein $R^y$ is H;

6.81 Compound 8-A or 8-B, as provided in Formula 6.79 or 6.80, wherein $R^2$ is H and $R^3$ is methyl;

6.82 Compound 8-A or 8-B, as provided in any of Formulas 6.79-6.81, wherein $R''$ is methyl;

6.83 Compound 6-K, wherein $R^y$ is H or $C_{1-6}$alkyl (e.g., methyl), $R^2$ and $R^3$ are independently H or $C_{1-6}$alkyl (e.g., methyl), $R''$ is selected from H, $C_{1-6}$alkyl (e.g., methyl, ethyl, propyl, isopropyl, n-butyl, isobutyl), halo$C_{1-6}$alkyl (e.g., trifluoromethyl, trichloromethyl), optionally substituted aryl (e.g., phenyl, 4-bromophenyl), and optionally substituted heteroaryl (e.g., 2-pyridyl), and $R^p$ is selected from an alkylcarbonyl group (e.g., —C(=O)—$C_{1-6}$alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.84 Compound 6-K, as provided in Formula 6.83, wherein $R^p$ is selected from C(=O)—$C_{1-6}$ alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.85 Compound 6-K, as provided in Formula 6.84, wherein $R^p$ is —C(=O)—O—$C_{1-6}$alkyl(aryl);

6.86 Compound 6-K, as provided in Formula 6.85, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.87 Compound 6-K, as provided in Formula 6.86, wherein $R^p$ is 1-phenylethoxycarbonyl, optionally in (R) or (S) form;

6.88 Compound 6-K, as provided in Formula 6.87, wherein $R^p$ is 1-phenylethoxycarbonyl, in (S) form;

6.89 Compound 6-K, as provided in any of Formulas 6.83-6.88, wherein $R^y$ is H;

6.90 Compound 6-K, as provided in any of Formulas 6.83-6.89, wherein $R^2$ is H and $R^3$ is methyl;

6.91 Compound 6-K, as provided in any of Formulas 6.83-6.90, wherein $R''$ is $C_{1-6}$alkyl (e.g., methyl, ethyl, propyl, isopropyl, n-butyl, isobutyl);

6.92 Compound 6-K, as provided in any of Formulas 6.83-6.91, wherein R" is methyl;

6.93 Compound 6-L, wherein $R^y$ is H or $C_{1-6}$alkyl (e.g., methyl), $R^2$ and $R^3$ are independently H or $C_{1-6}$alkyl (e.g., methyl), and $R^p$ is selected from an alkylcarbonyl group (e.g., —C(=O)—$C_{1-6}$ alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.94 Compound 6-L, as provided in Formula 6.93, wherein $R^p$ is selected from C(=O)—$C_{1-6}$ alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.95 Compound 6-L, as provided in Formula 6.94, wherein $R^p$ is —C(=O)—O—$C_{1-6}$alkyl(aryl);

6.96 Compound 6-L, as provided in Formula 6.95, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.97 Compound 6-L, as provided in Formula 6.96 wherein $R^p$ is 1-phenylethoxycarbonyl, optionally in (R) or (S) form;

6.98 Compound 6-L, as provided in Formula 6.97, wherein $R^p$ is 1-phenylethoxycarbonyl, in (S) form;

6.99 Compound 6-L, as provided in any of Formulas 6.93-6.98, wherein $R^y$ is H;

6.100 Compound 6-L, as provided in any of Formulas 6.93-6.99, wherein $R^2$ is H and $R^3$ is methyl;

6.101 Compound 6-J, wherein $R^y$ is H or $C_{1-6}$alkyl (e.g., methyl), $R^2$ and $R^3$ are independently H or $C_{1-6}$alkyl (e.g., methyl), and $R^p$ is selected from an alkylcarbonyl group (e.g., —C(=O)—$C_{1-6}$ alkyl, such as acetyl, isobutyryl, pivaloyl, or —C(=O)—$C_{1-6}$alkyl(aryl), such as 2-phenylethylcarbonyl or 1-phenylethylcarbonyl), an arylcarbonyl group (e.g. benzoyl), an alkoxycarbonyl group (e.g., —C(=O)—O—$C_{1-6}$alkyl, such as methoxycarbonyl, ethoxycarbonyl, t-butoxycarbonyl, or benzyloxycarbonyl, or —C(=O)—O—$C_{1-6}$alkyl(aryl), such as 2-phenylethoxycarbonyl or 1-phenylethoxycarbonyl), and an aryloxycarbonyl group (e.g., phenoxycarbonyl);

6.102 Compound 6-J, as provided in Formula 6.101, wherein $R^p$ is selected from C(=O)—$C_{1-6}$ alkyl (e.g., acetyl, isobutyryl, pivaloyl), —C(=O)-aryl (e.g. benzoyl), —C(=O)—O—$C_{1-6}$alkyl (e.g., methoxycarbonyl, ethoxycarbonyl, t-butoxycarbonyl, or benzyloxycarbonyl), —C(=O)—O—$C_{1-6}$alkyl(aryl) (e.g., 2-phenylethoxycarbonyl or 1-phenylethoxycarbonyl), and —C(=O)—O-aryl (e.g., phenoxycarbonyl);

6.103 Compound 6-J, as provided in Formula 6.102, wherein $R^p$ is —C(=O)—O—$C_{1-6}$alkyl(aryl);

6.104 Compound 6-J, as provided in Formula 6.103, wherein $R^p$ is selected from 1-phenylethoxycarbonyl, ethoxycarbonyl, methoxycarbonyl, t-butoxycarbonyl, isopropoxycarbonyl, phenoxycarbonyl, 4-methoxyphenoxycarbonyl, and benzyloxycarbonyl;

6.105 Compound 6-J, as provided in Formula 6.104 wherein $R^p$ is 1-phenylethoxycarbonyl, optionally in (R) or (S) form;

6.106 Compound 6-J, as provided in Formula 6.105, wherein $R^p$ is 1-phenylethoxycarbonyl, in (S) form;

6.107 Compound 6-J, as provided in any of Formulas 6.101-6.106, wherein $R^y$ is H;

6.108 Compound 6-J, as provided in any of Formulas 6.101-6.107, wherein $R^2$ is H and $R^3$ is methyl;

6.109 Compound 1-H, wherein $R^5$ is $C_{1-6}$alkyl (e.g., methyl), and $R^x$ is H, $C_{1-6}$alkyl, or $C_{6-10}$aryl, wherein the alkyl is optionally substituted with $C_{6-10}$aryl;

6.110 Compound 1-H, as provided in Formula 6.109, wherein $R^x$ is H;

6.111 Compound 1-H, as provided in Formula 6.109 or 6.110, wherein $R^5$ is methyl;

6.112 Compound 1-E or 1-F, wherein $R^x$ is H, $C_{1-6}$alkyl, or $C_{6-10}$aryl, wherein the alkyl is optionally substituted with $C_{6-10}$aryl, and PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

6.113 Compound 1-E or 1-F, as provided in Formula 6.112, wherein PG is an alkyldiaryl silyl group (e.g., t-butyldiphenylsilyl);

6.114 Compound 1-E or 1-F, as provided in Formula 6.113, wherein PG is a tert-butyldiphenyl silyl;

6.115 Compound 1-E or 1-F, as provided in any of Formulas 6.112-6.114, wherein $R^x$ is H;

6.116 Compound 1-D, wherein $R^x$ is H, $C_{1-6}$alkyl, or $C_{6-10}$aryl, wherein the alkyl is optionally substituted with $C_{6-10}$aryl, X is Br, Cl or I, and PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

6.117 Compound 1-D, as provided in Formula 6.116, wherein PG is an alkyldiaryl silyl group (e.g., t-butyldiphenylsilyl);

6.118 Compound 1-D, as provided in Formula 6.117, wherein PG is a tert-butyldiphenyl silyl;

6.119 Compound 1-D, as provided in any of Formulas 6.116-6.118, wherein $R^x$ is H;

6.120 Compound 1-D, as provided in any of Formulas 6.116-6.119, wherein X is Br;

6.121 Compound 1-D, as provided in any of Formulas 6.116-6.119, wherein X is I;

6.122 Compound 1-D, as provided in any of Formulas 6.116-6.119, wherein X is Cl;

6.123 Compound 1-C, wherein PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl);

6.124 Compound 1-C, as provided in Formula 6.123, wherein PG is an alkyldiaryl silyl group (e.g., t-butyldiphenylsilyl);

6.125 Compound 1-C, as provided in Formula 6.124, wherein PG is a tert-butyldiphenyl silyl;

6.126 Compound 1-B, wherein PG is selected from a trialkyl silyl group (e.g., trimethylsilyl, triethylsilyl, tripropylsilyl, triisopropylsilyl, t-butyldimethylsilyl), a dialkylaryl silyl group (e.g., dimethylphenylsilyl), an alkyldiaryl silyl group (e.g., t-butyldiphenylsilyl), and a triarylsilyl group (e.g., triphenylsilyl), and R' is $C_{1-6}$alkyl (e.g., methyl, ethyl, propyl, isopropyl, n-butyl, or t-butyl);

6.127 Compound 1-B, as provided in Formula 6.126, wherein PG is an alkyldiaryl silyl group (e.g., t-butyldiphenylsilyl);

6.128 Compound 1-B, as provided in Formula 6.127, wherein PG is a tert-butyldiphenyl silyl;

6.129 Compound 1-B, as provided in any of Formulas 6.126-6.128, wherein R' is methyl;

6.130 Compound 5-D, wherein $R^6$ is halogen (e.g., chloro), $R^m$ is selected from H, $C_{1-6}$alkyl (e.g., methyl, ethyl, propyl, isopropyl, n-butyl, isobutyl,), halo$C_{1-6}$alkyl (e.g., trifluoromethyl, trichloromethyl), carboxy$C_{1-6}$ alkyl (e.g., 3-carboxypropyl), optionally substituted aryl (e.g., phenyl, 4-halophenyl), or optionally substituted heteroaryl (e.g., pyridyl, such as 2-pyridyl), and each $R''$ is independently $C_{1-6}$alkyl (e.g., methyl, ethyl or isopropyl), or the two $R''$ moieties join together to form a $C_{2-10}$ alkyl or $C_{2-10}$ alkenyl bridge (i.e., a cyclic acetal), wherein said bridge is optionally substituted by 1-4 halogen or aryl, or wherein the two $R''$ moieties join together to form an optionally substituted 1,2-hydroxyaryl bridge (e.g., a catechol bridge);

6.131 Compound 5-D, as provided in Formula 6.130, wherein the two $R''$ moieties join together to form a bridge selected from —$CH_2CH_2$—, —$CH(CH_3)CH(CH_3)$—, —$CH_2CH(CH_3)$—, —$CH_2CH(Ph)$-, —$C(CH_3)_2C(CH_3)_2$—, —$CH_2CH_2CH_2$—, —$CH_2CBr_2CH_2$—, —$CH_2(C=CH)CH_2$—, —$CH_2CH(Ph)CH_2$—, —$CH(CH_3)CH_2CH(CH_3)$—, —$CH_2CH(CH_3)CH_2$—, —$CH_2C(CH_3)_2CH_2$—, —$CH_2C(CH_2CH_3)_2CH_2$—, —$CH_2CH_2CH_2CH_2$—, —$CH_2CH_2CH_2CH_2CH_2$—, and -(o-$C_6H_4$)—;

6.132 Compound 5-D, as provided in Formula 6.131, wherein the two $R''$ moieties join together to form a bridge selected from —$CH_2CH_2$—, —$C(CH_3)_2C(CH_3)_2$—, —$CH_2CH_2CH_2$—, and $CH_2C(CH_3)_2CH_2$—;

6.133 Compound 5-D, as provided in Formula 6.132, wherein each $R''$ is independently $C_{1-6}$alkyl (e.g., methyl, ethyl or isopropyl);

6.134 Compound 5-D, as provided in Formula 6.133, wherein each $R''$ is methyl;

6.135 Compound 5-D, as provided in any of Formulas 6.130-6.134, wherein $R^m$ is $C_{1-6}$alkyl, 6.136 Compound 5-D, as provided in Formula 6.135, wherein $R^m$ is methyl;

6.137 Compound 5-D, as provided in any of Formulas 6.130-6.136, wherein $R^6$ is chloro;

6.138 Compound 5-B or 5-C, wherein $R^6$ is halogen (e.g., chloro), and $R^m$ is selected from H, $C_{1-6}$alkyl (e.g., methyl, ethyl, propyl, isopropyl, n-butyl, isobutyl,), halo$C_{1-6}$alkyl (e.g., trifluoromethyl, trichloromethyl), carboxy$C_{1-6}$ alkyl (e.g., 3-carboxypropyl), optionally substituted aryl (e.g., phenyl, 4-halophenyl), or optionally substituted heteroaryl (e.g., pyridyl, such as 2-pyridyl);

6.139 Compound 5-B or 5-C, as provided in Formula 6.138, wherein $R^m$ is $C_{1-6}$alkyl, 6.140 Compound 5-B or 5-C, as provided in Formula 6.139, wherein $R^m$ is methyl;

6.141 Compound 5-B or 5-C, as provided in any of Formulas 6.138-6.140, wherein $R^6$ is chloro;

6.142 Compound 7-A, wherein $R^y$ is H or $C_{1-6}$alkyl (e.g., methyl), and $R^2$ and $R^3$ are independently H or $C_{1-6}$alkyl (e.g., methyl);

6.143 Compound 7-A, as provided in Formula 6.142, wherein $R^y$ is H;

6.144 Compound 7-A, as provided in Formula 6.142 or 6.143, wherein $R^2$ is H and $R^3$ is methyl;

6.145 Compound 6-F, wherein $R^y$ is H or $C_{1-6}$alkyl (e.g., methyl), and $R^2$ and $R^3$ are independently H or $C_{1-6}$alkyl (e.g., methyl);

6.146 Compound 6-F, as provided in Formula 6.145, wherein $R^y$ is H;

6.147 Compound 6-F, as provided in Formula 6.145 or 6.146, wherein $R^2$ is H and $R^3$ is methyl;

6.148 Compound 6-C, wherein $R^y$ is H or $C_{1-6}$alkyl (e.g., methyl), $R^2$ and $R^3$ are independently H or $C_{1-6}$alkyl (e.g., methyl), and $R^e$ is selected from optionally substituted 5-10 membered heteroaryl (e.g., optionally substituted pyridyl or pyrimidinyl), —C(=NH)NH($C_{1-6}$ alkyl), —C(=NH)N($C_{1-6}$ alkyl)$_2$, and —C(=NH)NH$_2$;

6.149 Compound 6-C, as provided in Formula 6.148, wherein $R^y$ is H;

6.150 Compound 6-C, as provided in Formula 6.148 or 6.149, wherein $R^2$ is H and $R^3$ is methyl;

6.151 Compound 6-C, as provided in any of Formulas 6.148-6.150, wherein $R^e$ is 5-10 membered heteroaryl, e.g., 6-membered heteroaryl (e.g., 2-pyridyl or 2-pyrimidinyl);

6.152 Compound 6-C, as provided in Formula 6.151, wherein $R^e$ is 2-pyrimidinyl;

6.153 Compound 5-I, wherein $R^6$ is halogen (e.g., chloro), and $R^z$ is selected from H, and unsubstituted $C_{1-6}$alkyl (e.g., methyl or ethyl), and $C_{1-6}$alkyl (e.g., methyl or ethyl) substituted by one $C_{1-6}$alkoxy, aryloxy, trialkylsilyl, aryl, or halo$C_{1-6}$alkyl;

6.154 Compound 5-I, as provided in Formula 6.153, wherein $R^z$ is H;

6.155 Compound 5-I, as provided in Formula 6.153, wherein $R^z$ is unsubstituted $C_{1-6}$alkyl (e.g., methyl or ethyl);

6.156 Compound 5-I, as provided in any of Formulas 6.153-6.155, wherein $R^6$ is chloro;

6.157 A compound according to any of Formulas 6.1-6.156, wherein the compound is selected from:

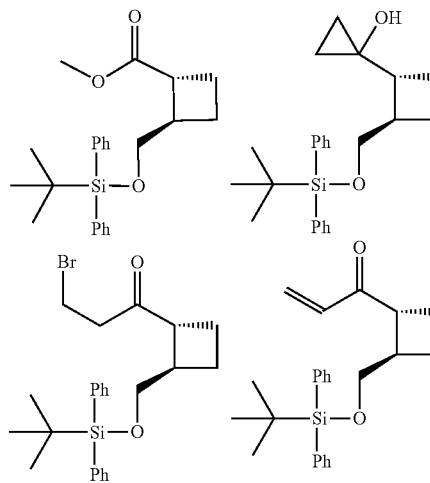

-continued
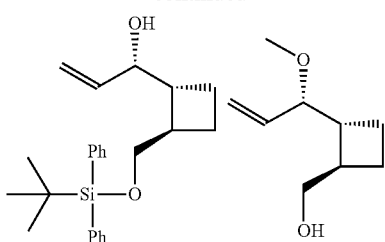
6.158 A compound according to any of Formulas 6.1-6.156, wherein the compound is selected from:
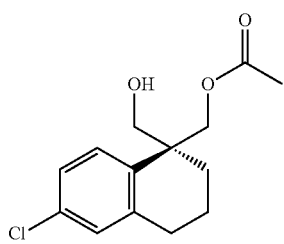
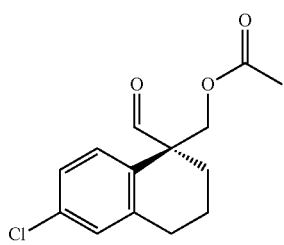
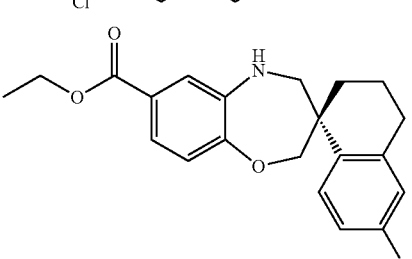
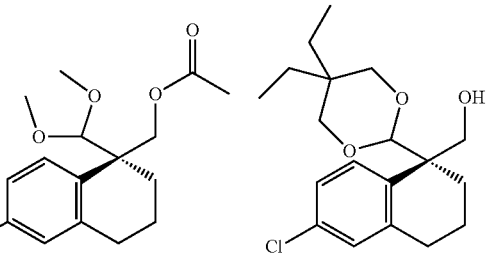
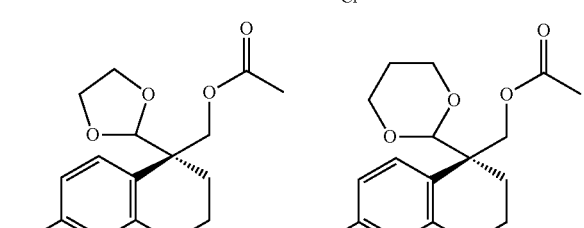
-continued
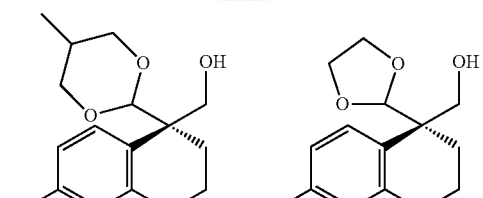
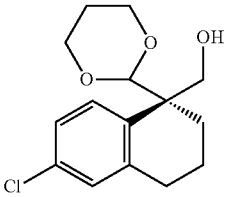
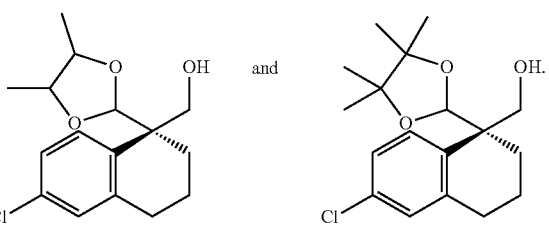
6.159 A compound according to any of Formulas 6.1-6.156, wherein the compound is selected from:
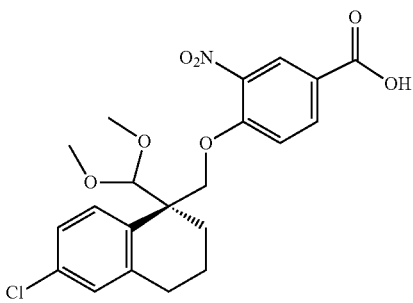
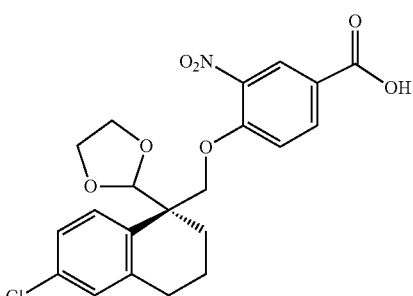
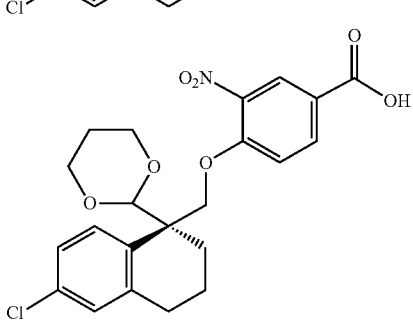

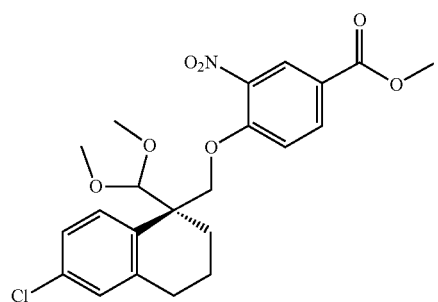
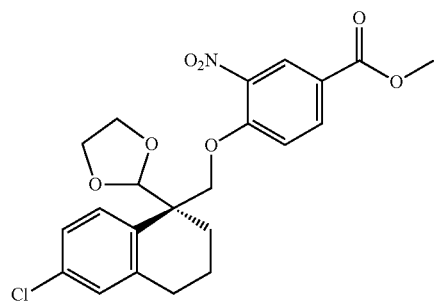
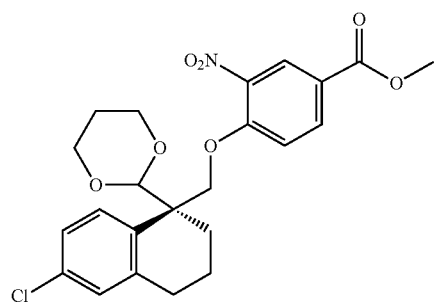
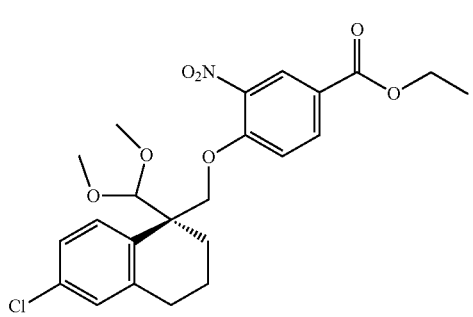
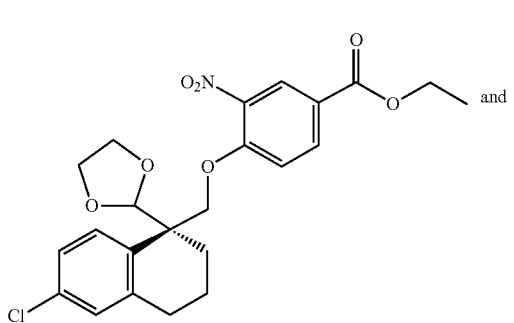
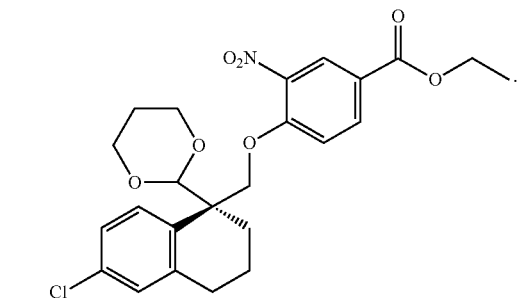
6.160 A compound according to any of Formulas 6.1-6.156, wherein the compound is selected from:
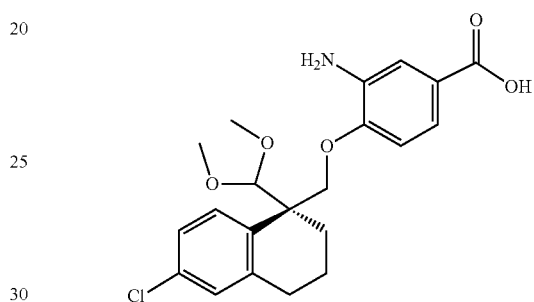
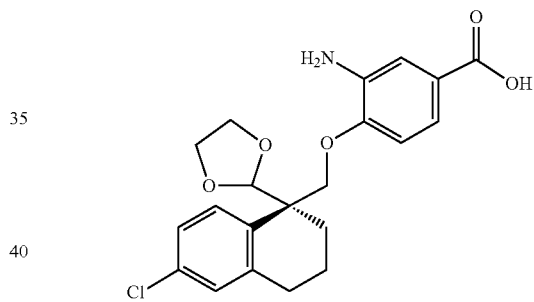
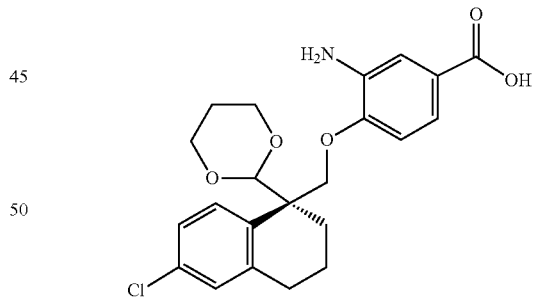
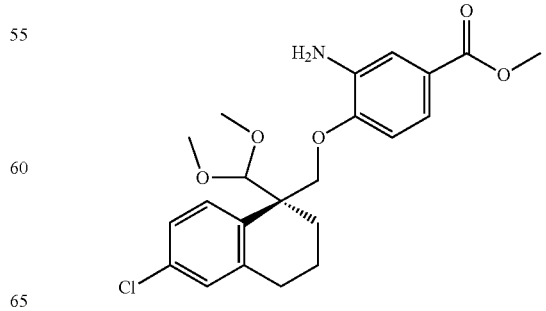

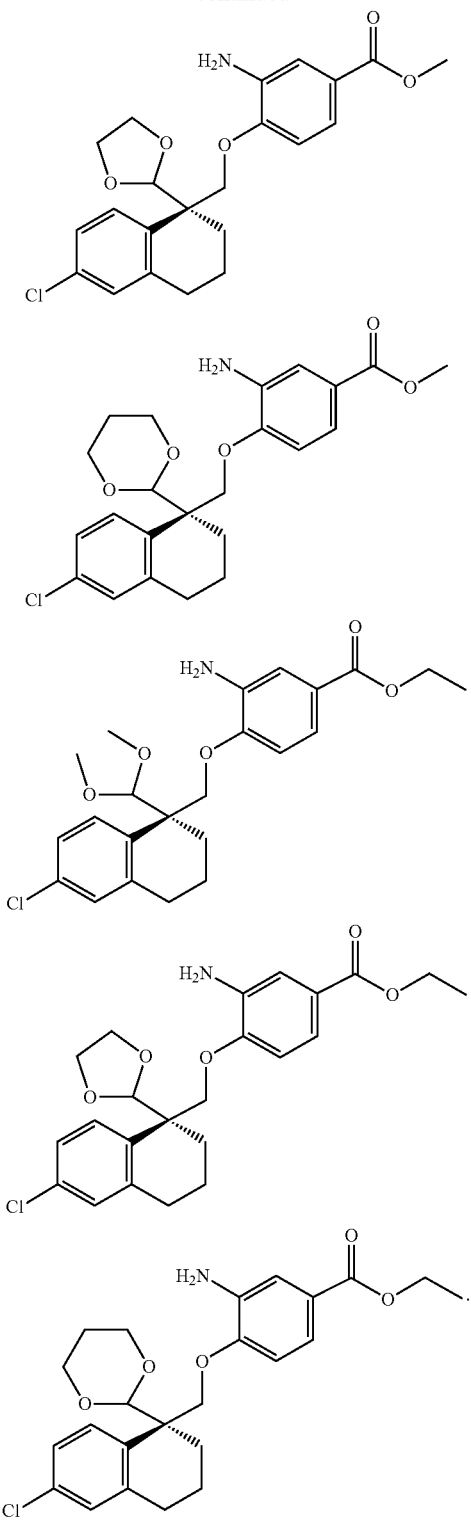
6.161 A compound according to any of Formulas 6.1-6.156, wherein the compound is selected from:
6.162 A compound according to any of Formulas 6.1-6.156, wherein the compound is selected from:

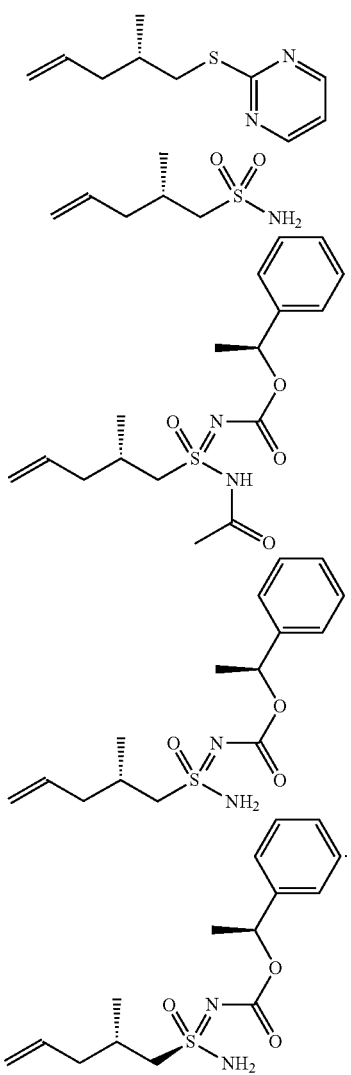
6.163 A compound according to any of Formulas 6.1-6.156, wherein the compound is selected from:
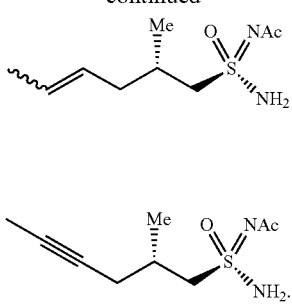
6.164 A compound according to any of Formulas 6.1-6.156, wherein the compound is selected from:
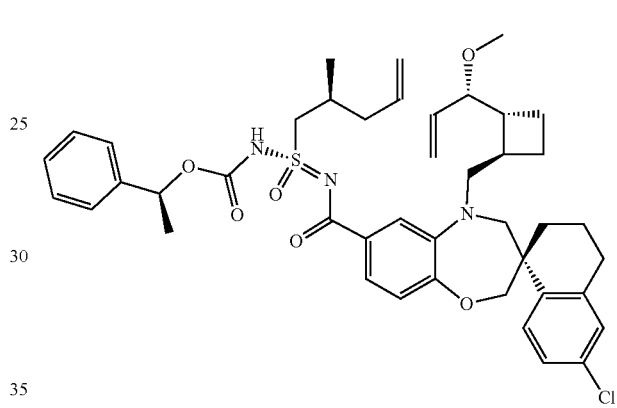
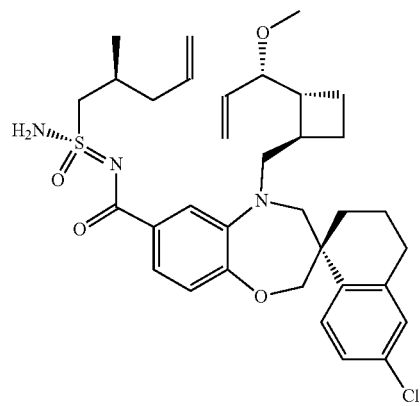
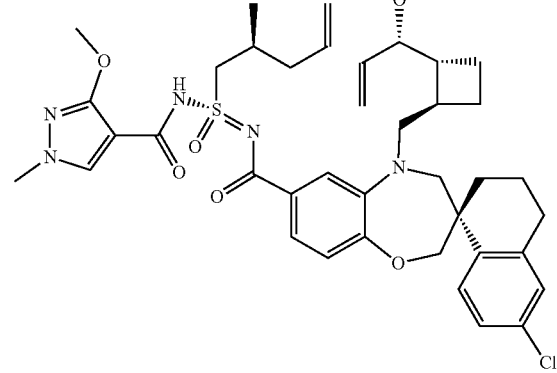

123
-continued
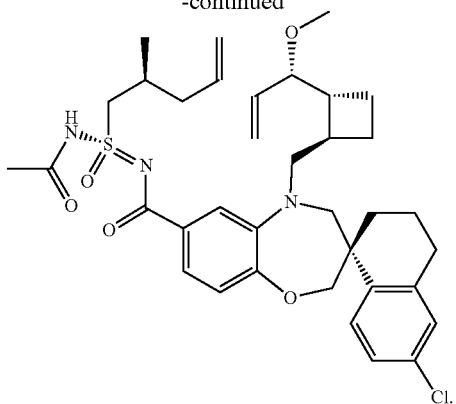
6.165 A compound according to any of Formulas 6.1-6.156, wherein the compound is:
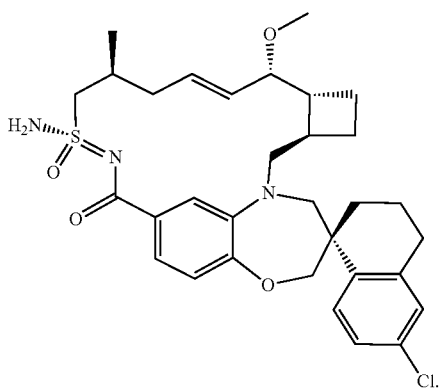 [SMILES: CO[C@H]1/C=C/C[C@H](C)C[S@](N)(=O)=NC(=O)c2ccc3c(c2)N(C[C@@H]2CC[C@H]21)C[C@@]1(CCCc2cc(Cl)ccc21)CO3]
6.166 A compound according to any of Formulas 6.1-6.156, wherein the compound is:
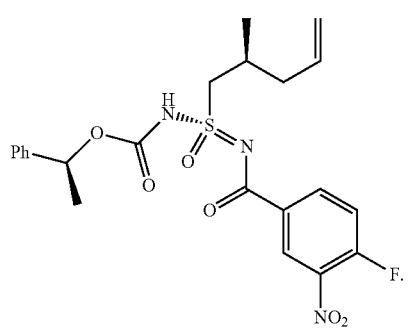 [SMILES: C=CC[C@H](C)C[S@](=O)(=NC(=O)c1ccc(F)c([N+](=O)[O-])c1)NC(=O)O[C@@H](C)c1ccccc1]
6.167 A compound according to any of Formulas 6.1-6.156, wherein the compound is selected from:
124
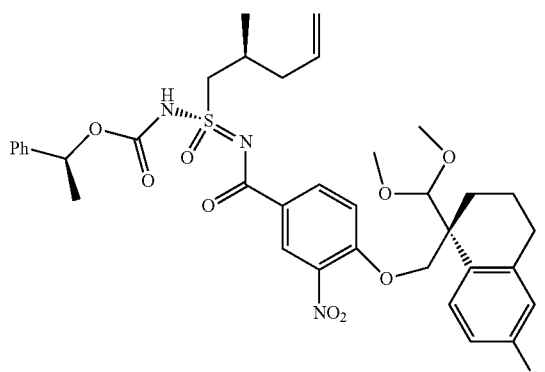
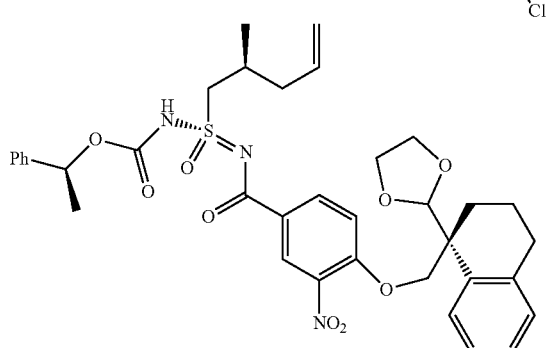
6.168 A compound according to any of Formulas 6.1-6.156, wherein the compound is selected from:
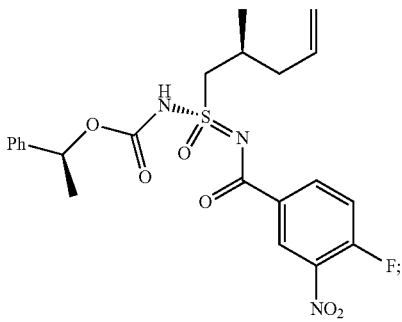

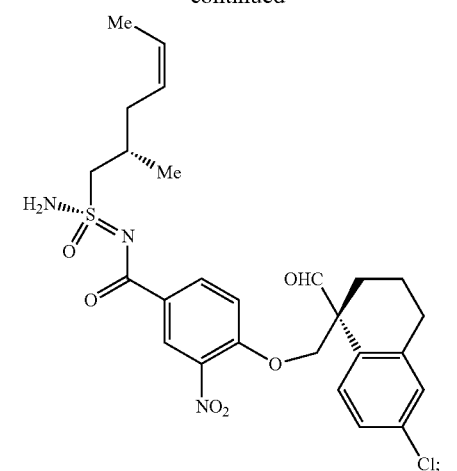
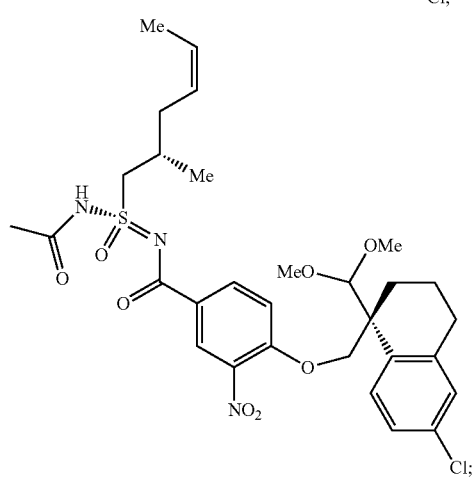
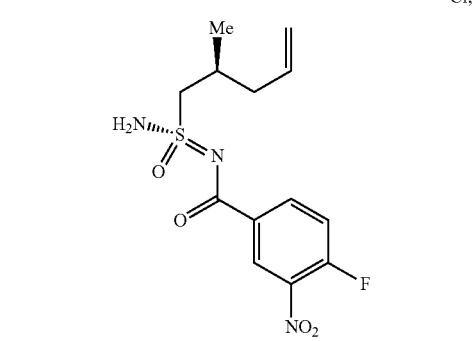
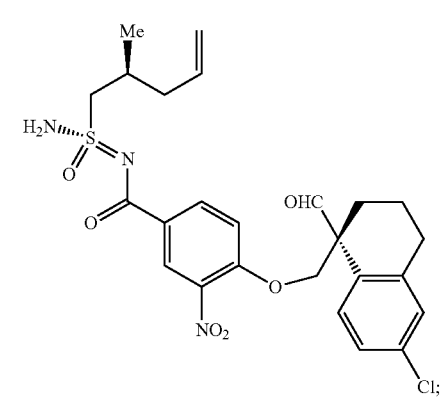
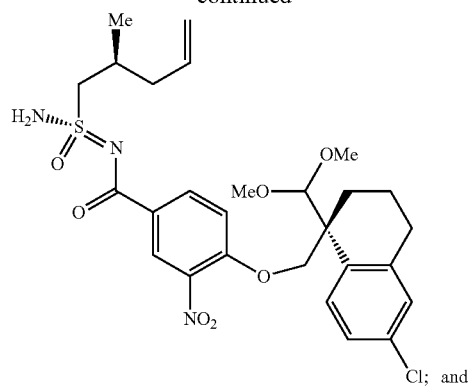
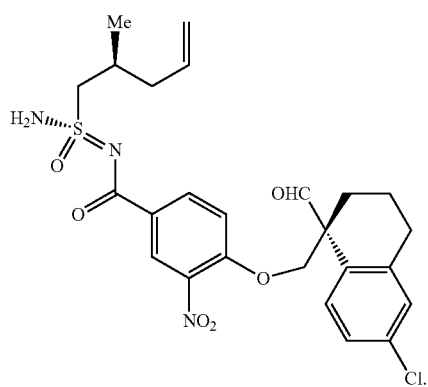
6.169 A compound according to any of Formulas 6.1-6.156, wherein the compound is:
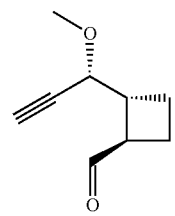
6.170 A compound according to any of Formulas 6.1-6.156, wherein the compound is selected from:
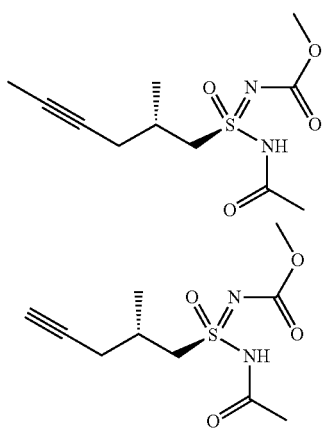

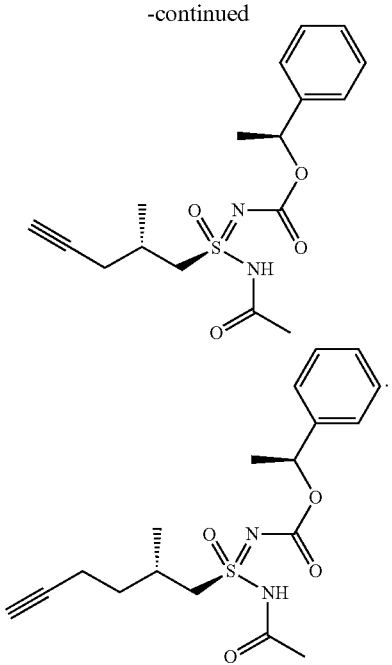

In one embodiment, the present disclosure provides a method of making a compound selected from 13-A, 13-B, 13-C, 13-D, 13-E, and 9-B, as shown in Scheme 13, wherein $R^x$ and $R^y$ are independently H, $C_{1-6}$alkyl, or $C_{6-10}$aryl, wherein the alkyl is optionally substituted with $C_{6-10}$aryl, $C_{6-10}$aryl (e.g. phenyl), and optionally substituted aryl (e.g., phenyl), $R^2$ and $R^3$ are independently H or $C_{1-6}$alkyl, $R^5$ is $C_{1-6}$ alkyl, $R^6$ is halogen, each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl, and $R^p$ is selected from H, —C(=O)—$C_{1-6}$alkyl, —C(=O)-heteroaryl, —C(=O)—O—$C_{1-6}$alkyl, and —C(=O)—O—$C_{1-6}$alkyl-phenyl, wherein each phenyl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members.

Scheme 13

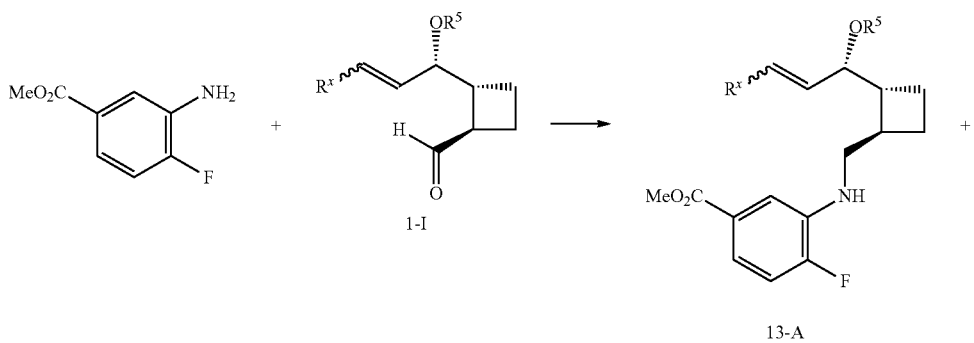

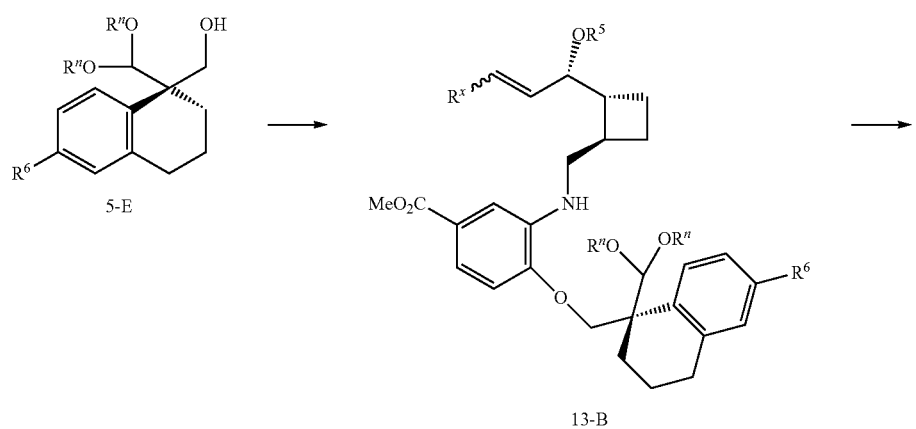

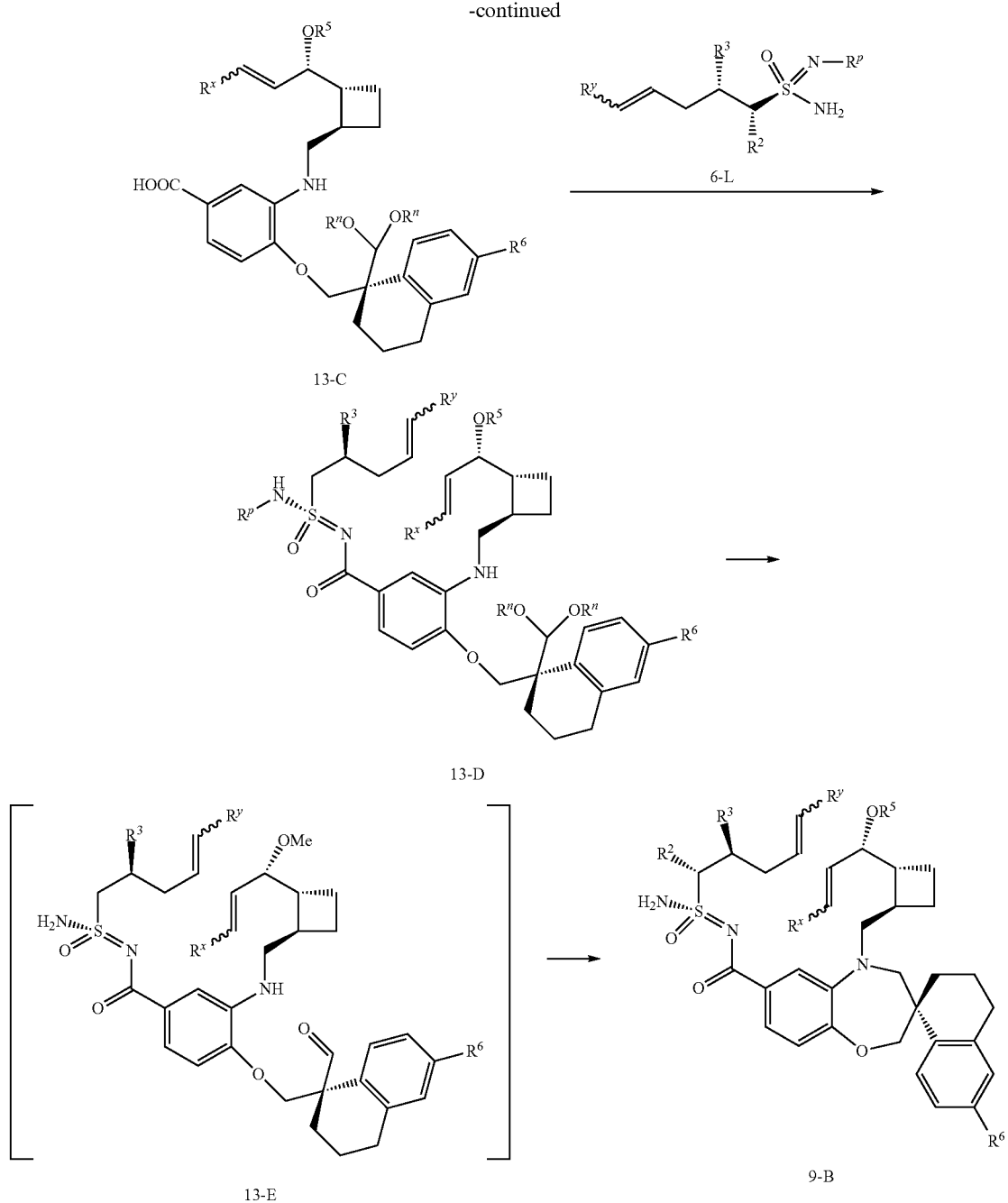

In one embodiment, the present disclosure provides a method to prepare a compound 13-A from a compound 1-I, wherein $R^x$ is H, $C_{1-6}$alkyl, or $C_{6-10}$aryl, wherein the alkyl is optionally substituted with $C_{6-10}$aryl, and $R^5$ is $C_{1-6}$alkyl. In one embodiment, $R^x$ is H, wherein $R^5$ is methyl.

In one embodiment, the method comprises the step of reacting a compound methyl 3-amino-4-fluorobenzoate with a compound 1-I under a reductive amination condition, using an acid, reducing agent, and dehydrating agent in a suitable solvent, for a time and under conditions effective to form a compound 13-A.

In one embodiment, the acid is selected from citric acid, pivalic acid, p-toluenesulfonic acid, methanesulfonic acid, hydrochloric acid, and trifluoroacetic acid (TFA). In one embodiment, the acid is trifluoroacetic acid (TFA).

In one embodiment, the reducing agent is selected from silanes (triisopropylsilane, triphenylsilane, diethylsilane, etc.), sodium borohydride, sodium borohydride/acetic acid, sodium cyanoborohydride, titanium isopropoxide/sodium cyanoborohydride, zinc/acetic acid, sodium borohydride/ magnesium perchlorate, zinc borohydride/zinc chloride, tetramethylammonium triacetoxyborohydride and triethylsilane ($Et_3SiH$). In one embodiment, the reducing agent is triethylsilane ($Et_3SiH$).

In one embodiment, the dehydrating agent is selected from molecular sieves, sodium sulfate, and magnesium sulfate (MgSO$_4$). In one embodiment, the dehydrating agent is magnesium sulfate (MgSO$_4$).

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., dichloromethane, 1,2-dichloroethane, chloroform, chlorobenzene), polar aprotic solvents (e.g., N,N-dimethylacetamide, N,N-dimethylformamide, N-methyl-2-pyrrolidinone, dimethyl sulfoxide), and acetonitrile (MeCN). In one embodiment, the solvent is acetonitrile (MeCN).

In one embodiment, the temperature of the reaction is from 0 to 40° C. In one embodiment, the temperature of the reaction is about 20° C.

In one embodiment, the present disclosure provides a method to prepare a compound 13-B from a compound 13-A and a compound 5-E, wherein $R^6$ is halogen, each $R''$ is independently $C_{1-6}$alkyl, or the two $R''$ moieties join together to form a $C_{2-4}$alkyl bridge, wherein the bridge is optionally substituted by one to four groups independently selected from $C_{1-3}$alkyl and phenyl. In one embodiment, $R^6$ is Cl. In one embodiment, each $R''$ is independently CH$_3$.

In one embodiment, the method comprises the step of reacting a compound 13-A with a compound 5-E, using a base in a suitable solvent, for a time and under conditions effective to form compound 13-B. In one embodiment, $R^6$ is Cl and each $R''$ is independently CH$_3$.

In one embodiment, the base is selected from alkoxides (sodium tert-butoxide, potassium tert-butoxide, sodium ethoxide, sodium methoxide, etc.), tertiary amines (triethylamine, tri-n-butylamine, N,N,N',N'-tetramethylethylenediamine, N-methylmorpholine, N-methylpiperidine, 1,4-diazabicylo[2.2.2]-octane, 1,8-diazabicyclo[5.4.0]undec-7-ene, 1,5-diazabicyclo-4.3.0]non-5-ene, etc.), inorganic bases (sodium bicarbonate, sodium carbonate, sodium phosphate monobasic, sodium phosphate dibasic, potassium bicarbonate, potassium carbonate, potassium phosphate monobasic, potassium phosphate dibasic, etc.), lithium bis(trimethylsilyl)amide, sodium bis(trimethylsilyl)amide and sodium tert-pentoxide (NaO$_t$-pentoxide). In one embodiment, the base is sodium tert-pentoxide (NaO$_t$-pentoxide).

In one embodiment, the solvent is selected from esters (ethyl acetate, butyl acetate, isobutyl acetate, etc.), ethers (methyl tert-butyl ether, tetrahydrofuran, 2-methyltetrahydronfuran, 1,4-dioxane, etc), aromatic solvents (toluene, benzene, xylenes, trifluorotoluene, etc.), polar aprotic (N,N-dimethylacetamide, N-methyl-2-pyrrolidone, dimethylsulfoxide, acetonitrile, propionitrile, butyronitrile, etc.), chlorinated solvents (1,2-dichloroethane, chlorobenzene, etc.), N,N-dimethylformamide (DMF) or any combination of listed solvents. In one embodiment, the solvent is N,N-dimethylformamide (DMF).

In one embodiment, the temperature of the reaction is from 50 to 100° C. In one embodiment, the temperature of the reaction is about 70° C.

In one embodiment, the present disclosure provides a method to prepare a compound 13-C from a compound 13-B.

In one embodiment, the method comprises the step of treating a compound 13-B with a base or an acid, in a suitable solvent, for a time and under conditions effective to form compound 13-C.

In one embodiment, the base is selected from inorganic bases (hydroxides such as sodium, potassium, lithium and cesium; carbonates such as lithium, sodium, potassium, and cesium; tribasic phosphates such as sodium, potassium.). In one embodiment, the base is lithium hydroxide (LiOH).

In one embodiment, the acid is selected from hydrochloric acid, sulfuric acid, hydrobromic acid, methanesulfonic acid, and trifluoroacetic acid.

In one embodiment, solvent is selected from alcohols (e.g. methanol, ethanol, and isopropanol), ethers (e.g. 2-methyltetrahydrofuran, tetrahydrofuran, and 1,4-dioxane), polar aprotic (e.g. N,N-dimethylformamide, and N,N-dimethylacetamide), with or without mixing with water. In one embodiment, the solvent is a mixture of tetrahydrofuran and water. In one embodiment, the solvent is a mixture of tetrahydrofuran and water at 1:1 volume ratio.

In one embodiment, the temperature of the reaction is from 30 to 100° C. In one embodiment, the temperature of the reaction is about 70° C.

In one embodiment, the present disclosure provides a method to prepare a compound 13-D from a compound 13-C and a compound 6-L. In one embodiment, $R^p$ is selected from —C(=O)—C$_{1-6}$alkyl, —C(=O)-phenyl, —C(=O)—O—C$_{1-6}$alkyl, —C(=O)—O—C$_{1-6}$alkyl-phenyl, and —C(=O)—O-phenyl. In one embodiment, $R^2$ is H. In one embodiment, $R^3$ is methyl. In one embodiment, $R^p$ is 1-phenylethoxycarbonyl, optionally in (R) or (S) form. In one embodiment, $R^p$ is 1-phenylethoxycarbonyl, in (S) form.

In one embodiment, the method comprises the step of reacting a compound 13-C with a compound 6-L, using an acid activator, a promoter, a base in a suitable solvent, for a time and under conditions effective to to form a compound 13-D.

In one embodiment, the acid activator is selected from carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methyl-morpholinium chloride (DMTMM), thionyl chloride, oxalyl chloride, (chloromethylene)-dimethyliminium chloride, isobutyl chloroformate, N,N,N,N'N'-tetramethylchloroformamidinium hexafluorophosphate (TCFH), N,N'-diisopropylcarbodiimide, N,N'-dicyclohexylcarbodiimide, diphenyl chlorophosphate, 2,4,6-trichlorobenzoyl chloride, 2-chloro-4,6-dimethoxy-1,3,5-triazine (CDMT), and N-(3-dimethylaminopropyl)-N'-ethylcarbodiimide hydrochloride (EDC.HCl). In one embodiment, the acid activator is N-(3-dimethylaminopropyl)-N'-ethylcarbodiimide hydrochloride (EDC.HCl).

In one embodiment, the promoter is selected from N-methylimidazole, 1-hydroxy-7-azabenzotriazole (HOAt), 1-hydroxybenzotriazole (HOBt), N,N-dimethylacetamide, N-methylimidazole, and 4-dimethylaminopyridine (DMAP). In one embodiment, the promoter is 4-dimethylaminopyridine (DMAP).

In one embodiment, the base is selected from tertiary amines (e.g., N-methylmorpholine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, collidine, 1-methylimidazole, N-methylimidazole), inorganic bases (e.g., lithium carbonate, sodium carbonate, potassium carbonate, calcium carbonate and bicarbonate derivatives, mono, di and tri basic potassium and sodium phosphate). In one embodiment, the base is N-methylimidazole (NMI).

In one embodiment, the solvent is selected from ethers (e.g., tetrahydrofuran, 2-methyltetrahydrofuran, methyl tert-butyl ether, cyclopentyl methyl ether), esters (e.g, ethyl acetate, isopropyl acetate), polar aprotic solvents (e.g., N,N-dimethylacetamide, N-methyl-2-pyrrolidinone, dimethyl sulfoxide), nitriles (e.g., acetonitrile), hydrocarbon solvents (e.g., toluene), halogenated solvents (e.g., dichloromethane, 1,2-dichloroethane, chloroform, chlorobenzene). In one embodiment, the solvent is acetonitrile (MeCN).

In one embodiment, the temperature of the reaction is from −50 to 50° C. In one embodiment, the temperature of the reaction is from 10 to 30° C.

In one embodiment, the present disclosure provides a method to prepare a compound 13-E from a compound 13-D.

In one embodiment, the method comprises the step of treating a compound 13-D with an acid in a suitable solvent, for a time and under conditions effective to form compound 13-E.

In one embodiment, the acid is selected from mineral acids (hydrochloric acid, hydrobromic acid, and sulfuric acid); sulfonic acids (p-toluenesulfonic acid, benzenesulfonic acid, and methanesulfonic acid); organic acids (trifluoroacetic acid, oxalic acid, and formic acid). In one embodiment, the acid is methanesulfonic acid (MsOH).

In one embodiment, the solvent is selected from ethers (e.g., tetrahydrofuran, 2-methyltetrahydrofuran, methyl tert-butyl ether, cyclopentyl methyl ether and tetrahydrofuran), esters (e.g, ethyl acetate, isopropyl acetate), polar aprotic solvents (e.g., N,N-dimethylacetamide, N-methyl-2-pyrrolidinone, dimethyl sulfoxide), nitriles (e.g., acetonitrile), hydrocarbon solvents (e.g., toluene), halogenated solvents (e.g., dichloromethane, 1,2-dichloroethane, chloroform, chlorobenzene), water, or a combination thereof. In one embodiment, the solvent is a mixture of tetrahydrofuran and water. In one embodiment, the solvent is a mixture of tetrahydrofuran and water at 1:1 volume ratio.

In one embodiment, the temperature of the reaction is from 40 to 100° C. the temperature of the reaction is from 60 to 70° C.

In one embodiment, the present disclosure provides a method to prepare a compound 9-B from a compound 13-E.

In one embodiment, the method comprises the step of treating a compound 13-E with an acid, a reducing agent, and a dehydrating agent in a suitable solvent, for a time and under conditions effective to form compound 9-B.

In one embodiment, the acid is selected from citric acid, pivalic acid, p-toluenesulfonic acid, methanesulfonic acid, hydrochloric acid and trifluoroacetic acid. In one embodiment, the acid is trifluoroacetic acid.

In one embodiment, the reducing agent is selected from silanes (triisopropylsilane, triphenylsilane, diethylsilane, triethylsilane), sodium borohydride, sodium borohydride/acetic acid, sodium cyanoborohydride, titanium isopropoxide/sodium cyanoborohydride, zinc/acetic acid, sodium borohydride/magnesium perchlorate, zinc borohydride/zinc chloride, tetramethylammonium triacetoxyborohydride. In one embodiment, the reducing agent is triethylsilane ($Et_3SiH$).

In one embodiment, the dehydrating agent is selected from molecular sieves, sodium sulfate and magnesium sulfate. In one embodiment, the dehydrating agent is magnesium sulfate.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., dichloromethane, 1,2-dichloroethane, chloroform, chlorobenzene), polar aprotic solvents (e.g., N,N-dimethylacetamide, N,N-dimethylformamide, N-methyl-2-pyrrolidinone, dimethyl sulfoxide, acetonitrile). In one embodiment, the solvent is acetonitrile.

In one embodiment, the temperature of the reaction is from 0 to 40° C. In one embodiment, the temperature of the reaction is about 20° C.

In one embodiment, the present disclosure provides a method to prepare a compound 9-B from a compound 13-A, 13-B, 13-C, 13-D, 13-E, 1-I, 5-E or 6-L.

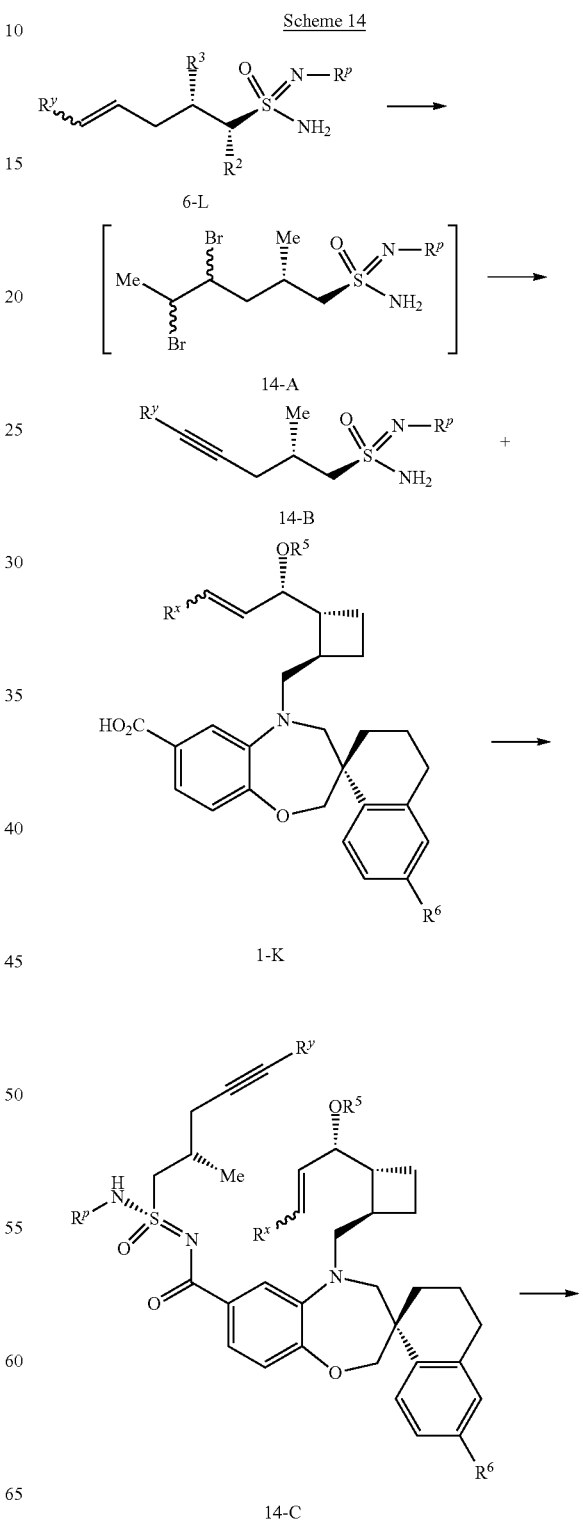

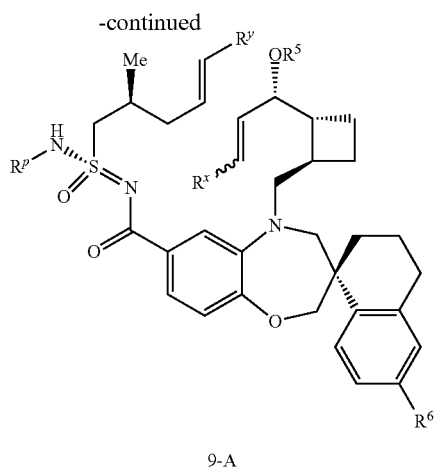

9-A

In one embodiment, the present disclosure provides a method of making a compound selected from 14-A, 14-B, 14-C and 9-A, as shown in Scheme 14, wherein $R^x$ and $R^y$ are independently H, $C_{1-6}$alkyl, or $C_{6-10}$aryl, wherein the alkyl is optionally substituted with $C_{6-10}$aryl, $R^2$ and $R^3$ are independently H or $C_{1-6}$alkyl, $R^5$ is $C_{1-6}$ alkyl, $R^6$ is halogen, $R^p$ is selected from H, —C(=O)—$C_{1-6}$alkyl, —C(=O)-heteroaryl, —C(=O)—O—$C_{1-6}$alkyl, and —C(=O)—O—$C_{1-6}$alkyl-phenyl, wherein each phenyl or heteroaryl is optionally substituted with one to four groups independently selected from $C_{1-3}$alkyl and —O$C_{1-3}$alkyl, wherein each heteroaryl has one to four heteroatoms; wherein each heteroatom is independently selected from N, O, and S, and wherein each heteroaryl has 5 to 10 ring members.

In one embodiment, the present disclosure provides a method to prepare a compound 14-A from a compound 6-L. In one embodiment, $R^p$ is selected from —C(=O)—$C_{1-6}$alkyl, —C(=O)-phenyl, —C(=O)—O—$C_{1-6}$alkyl, —C(=O)—O—$C_{1-6}$alkyl-phenyl, and —C(=O)—O-phenyl. In one embodiment, $R^p$ is —C(=O)—$CH_3$. In one embodiment, $R^y$ is methyl. In one embodiment, $R^2$ is H. In one embodiment, $R^3$ is methyl.

In one embodiment, the method comprises the step of treating a compound 6-L with a promotor in a suitable solvent, for a time and under conditions effective to form a compound 14-A. In one embodiment, $R^y$ is methyl, $R^2$ is H, $R^3$ is methyl, and $R^p$ is —C(=O)—$CH_3$.

In one embodiment, the promoter is selected from pyridinium hydrobromide perbromide, hydrobromic acid in combination with oxidants (e.g. potassium permanganate), hydrogen peroxide, or dimethylsulfoxide, oxalyl bromide in combination with dimethylsulfoxide; lithium bromide, sodium bromide, or potassium bromide in combination with oxidants (e.g. periodic acid, oxone, or ammonium cerium (IV) nitrate), and bromine. In one embodiment, the promoter is bromine.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., dichloromethane, 1,2-dichloroethane, chloroform, chlorobenzene), and polar aprotic solvents (e.g., N,N-dimethylacetamide, N,N-dimethylformamide, N-methyl-2-pyrrolidinone, dimethyl sulfoxide). In one embodiment, the solvent is dichloromethane.

In one embodiment, the temperature of the reaction is from −80 to 80° C. In one embodiment, the temperature of the reaction is from −80 to 10° C.

In one embodiment, the present disclosure provides a method to prepare a compound 14-B from a compound 14-A.

In one embodiment, the method comprises the step of treating a compound 14-A with a base in a suitable solvent, for a time and under conditions effective to to form a compound 14-B.

In one embodiment, the base is selected from sodium hydride, potassium hydride, calcium hydride, potassium tert-butoxide, sodium tert-butoxide, lithium tert-butoxide, magnesium di-tert-butoxide, sodium hydroxide, potassium hydroxide, lithium hydroxide, potassium tert-pentoxide, sodium tert-pentoxide, lithium tert-pentoxide, sodium hexamethyldisilazide, lithium hexamethyldisilazide, potassium hexamethyldisilazide, lithium diisopropylamide, sodium diisopropylamide, potassium diisopropylamide, n-butyllithium, s-butyllithium, t-butyllithium, or a combination thereof. In one embodiment, the base is potassium tert-butoxide.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., dichloromethane, 1,2-dichloroethane, chloroform, chlorobenzene), polar aprotic solvents (e.g., N,N-dimethylacetamide, N,N-dimethylformamide, N-methyl-2-pyrrolidinone, dimethyl sulfoxide). In one embodiment, the solvent is N,N-dimethylformamide.

In one embodiment, the temperature of the reaction is from −80 to 80° C. In one embodiment, the temperature of the reaction is from −80 to 20° C.

In one embodiment, the present disclosure provides a method to prepare a compound 14-C from a compound 14-B and a compound 1-K, wherein $R^x$ is H or $C_{1-6}$alkyl, $R^6$ is halogen, and $R^5$ is $C_{1-6}$ alkyl. In one embodiment, $R^x$ is H. In one embodiment, $R^6$ is Cl. In one embodiment, and $R^5$ is methyl.

In one embodiment, the method comprises the step of reacting a compound 14-B with a compound 1-K, with an activating agent, a promotor, and a base in a suitable solvent, for a time and under conditions effective to form a compound 14-C. In one embodiment, $R^x$ is H, $R^6$ is Cl, and $R^5$ is methyl.

In one embodiment, the activating agent is selected from carbonyldiimidazole (CDI), propylphosphonic anhydride (T3P), 1-[bis(dimethylamino)methylene]-1H-1,2,3-triazolo[4,5-b]pyridinium 3-oxide hexafluorophosphate (HATU), 4-(4,6-dimethoxy-1,3,5-triazin-2-yl)-4-methyl-morpholinium chloride (DMTMM), thionyl chloride, oxalyl chloride, (chloromethylene)-dimethyliminium chloride, isobutyl chloroformate, N,N,N,N'N'-tetramethylchloroformamidinium hexafluorophosphate (TCFH), N,N'-diisopropylcarbodiimide, N,N'-dicyclohexylcarbodiimide, diphenyl chlorophosphate, 2,4,6-trichlorobenzoyl chloride, 2-chloro-4,6-dimethoxy-1,3,5-triazine (CDMT), and N-(3-dimethylaminopropyl)-N'-ethylcarbodiimide hydrochloride (EDC-HCl). In one embodiment, the activating agent is N-(3-dimethylaminopropyl)-N'-ethylcarbodiimide hydrochloride (EDC-HCl).

In one embodiment, the promotor is selected from 1-hydroxy-7-azabenzotriazole (HOAt), 1-hydroxybenzotriazole (HOBt), N,N-dimethylacetamide, N-methylimidazole, and 4-dimethylaminopyridine (DMAP). In one embodiment, the promotor is 4-dimethylaminopyridine (DMAP).

In one embodiment, the base is selected from 1-methylimidazole, tertiary amines (e.g., N-methylmorpholine, triethyl amine, tripropylamine, N,N-diisopropylethylamine, tributylamine, 1,8-diazabicyclo[5.4.0]undec-7-ene, 1,4-diazabicyclo[2.2.2]octane, DABCO), aromatic amines (e.g., pyridine, 2,6-lutidine, collidine), inorganic bases (e.g., lithium carbonate, sodium carbonate, potassium carbonate, calcium carbonate and bicarbonate derivatives, mono, di and tri basic potassium and sodium phosphate). In one embodiment, the base is 1-methylimidazole.

In one embodiment, the solvent is selected from esters (e.g., ethyl acetate, isopropyl acetate), carbonates (e.g., dimethyl carbonate), ethers (e.g., tetrahydrofuran, 2-methyltetrahydrofuran, methyl tert-butyl ether, cyclopentyl methyl ether), chlorinated solvents (e.g., dichloromethane, 1,2-dichloroethane, chloroform), hydrocarbon solvents (e.g., toluene), polar aprotic solvents (e.g., N,N-dimethylformamide, N,N-dimethylacetamide, dimethylsulfoxide, N-methyl-2-pyrrolidone), nitriles (e.g., acetonitrile, propionitrile), water, or a combination thereof. In one embodiment, the solvent is acetonitrile.

In one embodiment, the temperature of the reaction is from 0 to 60° C. In one embodiment, the temperature of the reaction is from 10 to 30° C.

In one embodiment, the present disclosure provides a method to prepare a compound 9-A from a compound 14-C.

In one embodiment, the method comprises the step of treating a compound 14-C with a promoter, a silane, and a fluoride source in a suitable solvent, for a time and under conditions effective to form a compound 9-A.

In one embodiment, the promotor is selected from benzenedichlororuthenium(II) dimer, dichloro(para-cymene)ruthenium(II) dimer, rhodium (bis(1,5-cyclooctadiene)rhodium(II) tetrafluoroborate hydrate, (biscyclo[2.2.21]hepta-2,5-diene)rhodium(I) chloride dimer, tris (triphenylphosphine)rhodium(I) chloride, platinum (chloroplatinic acid hydrate, platinum(0)-1,3-divinyl-1,1,3,3-tetramethyldisiloxane complex), and pentamethylcyclopentadienyltris (acetonitrile)ruthenium(II) hexafluorophosphate ([Cp*Ru(MeCN)$_3$]PF$_6$). In one embodiment, the promotor is pentamethylcyclopentadienyltris (acetonitrile) ruthenium(II) hexafluorophosphate ([Cp*Ru(MeCN)$_3$]PF$_6$).

In one embodiment, the silane is selected from 1,1,3,3-tetramethyldisiloxane, trimethoxyhydrosilane, trimethylhydrosilane, benzyldimethylsilane, dimethylchlorosilane, ethoxy(dimethyl)silane, triethylsilane and triethoxysilane. In one embodiment, the silane is triethoxysilane.

In one embodiment, the fluoride source is selected from tetrabutylammonium fluoride, pyridine hydrogen fluoride, triethylamine trihydrofluoride, tetrabutylammonium difluorotriphenylsilicate and silver(I) fluoride. In one embodiment, the fluoride source is silver(I) fluoride.

In one embodiment, the solvent is selected from ethers (e.g., 2-methyltetrahydrofuran, tetrahydrofuran, methyl tert-butyl ether, cyclopentyl methyl ether), hydrocarbon solvents (e.g., toluene, n-heptane), alcohols (e.g., methanol, ethanol), halogenated solvents (e.g., dichloromethane, 1,2-dichloroethane, chloroform, chlorobenzene), polar aprotic solvents (e.g., N,N-dimethylacetamide, N,N-dimethylformamide, N-methyl-2-pyrrolidinone, dimethyl sulfoxide), or a combination of above listed solvents thereof. In one embodiment, the solvent is a combination of dichloromethanne (DCM), tetrahydrofuran (THF), and methanol (MeOH).

In one embodiment, the temperature of the reaction is from −80 to 100° C. In one embodiment, the temperature of the reaction is from 0 to 30° C.

In one embodiment, the present disclosure provides a method to prepare a compound 9-A from a compound 6-L, 14-A, 14-B, 1-K, or 14-C.

In one embodiment, the present disclosure provides a method of making a compound selected from 15-B, 15-C, and 1-A, as shown in Scheme 15, wherein $R^{16}$ is $C_{1-6}$alkyl or $C_{1-6}$alkylphenyl.

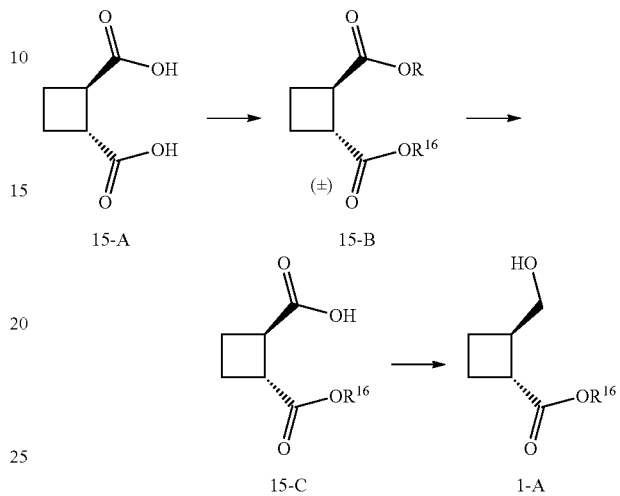

Scheme 15

In one embodiment, the present disclosure provides a method to prepare a compound 15-B from a compound 15-A.

In one embodiment, the method comprises the step of treating a compound 15-A with an acid or an alternative agent in a suitable solvent for a time and under conditions effective to form a compound 15-B. In one embodiment, $R^{16}$ is methyl, ethyl, iso-propyl, n-butyl or benzyl. In one embodiment, $R^{16}$ is methyl.

In one embodiment, the acid is selected from hydrochloric acid, pivalic acid, p-toluenesulfonic acid, methanesulfonic acid, sulfonyl chloride, acetyl chloride, chlorotrimethylsilane, and sulfuric acid. In one embodiment, the acid is sulfuric acid.

In one embodiment, the alternative agent is selected from iodomethane, dimethyl sulfate, methyl trifluoromethanesulfonate, chloroethane, bromoethane, iodoethane, isopropyl bromide, isopropyl iodide, benzyl bromide, benzyl chloride, benzyl iodide, carbonyldiimidazole, ethylcarbodiimide hydrochloride, and other coupling reagents known in the state of the art to promote esterification of esters, potassium carbonate, other bases that are known in the state of the art to promote the esterification of carboxylic acids.

In one embodiment, the solvent is selected from methanol, ethanol, isopropanol, benzyl alcohol, ethers (e.g., 2-methyltetrahydrofuran, tetrahydrofuran, methyl tert-butyl ether, cyclopentyl methyl ether), hydrocarbon solvents (e.g., toluene, n-heptane), halogenated solvents (e.g., 1,2-dichloroethane, chloroform, chlorobenzene), polar aprotic solvents (e.g., N,N-dimethylacetamide, N,N-dimethylformamide, N-methyl-2-pyrrolidinone, dimethyl sulfoxide). In one embodiment, the solvent is methanol.

In one embodiment, the temperature of the reaction is from −20 to 125° C. In one embodiment, the temperature of the reaction is about 65° C.

In one embodiment, the present disclosure provides a method to prepare a compound 15-C from a compound 15-B.

In one embodiment, the method comprises the step of treating a compound 15-B in a suitable solvent, with an enzyme in a suitable buffer solution, for a time and under conditions effective to form a compound 15-C.

In one embodiment, the enzyme is selected from Lipozyme CALB L, Novozyme 435, Novozyme 40086, Novozyme 51032, Palatase 20000L, Resinase HT, Lipase TL, and esterases. In one embodiment, the enzyme is Lipozyme CALB L.

In one embodiment, the buffer is selected an aqueous buffer, e.g., sodium phosphate buffer or potassium phosphate buffer, optionally having a pH of 5-8 (e.g., about pH 7). In one embodiment, the buffer is pH 7 phosphate buffer.

In one embodiment, the solvent is selected from ketones (e.g., acetone, methyl ethyl ketone), ethers (e.g., tetrahydrofuran, 2-methyltetrahydrofuran, methyl tert-butyl ether, cyclopentyl methyl ether), polar aprotic solvents (e.g., N,N-dimethylacetamide, N,N-dimethylformamide, N-methylpyrrolidinone, dimethyl sulfoxide), nitriles (e.g., acetonitrile), hydrocarbon solvents (e.g., toluene, n-heptane), halogenated solvents (e.g., dichloromethane, 1,2-dichloroethane, chloroform, chlorobenzene), water, or combinations of above listed solvents thereof. In one embodiment, the solvent is acetone.

In one embodiment, the temperature of the reaction is from 10 to 60° C. In one embodiment, the temperature of the reaction is about 35° C.

In one embodiment, the present disclosure provides a method to prepare a compound 1-A from a compound 15-C.

In one embodiment, the method comprises the step of treating a compound 15-C, with a reducing agent in a suitable solvent with for a time and under conditions effective to form a compound 1-A.

In one embodiment, the reducing agent is selected from borane tetrahydrofuran complex, diborane, other complexes of borane known in the state of the art that promote the reduction of carboxylic acids, $I_2$/NaBH$_4$, phenyl chloroformate/NaBH$_4$ or other chloroformates known in the state of the art that promote the reduction of mixed anhydrides with NaBH$_4$, borane dimethyl sulfide complex. In one embodiment, the reducing agent is borane dimethyl sulfide complex.

In one embodiment, the solvent is selected from ethers (e.g., tetrahydrofuran, 2-methyltetrahydrofuran, methyl tert-butyl ether, cyclopentyl methyl ether), polar aprotic solvents (e.g., N,N-dimethylacetamide, N,N-dimethylformamide, N-methylpyrrolidinone, dimethyl sulfoxide), nitriles (e.g., acetonitrile), hydrocarbon solvents (e.g., toluene, n-heptane), halogenated solvents (e.g., dichloromethane, 1,2-dichloroethane, chloroform, chlorobenzene), water, or a combination thereof. In one embodiment, the solvent is 2-methyltetrahydrofuran.

In one embodiment, the temperature of the reaction is from −10 to 40° C. In one embodiment, the temperature of the reaction is from 0 to 20° C.

In one embodiment, the present disclosure provides a method to prepare a compound 1-A from a compound 15-A, 15-B, or 15-C.

In one embodiment, the present disclosure provides a method to prepare a salt 9-C Base from a compound 9-C, as shown in Scheme 16, wherein $R^x$ and $R^y$ are independently H, $C_{1-6}$alkyl, or $C_{6-10}$aryl, wherein the alkyl is optionally substituted with $C_{6-10}$aryl, $R^2$ and $R^3$ are independently H or $C_{1-6}$alkyl, $R^5$ is $C_{1-6}$ alkyl, $R^6$ is halogen, and $R^{12}$ is H or —C(O)—$R^1$, wherein $R^1$ is selected from optionally substituted $C_{1-6}$alkyl (e.g., methyl), optionally substituted $C_{1-6}$alkoxy (e.g., (S)-1-phenylethoxy), or optionally substituted 5-10 membered heteroaryl (e.g., 1-methyl-3-methoxy-1H-pyrazol-4-yl). In one embodiment, $R^x$ and $R^y$ are independently H. In one embodiment, $R^5$ is methyl. In one embodiment, $R^6$ is Cl. In one embodiment, $R^{12}$ is —C(O)-1-methyl-3-methoxy-1H-pyrazol-4-yl.

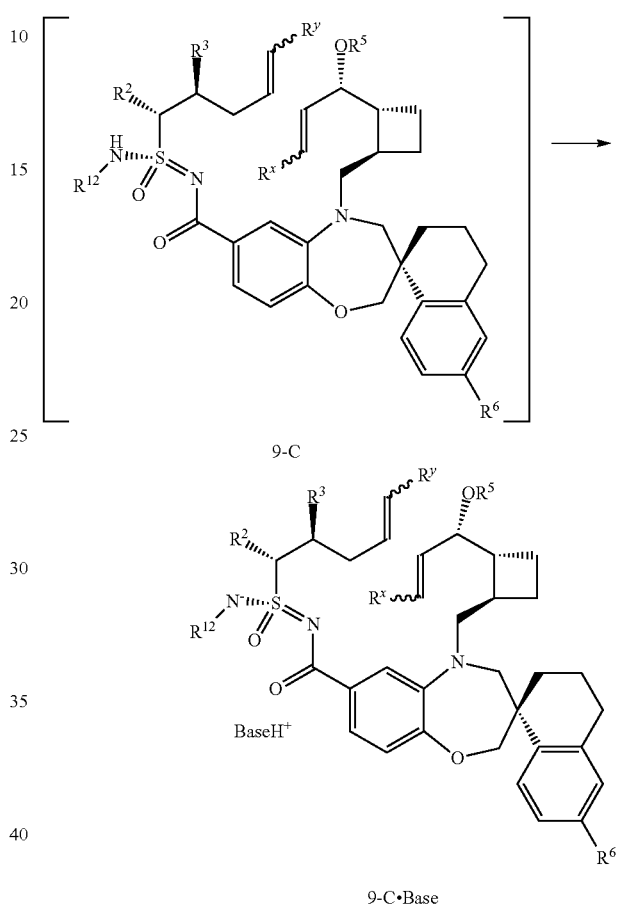

In one embodiment, the method comprises the step of reacting a compound 9-C with a base in a suitable solvent for a time and under conditions effective to form a salt 9-C Base.

In one embodiment, the base is selected from 1,5,7-triazabicyclo[4.4.0]dec-5-ene, (−)-cinchonidine, (−)-quinine and dicyclohexylamine. In one embodiment, the base is dicyclohexylamine.

In one embodiment, the solvent is selected from ethers (e.g., dibutyl ether, methyl tert-butyl ether), hydrocarbon solvents (e.g., methylcyclohexane, heptane, toluene), alcohols (e.g., isopropyl alcohol). In one embodiment, the solvent is a combination of methyl tert-butyl ether and heptane.

In one embodiment, the temperature of the reaction is from 0 to 60° C. In one embodiment, the temperature of the reaction is from 10 to 30° C.

In one embodiment, the present disclosure provides a method to prepare a compound 1 from a compound 9-C or a salt 9-C Base.

In one embodiment, the present disclosure provides a method to prepare a compound 9-C from a salt 9-C Base, as shown in Scheme 17, wherein $R^x$ and $R^y$ are independently H, $C_{1-6}$alkyl, or $C_{6-10}$aryl, wherein the alkyl is optionally substituted with $C_{6-10}$aryl, $R^2$ and $R^3$ are independently H or $C_{1-6}$alkyl, $R^5$ is $C_{1-6}$ alkyl, $R^6$ is halogen, and $R^{12}$ is H or —C(O)—$R^1$, wherein $R^1$ is selected from optionally substituted $C_{1-6}$alkyl (e.g., methyl), optionally substituted $C_{1-6}$alkoxy (e.g., (S)-1-phenylethoxy), or optionally substituted 5-10 membered heteroaryl (e.g., 1-methyl-3-methoxy-1H-pyrazol-4-yl). In one embodiment, $R^x$ and $R^y$ are independently H. In one embodiment, $R^5$ is methyl. In one embodiment, $R^6$ is Cl. In one embodiment, $R^{12}$ is —C(O)-1-methyl-3-methoxy-1H-pyrazol-4-yl.

Scheme 17

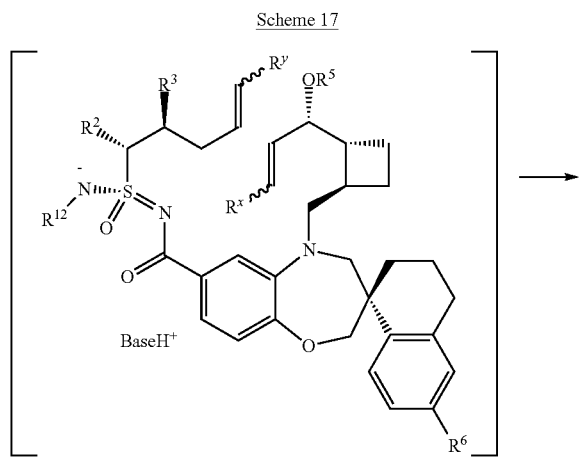

9-C·Base

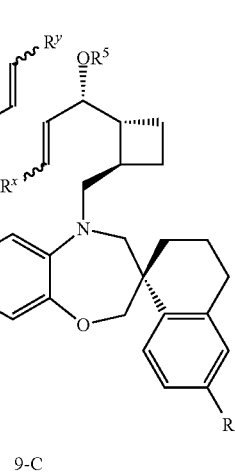

9-C

In one embodiment, the method comprises the step of reacting a salt 9-C Base with an acid in a suitable solvent for a time and under conditions effective to form a compound 9-C.

In one embodiment, the acid is selected from aqueous hydrochloric acid, aqueous sulfuric acid, aqueous phosphoric acid, aqueous citric acid, aqueous acetic acid, aqueous formic acid. In one embodiment, the acid is aqueous hydrochloric acid.

In one embodiment, the solvent is selected from ethyl acetate, isopropyl acetate and toluene. In one embodiment, the solvent is ethyl acetate, isopropyl acetate.

In one embodiment, the temperature of the reaction is from 0° C. to 60° C. In one embodiment, the temperature of the reaction is from 10 to 30° C.

In one embodiment, the present disclosure provides a method to prepare a compound 1 from a compound 9-C or a salt 9-C Base.

The description set forth herein is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading. Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" or "diastereomers" are stereoisomers that have at least two asymmetric atoms, but which are not mirror-images of each other.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and/or hindered rotation about a bond axis and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, diastereomeric mixtures, optically pure forms and intermediate mixtures. Optically active (R)- and (S)-isomers may be prepared using chiral synthons or chiral reagents, or resolved using conventional techniques.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing an amide (e.g., by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

Compounds described herein may have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s).

In some embodiments disclosed herein, a catalyst used for a reaction may be an "asymmetric" or catalyst. The term "asymmetric catalyst" as used herein refers to a catalyst that promotes the enantioselective and/or diastereoselective transformation of an achiral center or molecule into a chiral center or molecule, respectively. For example, an asymmetric catalyst may generate an enantiomeric excess of a product. Exemplary asymmetric catalysts comprise a transition metal and a chiral ligand. Non-limiting examples of chiral ligands include BINAP/SEGPHOS®, salens, bisoxazolines, tartrate ligands, cinchona alkaloids, DuPhos phospholanes, BPE phospholanes, DSM phosphoramidites, Solvias® Josiphos families, phosphine-oxazolines, the Reetz and Trost ligands, and ChiralQuest phosphines.

Also provided are pharmaceutically acceptable hydrates, solvates, co-crystals, tautomeric forms, polymorphs, and prodrugs of the compounds described herein.

The term "hydrate" refers to the complex formed by the combining of a compound of Formula I, or any Formula disclosed herein, and water.

The term "solvate" refers to a complex formed by the combining of a compound of Formula I, or any other Formula as disclosed herein, and a solvent or a crystalline solid containing amounts of a solvent incorporated within the crystal structure. As used herein, the term "solvate" includes hydrates.

Any formula or structure given herein, including Formula A or Formula I or Formula I(a), or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula A or Formula I or Formula I(a), or any Formula disclosed herein, in which from 1 to "n" hydrogens attached to a carbon atom is/are replaced by deuterium, in which n is the number of hydrogens in the molecule. Such compounds exhibit increased resistance to metabolism and thus may be useful for increasing the half-life of any compound of Formula I when administered to a mammal. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The modifier "about" used in connection with a quantity is inclusive of the stated value and has the meaning dictated by the context (e.g., includes the degree of error associated with measurement of the particular quantity). Absent any other definition or any context to the contrary, the term about may be interpreted as ±10%, ±5%, ±3%, or ±2%, or ±1%.

The term "chiral" refers to molecules which have the property of non-superimposability of the mirror image partner, and the term "achiral" refers to molecules which are superimposable on their mirror image partner.

A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

A dash ("–" or "-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line " " that is between two chemical groups is used to indicate a mixture of isomers at this point.

A squiggly line on a chemical group as shown below, for example,

indicates a point of attachment, i.e., it shows the broken bond by which the group is connected to another described group.

The term "substituted" or "optionally substituted" means that one or more hydrogen atoms on a carbon atom (either aliphatic or aromatic) is replaced with one or more atoms or groups other than hydrogen, provided that the designated carbon atom's normal valence is not exceeded. A "substituent" is an atom or group that replaces a hydrogen atom on a carbon when it is "substituted." Unless specified otherwise, where a group is described as optionally substituted, any substituents of the group are themselves unsubstituted. The term "optionally substituted," if not otherwise modified, includes at least the following optional substituents: halogen, hydroxy, amino, thiol, $C_{1-6}$alkyl, $C_{1-6}$haloalkyl, $C_{2-6}$alkynyl, $C_{3-10}$ cycloalkyl, $C_{6-10}$aryl, 3-12 membered heterocycloalkyl, and 5-10 membered heteroaryl, —O$C_{1-6}$alkyl, —C(O)—$C_{1-6}$alkyl, —C(O)O—$C_{1-6}$alkyl, —C(O)—OH, —C(O)—$NH_2$, —C(O)N($C_{1-6}$alkyl)($C_{1-6}$alkyl), —C(O)NH($C_{1-6}$alkyl), OC(O)N($C_{1-6}$alkyl)($C_{1-6}$alkyl)-, OC(O)NH($C_{1-6}$alkyl), —N($C_{1-6}$alkyl)($C_{1-6}$alkyl), —NH($C_{1-6}$alkyl), —N($C_{1-6}$alkyl)-C(O)—($C_{1-6}$alkyl), NH—C(O)—($C_{1-6}$alkyl), —N($C_{1-6}$alkyl)-C(O)O—($C_{1-6}$alkyl), —S(O)$_2$$NH_2$, —S(O)$_{(1\ or\ 2)}$($C_{1-6}$alkyl), —S(O)$_2$N($C_{1-6}$alkyl)($C_{1-6}$alkyl), —N($C_{1-6}$alkyl)S(O)$_2$$R^b$, —$N_3$, —CN, and —$NO_2$.

As used herein, "alkyl" is a linear or branched saturated monovalent hydrocarbon. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2$CH($CH_3$)$_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2$$CH_2CH_3$), 3-methyl-2-butyl (—CH($CH_3$)CH($CH_3$)$_2$), 3-methyl-1-butyl (—$CH_2CH_2$CH($CH_3$)$_2$), 2-methyl-1-butyl (—$CH_2$CH($CH_3$)$CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2$$CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), and 2,3-dimethyl-2-butyl (—C($CH_3$)$_2$CH($CH_3$)$_2$), 3,3-dimethyl-2-butyl (—CH($CH_3$)C($CH_3$)$_3$. Whenever any alkyl group may exist in more than one isomeric form, for example n-butyl, sec-butyl, and tert-butyl, any reference herein that lacks a prefix, e.g., "butyl", should be interpreted as the normal isomer (e.g., "n-butyl"). Thus, "propyl" means "n-propyl," and "butyl" means "n-butyl."

"Alkenyl" refers to an aliphatic group containing at least one carbon-carbon double bond. Examples of alkenyl groups include ethenyl, propenyl, butadienyl (including 1,2-butadienyl, and 1,3-butadienyl).

"Alkoxy" as used herein refers to a radical of the formula —$OR_A$ where $R_A$ is an alkyl radical as defined above. Non-limiting examples of alkoxy include methoxy, ethoxy, propoxy, and butoxy.

"Alkynyl" refers to an aliphatic group containing at least one carbon-carbon triple bond.

"Aryl" refers to a monoradical or diradical aromatic carbocyclic group having a single ring (e.g., monocyclic) or multiple rings (e.g., bicyclic or tricyclic) including fused ring systems wherein one or more fused rings is/are fully or partially unsaturated. Non-limiting examples of aryl groups as used herein include phenyl, naphthyl, fluorenyl, indanyl, tetrahydroindanyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "aryloxy" refers to the group —O-aryl.

"Cycloalkyl" refers to a saturated or partially saturated cyclic alkyl group having a single ring or multiple rings including fused, bridged, and spiro ring systems. Examples of cycloalkyl groups include cyclopropyl, cyclobutyl, cyclopentyl, and cyclohexyl. "Cycloalkyl" does not include any rings containing heteroatoms in the ring.

"Halo" and "halogen" are used herein to refer to fluoro (—F), chloro (—Cl), bromo (—Br) and iodo (—I).

When the prefix "halo" is appended to another term it refers to any one or more of the hydrogen associated with that term being independently replaced by a halogen atom. Thus, the term "haloalkyl" as used herein refers to an alkyl as defined herein, wherein one or more hydrogen atoms of the alkyl are independently replaced by a halogen substituent, which may be the same or different. For example, $C_{1-6}$haloalkyl (or halo$C_{1-6}$alkyl) is a $C_{1-6}$alkyl wherein one or more of the hydrogen atoms of the $C_{1-6}$alkyl have been replaced by a halo substituent. Examples of haloalkyl groups include, but are not limited to, fluoromethyl, fluorochloromethyl, difluoromethyl, difluorochloromethyl, trifluoromethyl, 1,1,1-trifluoroethyl, and pentafluoroethyl. Up to all hydrogen atoms of the associated term may be replaced by halogen, thus resulting in a perfluorinated substituent (e.g., perfluoroalkyl).

"Heteroaryl" refers to a monoradical or diradical aromatic group having a single ring, multiple rings, or multiple fused rings, with one or more ring heteroatoms independently selected from nitrogen, oxygen, and sulfur. The heteroatoms within the "heteroaryl" may be oxidized, e.g., —N(O)—, —S(O)—, —S(O)$_2$—. The term includes fused ring systems wherein one or more fused rings is/are fully or partially unsaturated. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above. Non-limiting examples of heteroaryl groups include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl.

The term "heteroaryloxy" refers to the group —O-heteroaryl.

The term "heterocyclyl," "heterocycle," or "heterocyclic" or "heterocycloalkyl" refers to a monoradical or diradical saturated or unsaturated group having a single ring or multiple condensed rings having one or more heteroatoms selected from nitrogen, sulfur, phosphorus, and/or oxygen within the ring. The heteroatoms within the "heterocyclyl" may be oxidized, e.g. —N(O)—, —S(O)—, —S(O)$_2$—. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Exemplary heterocyclic groups include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl.

The term "cyano" refers to the group —CN.

The term "oxo" refers to a group =O.

The term "carboxy" refers to a group —C(O)—OH.

The term "dioxane" refers to "1,4-dioxane."

Compounds described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Non-limiting examples of "pharmaceutically acceptable salts" of the compounds disclosed herein also include salts derived from an appropriate base, such as an alkali metal (for example, sodium, potassium), an alkaline earth metal (for example, magnesium), ammonium, and $NX_4^+$ wherein X is $C_1$-$C_4$ alkyl). Also included are base addition salts, such as sodium or potassium salts.

"Salt" refers to acid or base salts of the compounds used in the methods of the present disclosure. Salts useful in the present disclosure include, but are not limited to, an alkali metal (for example, sodium, potassium), an alkaline earth metal (for example, magnesium), ammonium, organic amine salts (for example, dicyclohexylamine (DCA) salt, 1,5,7-Triazabicyclo[4.4.0]dec-5-ene (TBD) salt, (−)-Cinchonidine salt, (−)-Quinine salt, and $NX_4^+$ salt, wherein X is $C_1$-$C_4$ alkyl).

The terms "nonpolar," "polar aprotic," and "polar protic" as used herein to refer to solvents, is intended as a means of classifying solvents for use in the various methods and steps described herein. For the purposes of classification herein, the term "nonpolar solvent" means any ethereal solvent, hydrocarbon solvent or halogenated solvent, carbon dioxide, and carbon disulfide, as well as other solvents traditionally classified as nonpolar solvents. Ethereal solvents include dimethyl ether, diethyl ether, dipropyl ether, diisopropyl ether, dibutyl ether, methyl isopropyl ether, methyl t-butyl ether, cyclopentyl methyl ether, tetrahydrofuran, 2-methyltetrahydrofuran, 1,4-dioxane, 1,2-dimethoxyethane, diethylene glycol diethyl ether, triethylene glycol dimethyl ether, and anisole. Hydrocarbon solvents include petroleum ether, pentane (or mixed pentanes), heptane (or mixed heptanes), hexane (or mixed hexanes), octane, isooctane, decane, dodecane, cyclopentane, cyclohexane, methylcyclohexane, benzene, toluene, o-xylene, m-xylene, p-xylene, pyridine, chlorobenzene, 1,2-dichlorobenzene, fluorobenzene, phenol, anisole, trifluorotoluene, hexachlorobenzene, hexafluorobenzene, and benzonitrile. Halogenated solvents include dichloromethane, tetrachloromethane, chloroform, 1,1-dichloroethane, 1,1,1-trichloroethane, vinyl chloride, vinylidene dichloride, trichloroethylene, perchloroethylene, chlorobenzene, 1,2-dichlorobenzene, fluorobenzene, trifluorotoluene, hexachlorobenzene, and hexafluorobenzene. For the purposes of classification herein, the term "polar aprotic solvent" means any ester, nitrile, or ketone solvent, as well as N,N-dimethylformamide, N,N-dimethylacetamide, dimethylsulfoxide, sulfolane, N-methyl-2-pyrrolidinone, N,N-dimethylethyleneurea, N,N-dimethylpropyleneurea, hexamethylphosphoric acid triamide, dimethyl carbonate, diethyl carbonate, ethylene carbonate, propylene carbonate, and nitromethane, as well as other solvents traditionally classified as polar protic solvents. Ester solvents include methyl acetate, ethyl acetate, propyl acetate, isopropyl acetate, butyl acetate, isobutyl acetate, t-butyl acetate, vinyl acetate, 2,2,2-trichloroethyl acetate, and 2-ethoxyethyl acetate. Nitrile solvents include acetonitrile, propionitrile, and benzonitrile. Ketone solvents include acetone, methyl ethyl ketone, methyl n-butyl ketone, methyl isobutyl ketone, methyl t-butyl ketone, 3-pentanone, cyclopentanone, cyclohexanone, and 2,5-hexanedione. For the purposes of classification herein, the term "polar protic solvents" means any alcohol or acid solvent, or water, or ammonia, as well as other solvents traditionally classified as polar protic solvents. Alcohol solvents include methanol, ethanol, n-propanol, isopropanol, n-butanol, isobutanol, sec-butanol, tert-butanol, pentanol, 3-methyl-1-butanol, cyclopentanol, cyclohexanol, phenol, 2-methyoxyethanol, 2-ethoxyethanol, ethylene glycol, 1,2-propylene glycol, 1,3-propylene glycol, glycerol, 1,4-butanediol, and 1,4-cyclohexanediol. Acid solvents include formic acid, acetic acid, trichloroacetic acid, and trifluoroacetic acid.

EXAMPLES

Protection of EX-1 to EX-2

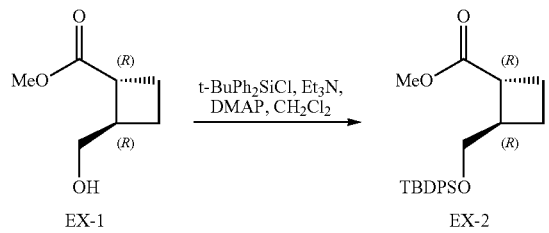

A reactor was charged with 4-(dimethylamino)pyridine (0.05 equiv.) followed by a solution of EX-1 (1.0 equiv., scaling factor) in dichloromethane (10 volumes) and triethylamine (1.2 equiv.) and cooled to about 0° C. tert-Butyldiphenylchlorosilane (1.05 equiv.) was added over about 2 min then the mixture was warmed to about 25° C. The reaction mixture was stirred for about 6 h then quenched with 15 wt % aqueous sodium bicarbonate solution (5 volumes). The phases were separated and the aqueous layer was washed with dichloromethane (10 volumes). The combined organic layers were washed with 15 wt % aqueous sodium chloride solution (10 volumes), dried over magnesium sulfate, filtered, and concentrated. The crude product was purified by silica gel chromatography using ethyl acetate and heptane to afford EX-2. $^1$H NMR (400 MHz, CDCl$_3$) δ 7.56-7.71 (m, 4H), 7.32-7.48 (m, 6H), 3.56-3.71 (m, 5H), 3.08 (q, J=8.8 Hz, 1H), 2.68-2.84 (m, 1H), 2.00-2.24 (m, 2H), 1.87 (ddd, J=5.7, 7.8, 9.3 Hz, 2H), 1.06 (s, 9H).

Kulinkovich Cyclopropanation of EX-2 to EX-5

A reactor was charged with EX-2 (1.0 equiv., scaling factor) and tetrahydrofuran (10 volumes) and cooled to about 0° C. Titanium(IV) isopropoxide (1.0 equiv.) was charged to the mixture at about 10° C. and then 40 wt % ethylmagnesium bromide in 2-methyltetrahydrofuran (3.0 equiv.) was added over about 2 h at about 0° C. The mixture was agitated for about 2 h at about 0° C. and then quenched with 25 wt % aqueous ammonium chloride solution (6 volumes) followed by 20 wt % citric acid solution (6 volumes) at about 0° C. The mixture was warmed to about 20° C. and the aqueous layer was removed and back-extracted with methyl tert-butyl ether (10 volumes). The organic layers were combined, washed with 15 wt % aqueous sodium chloride solution (5 volumes), dried over magnesium sulfate, filtered, and concentrated to afford EX-3. $^1$H NMR (400 MHz, CDCl$_3$) δ 7.62-7.76 (m, 4H), 7.34-7.51 (m, 6H), 3.62 (dd, J=4.5, 10.0, 1H), 3.51 (t, J=9.7 Hz, 1H), 2.62 (q, J=8.7 Hz, 1H), 2.32-2.46 (m, 1H), 1.63-1.80 (m, 2H), 1.41-1.54 (m, 1H), 1.22-1.37 (m, 1H), 1.04 (s, 9H), 0.74-0.82 (m, 1H), 0.60-0.67 (m, 2H), 0.41 (ddd, J=5.1, 7.7, 9.1 Hz, 1H).

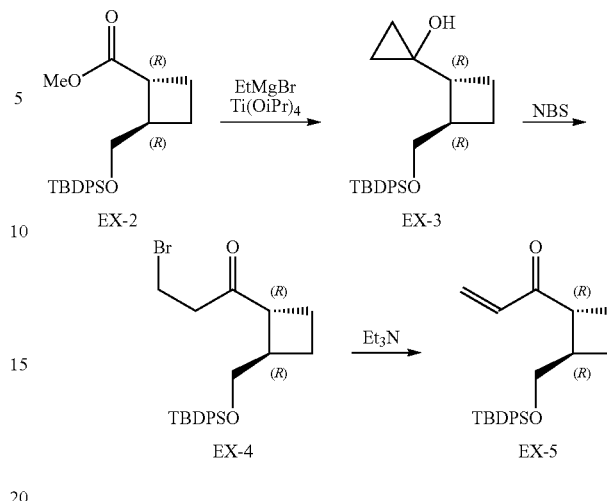

A reactor was charged with EX-3 (1.0 equiv., scaling factor) in dichloromethane (10 volumes) and cooled to about 0° C. N-Bromosuccinimide (1.05 equiv.) was charged in one portion and agitated for about 1.5 h at about 0° C. Triethylamine (2.0 equiv.) was charged at 0° C. and agitated for about 2.5 h at about 0° C. The reaction mixture was quenched with 20 wt % citric acid solution (10 volumes) and warmed to about 20° C. The layers were separated and the organic layer was washed with 5 wt % sodium bicarbonate solution (10 volumes) followed by 15 wt % aqueous sodium chloride solution (5 volumes), dried over magnesium sulfate, filtered, then concentrated to afford EX-5. $^1$H NMR (400 MHz, CDCl$_3$) δ 7.66 (ddt, J=1.1, 2.8, 6.4 Hz, 4H), 7.33-7.47 (m, 6H), 6.28-6.39 (m, 1H), 6.19 (dd, J=1.4, 17.7 Hz, 1H), 5.74 (dt, J=1.1, 10.5 Hz, 1H), 3.67 (d, J=5.0 Hz, 2H), 3.48 (q, J=8.4 Hz, 1H), 2.73 (ddt, J=4.2, 8.4, 13.4 Hz, 1H), 2.19 (dq, J=8.9, 10.8 Hz, 1H), 1.98-2.11 (m, 1H), 1.83-1.94 (m, 2H), 1.07 (s, 9H).

Reduction of EX-5 to EX-6

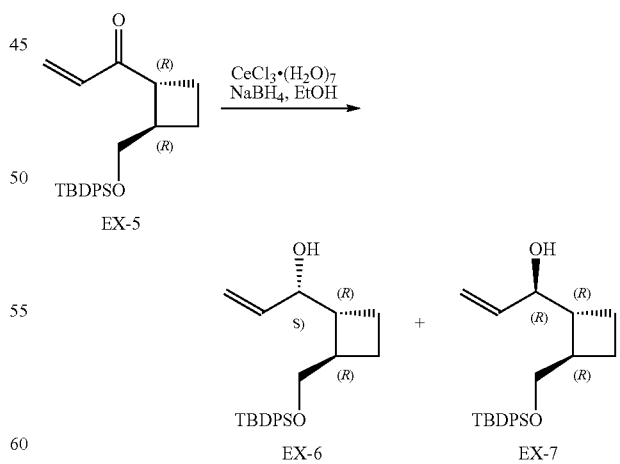

A reactor was charged with cerium(III) chloride heptahydrate (0.30 equiv.) followed by EtOH (5 volumes) and warmed to about 30° C. The contents of the reactor were agitated until homogeneous and then cooled to about −10° C. A solution of EX-5 (1.0 equiv., scaling factor) in ethanol (5 volumes) was added at about −10° C. Sodium borohydride (1.50 equiv.) was added in three equal portions at about 30 min intervals maintaining the internal temperature below about −10° C. The reaction mixture was agitated for about 2 h, and then acetone (10 equiv.) was charged and the mixture was warmed to about 0° C. A 10 wt % citric acid solution (10 volumes) was charged slowly to the reaction mixture at about 0° C., and then the mixture was diluted with dichloromethane (10 volumes) and warmed to about 20° C. The aqueous layer was separated and back-extracted twice with dichloromethane (5 volumes). The combined organic layers were washed with 15 wt % aqueous sodium chloride solution (5 volumes), dried over magnesium sulfate, filtered, and then concentrated. EX-6 and EX-7 was purified by chromatography using ethyl acetate and heptane. EX-6: $^1$H NMR (400 MHz, CDCl$_3$) δ 7.69 (tt, J=1.7, 6.1 Hz, 4H), 7.34-7.50 (m, 6H), 5.77 (ddd, J=6.5, 10.4, 17.0 Hz, 1H), 5.29 (td, J=1.5, 17.1 Hz, 1H), 5.10 (ddd, J=1.0, 1.9, 10.4 1H), 3.91-4.01 (m, 1H), 3.76 (s, 1H), 3.61 (dd, J=4.4, 10.0 Hz, 1H), 3.42 (t, J=10.1 Hz, 1H), 2.33-2.48 (m, 1H), 2.14 (p, J=8.7 Hz, 1H), 1.36-1.89 (m, 4H), 1.05 (s, 9H). EX-7: $^1$H NMR (400 MHz, CDCl$_3$) δ 7.67 (ddd, J=1.6, 5.0, 8.0 Hz, 4H), 7.34-7.48 (m, 6H), 5.89 (ddd, J=5.9, 10.5, 17.2 1H), 5.24-5.32 (m, 1H), 5.17 (td, J=1.6, 10.5 Hz, 1H), 4.06 (t, J=5.5 Hz, 1H), 3.57 (dd, J=4.5, 10.1 Hz, 1H), 3.47 (dd, J=7.5, 10.1 Hz, 1H), 2.66 (s, 1H), 2.47-2.35 (m, 2H), 1.66-1.94 (m, 3H), 1.50-1.65 (m, 1H), 1.06 (s, 9H).

Resolution of a Mixture of EX-6 and EX-7

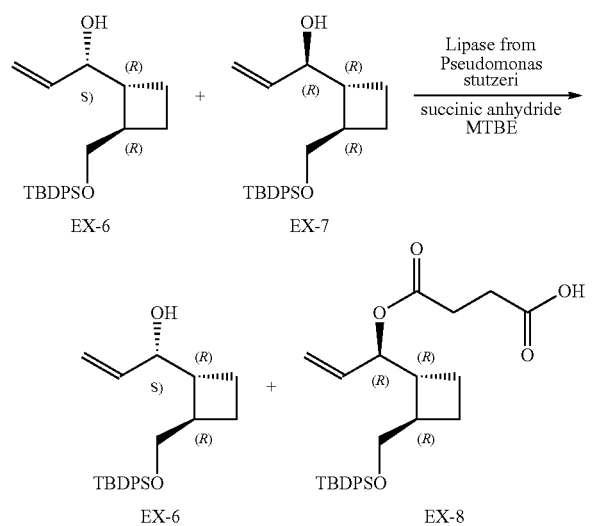

A reactor was charged with a mixture of EX-6 and EX-7 (1.0 equiv., scaling factor; mixture of alcohols), methyl tert-butyl ether (20 volumes), succinic anhydride (1.5 equiv.), and *Pseudomonas stutzeri* lipase (10 wt %). The mixture was agitated at about 20° C. for about 24 h, filtered through a pad of Celite, and concentrated. The crude product was purified by chromatography using ethyl acetate and hexanes to separate EX-6 and EX-8. $^1$H NMR data for EX-6 matches the previous entry. EX-8: $^1$H NMR (400 MHz, CDCl$_3$) δ 7.65 (d, 4H), 7.36-7.44 (m, 6H), 5.59-5.67 (m, 1H), 5.16-5.23 (m, 2H), 5.07-5.10 (d, 1H), 3.54-3.61 (m, 2H), 2.60-2.69 (m, 4H), 2.37-2.43 (m, 1H), 2.22-2.31 (m, 1H), 1.84-1.91 (m, 2H), 1.68-1.82 (m, 2H), 1.06 (s, 9H).

Methylation of EX-6 to EX-9

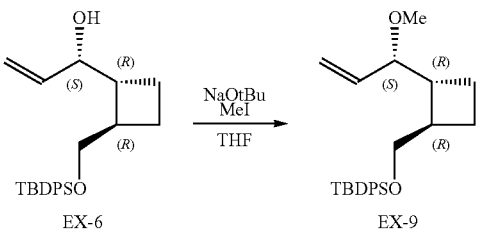

A reactor was charged with EX-6 (1.0 equiv., scaling factor), tetrahydrofuran (10 volumes) and iodomethane (4.7 equiv.) and cooled to about 0° C. Sodium tert-butoxide (1.4 equiv., 2 M in tetrahydrofuran) was charged and the mixture was agitated at about 0° C. for about 2 h. Triethylamine (4.1 equiv.) was charged and the mixture was diluted with methyl tert-butyl ether (20 volumes) and water (10 volumes). The layers were separated and the aqueous layer was back-extracted with methyl tert-butyl ether (20 volumes). The combined organic layers were washed with a solution of sodium metabisulfite (5 equiv.) in water (10 volumes), then saturated aqueous sodium chloride solution (10 volumes), and then dried over magnesium sulfate, filtered, and concentrated. The crude product was purified by chromatography with ethyl acetate and hexanes to afford EX-9. $^1$H NMR (400 MHz, CDCl$_3$) δ 7.67 (d, J=7.5 Hz, 4H), 7.38 (m, 6H), 5.59 (m, 1H), 5.19 (s, 1H), 5.15 (d, J=7.6 Hz, 1H), 3.69 (dd, 4.9, J=10.3 Hz, 1H), 3.60 (dd, 6.1, J=10.3 Hz, 1H), 3.44 (t, J=7.2 Hz, 1H), 3.23 (s, 3H), 2.37 (m, 1H), 2.27 (m, 1H), 1.76 (m, 4H), 1.06, (s, 9H).

Deprotection of EX-9 to EX-10

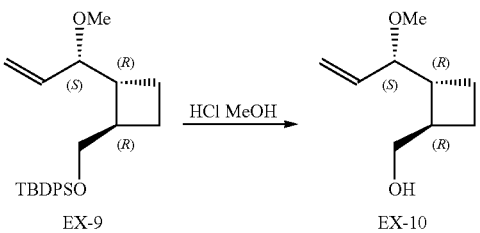

A reactor was charged with EX-9 (1.0 equiv, scale factor) and methanol (10 volumes) at about 20° C. Hydrochloric acid (37% in water, 3 equiv) was added to the reaction mixture over about 5 minutes and then the reaction mixture was aged for about 4 hours. The reaction mixture was combined with aqueous sodium bicarbonate (4 equiv in 10 volumes of water) and dichloromethane (10 volumes). The layers were separated and the organic layer collected. The aqueous layer was extracted two additional times with dichloromethane (10 volumes each) and the organic extracts were combined, concentrated, and purified by column chromatography using ethyl acetate and hexanes to afford EX-10. $^1$H NMR (400 MHz, CDCl$_3$) δ 5.50 (m, 1H), 5.25 (s, 1H), 5.22 (dd, 1.6, J=7.6 Hz, 1H), 3.58 (dd, J=4.3, 10.3 Hz, 1H), 3.36 (m, 2H), 3.29 (s, 3H), 2.32 (m, 1H), 2.03 (m, 1H), 1.82 (m, 2H), 1.55 (m, 2H).

Deprotection of EX-9 to EX-10

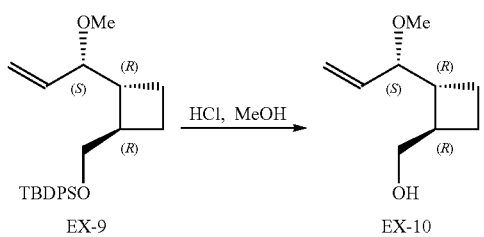

A reactor was charged with EX-9 (1.0 equiv, scale factor) and methanol (10 volumes) at about 20° C. Hydrochloric acid (37% in water, 3 equiv) was added to the reaction mixture over about 5 minutes and then the reaction mixture was aged for about 4 hours. The reaction mixture was combined with aqueous sodium bicarbonate (4 equiv in 10 volumes of water) and dichloromethane (10 volumes). The layers were separated and the organic layer collected. The aqueous layer was extracted two additional times with dichloromethane (10 volumes each) and the organic extracts were combined, concentrated, and purified by column chromatography using ethyl acetate and hexanes to afford EX-10. $^1$H NMR (400 MHz, CDCl$_3$) δ 5.50 (m, 1H), 5.25 (s, 1H), 5.22 (dd, 1.6, J=7.6 Hz, 1H), 3.58 (dd, J=4.3, 10.3 Hz, 1H), 3.36 (m, 2H), 3.29 (s, 3H), 2.32 (m, 1H), 2.03 (m, 1H), 1.82 (m, 2H), 1.55 (m, 2H).

Oxidation EX-10 to EX-11

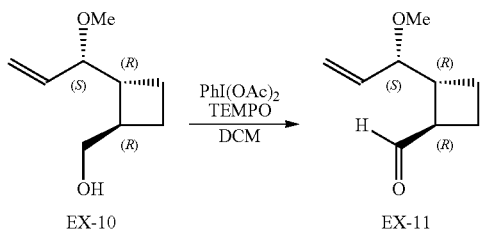

A reactor was charged with EX-10 (1.0 equiv., scaling factor) and dichloromethane (10 volumes). The contents were adjusted to about 20° C. and iodobenzene diacetate (1.05 equiv.) and (2,2,6,6-tetramethylpiperidin-1-yl)oxyl (0.025 equiv.) were added. The mixture was agitated for about 20 h to generate a solution of EX-11 in dichloromethane that was used directly in the next step.

Oxidation EX-10 to EX-11

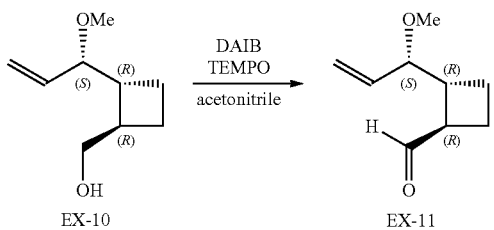

A reactor was charged with EX-10 (1.0 equiv, scaling factor) and acetonitrile (9 volumes). The contents were adjusted to about 20° C. and iodobenzene diacetate (1.05 equiv) was added. A solution of (2,2,6,6-tetramethylpiperidin-1-yl)oxyl (0.05 equiv) in acetonitrile (1 volume) was added over about 1 hour. The mixture was agitated for about 3 h, which yielded a solution of EX-11 in acetonitrile that was used directly in the next step.

Reductive Amination of EX-11 to EX-13

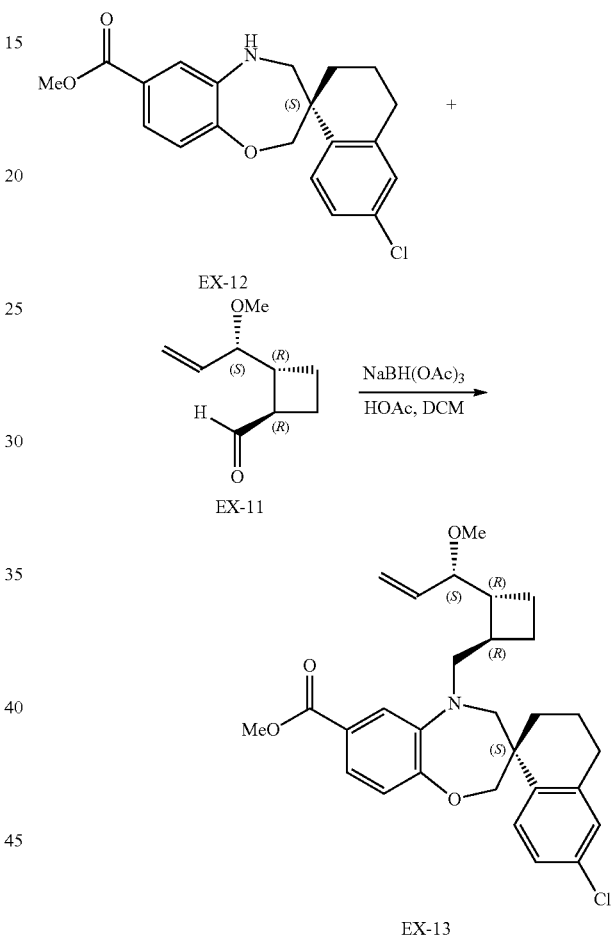

A reactor was charged with EX-12 (1 equiv., scaling factor) and a solution of EX-11 (1.2 equiv.) in dichloromethane (3 volumes). Acetic acid (1 equiv.) was added, the contents were cooled to about −20° C., and sodium triacetoxyborohydride (1.6 equiv.) was added. The mixture was agitated for about 20 h at about −20° C. The temperature was adjusted to about 0° C. and saturated sodium bicarbonate (6 volumes) was added. The layers were separated and the aqueous phase was washed with dichloromethane (6 volumes). The combined organic layers were dried over magnesium sulfate, filtered, and concentrated. The crude product was purified by chromatography using ethyl acetate and hexanes to afford EX-13. $^1$H NMR (400 MHz, CDCl$_3$) δ 7.63 (d, J=8.5 Hz, 1H), 7.32 (m, 2H), 7.09 (dd, 2.3, J=8.4 Hz, 1H), 7.01 (d, J=2.3 Hz, 1H), 6.83 (d, J=8.3 Hz, 1H), 5.51 (m, 1H), 5.14 (s, 1H), 5.11 (m, 1H), 4.01 (m, 2H), 3.80 (s, 3H), 3.64 (dd, 3.5, 14.9 Hz, 1H), 3.57 (d, J=14.3 Hz, 1H), 3.42 (t, J=7.8 Hz, 1H), 3.24 (m, 3H), 3.12 (dd, 9.3, J=14.9 Hz, 1H), 2.69 (m, 2H), 2.46 (m, 1H), 1.97 (m, 3H), 1.76 (m, 3H), 1.50 (m, 3H).

Kulinkovich Cyclopropanation of EX-14 to EX-15

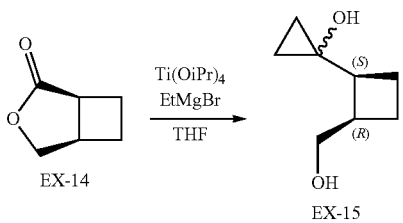

A reactor was charged with EX-14 (1 equiv., scaling factor) and tetrahydrofuran (20 volumes). The mixture was cooled to about 0° C. and titanium tetraisopropoxide (1.1 equiv.) was charged to the reactor. Ethylmagnesium bromide (1 M in tetrahydrofuran, 3.0 equiv.) was charged over about 4 h. The contents of the reactor were adjusted to about 10° C. and agitated for about 20 h. The contents were cooled to about 0° C. and aqueous ammonium chloride (20 wt % in water, 10 volumes) was charged to the reactor while maintaining the contents at not more than about 5° C. After addition was complete, the reactor contents were warmed to about 20° C. and filtered. The filtrate was concentrated and filtered through silica gel using methanol and dichloromethane to afford EX-15. $^1$H NMR (400 MHz, CDCl$_3$) δ 4.05 (t, J=10.6 Hz, 1H), 3.70 (dd, J=4.2, 10.9 Hz, 1H), 2.99 (br s, 2H), 2.81-2.89 (m, 1H), 2.69-2.81 (m, 1H), 1.89-2.06 (m, 2H), 1.45-1.57 (m, 2H), 0.61-0.83 (m, 3H), 0.33 (ddd, J=4.9, 6.8, 10.2 Hz, 1H).

Protection of EX-15 to EX-16

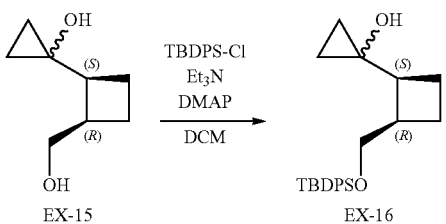

A reactor was charged with EX-15 (1.0 equiv., scaling factor) and dichloromethane (15 volumes) and cooled to about 0° C. Triethylamine (1.2 equiv.) and 4-(dimethylamino)pyridine (0.05 equiv.) were charged to the reactor, and then tert-butyldiphenylchlorosilane (1.1 equivalents) was charged over about 5 min. The reaction mixture was allowed to warm to about 20° C. and agitated for about 15 h. Water (5 volumes) was charged to the reactor and 20 wt % aqueous citric acid was added until the mixture pH was about 7. The aqueous layer was separated and back-extracted with dichloromethane (5 volumes). The combined organic layers were combined and concentrated and purified by chromatography using ethyl acetate and dichloromethane to afford EX-16. $^1$H NMR (400 MHz, CDCl$_3$) δ 7.66-7.74 (m, 4H), 7.35-7.50 (m, 6H), 4.87 (s, 1H), 4.13 (t, J=10.9 Hz, 1H), 3.60 (dd, J=4.2, 10.8 Hz, 1H), 2.91-3.00 (m, 1H), 2.71-2.83 (m, 1H), 1.80-1.95 (m, 2H), 1.41-1.53 (m, 1H), 1.28-1.40 (m, 1H), 1.04 (s, 9H), 0.78-0.85 (m, 1H), 0.68-0.77 (m, 2H), 0.28-0.38 (m, 1H).

Ring-Opening and Elimination EX-16 to EX-18

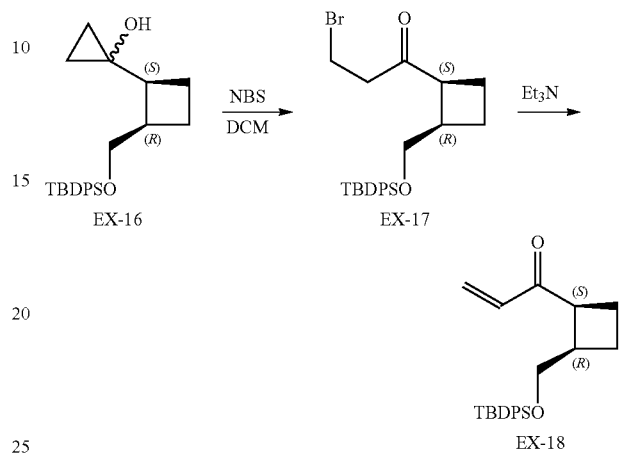

A reactor was charged with EX-16 (1.0 equiv., scaling factor) and dichloromethane (8 volumes) and cooled to about 0° C. N-Bromosuccinimide (1.0 equiv.) was charged portionwise over about 10 min and the mixture was agitated for about 30 min. Triethylamine (2 equiv.) was charged and the resulting mixture was agitated for about 6 h. The organic layer was washed with 20 wt % aqueous citric acid solution (6 volumes) followed by a mixture of water (4 volumes) and 5 wt % aqueous sodium bicarbonate solution (1 volume). The resulting organic layer was concentrated and purified by chromatography using ethyl acetate and heptane to afford EX-18. $^1$H NMR (400 MHz, CDCl$_3$) δ 7.59-7.63 (m, 4H), 7.33-7.44 (m, 6H), 6.36 (dd, J=10.7, 17.7 Hz, 1H), 6.12 (dd, J=1.2, 17.7 Hz, 1H), 5.70 (dd, J=1.2, 10.6 Hz, 1H), 3.65-3.74 (m, 2H), 3.58 (dd, J=6.1, 10.7 Hz, 1H), 2.98-2.85 (m, 1H), 2.46-2.59 (m, 1H), 2.04 (qd, J=8.5, 11.1 Hz, 1H), 1.85-1.97 (m, 1H), 1.61-1.74 (m, 1H), 1.00 (s, 9H).

Epimerization of EX-18 to EX-5

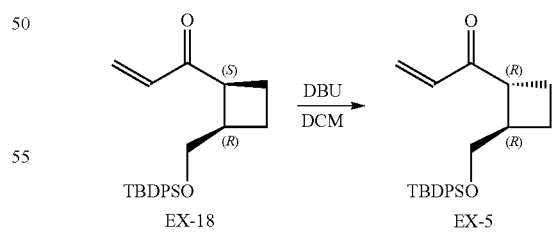

A reactor was charged with EX-18 (1.0 equiv., scaling factor) and dichloromethane (20 volumes). The contents were adjusted to about 20° C. and 1,8-diazabicyclo[5.4.0]undec-7-ene (0.4 equiv.) was charged. The mixture was agitated for about 16 h, after which water (8 volumes) was charged. Aqueous citric acid (20 wt %) was added until the aqueous layer was about pH 5-6, and then the organic layer was dried over solid sodium sulfate, filtered, and concentrated to afford EX-5. ¹H NMR (400 MHz, CDCl₃) δ 7.63-7.68 (m, 4H), 7.32-7.48 (m, 6H), 6.33 (dd, J=10.5, 17.7 Hz, 1H), 6.19 (dd, J=1.4, 17.7 Hz, 1H), 5.74 (dd, J=1.4, 10.5 Hz, 1H), 3.67 (d, J=5.1 Hz, 2H), 3.48 (q, J=8.4 Hz, 1H), 2.73 (dtd, J=5.0, 8.4, 13.3 Hz, 1H), 2.19 (qd, J=8.9, 11.0 Hz, 1H), 1.99-2.11 (m, 1H), 1.82-1.95 (m, 2H), 1.07 (s, 9H).

Thiolation of EX-5 to EX-19

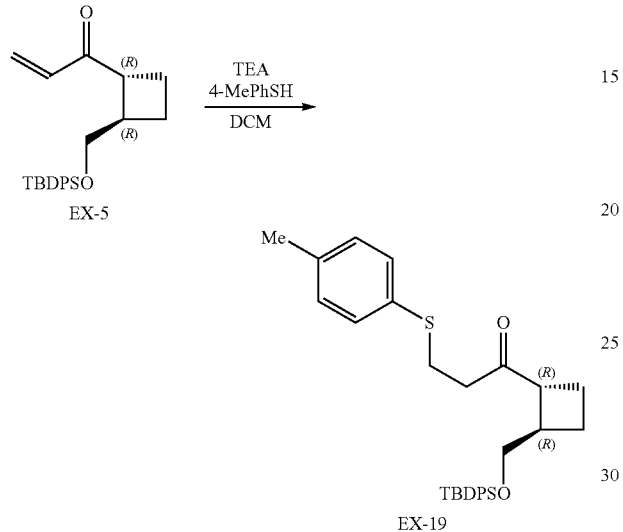

A reactor was charged with EX-5 (1.0 equiv., scaling factor), 4-methylbenzenethiol (1.05 equiv.), and dichloromethane (10 volumes). The contents were adjusted to about 20° C. and triethylamine (1.2 equivalents) was charged. The reaction mixture was agitated for about 24 h after which 1 N sodium hydroxide (6 volumes) was charged. The organic layer was separated and washed with 15 wt % aqueous sodium chloride solution (5 volumes), dried over magnesium sulfate, concentrated, and purified by chromatography using ethyl acetate and heptane to afford EX-19. ¹H NMR (400 MHz, CDCl₃) δ 7.63 (qd, J=1.6, 6.6 Hz, 4H), 7.31-7.48 (m, 6H), 7.22 (d, J=8.2 Hz, 2H), 7.07 (d, J=7.9 Hz, 2H), 3.61 (d, J=5.2 Hz, 2H), 2.99-3.20 (m, 3H), 2.54-2.71 (m, 3H), 2.30 (s, 3H), 2.03-2.18 (m, 1H), 1.90-2.01 (m, 1H), 1.81 (dt, J=6.5, 8.9 Hz, 2H), 1.05 (s, 9H).

Reduction of EX-19 to EX-20

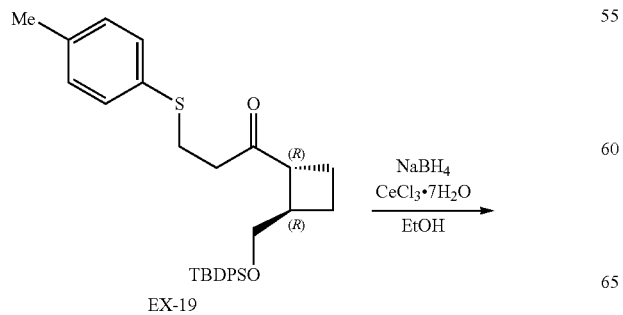

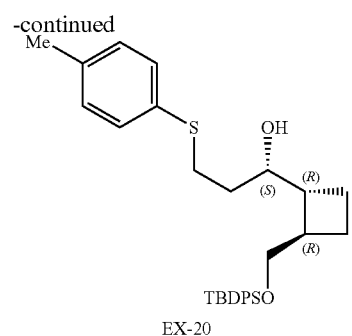

A reactor was charged with EX-19 (1.0 equiv., scaling factor), cerium(III) chloride heptahydrate (0.3 equiv.), and ethanol (10 volumes) and cooled to about −15° C. Sodium borohydride (1.5 equiv.) was added and the mixture was allowed to warm to about 20° C. and agitated for about 70 h to afford a solution of EX-20. ¹H NMR (400 MHz, CDCl₃) δ 7.63-7.66 (m, 4H), 7.33-7.49 (m, 6H), 7.25 (d, J=7.9 Hz, 2H), 7.08 (d, J=7.9 Hz, 2H), 3.68 (ddd, J=2.8, 5.3, 9.2 Hz, 2H), 3.56 (dd, J=4.5, 10.3 Hz, 1H), 3.49 (dd, J=6.7, 10.3 Hz, 1H) 3.12 (ddd, J=5.1, 8.6, 13.4 Hz, 1H), 2.94 (ddd, J=7.2, 8.4, 13.0 Hz, 1H), 2.24-2.33 (m, 4H), 1.54-1.87 (m, 6H), 1.05 (s, 9H).

Methylation of EX-21 to EX-22

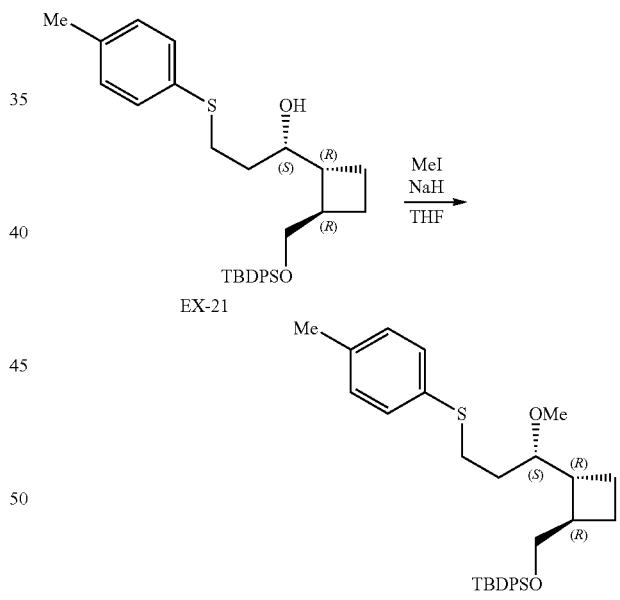

A reactor was charged with EX-21 (1.0 equiv., scaling factor), tetrahydrofuran (10 volumes), and iodomethane (5 equivalents) at about 20° C. Sodium hydride in mineral oil (60 wt %, 3 equiv.) was charged and the reaction was agitated at about 20° C. for about 17 h. The reaction mixture was diluted with heptane (20 volumes), filtered through Celite, and concentrated to dryness. The crude product was purified by chromatography using ethyl acetate and heptane to afford EX-22. ¹H NMR (400 MHz, CDCl₃) δ 7.65-7.67 (m, 4H), 7.32-7.45 (m, 6H), 7.23 (d, J=8.2 Hz, 2H), 7.08 (d, J=7.8 Hz, 2H), 3.67 (dd, J=4.4, 10.3 Hz, 1H), 3.59 (dd, J=5.9, 10.3 Hz, 1H), 3.22-3.28 (m, 4H), 2.90 (ddq, J=6.7, 8.3, 12.7 Hz, 2H), 2.24-2.36 (m, 5H), 1.54-1.89 (m, 6H), 1.05 (s, 9H).

Oxidation of EX-22 to EX-23

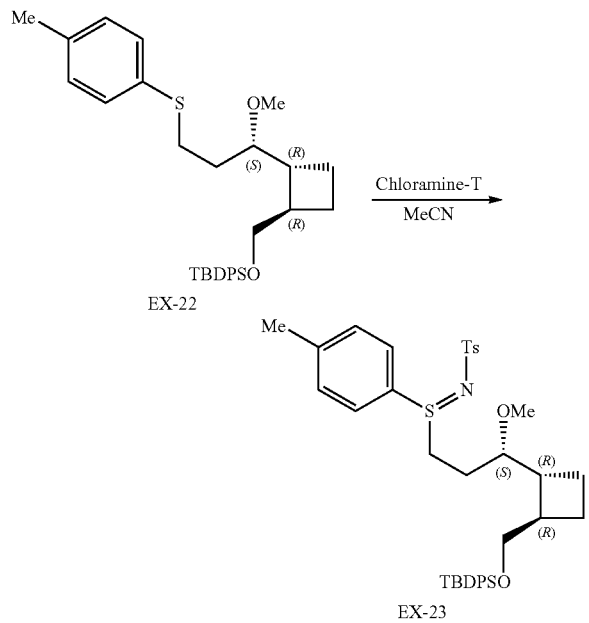

A reactor was charged with EX-22 (1.0 equiv., scaling factor), acetonitrile (20 volumes), and chloramine-T (1.2 equiv.) at about 20° C. and agitated for about 3 h. The reaction mixture was diluted with methyl tert-butyl ether (20 volumes), filtered through Celite, and concentrated to afford EX-23.

Thermolysis of EX-23 to EX-9

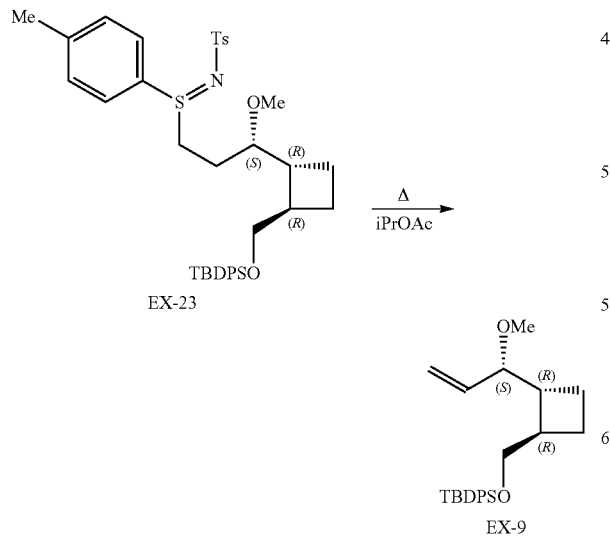

A reactor was charged with EX-23 and isopropyl acetate (10 volumes) and heated to about 90° C. for about 24 h. The reaction mixture was concentrated to afford EX-9. ¹H NMR (400 MHz, CDCl₃) δ 7.69-7.71 (m, 4H), 7.32-7.48 (m, 6H), 5.51-5.72 (m, 1H), 5.08-5.26 (m, 2H), 3.71 (dd, J=4.8, 10.2 Hz, 1H), 3.63 (dd, J=6.2, 10.2 Hz, 1H), 3.46 (dd, J=6.7, 7.8 Hz, 1H), 3.25 (s, 3H), 2.26-2.44 (m, 2H), 1.63-1.96 (m, 4H), 1.08 (s, 9H).

Triflation of EX-24 to EX-25

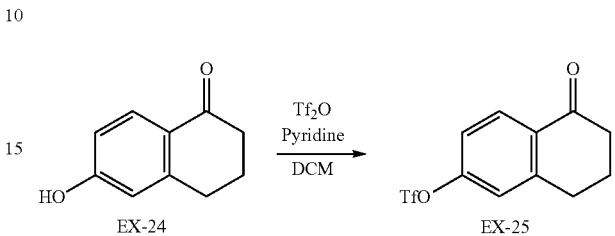

A reactor was charged with EX-24 (1.0 equiv., scaling factor) and dichloromethane (15 volumes). The mixture was cooled to about 0° C., and pyridine (1.4 equiv.) was charged to the reactor. Triflic anhydride (1.2 equiv.) was then charged while maintaining an internal temperature below about 10° C. The reaction mixture was agitated at about 0° C. for about 30 min, and then quenched by charging a saturated aqueous sodium carbonate solution (10 volumes) and mixing the biphasic mixture for about 5 min. The mixture was adjusted to about 20° C., and the organic layer was separated, washed with water (10 volumes), dried over sodium sulfate, filtered, and concentrated. The crude product was purified by chromatography using ethyl acetate and hexanes to afford EX-25. ¹H NMR (400 MHz, CDCl₃) δ 8.16 (d, J=8.4 Hz, 1H), 7.18-7.27 (m, 2H), 3.04 (t, J=6.1 Hz, 2H), 2.67-2.75 (m, 2H), 2.15-2.26 (m, 2H).

Chlorination of EX-25 to EX-26

A reactor was charged with EX-25 (1.0 equiv., scaling factor), lithium chloride (1.4 equiv.) and N-methyl-2-pyrrolidinone (8 volumes). The reaction mixture was heated to about 140° C. and agitated for about 72 h. The reaction mixture was cooled to about 40° C., and then 1 M aqueous sodium hydroxide solution (15 volumes) was charged and the mixture was agitated for about 1 h at about 40° C. The reaction mixture was cooled to about 20° C., and then heptane (15 volumes) was charged and the biphasic mixture was agitated for about 5 min. The layers were separated and the aqueous layer was extracted with heptane (10 volumes). The combined organic layers were washed with saturated aqueous sodium chloride solution (5 volumes), dried over sodium sulfate, filtered, and concentrated to provide EX-26. ¹H NMR (400 MHz, CDCl₃) δ 7.97 (d, J=8.2 Hz, 1H), 7.23-7.31 (m, 2H), 2.94 (t, J=6.1 Hz, 2H), 2.61-2.69 (m, 2H), 2.08-2.19 (m, 2H).

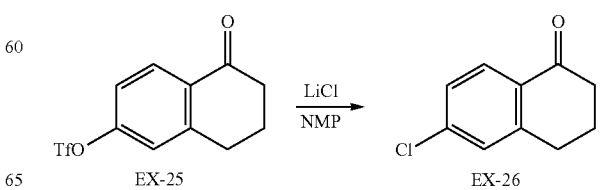

Enzymatic Acetylation and Oxidation of EX-27 to EX-29

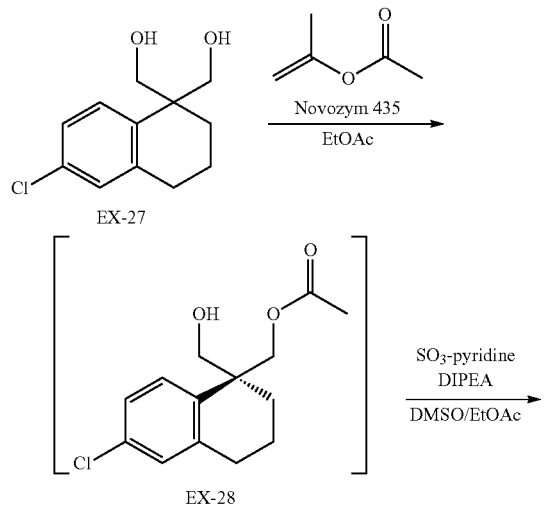

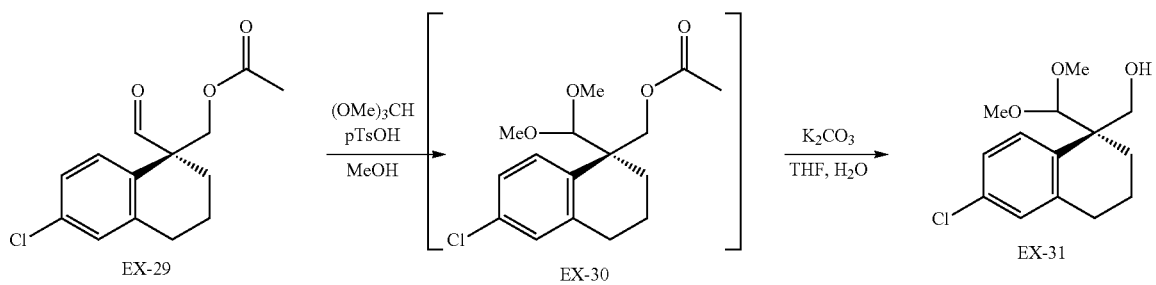

-continued

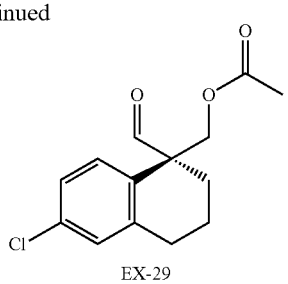

EX-29

A reactor was charged with EX-27 (1.0 equiv., scaling factor) and ethyl acetate (10 volumes) and warmed to about 25° C. to dissolve the solids. The solution was cooled to about 20° C. and charged with isopropenyl acetate (1.12 equiv.) and Novozym 435 (20 wt %). The reaction mixture was agitated at about 20° C. for about 17 h. The enzyme beads were removed via filtration, and the reactor was rinsed forward with ethyl acetate (1 volume) to afford a solution of EX-28 in ethyl acetate. A portion was purified by chromatography using ethyl acetate and hexanes to afford a sample of EX-28. $^1$H NMR (400 MHz, CDCl$_3$): δ 7.37 (d, J=8.2 Hz, 1H), 7.08-7.17 (m, 2H), 4.23, 4.22 (ABq, 2H, J=11.5 Hz), 3.71, 3.67 (ABq, 2H, J=11.5 Hz), 2.75 (t, J=6.1 Hz, 2H), 2.08 (s, 3H), 1.74-1.87 (m, 4H).

A reactor was charged with the solution of EX-28 in ethyl acetate and cooled to about 0° C. N,N-Diisopropylethylamine (3.5 equiv.) was charged to the reactor, followed by a solution of sulfur trioxide-pyridine (2.5 equiv.) in dimethyl sulfoxide (6 volumes). The reaction mixture was agitated at about 0° C. for about 30 min. Water (6 volumes) was added, and the biphasic mixture was agitated for about 5 min. The mixture was adjusted to about 20° C., and the layers were separated. The organic layer was washed two times with a 10 wt % aqueous citric acid solution (5 volumes) and once with saturated aqueous sodium chloride solution (7 volumes). The organic layer was dried over sodium sulfate, filtered, and concentrated to afford EX-29. $^1$H NMR (400 MHz, CDCl$_3$): δ 9.51 (s, 1H), 7.13-7.21 (m, 2H), 7.04-7.12 (m, 1H), 4.51 (d, J=11.4 Hz, 1H), 4.27 (d, J=11.4, 1H), 2.76-2.83 (m, 2H), 2.07-2.18 (m, 1H), 2.03 (s, 3H), 1.82-1.97 (m, 3H).

Acetal Formation and Acetate Hydrolysis of EX-29 to EX-31

A reactor was charged with EX-29 (1.0 equiv, scaling factor), trimethyl orthoformate (3.0 equiv), p-toluenesulfonic acid (0.05 equiv), and methanol (15 volumes). The reaction mixture was heated to about 45° C. and agitated for about 2 h. The reaction mixture was cooled to about 15° C., and potassium carbonate (3.0 equiv) was charged to the reactor. The temperature was adjusted to about 45° C. and the reaction mixture was agitated for about 3 h. The reaction mixture was cooled to about 15° C. and quenched with water (10 volumes) and then concentrated to remove methanol. Ethyl acetate (10 volumes) was charged, and the biphasic mixture was agitated for about 5 min. The layers were separated, and the aqueous layer was back-extracted once with ethyl acetate (5 volumes). The organic layers were combined and washed with 1 M aqueous sodium hydroxide solution (10 volumes), saturated aqueous sodium chloride solution (10 volumes), dried over magnesium sulfate, filtered, and concentrated to afford EX-31. $^1$H NMR (400 MHz, CDCl$_3$): δ 7.35 (d, 1H), 7.07-7.13 (m, 2H), 4.49 (s, 1H), 3.90 (d, J=11.3 Hz, 1H), 3.49-3.57 (m, 1H), 3.46 (s, 3H), 3.33 (s, 3H), 2.64-2.82 (m, 2H), 1.79-2.08 (m, 3H), 1.65-1.81 (m, 1H).

General Procedure for Transacetalization of EX-31 to EX-32-39

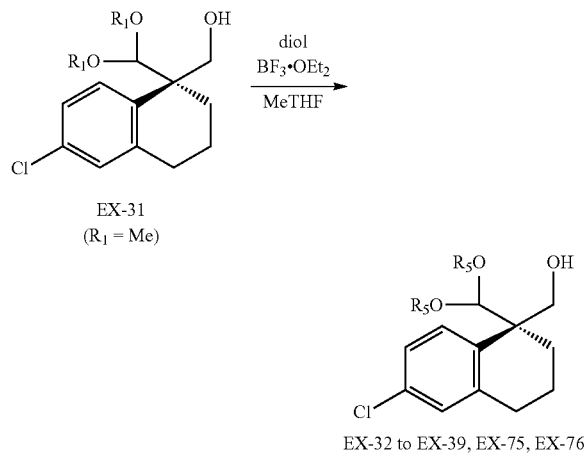

EX-31
(R₁ = Me)

EX-32 to EX-39, EX-75, EX-76

A reactor was charged with EX-31 (1.0 equiv., scaling factor), diol (2 equiv.), boron trifluoride diethyl etherate (1 equiv.), and 2-methyltetrahydrofuran (10 volumes). The mixture was heated to about 50° C. for about 15 minutes. The temperature was adjusted to about 20° C. and the reaction mixture was diluted with ethyl acetate (30 volumes). The organic layer was washed twice with water (20 volumes), dried over sodium sulfate, filtered, and concentrated. The crude product was purified by chromatography using ethyl acetate and heptane to afford EX-32 through EX-39, EX-75 and EX-76 depending on the diol, as shown below.

EX-32: diol=ethylene glycol, $R_5$=—$CH_2CH_2$—, ¹H NMR (400 MHz, CDCl₃): δ 7.37 (d, J=8.2 Hz, 1H), 7.12 (m, 2H), 5.11 (s, 1H), 4.05-3.88 (m, 4H), 3.81 (dd, J=7.4, 3.5 Hz, 1H), 3.64 (d, J=11.4 Hz, 1H), 2.74 (q, J=6.6, 5.8 Hz, 2H), 2.31 (s, 1H), 2.13-1.97 (m, 1H), 1.91 (ddd, J=14.4, 8.4, 3.3 Hz, 2H), 1.77 (tdt, J=8.2, 6.7, 4.1 Hz, 1H).

EX-33: diol=2,3-butanediol, $R_5$=—$CH(CH_3)CH(CH_3)$—, ¹H NMR (400 MHz, CDCl₃): δ 7.40-7.33 (m, 1H), 7.11 (m, 2H), 5.46-5.04 (m, 1H), 4.31-4.01 (m, 1H), 3.99-3.81 (m, 1H), 3.73-3.49 (m, 2H), 2.74 (q, J=6.3, 5.4 Hz, 1H), 2.40 (s, 1H), 2.06-1.84 (m, 3H), 1.83-1.70 (m, 1H), 1.37-1.04 (m, 6H).

EX-34: diol=pinacol, $R_5$=—$C(CH_3)_2C(CH_3)_2$—, ¹H NMR (400 MHz, CDCl₃): δ 7.37 (d, J=8.3 Hz, 1H), 7.10 (d, J=9.0 Hz, 2H), 5.27 (s, 1H), 3.89 (d, J=11.3 Hz, 1H), 3.56 (d, J=11.4 Hz, 1H), 2.74 (q, J=7.2, 6.1 Hz, 2H), 2.04-1.88 (m, 3H), 1.83-1.69 (m, 1H), 1.59 (s, 1H), 1.26-1.14 (m, 12H).

EX-35: diol=propylene glycol, $R_5$=—$CH_2CH_2CH_2$—, ¹H NMR (400 MHz, CDCl₃): δ 7.35 (d, J=8.3 Hz, 1H), 7.11-7.04 (m, 2H), 4.83 (s, 1H), 4.14 (dddt, J=35.4, 11.6, 5.3, 1.8 Hz, 2H), 3.90 (d, J=11.4 Hz, 1H), 3.86-3.75 (m, 1H), 3.68 (td, J=12.0, 2.5 Hz, 1H), 3.50 (d, J=11.4 Hz, 1H), 2.83-2.63 (m, 2H), 2.05 (ddd, J=21.6, 8.1, 5.2 Hz, 3H), 1.86 (dt, J=13.4, 5.4 Hz, 1H), 1.74 (td, J=8.1, 4.0 Hz, 1H), 1.42-1.30 (m, 1H).

EX-36: diol=2,4-pentanediol, $R_5$=—$CH(CH_3)CH_2CH(CH_3)$—, ¹H NMR (400 MHz, CDCl₃): δ 7.38 (d, J=9.2 Hz, 1H), 7.07 (m, 2H), 4.79 (s, 1H), 4.02 (d, J=11.2 Hz, 1H), 3.74 (dqd, J=12.3, 6.0, 2.2 Hz, 1H), 3.62 (ddd, J=11.1, 6.5, 2.6 Hz, 1H), 3.45 (d, J=11.2 Hz, 1H), 2.73 (q, J=7.3, 6.5 Hz, 2H), 2.17-1.94 (m, 2H), 1.87-1.63 (m, 1H), 1.52 (dt, J=13.2, 2.4 Hz, 1H), 1.23 (d, J=6.1 Hz, 4H), 1.15 (d, J=6.2 Hz, 3H).

EX-37: diol=2-methyl-1,3-propanediol, $R_5$=—$CH_2CH(CH_3)CH_2$—, ¹H NMR (400 MHz, CDCl₃): δ 7.35 (d, J=8.1 Hz, 1H), 7.09 (m, 2H), 4.74 (s, 1H), 4.05 (dddd, J=36.2, 11.2, 4.7, 2.3 Hz, 2H), 3.89 (d, J=11.4 Hz, 1H), 3.50 (d, J=11.4 Hz, 1H), 3.32 (t, J=11.1 Hz, 1H), 3.20 (t, J=11.2 Hz, 1H), 2.79-2.62 (m, 2H), 2.20-1.97 (m, 2H), 1.93-1.80 (m, 1H), 1.80-1.66 (m, 1H), 0.69 (d, J=6.7 Hz, 3H).

EX-38: diol=2,2-dimethyl-1,3-propanediol, $R_5$=—$CH_2C(CH_3)_2CH_2$—, ¹H NMR (400 MHz, CDCl₃): δ 7.35 (d, J=8.3 Hz, 1H), 7.09 (m, 2H), 4.74 (s, 1H), 3.90 (d, J=11.4 Hz, 1H), 3.68 (dd, J=11.0, 2.8 Hz, 1H), 3.59 (dd, J=11.1, 2.8 Hz, 1H), 3.53 (d, J=11.4 Hz, 1H), 3.47 (d, J=11.0 Hz, 1H), 3.35 (d, J=11.1 Hz, 1H), 2.83-2.66 (m, 2H), 2.07 (dd, J=7.4, 4.8 Hz, 2H), 1.88 (dt, J=13.4, 5.4 Hz, 1H), 1.78-1.67 (m, 1H), 1.17 (s, 3H), 0.71 (s, 3H).

EX-39: diol=2,2-diethyl-1,3-propanediol, $R_5$=—$CH_2C(CH_2CH_3)_2CH_2$—, ¹H NMR (400 MHz, CDCl₃): δ 7.33-7.30 (m, 1H), 7.09 (m, 2H), 4.75 (s, 1H), 3.95-3.82 (m, 2H), 3.78 (dd, J=11.3, 2.9 Hz, 1H), 3.51 (d, J=11.4 Hz, 1H), 3.43 (d, J=11.2 Hz, 1H), 3.29 (d, J=11.3 Hz, 1H), 2.85-2.67 (m, 2H), 2.05 (dd, J=7.1, 5.1 Hz, 2H), 1.87 (dt, J=13.5, 5.4 Hz, 1H), 1.79-1.64 (m, 3H), 1.05 (q, J=7.6 Hz, 2H), 0.84 (t, J=7.6 Hz, 3H), 0.75 (t, J=7.6 Hz, 3H).

EX-75: diol=meso-1,2-diphenyl-1,2-ethanediol, $R_5$=—$CH(C_6H_5)CH(C_6H_5)$—, ¹H NMR (400 MHz, CDCl₃) δ 7.54-7.47 (m, 1H), 7.36-6.68 (m, 12H), 5.28 (d, J=7.7 Hz, 2H), 5.25-5.12 (m, 1H), 4.05 (dd, J=11.5, 4.3 Hz, 1H), 3.79 (ddd, J=28.1, 11.4, 6.6 Hz, 1H), 2.73 (tt, J=16.3, 6.6 Hz, 2H), 2.21 (dddt, J=22.2, 13.6, 8.4, 3.9 Hz, 2H), 2.08-1.94 (m, 2H), 1.87-1.64 (m, 1H).

EX-76: diol=2-phenyl-1,3-propanediol, $R_5$=—$CH_2CH(C_6H_5)CH_2$—, ¹H NMR (400 MHz, CDCl₃) δ 7.42 (d, J=8.4 Hz, 1H), 7.33 (dd, J=8.1, 6.3 Hz, 2H), 7.27 (t, J=7.3 Hz, 2H), 7.20-7.14 (m, 2H), 7.11 (t, J=2.9 Hz, 1H), 4.91 (s, 1H), 4.27 (ddd, J=11.2, 4.7, 2.3 Hz, 1H), 4.19 (ddd, J=11.3, 4.7, 2.4 Hz, 1H), 3.95 (dd, J=11.5, 3.4 Hz, 1H), 3.87 (d, J=11.2 Hz, 1H), 3.76 (d, J=11.4 Hz, 1H), 3.57 (dd, J=11.4, 8.9 Hz, 1H), 3.21 (ddd, J=11.4, 6.8, 4.5 Hz, 1H), 2.74 (tq, J=11.0, 5.6 Hz, 2H), 2.60 (dd, J=9.1, 3.8 Hz, 1H), 2.17-2.01 (m, 2H), 1.99-1.84 (m, 1H), 1.84-1.68 (m, 1H).

Conversion of EX-40 to EX-41

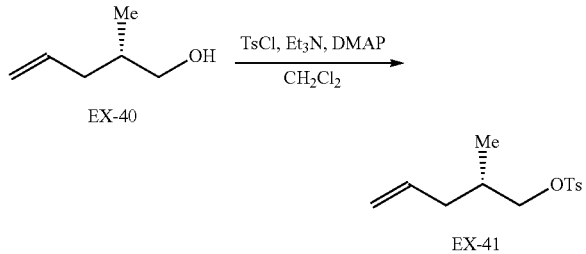

A reactor was charged with EX-40 (1.0 equiv., scaling factor) and dichloromethane (8 volumes). The reaction mixture was cooled to about 0° C., and dosed sequentially with 4-dimethylaminopyridine (0.1 equiv.), 4-toluenesulfonyl chloride (1.0 equiv.) and triethylamine (1.3 equiv.). The mixture was warmed to about 20° C. and agitated for about 2 h. The mixture was washed sequentially with 0.5 M HCl (5 volumes), 5 wt % aqueous sodium bicarbonate solution (5 volumes), and water (5 volumes). The organic layer was concentrated to afford EX-41. ¹H NMR (400 MHz, CDCl₃): δ 7.67 (d, J=8.4 Hz, 2H), 7.24 (d, J=8.4 Hz, 2H), 5.55 (m, 1H), 4.81-4.89 (m, 2H), 3.78 (dd, J=5.6, 9.2 Hz, 1H), 3.72 (dd, J=5.6, 9.2 Hz, 1H), 2.33 (s, 3H), 1.70-2.05 (m, 3H), 0.78 (d, J=6.8 Hz, 3H).

Conversion of EX-41 to Thiopyrimidine EX-42

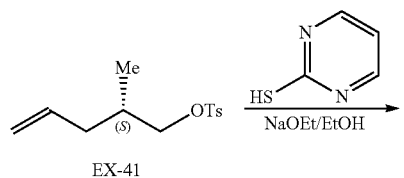

A reactor was charged with 2-mercaptopyrimidine (1.05 equiv.), ethanol (6 volumes), sodium ethoxide (1.05 equiv.), and a solution of EX-41 (1.0 equiv., scaling factor) in ethanol (0.5 volumes). The reaction mixture was warmed to about 65° C. and agitated for about 4 h before cooling to about 20° C. The reaction mixture was quenched with 5 wt % aqueous ammonium chloride solution (3 volumes) and diluted with dichloromethane (10 volumes). The layers were separated, and the aqueous layer was back-extracted with dichloromethane (5 volumes). The organic layers were combined and washed two times with saturated aqueous sodium chloride solution (3 volumes each). The organic layer was concentrated under reduced pressure to afford EX-42. ¹H NMR (400 MHz, DMSO-d₆): δ 8.58 (d, J=4.9 Hz, 2H), 7.16 (t, J=4.9 Hz, 1H), 5.75 (m, 1H), 4.90-5.10 (m, 2H), 3.13 (dd, J=6.3, 13.3 Hz, 1H), 2.96 (dd, J=7.4, 13.3 Hz, 1H), 2.26 (m, 1H), 1.85-2.05 (m, 2H), 0.93 (d, J=6.7 Hz, 3H).

Oxidation of EX-42 to EX-43

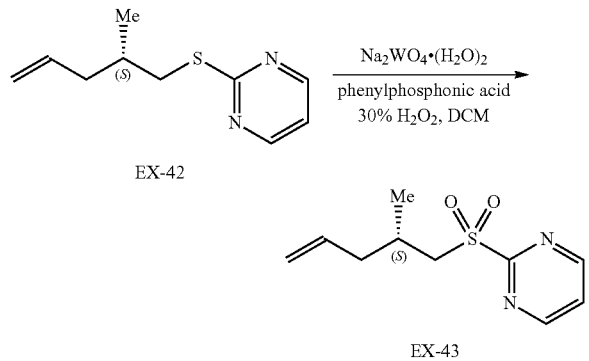

A reactor was charged with EX-42 (1.0 equiv., scaling factor), toluene (4 volumes), sodium tungstate dihydrate (0.1 equiv.), phenylphosphonic acid (0.1 equiv.) and tetrabutylammonium hydrogen sulfate (0.1 equiv.). The reaction mixture was cooled to about 10° C. and dosed with 30 wt % aqueous hydrogen peroxide solution (2.0 equiv.). The reaction mixture was warmed to about 20° C., agitated for about 1 h, cooled to about 10° C., and quenched with a 10 wt % aqueous sodium sulfite solution (5 volumes). The mixture was diluted with ethyl acetate (4 volumes), the phases were separated and the aqueous layer was back-extracted with ethyl acetate (4 volumes). The combined organic layers were washed sequentially with 15 wt % aqueous sodium bicarbonate solution (3 volumes), saturated aqueous sodium chloride solution (3 volumes) and water (3 volumes). The organic layer was concentrated under reduced pressure to afford EX-43. ¹H NMR (400 MHz, CDCl₃): δ 8.91 (d, J=4.7 Hz, 2H), 7.56 (t, J=4.7 Hz, 1H), 5.72 (m, 1H), 5.04-5.12 (m, 2H), 3.53 (dd, J=4.7, 14.5 Hz, 1H), 3.30 (dd, J=8.2, 14.5 Hz, 1H), 2.13-2.40 (m, 3H), 1.07 (d, J=7.0 Hz, 3H).

Conversion of EX-43 to EX-45

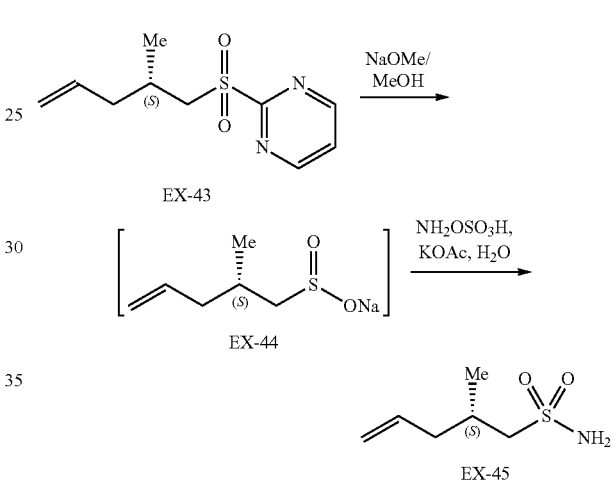

A reactor was charged with EX-43 (1.0 equiv., scaling factor) and methanol (8 volumes). The reaction mixture was cooled to about 0° C. and dosed with sodium methoxide (1.1 equiv.) solution in methanol (2 volumes). The reaction mixture was warmed to about 20° C. and agitated for about 1 h. Volatiles were removed under reduced pressure to give the crude EX-44.

Crude EX-44 was dissolved in water (6 volumes), washed two times with methyl tert-butyl ether (4 volumes each), and two times with dichloromethane (2 volumes each). Potassium acetate (2.5 equiv.) was charged to the aqueous EX-44 solution, the mixture was warmed to about 45° C., and hydroxylamine-O-sulfonic acid (1.0 equiv.) was charged. The reaction mixture was then agitated at about 45° C. for about 1.5 h. Upon cooling to about 20° C., the reaction mixture was extracted with ethyl acetate (13 volumes), the layers were separated, and the organic layer was washed sequentially with 1 M aqueous HCl solution (2.5 volumes), 15 wt % aqueous sodium bicarbonate solution (2.5 volumes) and saturated aqueous sodium chloride solution (2.5 volumes). The organic layer was concentrated to afford EX-45. ¹H NMR (400 MHz, CDCl₃): δ 5.75 (m, 1H), 5.39 (s, br, 2H), 5.04-5.11 (m, 2H), 3.20 (dd, J=4.4, 14.0 Hz, 1H), 2.96 (dd, J=7.2, 14.0 Hz, 1H), 2.05-2.30 (m, 3H), 1.13 (d, J=6.8 Hz, 3H).

Silylation of EX-45 to EX-46

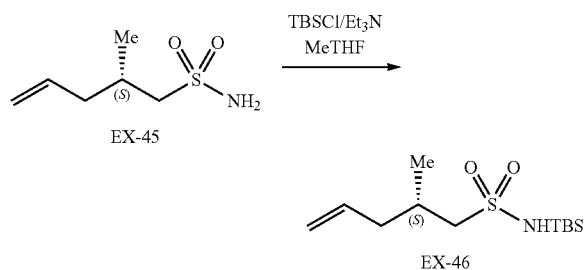

A reactor was charged with EX-45 (1.0 equiv., scaling factor), 2-methyltetrahydrofuran (4.5 volumes) and tert-butyldimethylchlorosilane (1.6 eqiuv). Triethylamine (2.3 equiv.) was charged and the reaction mixture was warmed to about 45° C. for about 20 h. The mixture was cooled to about 20° C., quenched with 5 wt % aqueous citric acid solution (20 volumes), and washed with methyl tert-butyl ether (20 volumes). The methyl tert-butyl ether layer was washed two times with water (10 volumes each) and concentrated to afford EX-46. $^1$H NMR (400 MHz, CDCl$_3$): δ 5.74 (m, 1H), 5.14-5.02 (m, 2H), 4.27 (s, br, 1H), 3.09 (dd, J=3.2, 14.0 Hz, 1H), 2.82 (dd, J=8.0, 14.0 Hz, 1H), 2.27-2.05 (m, 3H), 1.14 (d, J=6.4 Hz, 3H), 0.94 (s, 9H), 0.28 (s, 6H).

Deoxychlorination and Amination of EX-46 to EX-48 with Stoichiometric Amount of Triphenylphosphine Oxide

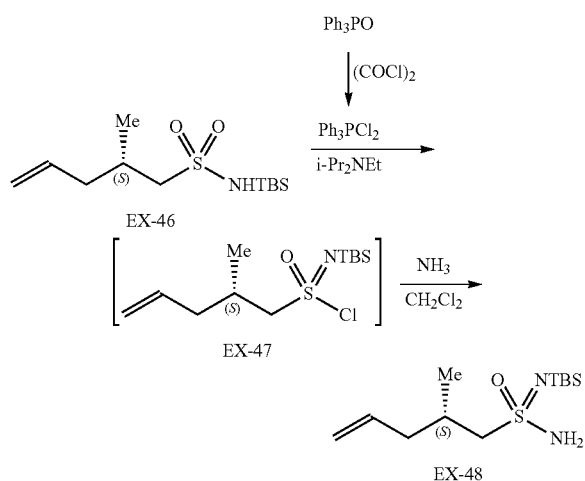

A reactor was charged with triphenylphosphine oxide (1.1 equiv.), and dichloromethane (10 volumes) and cooled to about 0° C. Oxalyl chloride (1.3 equiv.) was charged. The mixture was agitated at about 0° C. for about 0.5 h and then cooled to about −10° C. N,N-diisopropylethylamine (2.0 equiv.) was charged followed by the addition of a solution of EX-46 (1.0 equiv., scaling factor) in dichloromethane (4 volumes). The resulting solution was warmed to about 0° C. and agitated for 1 h to afford a solution of EX-47.

Another reactor was charged with dichloromethane (4 volumes), cooled to about −10° C., and charged with anhydrous ammonia via subsurface sparging until the solution is saturated. The EX-47 solution was transferred to this ammonia solution that had been precooled to about −10° C.) while maintaining a stream of ammonia gas via subsurface sparging and maintaining the reaction temperature below about 0° C. The resulting slurry was then agitated at about 0° C. for about 0.5 h and warmed to about 20° C. The reaction mixture was washed two times with 20% w/v aqueous ammonium chloride solution (12 volumes), and two times with water (5 volumes each) and concentrated to afford EX-48. $^1$H NMR (400 MHz, CDCl$_3$, mixture of about 1:1 diastereomers): δ 5.76 ppm (m, 1H), 5.02-5.13 (m, 2H), 4.37 (s, br, 2H), 3.16 (dd, J=4.2, 13.7 Hz, 0.5H), 3.13 (dd, J=4.8, 13.8 Hz, 0.5H), 2.93 (dd, J=6.9, 13.8 Hz, 0.5H), 2.88 (dd, J=7.4, 13.7 Hz, 0.5H), 2.05-2.30 (m, 3H), 1.13 (d, J=6.4 Hz, 1.5H), 1.11 (d, J=6.5 Hz, 1.5H), 0.89 (s, 9H), 0.12 (s, 3H), 0.11 (s, 3H).

Deoxychlorination and Amination of EX-46 to EX-48 with Catalytic Amount of Triphenylphosphine Oxide A reactor was charged with EX-46 (1.0 equiv., scaling factor), triphenylphosphine oxide (0.05 equiv.), 2,6-lutidine (2.0 equiv.) and dichloromethane (8 volumes) and cooled to about −10° C. Oxalyl chloride (1.4 equiv.) was added over about 1 h. The mixture was agitated at about 0° C. for about 4 h to afford a solution of EX-47.

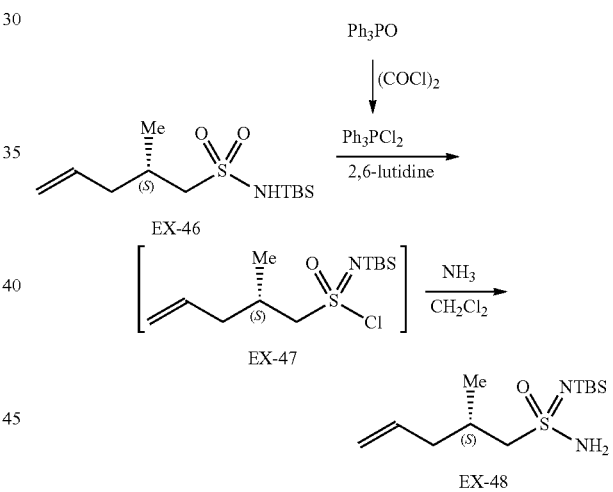

Another reactor was charged with dichloromethane (8 volumes), cooled to about −10° C., and charged with anhydrous ammonia via subsurface sparging until the solution was saturated. The EX-47 solution was transferred to this ammonia solution that had been precooled to about −10° C. while maintaining a stream of ammonia gas via subsurface sparging and maintaining the reaction temperature below about 0° C. The resulting slurry was then agitated at about 0° C. for about 1 h and warmed to about 20° C. and filtered. The cake was rinsed with dichloromethane (2 volumes) and the filtrate was returned to the reactor. The combined filtrate was washed with 20% w/v aqueous ammonium chloride solution (6 volumes), and two times with 5% w/v aqueous citric acid solution (8 volumes each). The organic layer was then washed two times with water (7 volumes each) and concentrated to afford EX-48. $^1$H NMR (400 MHz, CDCl$_3$, mixture of about 1:1 diastereomers): δ 5.76 ppm (m, 1H), 5.02-5.13 (m, 2H), 4.37 (s, br, 2H), 3.16 (dd, J=4.2, 13.7 Hz, 0.5H), 3.13 (dd, J=4.8, 13.8 Hz, 0.5H), 2.93 (dd, J=6.9, 13.8 Hz, 0.5H), 2.88 (dd, J=7.4, 13.7 Hz, 0.5H), 2.05-2.30 (m, 3H), 1.13 (d, J=6.4 Hz, 1.5H), 1.11 (d, J=6.5 Hz, 1.5H), 0.89 (s, 9H), 0.12 (s, 3H), 0.11 (s, 3H).

Conversion of EX-48 to EX-51

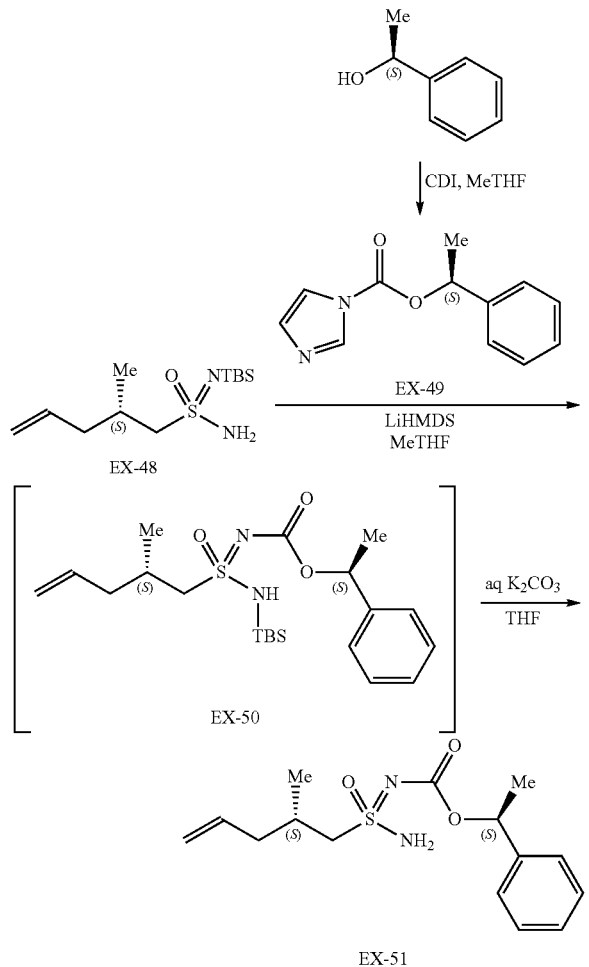

A reactor was charged with 1,1'-carbonyldiimidazole (CDI, 1.30 equiv.), (S)-1-phenylethanol (1.36 equiv.) and 2-methyltetrahydrofuran (7 volumes) and agitated at about 25° C. for 1 h. A solution of EX-48 (1.0 equiv., scaling factor) in 2-methyltetrahydrofuran (7 volumes) was added and the mixture was cooled to about −10° C. Lithium bis(trimethylsilyl)amide (1 M in tetrahydrofuran, 1.8 equiv.) was added and the mixture was warmed to about 0° C. and agitated for about 1 h. The reaction mixture was washed with 0.5 M aqueous HCl solution (10 volumes). The separated organic layer was combined with 2.5 M aqueous potassium carbonate solution (10 volumes) and the mixture was heated to about 50° C. and agitated for about 16 h. The aqueous layer was removed, and the organic layer was diluted with heptane (4 volumes) and extracted with two portions of 0.1 M aqueous sodium hydroxide solution (10 volumes). The combined aqueous sodium hydroxide phases were washed with toluene (10 volumes), and the aqueous layer was dosed with 2 M aqueous phosphoric acid to about pH 7. The aqueous layer was extracted with 10 volumes, and the organic layer was concentrated to afford EX-51. $^1$H NMR (400 MHz, CDCl$_3$, mixture of about 1:1 diastereomers, NH$_2$ signal appeared as a broad peak between 4-6 ppm): δ 7.21-7.40 (m, 5H), 5.55-5.76 (m, 2H), 4.95-5.12 (m, 2H), 3.40 (dd, J=4.4, 14.4 Hz, 0.5H), 3.34 (dd, J=4.4, 14.4 Hz, 0.5H), 3.17 (dd, J=7.6, 14.4 Hz, 0.5H), 3.05 (dd, J=7.6, 14.4 Hz, 0.5H), 2.00-2.29 (m, 3H), 1.55 (d, J=6.8 Hz, 3H), 1.10 (d, J=6.4 Hz, 3H).

Acylation of EX-51 to EX-52

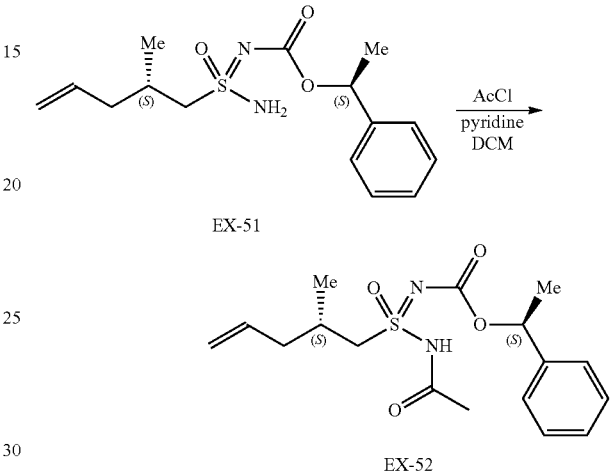

A reactor was charged with EX-51 (1.0 equiv., scaling factor), dichloromethane (8 volumes), and pyridine (1.5 equiv.). A solution of acetyl chloride in dichloromethane (1.0 M, 1.2 equiv.) was added and the mixture was agitated at about 20° C. for about 1 h. The mixture was diluted with water (0.5 volumes) and 1.0 M aqueous HCl solution (10 volumes). The organic layer was separated and washed with water (10 volumes) and concentrated to dryness. The crude concentrate was dissolved in isopropyl acetate (5 volumes), diluted with heptane (20 volumes), and the slurry was cooled to about 0° C. The slurry was agitated at about 0° C. for about 20 h and filtered to afford EX-52. $^1$H NMR (400 MHz, CDCl$_3$, mixture of about 1:1 diastereomers, NH signal appears as a broad peak from 9.5-10.5 ppm) 7.25-7.37 (m, 5H), 5.54-5.80 (m, 2H), 4.97-5.14 (m, 2H), 3.67 (dd, J=4.5, 11.8 Hz, 0.5H), 3.63 (dd, J=4.5, 11.8 Hz, 0.5H), 3.45 (dd, J=8.0, 11.0 Hz, 0.5H), 3.41 (dd, J=8.0, 11.0 Hz, 0.5H), 1.96-2.32 (m, 6H), 1.58 (d, J=1.8 Hz, 1.5H), 1.56 (d, J=1.8 Hz, 1.5H), 1.11 (d, J=3.3 Hz, 1.5H), 1.09 (d, J=3.3 Hz, 1.5H).

Resolution of EX-52 to EX-53

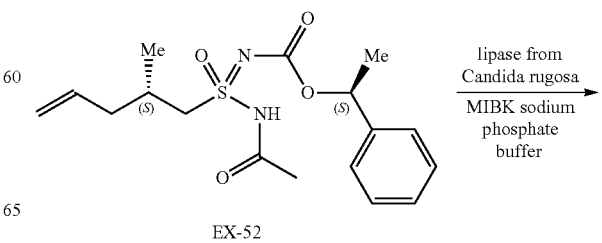

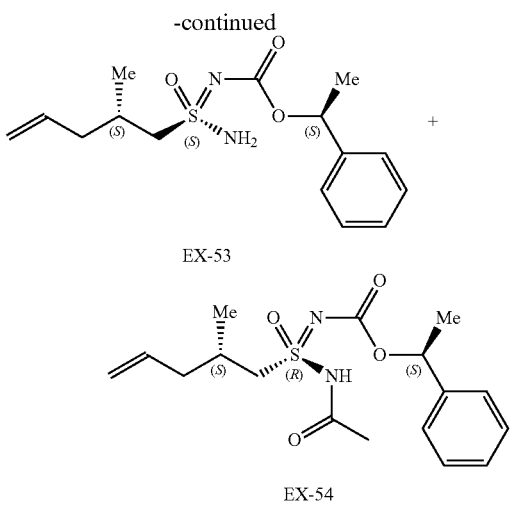

A reactor was charged with EX-52 (1.0 equiv., scaling factor), MIBK (5 volumes), sodium phosphate buffer (0.1 M, pH 7, 25 volumes), and *Candida rugosa* lipase (30 wt %). The mixture was agitated at about 20° C. for about 3 days. The mixture was diluted with MIBK (10 volumes) and the aqueous layer was removed. The organic layer was charged with filter aid and filtered with MIBK rinse (5 volumes). The filtered solution was washed about three times with 0.1 M NaHCO$_3$ solution (20 volumes) and one time with water (20 volumes). The solution was concentrated, diluted with heptane (10 volumes), and re-concentrated. The resulting solids were recrystallized in heptane (5 volumes) from about 40° C. to about 20° C., filtered, and rinsed with heptane (2 volumes). The cake was dried at about 40° C. to afford EX-53. EX-53 $^1$H NMR (400 MHz, CDCl$_3$): δ 7.26-7.40 (m, 5H), 5.71 (q, J=6.8 Hz, 1H), 5.60 (m, 1H), 5.41 (br s, 2H), 5.01 (m, 2H), 3.41 (dd, J=4.4, 14.4 Hz, 1H), 3.04 (dd, J=8.0, 14.4 Hz, 1H), 2.24 (m, 1H), 2.09 (m, 2H), 1.56 (d, J=6.8 Hz, 3H), 1.11 (d, J=6.8 Hz, 3H). EX-54 $^1$H NMR (400 MHz, CDCl$_3$): δ 7.24-7.39 (m, 5H), 5.75 (q, J=6.6 Hz, 1H), 5.65 (m, 1H), 4.99-5.01 (m, 2H), 3.67 (dd, J=4.6, 14.5 Hz, 1H), 3.04 (dd, J=7.8, 14.5 Hz, 1H), 2.07-2.30 (m, 3H), 2.05 (s, 3H), 1.57 (d, J=6.6 Hz, 3H), 1.09 (d, J=6.7 Hz, 3H).

Displacement of EX-41 to Form EX-56

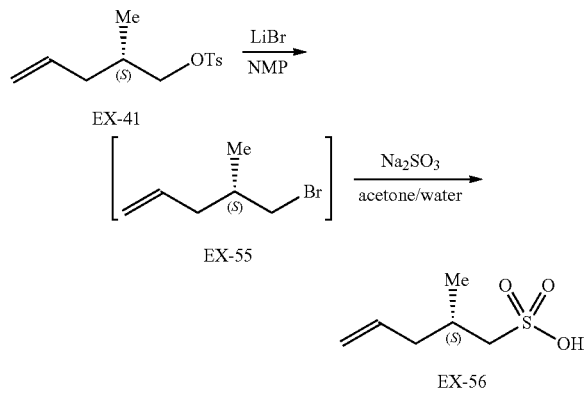

A reactor was charged with EX-41 (1.0 equiv., scaling factor), lithium bromide (1.8 equiv.), NMP (5 volumes), and heated to about 50° C. for about 2 h. The mixture was cooled to about 20° C. and diluted with methyl tert-butyl ether (23 volumes) and water (23 volumes). The organic layer was separated and washed with water (8 volumes) and concentrated to about 4 volumes to afford EX-55 as a solution in methyl tert-butyl ether. $^1$H NMR (400 MHz, CD$_3$OD) δ 5.91 (ddt, J=7.1, 10.2, 17.3 Hz, 1H), 5.15-5.24 (m, 2H), 3.47-3.62 (m, 2H), 2.27-2.38 (m, 1H), 2.17 (dtt, J=1.3, 7.1, 13.9 Hz, 1H), 2.00 (qt, J=5.4, 6.7 Hz, 1H), 1.15 (d, J=6.7 Hz, 3H).

A solution of EX-55 in methyl tert-butyl ether (4 volumes) was charged with sodium sulfite (1.5 equiv.), acetone (4 volumes), and water (3 volumes). The mixture was heated to about 65° C. for about 17 h as methyl tert-butyl ether was distilled off under atmospheric pressure. Sodium sulfite (1.5 equiv.) and water (1 volume) were added and the reaction was heated at about 65° C. for about 48 h. The mixture was cooled to about 20° C. and acetone (70 volumes) was added. The slurry was filtered to remove solids, and the filtrate was concentrated to afford EX-56. $^1$H NMR (400 MHz, CD$_3$OD) δ 5.76-5.91 (m, 1H), 5.01-5.16 (m, 2H), 2.89 (dd, J=5.0, 13.9 Hz, 1H), 2.64 (dd, J=7.4, 13.9 Hz, 1H), 2.24-2.35 (m, 1H), 2.03-2.23 (m, 2H), 1.12 (d, J=6.6 Hz, 3H).

Chlorination of EX-56 and Amidation to Form EX-45

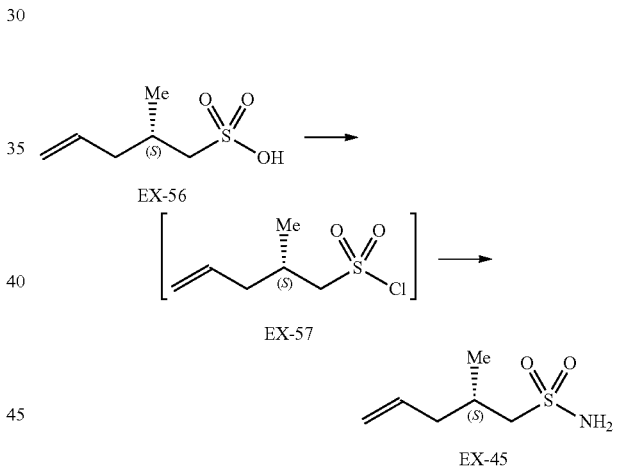

A reactor was charged with EX-56 (1.0 equiv. scaling factor), tetrahydrofuran (10 volumes), and DMF (0.5 equiv.). Thionyl chloride (2.3 equiv.) was then added dropwise and the mixture was agitated at about 20° C. for about 30 min to afford a solution of EX-57.

Another reactor containing concentrated ammonium hydroxide (about 28 wt %, 10 volumes) was charged with the EX-57 solution, and the reaction mixture was agitated for 10 min. The mixture was diluted with ethyl acetate (40 volumes) and water (20 volumes), and the organic layer was concentrated to afford EX-45. $^1$H NMR (400 MHz, CDCl$_3$): δ 5.75 (m, 1H), 5.39 (s, br, 2H), 5.04-5.11 (m, 2H), 3.20 (dd, J=4.4, 14.0 Hz, 1H), 2.96 (dd, J=7.2, 14.0 Hz, 1H), 2.05-2.30 (m, 3H), 1.13 (d, J=6.8 Hz, 3H).

Bis-acetylation of EX-48 to EX-58

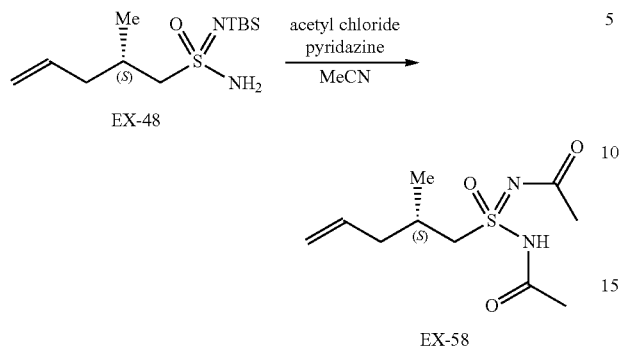

A reactor was charged with EX-48 (1.0 equiv., scaling factor) and acetonitrile (10 volumes). The solution was charged with a mixture of acetyl chloride (3.0 equiv.) and pyridazine (3.0 equiv.) in acetonitrile (18 volumes) and agitated at about 20° C. for about 4 h. Methanol (5.0 equiv.) was added and the mixture was agitated at about 20° C. for about 1 h. The mixture was diluted with ethyl acetate (30 volumes) and washed with 1 M aqueous HCl solution (5 volumes). The organic layer was concentrated and purified by chromatography using ethyl acetate and heptane to afford EX-58. $^1$H NMR (400 MHz, CDCl$_3$): δ 5.74 (m, 1H), 5.11 (m, 2H), 3.65 (dd, J=4.4, 14.4 Hz, 1H), 3.45 (dd, J=8.0, 14.4 Hz, 1H), 2.32 (m, 1H), 2.18 (m, 2H), 2.17 (s, 6H), 1.15 (d, J=6.8, 3H).

Desymmetrization of EX-58 to EX-59

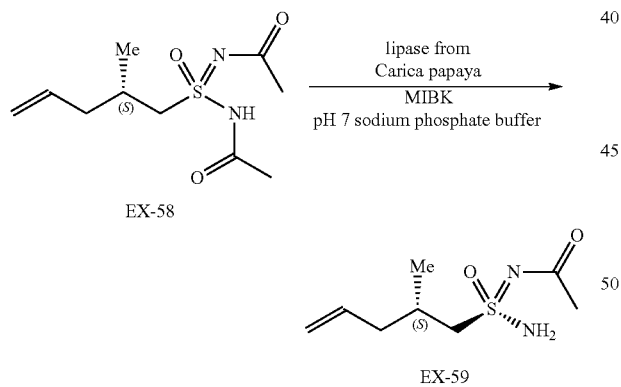

A reactor was charged with EX-58 (1.0 equiv., scaling factor), methyl isobutyl ketone (5 volumes), sodium phosphate buffer (0.1 M, pH 7, 25 volumes), and *Carica papaya* lipase (50 wt %). The mixture was stirred at about 30° C. for about 48 h. The mixture was extracted with dichloromethane. The organic layer was concentrated and purified by chromatography using ethyl acetate and heptane to afford EX-59. $^1$H NMR (400 MHz, CDCl$_3$): δ 5.74 (m, 1H), 5.11 (m, 2H), 3.47 (dd, J=4.8, 14.4 Hz, 1H), 3.11 (dd, J=7.2, 14.4 Hz, 1H), 2.28 (m, 1H), 2.18 (m, 2H), 2.13 (s, 3H), 1.17 (d, J=6.8 Hz, 3H).

Deprotection of EX-54 to EX-59

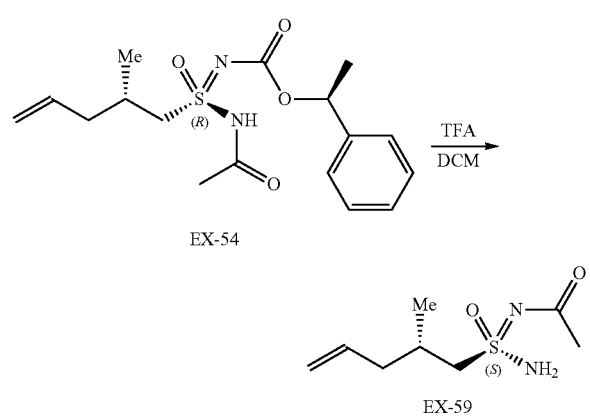

A reactor was charged with EX-54 (1.0 equiv., scaling factor), dichloromethane (20 volumes), and trifluoroacetic acid (10 equiv.). The reaction mixture was stirred at about 20° C. for about 2.5 h. The mixture was concentrated and then concentrated with the aid of isopropyl acetate followed by heptane. The concentrated reaction mixture was dissolved in heptane (5 volumes) and the resulting solids were collected by vacuum filtration and dried to afford EX-59. $^1$H NMR (400 MHz, CDCl$_3$): δ 5.71 (m, 1H), 5.52 (br. s, 1H), 5.08 (m, 2H), 3.45 (dd, J=14.4, 4.7 Hz, 1H), 3.09 (dd, J=14.4, 7.5 Hz, 1H), 2.26 (m, 1H), 2.26 (m, 2H), 2.11 (s, 3H), 1.15 (d, J=6.9 Hz, 3H).

Coupling of EX-59 and EX-60 to EX-61

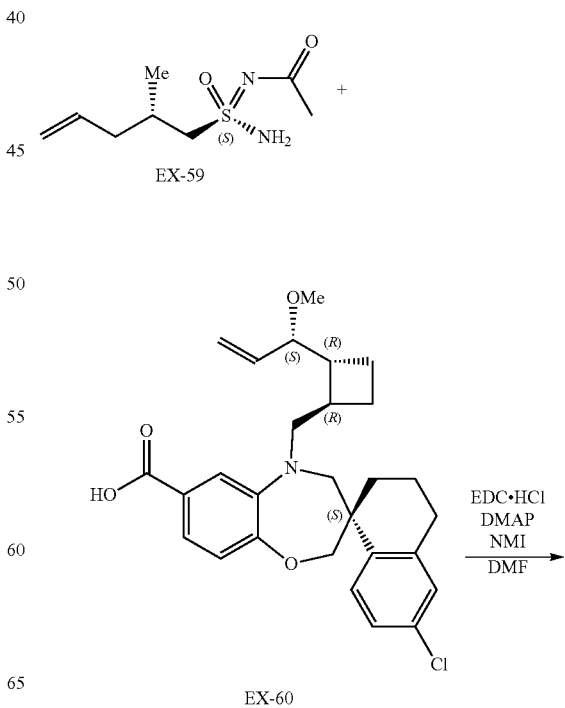

-continued

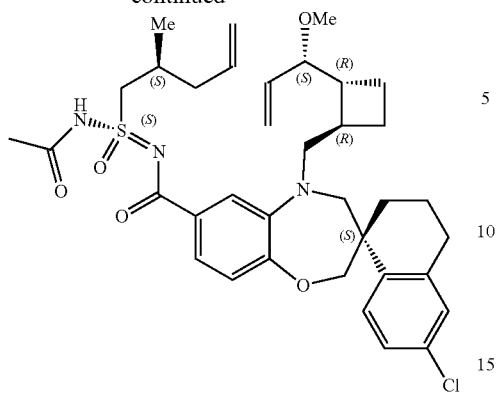

EX-61

-continued

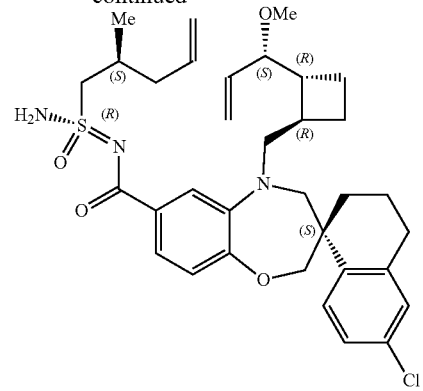

EX-62

A reactor was charged with EX-60 (1.0 equiv., scaling factor), N,N-dimethylformamide (10 volumes), and 1-methylimidazole (3.0 equiv.). 4-dimethylaminopyridine (1.0 equiv.) followed by 1-(3-dimethylaminopyropyl)-3-ethylcarbodiimide hydrochloride (1.30 equiv.) were added to the reactor. Contents are agitated for about 5 min at about 20° C. EX-59 (1.06 equiv.) was then added to the reactor. Contents were agitated for about 8 h at about 20° C. The reaction mixture was diluted with isopropyl acetate (10 volumes) and washed with an aqueous solution of sodium chloride (24 wt %, 10 volumes). The organic layer was washed with 5 wt % aqueous citric acid (10 volumes), 0.1 M aqueous sodium carbonate solution (10 volumes) twice, and then an aqueous solution of sodium chloride (24 wt %, 10 volumes). The organic layer was concentrated to dryness and purified by flash column chromatography using ethyl acetate and heptane to afford EX-61. $^1$H NMR (400 MHz, DMSO-$d_6$): 7.67 (d, J=8.6 Hz, 1H), 7.45 (d, J=1.9 Hz, 1H), 7.38 (dd, J=8.2, 1.8 Hz, 1H), 7.26 (dd, J=8.6, 2.4 Hz, 1H), 7.20 (d, J=2.4 Hz, 1H), 6.89 (d, J=8.2 Hz, 1H), 5.85-5.71 (m, 1H), 5.54-5.65 (m, 1H), 5.15-5.24 (m, 2H), 5.02-5.11 (m, 2H), 4.01-4.10 (m, 2H), 3.43-3.72 (m, 6H), 3.17-3.33 (m, 5H), 2.68-2.87 (m, 2H), 2.47 (dd, J=11.0, 5.7 Hz, 1H), 2.05-2.34 (m, 3H), 1.78-2.04 (m, 7H), 1.47-1.78 (m, 4H), 1.07 (d, J=6.4 Hz, 3H).

A reactor was charged with EX-61 (1.0 equiv., scaling factor), methyl tert-butyl ether (30 volumes), potassium phosphate buffer (0.1 M, pH 7, 90 volumes), and *Pseudomonas stutzeri* lipase (100 wt %). The mixture was stirred at about 20° C. for about 40 h. The mixture was heated at about 40° C. for about 6 days and cooled to about 20° C. The mixture was diluted with methyl tert-butyl ether (50 volumes) and dichloromethane (100 volumes) and filtered. The mixture was diluted with water (100 volumes) and the phases were separated. The aqueous layer was back-extracted three times with dichloromethane (200 volumes per extraction), and the combined organic layers were concentrated to get EX-62. $^1$H NMR (400 MHz, CDCl$_3$): δ 7.70 (d, J=8.4 Hz, 1H), 7.49-7.55 (m, 2H), 7.17 (dd, J=8.8, 2.4 Hz, 1H), 7.09 (d, J=2.0 Hz, 1H), 6.91 (d, J=8.0 Hz, 1H), 5.70-5.83 (m, 3H), 5.59 (ddd, J=16.8, 10.4, 7.6 Hz, 1H), 5.04-5.22 (m, 4H), 4.12, 4.06 (ABq, J=12.0 Hz, 2H), 3.57-3.69 (m, 2H), 3.41-3.54 (m, 2H), 3.17-3.36 (m, 6H), 2.70-2.84 (m, 2H), 2.48-2.59 (m, 1H), 2.31-2.40 (m, 1H), 2.08-2.29 (m, 3H), 1.95-2.06 (m, 2H), 1.46-1.94 (m, 6H), 1.15 (d, J=6.8 Hz, 3H).

S$_N$Ar of A and 4-fluoro-3-nitrobenzoic Acid to B

Deacetylation of EX-61 to EX-62

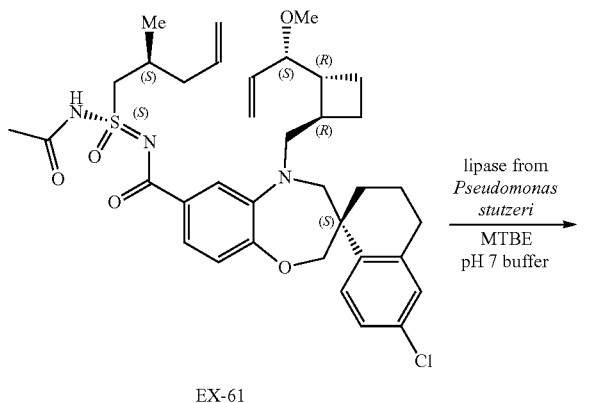

EX-61

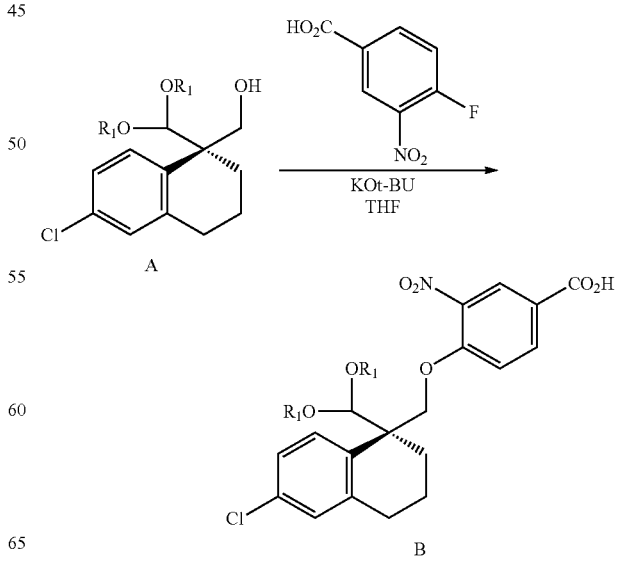

A reactor was charged with A (EX-31, EX-32, or EX-35) (1.0 equiv., scaling factor), 4-fluoro-3-nitrobenzoic acid (1.2 equiv.), and tetrahydrofuran (15 volumes). The reaction mixture was charged with a solution of potassium tert-butoxide in tetrahydrofuran (2.5 equiv.) over about 10 minutes. The reaction mixture was agitated at about 20° C. for about 1 hour. The reaction mixture was quenched with saturated aqueous ammonium chloride (20 volumes) and extracted with ethyl acetate (80 volumes). The organic layer was washed with water (20 volumes), dried over sodium sulfate, filtered, and concentrated. The crude product was purified by chromatography using ethyl acetate, heptane, and acetic acid to afford B (EX-63, EX-64, EX-65).

EX-63: $R_1$=CH$_3$, $^1$H NMR (400 MHz, CDCl$_3$) δ 8.59 (s, 1H), 8.36-8.16 (m, 1H), 7.69 (d, J=8.3 Hz, 1H), 7.15-7.06 (m, 3H), 4.73 (s, 1H), 4.28 (d, J=8.7 Hz, 1H), 4.19 (d, J=8.7 Hz, 1H), 3.48 (s, 3H), 3.42 (s, 3H), 2.75 (td, J=16.7, 13.4, 8.4 Hz, 2H), 2.11 (t, J=10.9 Hz, 1H), 2.04-1.90 (m, 2H), 1.71 (dt, J=10.6, 5.2 Hz, 1H).

EX-64: $R_1$=cyclic, —CH$_2$CH$_2$—, $^1$H NMR (400 MHz, CDCl$_3$) δ 8.57 (d, J=2.2 Hz, 1H), 8.21 (dd, J=8.8, 2.2 Hz, 1H), 7.71-7.43 (m, 1H), 7.13 (dd, J=5.7, 3.3 Hz, 3H), 5.30 (d, J=3.1 Hz, 1H), 4.44 (d, J=8.8 Hz, 1H), 4.27 (d, J=8.8 Hz, 1H), 4.01-3.77 (m, 4H), 2.79 (q, J=5.4 Hz, 2H), 2.23-2.09 (m, 1H), 2.09-1.96 (m, 2H), 1.85-1.72 (m, 1H).

EX-65: $R_1$=cyclic, —CH$_2$CH$_2$CH$_2$—, H NMR (400 MHz, CDCl$_3$) δ 8.59 (d, J=2.2 Hz, 1H), 8.22 (dd, J=8.8, 2.2 Hz, 1H), 7.73 (d, J=8.5 Hz, 1H), 7.17-7.09 (m, 3H), 4.96 (s, 1H), 4.31 (d, J=8.7 Hz, 1H), 4.19 (d, J=8.7 Hz, 1H), 4.08 (dt, J=11.5, 3.5 Hz, 2H), 3.77 (dtd, J=18.6, 12.0, 2.5 Hz, 2H), 2.76 (dt, J=12.6, 5.4 Hz, 2H), 2.23-2.09 (m, 1H), 2.09-1.87 (m, 2H), 1.78-1.65 (m, 1H), 1.35-1.23 (m, 2H).

Coupling of EX-63 and EX-53 to EX-66

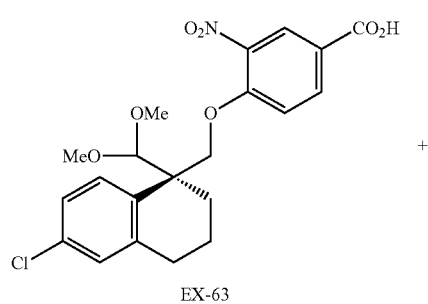

EX-63

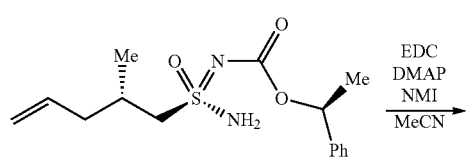

EX-53

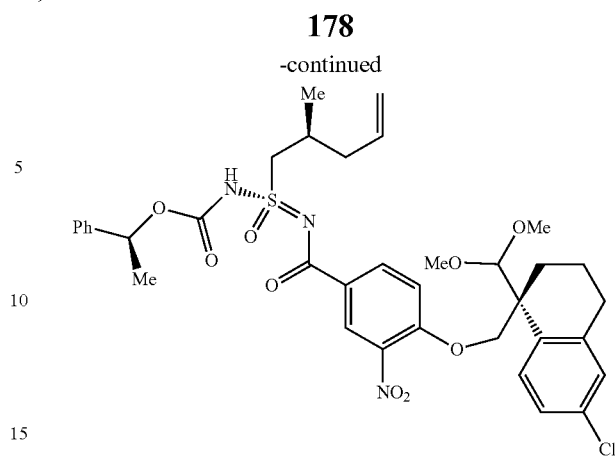

EX-66

A reactor was charged with EX-63 (1.0 equiv., scaling factor), EDC.HCl (1.3 equiv.), DMAP (1.0 equiv.), acetonitrile (50 volumes), NMI (3.0 equiv.), and EX-53 (1.1 equiv.). The mixture was agitated at about 20° C. for about 5 hours. The mixture was diluted with ethyl acetate (300 volumes) and the organic layer was washed with 5 wt % aqueous citric acid (150 volumes), 10% aqueous NaOH (150 volumes), and water (150 volumes). The organic layer was dried over sodium sulfate, filtered, and concentrated. The crude product was purified by chromatography using ethyl acetate to afford EX-66. $^1$H NMR (400 MHz, CDCl$_3$) δ 8.51 (d, J=2.1 Hz, 1H), 8.22-8.04 (m, 1H), 7.70 (d, J=8.4 Hz, 1H), 7.32 (dd, J=13.2, 6.1 Hz, 1H), 7.21-7.06 (m, 7H), 6.83 (d, J=8.8 Hz, 1H), 5.57 (dddd, J=37.3, 31.1, 17.6, 7.2 Hz, 3H), 4.97 (dd, J=13.6, 8.6 Hz, 2H), 4.73 (s, 1H), 4.28-4.00 (m, 2H), 3.46 (s, 3H), 3.38 (s, 3H), 3.24-2.90 (m, 2H), 2.83-2.62 (m, 2H), 2.12-2.00 (m, 2H), 1.95-1.83 (m, 2H), 1.69 (d, J=11.2 Hz, 2H), 1.32 (d, J=6.5 Hz, 3H), 0.96 (d, J=6.1 Hz, 3H).

Deprotection of EX-66 to EX-67

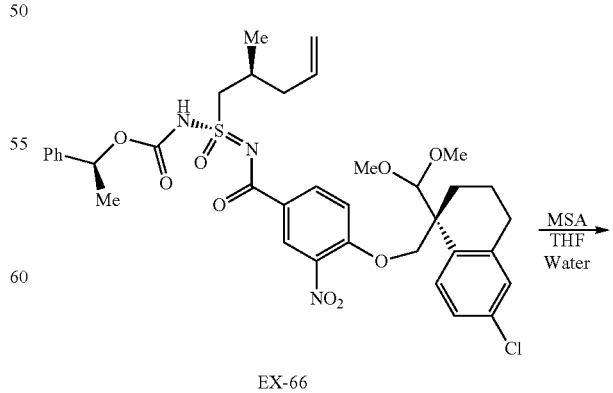

EX-66

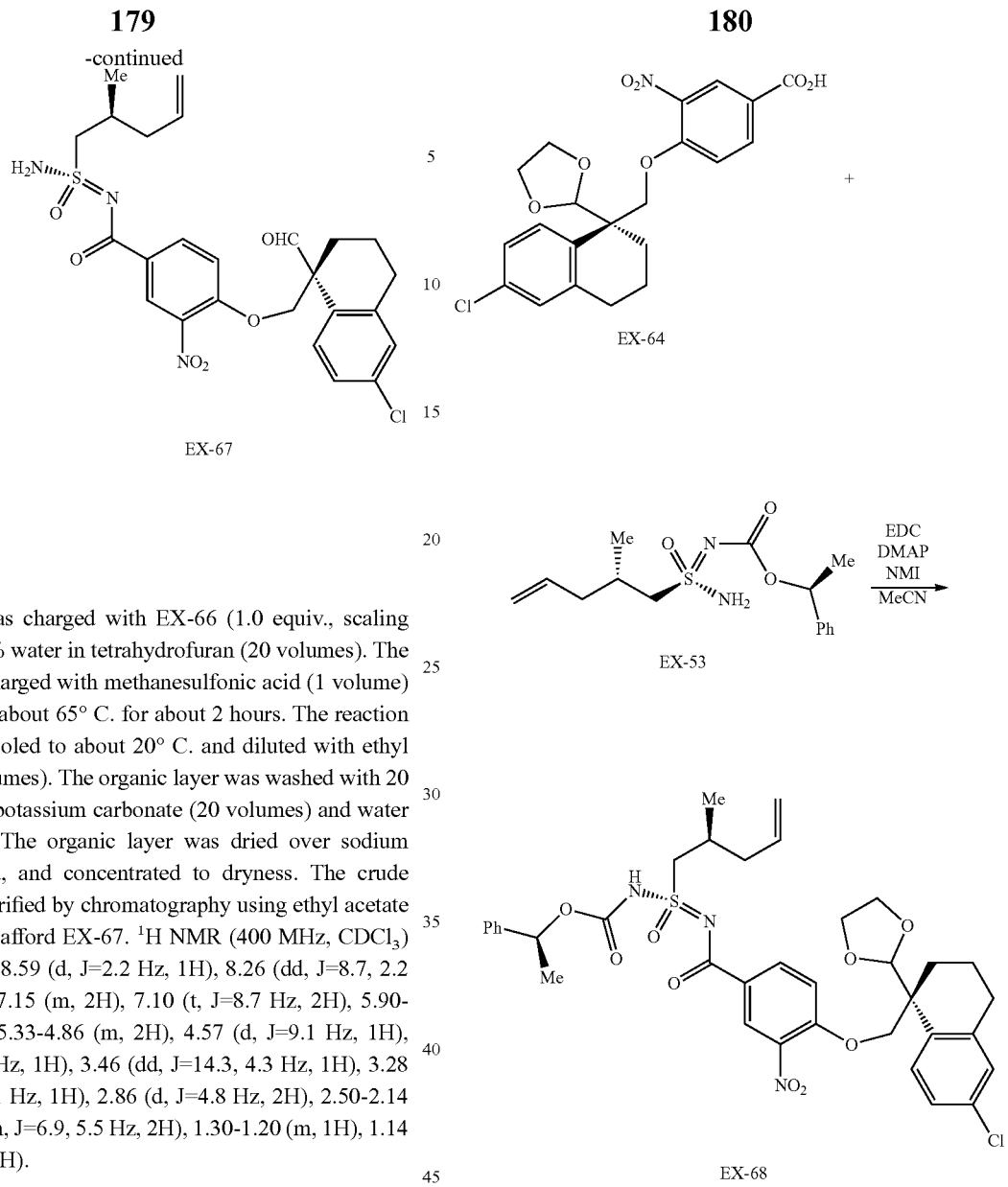

EX-67

EX-64

EX-53

EX-68

A reactor was charged with EX-66 (1.0 equiv., scaling factor) and 15% water in tetrahydrofuran (20 volumes). The solution was charged with methanesulfonic acid (1 volume) and agitated at about 65° C. for about 2 hours. The reaction mixture was cooled to about 20° C. and diluted with ethyl acetate (40 volumes). The organic layer was washed with 20 wt % aqueous potassium carbonate (20 volumes) and water (20 volumes). The organic layer was dried over sodium sulfate, filtered, and concentrated to dryness. The crude product was purified by chromatography using ethyl acetate and heptane to afford EX-67. $^1$H NMR (400 MHz, CDCl$_3$) δ 9.55 (s, 1H), 8.59 (d, J=2.2 Hz, 1H), 8.26 (dd, J=8.7, 2.2 Hz, 1H), 7.24-7.15 (m, 2H), 7.10 (t, J=8.7 Hz, 2H), 5.90-5.61 (m, 3H), 5.33-4.86 (m, 2H), 4.57 (d, J=9.1 Hz, 1H), 4.25 (d, J=8.9 Hz, 1H), 3.46 (dd, J=14.3, 4.3 Hz, 1H), 3.28 (dd, J=14.4, 8.1 Hz, 1H), 2.86 (d, J=4.8 Hz, 2H), 2.50-2.14 (m, 4H), 1.95 (h, J=6.9, 5.5 Hz, 2H), 1.30-1.20 (m, 1H), 1.14 (d, J=6.6 Hz, 3H).

Coupling of EX-64 and EX-53 to EX-68

A reactor was charged with EX-64 (1.0 equiv., scaling factor), EDC.HCl (1.3 equiv.), DMAP (1.0 equiv.), acetonitrile (10 volumes), NMI (3.0 equiv.), and EX-53 (1.1 equiv.). The mixture was agitated at about 20° C. for about 5 hours. The mixture was diluted with ethyl acetate (50 volumes) and the organic layer was washed with 5 wt % aqueous citric acid (25 volumes), 10% aqueous NaOH (25 volumes), and water (25 volumes). The organic layer was dried over sodium sulfate, filtered, and concentrated. The crude product was purified by chromatography using ethyl acetate and heptane to afford EX-68. $^1$H NMR (400 MHz, CDCl$_3$) δ 8.58 (d, J=2.2 Hz, 1H), 8.21 (dd, J=8.8, 2.2 Hz, 1H), 7.60 (d, J=9.3 Hz, 1H), 7.41-7.30 (m, 6H), 7.17-7.03 (m, 3H), 5.89 (q, J=6.6 Hz, 1H), 5.68 (ddt, J=17.2, 10.2, 6.9 Hz, 1H), 5.30 (s, 1H), 5.19-4.99 (m, 2H), 4.41 (d, J=8.8 Hz, 1H), 4.24 (d, J=8.8 Hz, 1H), 3.94-3.68 (m, 5H), 3.55 (dd, J=14.5, 7.8 Hz, 1H), 2.80-2.73 (m, 2H), 2.31 (qd, J=6.9, 4.4 Hz, 1H), 2.19-2.08 (m, 4H), 2.03-1.91 (m, 1H), 1.77 (td, J=10.9, 9.2, 4.6 Hz, 1H), 1.63 (d, J=6.6 Hz, 3H), 1.13 (d, J=6.7 Hz, 3H).

Deprotection of EX-68 to EX-67

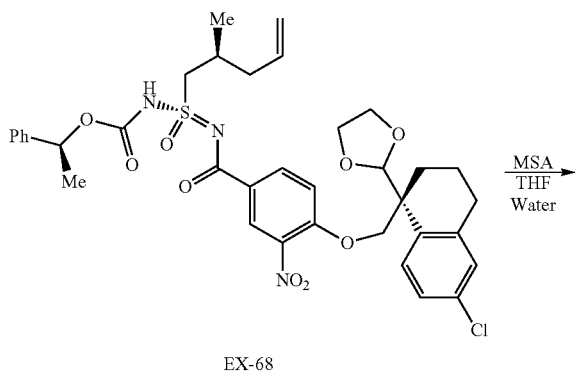

EX-68

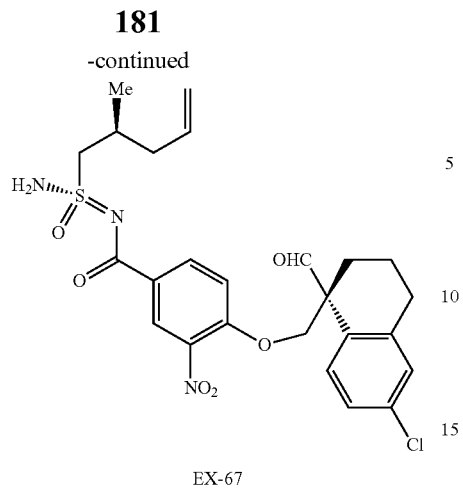

EX-67

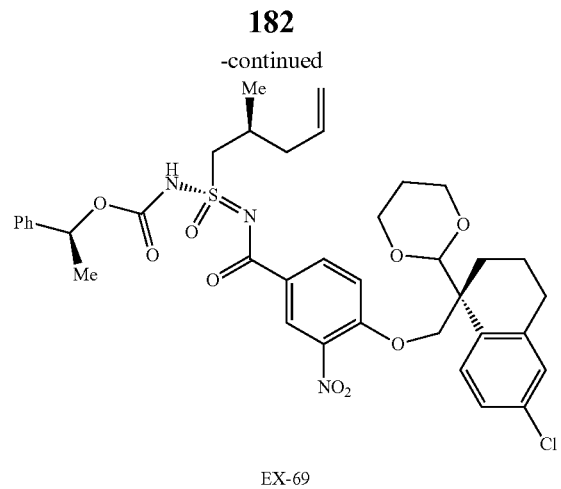

EX-69

A reactor was charged with EX-68 (1.0 equiv., scaling factor) and 15% water in tetrahydrofuran (30 volumes). The solution was charged with methanesulfonic acid (1 volume) and agitated at about 65° C. for about 6 hours. The reaction mixture was cooled to about 20° C. and diluted with ethyl acetate (300 volumes). The organic layer was washed with 20 wt % aqueous potassium carbonate (150 volumes) and water (150 volumes). The organic layer was dried over sodium sulfate, filtered, and concentrated to dryness. The crude product was purified by chromatography using ethyl acetate and heptane to afford EX-67. $^1$H NMR (400 MHz, CDCl$_3$) δ 9.55 (s, 1H), 8.59 (d, J=2.2 Hz, 1H), 8.26 (dd, J=8.7, 2.2 Hz, 1H), 7.24-7.15 (m, 2H), 7.10 (t, J=8.7 Hz, 2H), 5.90-5.61 (m, 3H), 5.33-4.86 (m, 2H), 4.57 (d, J=9.1 Hz, 1H), 4.25 (d, J=8.9 Hz, 1H), 3.46 (dd, J=14.3, 4.3 Hz, 1H), 3.28 (dd, J=14.4, 8.1 Hz, 1H), 2.86 (d, J=4.8 Hz, 2H), 2.50-2.14 (m, 4H), 1.95 (h, J=6.9, 5.5 Hz, 2H), 1.30-1.20 (m, 1H), 1.14 (d, J=6.6 Hz, 3H).

Coupling of EX-65 and EX-53 to EX-69

A reactor was charged with EX-65 (1.0 equiv., scaling factor), EDC.HCl (1.3 equiv.), DMAP (1.0 equiv.), acetonitrile (10 volumes), NMI (3.0 equiv.), and EX-53 (1.1 equiv.). The mixture was agitated at about 20° C. for about 5 hours. The mixture was diluted with ethyl acetate (100 volumes) and the organic layer was washed with 5 wt % aqueous citric acid (50 volumes), 10% aqueous NaOH (50 volumes), and water (50 volumes). The organic layer was dried over sodium sulfate, filtered, and concentrated. The crude product was purified by chromatography using ethyl acetate to afford EX-69. $^1$H NMR (400 MHz, CDCl$_3$) δ 8.58 (d, J=2.2 Hz, 1H), 8.20 (dd, J=8.8, 2.2 Hz, 1H), 7.74 (d, J=8.5 Hz, 1H), 7.35 (q, J=4.2, 3.6 Hz, 7H), 7.18-6.95 (m, 3H), 5.88 (q, J=6.6 Hz, 1H), 5.77-5.49 (m, 1H), 5.14-4.93 (m, 4H), 4.27 (d, J=8.7 Hz, 1H), 4.20-4.03 (m, 4H), 3.90-3.68 (m, 3H), 3.55 (dd, J=14.5, 7.8 Hz, 1H), 2.75 (dt, J=13.7, 5.2 Hz, 2H), 2.32 (td, J=7.0, 4.5 Hz, 1H), 2.23-2.08 (m, 4H), 1.98 (td, J=10.0, 9.3, 4.5 Hz, 1H), 1.62 (d, J=6.6 Hz, 3H), 1.13 (d, J=6.7 Hz, 3H).

Deprotection of EX-69 to EX-67

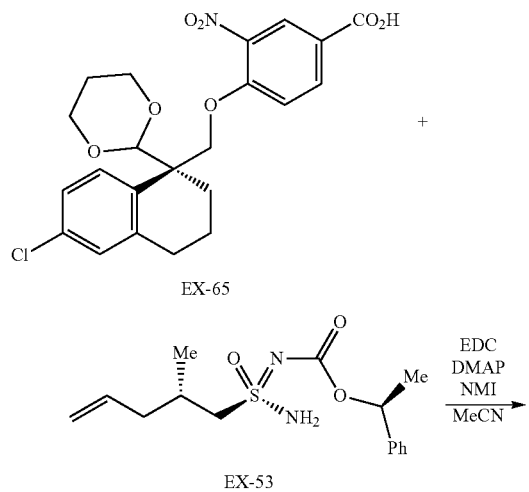

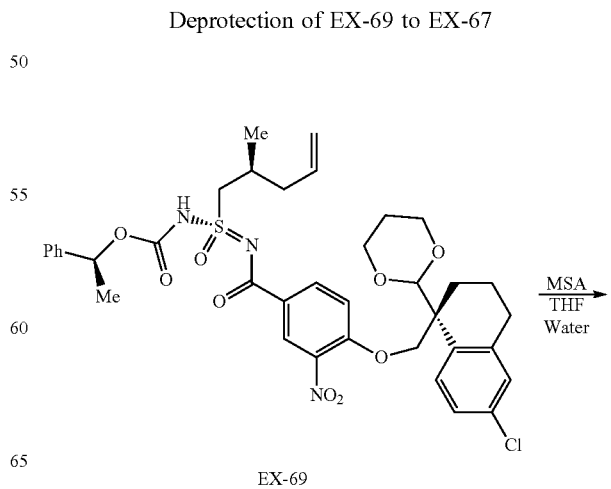

EX-69

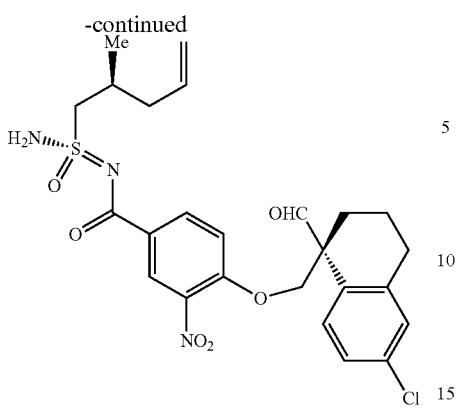

EX-67

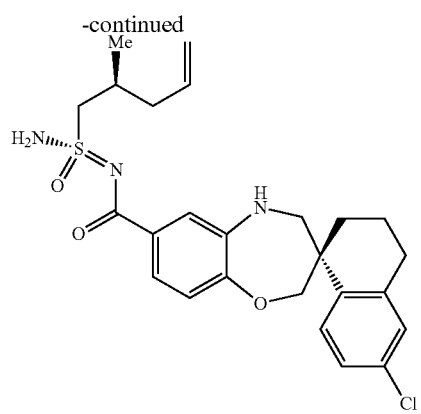

EX-70

A reactor was charged with EX-69 (1.0 equiv., scaling factor) and 15% water in tetrahydrofuran (30 volumes). The solution was charged with methanesulfonic acid (1 volume) and agitated at about 65° C. for about 24 hours. The reaction mixture was cooled to about 20° C. and diluted with ethyl acetate (300 volumes). The organic layer was washed with 20 wt % aqueous potassium carbonate (150 volumes) and water (150 volumes). The organic layer was dried over sodium sulfate, filtered, and concentrated to dryness. The crude product was purified by chromatography using ethyl acetate and heptane to afford EX-67. $^1$H NMR (400 MHz, CDCl$_3$) δ 9.55 (s, 1H), 8.59 (d, J=2.2 Hz, 1H), 8.26 (dd, J=8.7, 2.2 Hz, 1H), 7.24-7.15 (m, 2H), 7.10 (t, J=8.7 Hz, 2H), 5.90-5.61 (m, 3H), 5.33-4.86 (m, 2H), 4.57 (d, J=9.1 Hz, 1H), 4.25 (d, J=8.9 Hz, 1H), 3.46 (dd, J=14.3, 4.3 Hz, 1H), 3.28 (dd, J=14.4, 8.1 Hz, 1H), 2.86 (d, J=4.8 Hz, 2H), 2.50-2.14 (m, 4H), 1.95 (h, J=6.9, 5.5 Hz, 2H), 1.30-1.20 (m, 1H), 1.14 (d, J=6.6 Hz, 3H).

A reactor was charged with EX-67 (1.0 equiv., scaling factor), iron (30 equiv.), and acetic acid (10 volumes). The mixture was agitated at about 70° C. for about 1 hour. The reaction mixture was cooled to about 20° C. and charged with sodium triacetoxyborohydride (3.0 equiv.). The mixture was agitated at about 20° C. for approximately 40 minutes. The reaction mixture was diluted with ethyl acetate (40 volumes) and filtered through Celite. The organic layer was washed twice with 20 wt % aqueous potassium carbonate (20 volumes) and once with water (20 volumes). The organic layer was dried over sodium sulfate, filtered, and concentrated to dryness. The crude product was purified by chromatography using ethyl acetate and heptane to afford EX-70. $^1$H NMR (400 MHz, CDCl$_3$) δ 7.86 (d, J=8.5 Hz, 1H), 7.68-7.38 (m, 2H), 7.16 (dd, J=8.5, 2.3 Hz, 1H), 7.08 (d, J=2.3 Hz, 1H), 6.90 (d, J=8.3 Hz, 1H), 5.83-5.67 (m, 3H), 5.25-4.80 (m, 2H), 4.28-4.03 (m, 3H), 3.63-3.38 (m, 2H), 3.38-3.22 (m, 2H), 2.73 (t, J=6.2 Hz, 2H), 2.33 (dq, J=11.1, 6.6 Hz, 1H), 2.23-2.09 (m, 2H), 2.05 (d, J=0.8 Hz, 1H), 1.97-1.61 (m, 2H), 1.26 (td, J=7.2, 0.8 Hz, 1H), 1.14 (d, J=6.6 Hz, 3H).

Reductive Cyclization of EX-67 to EX-70

Coupling of EX-70 and EX-11 to EX-71

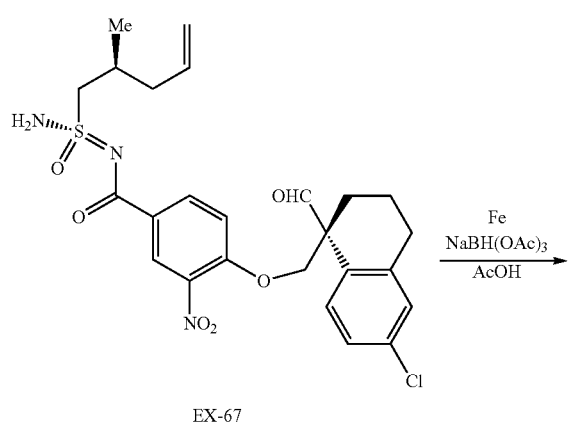

EX-67

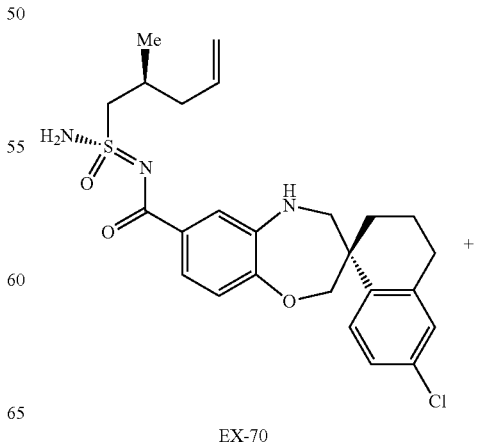

EX-70

-continued

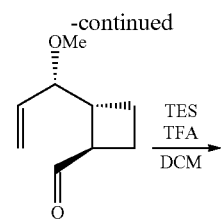

EX-11

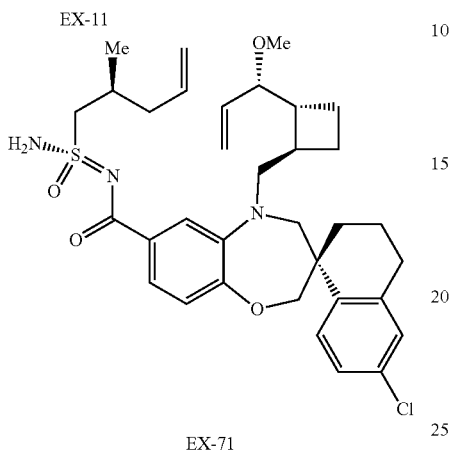

EX-71

A reactor was charged with EX-70 (1 equiv., scaling factor), EX-11 (1.1 equiv.), magnesium sulfate (200 wt %) and dichloromethane (20 volumes). The mixture was stirred at about 20° C. for about 1 hour. The mixture was charged with triethylsilane (2.0 equiv.) and TFA (2 equiv.) and agitated at about 20° C. for about 3 hours. The reaction mixture was diluted with dichloromethane (100 volumes) and filtered through Celite. The organic layer was washed with 2M aqueous potassium carbonate (50 volumes) and water (50 volumes). The organic layer was dried over sodium sulfate, filtered, and concentrated to dryness. The crude product was purified by chromatography using ethyl acetate and heptane to afford EX-71. $^1$H NMR (400 MHz, CDCl$_3$) δ 7.68 (d, J=8.5 Hz, 1H), 7.59-7.43 (m, 2H), 7.16 (dd, J=8.5, 2.3 Hz, 1H), 7.08 (d, J=2.3 Hz, 1H), 6.90 (d, J=8.2 Hz, 1H), 5.75 (ddt, J=17.2, 10.4, 7.1 Hz, 1H), 5.58 (ddd, J=16.9, 10.7, 7.8 Hz, 1H), 5.22-4.96 (m, 4H), 4.08 (q, J=12.0 Hz, 2H), 3.72-3.55 (m, 2H), 3.53-3.39 (m, 2H), 3.35-3.18 (m, 6H), 2.76 (d, J=5.1 Hz, 2H), 2.52 (td, J=8.5, 3.6 Hz, 1H), 2.40-2.26 (m, 1H), 2.15 (dt, J=29.2, 8.4 Hz, 3H), 2.06-1.94 (m, 2H), 1.93-1.46 (m, 6H), 1.15 (d, J=6.7 Hz, 3H).

Reductive Amination of EX-11 to EX-13 and Hydrolysis of EX13 to EX-60

Step 1

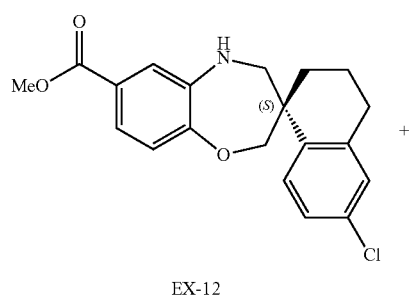

EX-12

Step 2

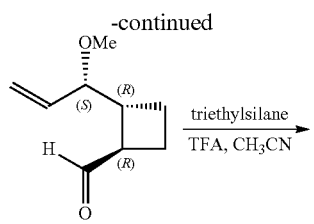

EX-11

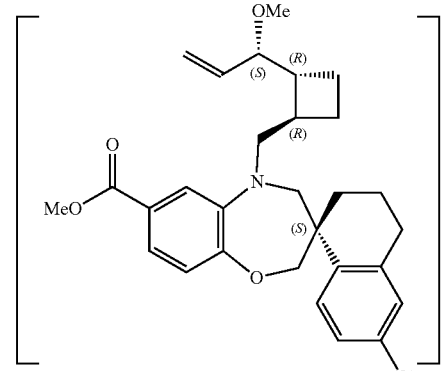

EX-13

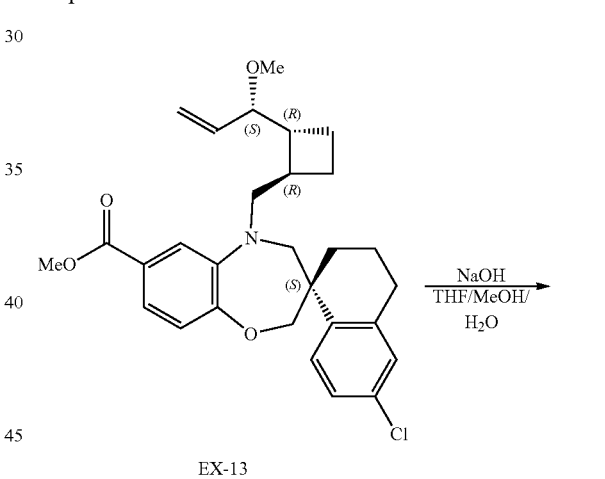

EX-13

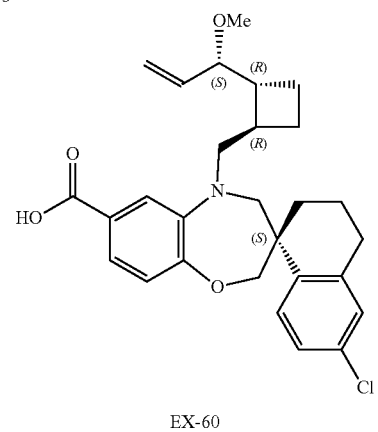

EX-60

A previously-prepared solution of EX-11 (1.2 equiv) in about 10 volumes of acetonitrile was combined with acetonitrile (4 volumes) and cooled to about 0° C., then combined with triethylsilane (2.0 equiv) and trifluoroacetic acid (0.5 equiv). A solution of EX-12 (1 equiv, scaling factor) in acetonitrile (1 volume) was charged to this mixture over about 10 minutes. The mixture was warmed to about 20° C. and then aged for about 25 hours. The reaction mixture was then combined with aqueous tribasic potassium phosphate (2 M, 5 volumes) and methyl tert-butyl ether (5 volumes). The layers were separated and the organic layer was washed with water (5 volumes), yielding EX-13. This solution was concentrated after which tetahydrofuran (4 volumes) was added. The solution was again concentrated and combined with tetrahydrofuran (4 volumes), methanol (4 volumes), water (0.7 volumes), and sodium hydroxide (50 wt % in water, 2 equiv). This mixture was heated to about 60° C. for about 13 h, then cooled to 20° C. and combined with methyl tert-butyl ether (8 volumes) and sodium bisulfate monohydrate (2.5 equiv) dissolved in water (8 volumes). After agitating for about 45 minutes, the layers were separated and the resulting organic solution washed three times with water (5 volumes each). The solution was concentrated to about 3 volumes after which 2-methyl-2-butanol (12 volumes) was charged. The mixture was further concentrated to a total volume of approximately 12 volumes and then adjusted to about 55° C. EX-60 seed crystals (ca. 0.1 wt %) were added, after which the mixture was adjusted to 5° C. over about 4 hours and aged for about 2 hours. The slurry was filtered and the resulting EX-60 bis(t-amyl alcohol) solvate was combined with acetonitrile (15 volumes) and aged at 20° C. for about 6 h, then cooled to 5° C. over 2 h and held for a further about 6 h. The slurry was filtered and dried in a vacuum oven at about 50° C. for about 23 h to afford EX-60. $^1$H NMR (400 MHz, CDCl$_3$) δ 7.71 (d, J=8.5 Hz, 1H), 7.54-7.42 (m, 2H), 7.17 (dd, J=8.5, 2.3 Hz, 1H), 7.08 (d, J=2.4 Hz, 1H), 6.93 (d, J=8.2 Hz, 1H), 5.64-5.51 (m, 1H), 5.26-5.15 (m, 2H), 4.18-4.05 (m, 2H), 3.76 (dd, J=14.8, 3.3 Hz, 1H), 3.67 (d, J=14.4 Hz, 1H), 3.49 (t, J=8.1 Hz, 1H), 3.39-3.27 (m, 4H), 3.19 (dd, J=14.9, 9.4 Hz, 1H), 2.87-2.68 (m, 2H), 2.54 (tq, J=11.8, 4.7, 3.0 Hz, 1H), 2.17-1.96 (m, 3H), 1.97-1.73 (m, 3H), 1.73-1.41 (m, 3H).

Amide Coupling of EX-51 and EX-60 to EX-74 and Deprotection of EX-74 to EX-62

Step 1

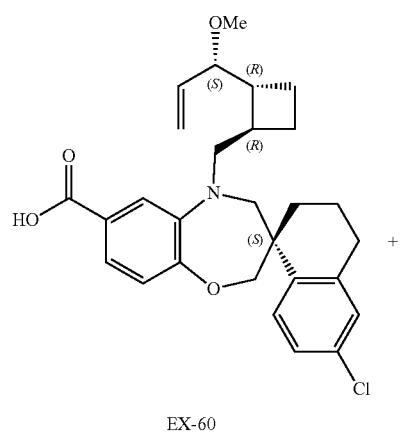

EX-60

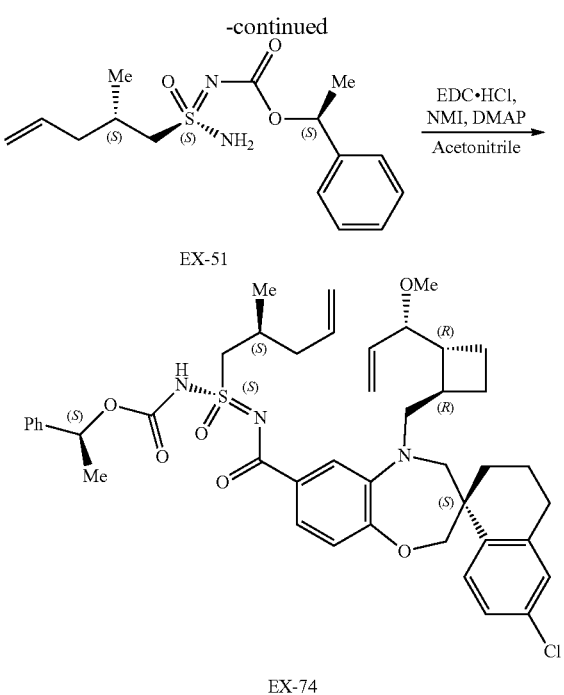

EX-51

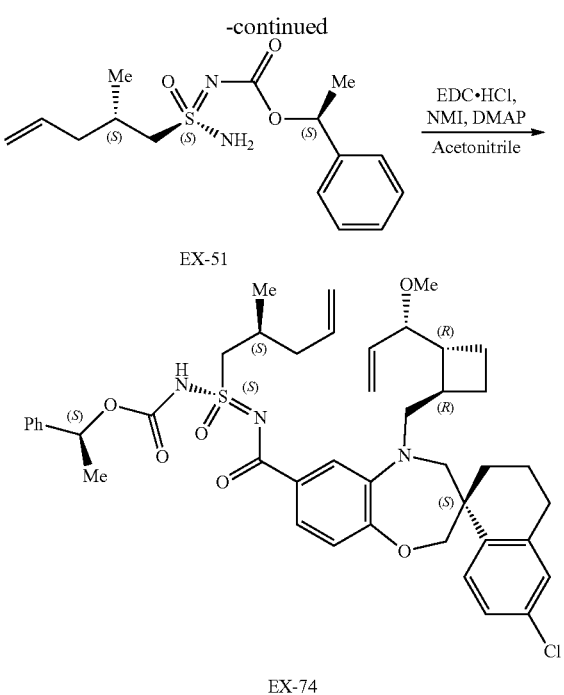

EX-74

Step 2

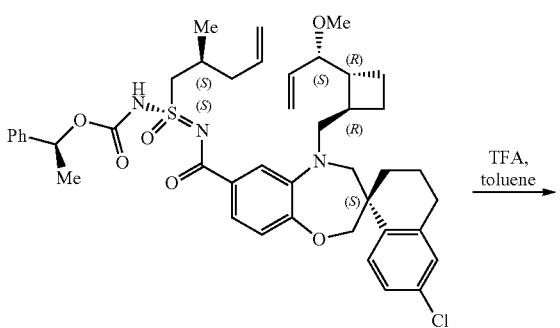

EX-74

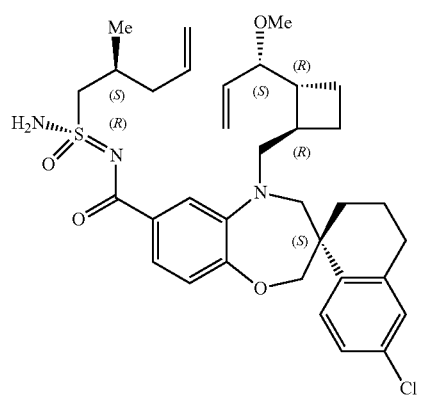

EX-62

A reactor was charged with EX-60 (1.0 equiv, scaling factor), EX-51 (1.06 equiv), 4-dimethylaminopyridine (1.0 equiv), and acetonitrile (8 volumes). The mixture was agitated at about 20° C. 1-methylimidazole (3.0 equiv), 1-(3-dimethylaminopropyl)-3-ethylcarbodiimide hydrochloride (1.3 equiv), and acetonitrile (2 volumes) were charged to the reactor. The reaction mixture was agitated at about 20° C. for about 22 hours. Toluene (10 volumes) and 0.2M sodium hydroxide (8 volumes) were charged to the reactor. The layers were separated. A second portion of 0.2M sodium hydroxide (8 volumes) was charged to the reactor. The mixture was heated to about 40° C. then the layers were separated. The organics were washed with 10% aqueous citric acid (8 volumes) at about 40° C. Then, the organics were heated to about 50° C. and distilled under vacuum to about 5 volumes. Toluene (3 volumes) was charged to the reactor, and the temperature of the mixture was adjusted to about 20° C. Trifluoroacetic acid (15.0 equiv) was charged to the reactor. The mixture was aged about three hours. Then, this stream was transferred into a separate reactor containing 2M sodium hydroxide (16 volumes) over about 20 minutes. The biphasic mixture was heated to about 40° C. and the layers were separated. The organics were washed with 10% aqueous citric acid (8 volumes) and water (16 volumes). The organics were transferred to a clean reactor and the temperature was adjusted to about 45° C. n-Heptane (3 volumes) was charged to the reactor followed by EX-62 seeds (0.01 equiv). The mixture was aged about 1 hour then was cooled to about 0° C. over about three hours. n-Heptane (9 volumes) was charged to the reactor over about two hours then the mixture was aged about 18 hours. The mixture was filtered, washed with 9:1 n-Heptane/toluene (5 volumes) and dried in a vacuum oven at about 50° C. for about 21 hours to afford EX-62. $^1$H NMR (400 MHz, CDCl$_3$) δ 7.71-7.65 (d, J=8.5 Hz, 1H), 7.56-7.47 (m, 2H), 7.18-7.13 (m, 1H), 7.09-7.06 (d, J=2.3 Hz, 1H), 6.92-6.87 (d, J=8.2 Hz, 1H), 5.82-5.69 (m, 1H), 5.63-5.52 (m, 1H), 5.22-5.04 (m, 4H), 4.14-4.02 (q, J=12.0 Hz, 2H), 3.68-3.57 (m, 2H), 3.53-3.41 (m, 2H), 3.35-3.21 (m, 6H), 2.81-2.71 (m, 2H), 2.58-2.46 (m, 1H), 2.40-2.28 (m, 1H), 2.22-2.07 (m, 3H), 2.05-1.95 (m, 2H), 1.94-1.47 (m, 6H), 1.18-1.10 (d, J=6.7 Hz, 3H).

Amidation EX-62 and EX-72 to EX-73

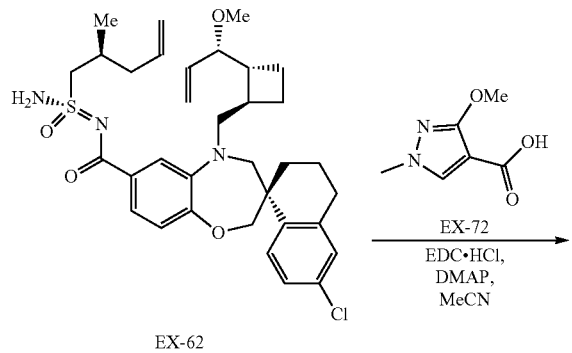

EX-62

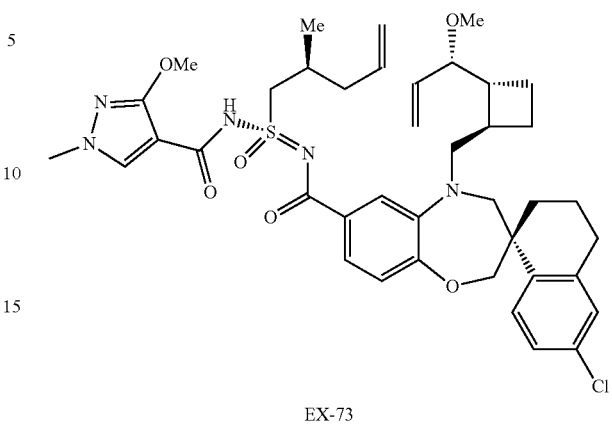

EX-73

A reaction vessel was charged with EX-62 (1.0 equiv, scaling factor), EX-72 (1.1 equiv), 4-dimethylaminopyridine (1.0 equiv), and acetonitrile (10 volumes). To this mixture was charged 1-methylimidazole (3.0 equiv), and N-(3-dimethylaminopropyl)-N'-ethylcarbodiimide hydrochloride (1.2 equiv), and the contents were agitated at about 20° C. for about 12 hours. Ethyl acetate (10 volumes) and 10% aqueous citric acid (10 volumes) were charged to the reactor, and the layers were separated. The organic layer was washed with 15 wt % aqueous sodium chloride (10 volumes), and the layers were separated. The organic layer was solvent switched into toluene and then carried into the next step. $^1$H NMR (400 MHz, CDCl$_3$) δ 11.25 (s, 1H), 7.77 (s, 1H), 7.68 (d, J=8.5 Hz, 1H), 7.54-7.48 (m, 2H), 7.16 (dd, J=8.5, 2.3 Hz, 1H), 7.08 (d, J=2.4 Hz, 1H), 6.90 (d, J=8.2 Hz, 1H), 5.76 (ddt, J=17.4, 10.5, 7.1 Hz, 1H), 5.55 (ddd, J=16.9, 10.4, 7.9 Hz, 1H), 5.21-5.03 (m, 4H), 4.11 (t, J=11.9 Hz, 2H), 4.06 (s, 3H), 3.85-3.56 (m, 3H), 3.78 (s, 3H), 3.46 (t, J=7.9 Hz, 1H), 3.32 (dd, J=14.4, 5.2 Hz, 2H), 3.27 (s, 3H), 2.81-2.72 (m, 2H), 2.58-1.56 (m, 14H), 1.15 (d, J=6.8 Hz, 3H).

Ring-Closing Metathesis of EX-73 to Compound 1

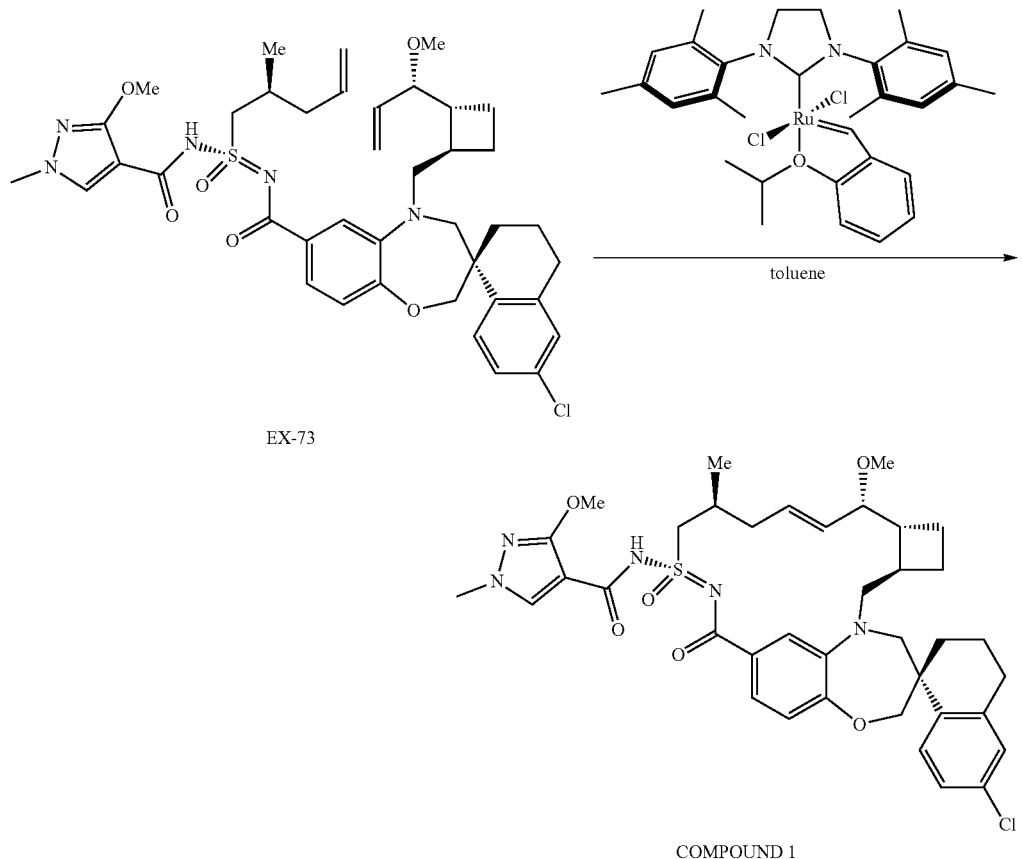

EX-73

COMPOUND 1

A reaction vessel was charged with a solution of EX-73 (1.0 equiv, scaling factor) in toluene (9 volumes). Toluene (180 volumes) was charged, and the contents were heated to about 85° C. A solution of Hoveyda-Grubbs II catalyst (0.10 equiv) in toluene (8 volumes) was charged over about 1 h. Toluene (2 volumes) was charged, and the contents were agitated for about 30 min. The reaction mixture was cooled to about 70° C. and acetonitrile (2 volumes) was charged. The contents were concentrated to afford Compound 1. $^1$H NMR (400 MHz, DMSO-$d_6$) δ 11.58 (s, 1H), 8.22 (s, 1H), 7.66 (d, J=8.5 Hz, 1H), 7.26 (dd, J=8.5, 2.2 Hz), 7.22 (dd, J=8.2 Hz, 1.0 Hz, 1H), 7.16 (d, J=2.0 Hz, 1H), 7.03 (s, 1H), 6.91 (d, J=8.1 Hz, 1H), 6.00 (ddd, J=14.2 Hz, 6.6 Hz, 6.6 Hz, 1H), 5.51 (dd, J=15.4 Hz, 8.1 Hz, 1H), 4.05 (d, J=12.5 Hz, 1H), 4.03 (m, 1H), 3.94 (d, J=12.4 Hz, 1H), 3.90 (s, 3H), 3.88 (m, 1H), 3.77 (m, 1H), 3.75 (s, 3H), 3.67 (dd, J=8.0H, 2.6 Hz, 1H), 3.61 (d, J=14.2 Hz, 1H), 3.26 (d, J 14.3 Hz, 1H), 3.16 (s, 3H), 3.01 (dd, J=15.0 Hz, 10.2 Hz, 1H), 2.80 (ddd, J=17.2 Hz, 3.3 Hz, 3.3 Hz, 1H), 2.69 (ddd, J=16.8 Hz, 8.3 Hz, 8.3 Hz, 1H), 2.41 (m, 1H), 2.37 (m, 1H), 2.36 ((m, 1H), 2.15 (m, 1H), 2.07 (m, 1H), 1.99 (d, J=13.7 Hz, 1H), 1.85 (m, 2H), 1.76 (m, 1H), 1.71 (m, 1H), 1.69 (m, 1H), 1.63 (m, 1H), 1.37 (ddd, J=14.3 Hz, 7.6 Hz, 7.6 Hz, 1H), 1.02 (d, J=6.6 Hz, 3H). $^1$H NMR (400 MHz, CDCl$_3$) δ 11.75 (s, 1H), 7.81 (s, 1H), 7.71 (d, J=8.4 Hz, 1H), 7.44 (m, 1H), 7.18 (m, 1H), 7.13 (dd, J=8.4 Hz, 2.0 Hz, 1H), 7.05 (d, J=2.0 Hz, 1H), 6.89 (d, J=8.0 Hz, 1H), 6.01 (dt, J=15.6 Hz, 6.4 Hz, 1H), 5.58 (dd, J=15.6 Hz, 7.2 Hz, 1H), 4.06 (s, 3H), 4.06 (d, J=12.0 Hz, 1H), 4.03 (m, 1H), 3.99 (d, J=12.0 Hz, 1H), 3.87 (m, 1H), 3.81 (dd, J=14.8 Hz, 2.5 Hz, 1H), 3.77 (s, 3H), 3.72 (m, 1H), 3.70 (m, 1H), 3.30 (d, J=14.4 Hz, 1H), 3.25 (s, 3H), 2.97 (dd, J=15.2 Hz, 11.2 Hz, 1H), 2.76 (m, 2H), 2.51 (m, 1H), 2.51 (m, 1H), 2.39 (m, 1H), 2.34 (m, 1H), 2.11 (m, 1H), 2.03 (m, 1H), 1.91 (m, 1H), 1.89 (m, 1H), 1.83 (m, 1H), 1.73 (m, 1H), 1.66 (m, 1H), 1.66 (m, 1H), 1.36 (m, 1H), 1.07 (d, J=7.2 Hz, 3H).

Coupling of EX-72 and EX-77 to Compound 1

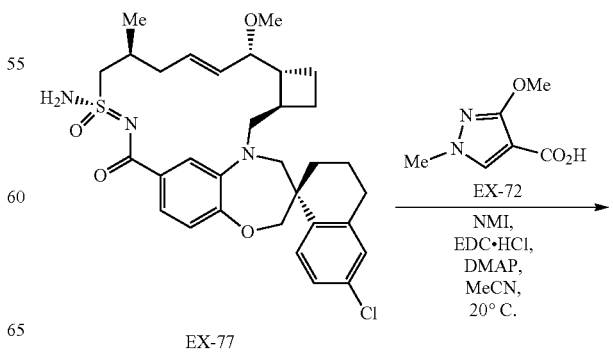

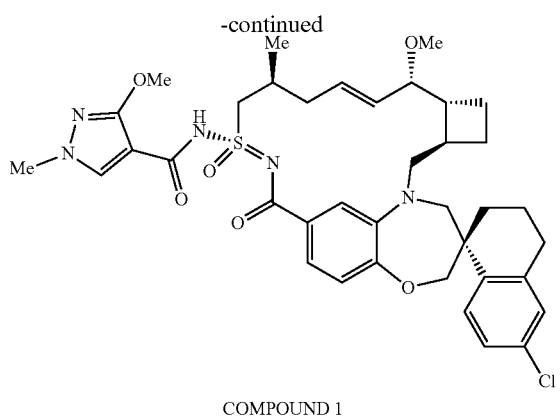

COMPOUND 1

A reactor was charged with EX-77 (1 equiv, scaling factor), EX-72 (1.25 equiv), DMAP (1.0 equiv), MeCN (10 V), NMI (2.0 equiv), and EDC HCl (1.5 equiv) at about 20° C. then stirred for about 14 h. The reaction mixture was diluted with EtOAc (20 V) followed by the addition of 10 wt % aqueous citric acid solution (10 V). The layers were separated then the organic layer was washed with water (10 V). The layers were separated and the organic layer was dried over sodium sulfate. The drying agent was removed via filtration then the filtrate was concentrated to dryness to afford Compound 1.

Salt Formation of Intermediate EX-73·DCA

A reaction vessel was charged with a solution of EX-73 in ethyl acetate. The solution was distilled under vacuum to 5 volumes. To this mixture, methyl tert-butyl ether (10 V) was charged, and the solution was distilled under vacuum to 3 volumes. To this mixture, methyl tert-butyl ether (10 V) was charged, and the solution was distilled under vacuum to 5 volumes. To this mixture, methyl tert-butyl ether (10 volumes) was charged, and the mixture was polish filtered into a clean reactor. To this reactor, dicyclohexylamine (1.1 equiv) was charged over about 30 minutes. At the end of addition, EX-73·DCA seeds (0.5 equiv) were charged, and the mixture was aged for about 2 hours. n-Heptane (10 volumes) was charged to the reactor over 2 hours, and the mixture was aged for about 12 hours. The slurry was filtered and was washed with 3:2 (v/v) MTBE/heptane (5 volumes), and then dried in a vacuum oven at 60° C. for about 24 hours to afford EX-73·DCA. $^1$H NMR (400 MHz, CDCl$_3$) δ 7.75 (s, 1H), 7.64 (d, J=8.5 Hz, 1H), 7.58-7.48 (m, 2H), 7.14 (dd, J=8.5, 2.4 Hz, 1H), 7.08 (d, J=2.3 Hz, 1H), 6.86 (d, J=8.1 Hz, 1H), 5.83-5.68 (m, 1H), 5.54 (ddd, J=17.1, 10.4, 7.9 Hz, 1H), 5.19-4.98 (m, 4H), 4.15-3.94 (m, 5H), 3.73 (s, 4H), 3.64 (dd, J=13.9, 7.8 Hz, 1H), 3.56-3.42 (m, 3H), 3.41-3.26 (m, 2H), 3.24 (s, 3H), 2.95-2.72 (m, 4H), 2.53-2.44 (m, 1H), 2.36 (m, J=6.4 Hz, 1H), 2.32-2.21 (m, 1H), 2.18-2.05 (m, 2H), 1.99 (d, J=10.2 Hz, 6H), 1.92-1.81 (m, 2H), 1.80-1.71 (m, 5H), 1.70-1.48 (m, 6H), 1.47-1.29 (m, 4H), 1.28-1.01 (m, 11H)

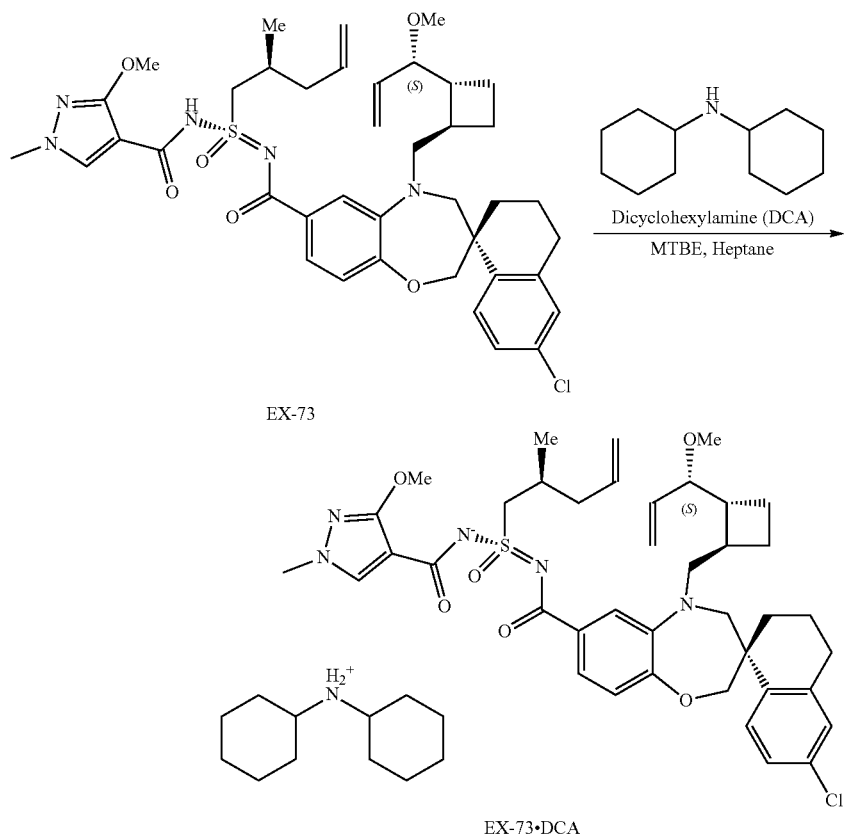

Salt Formation of Intermediate EX-73·TBD

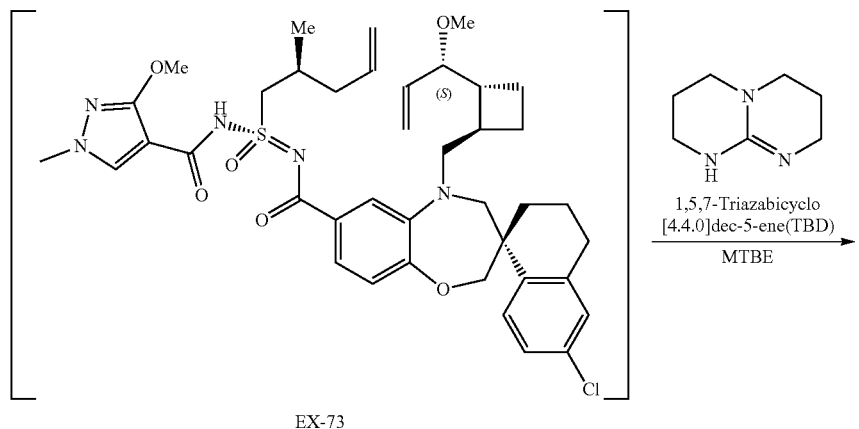

EX-73

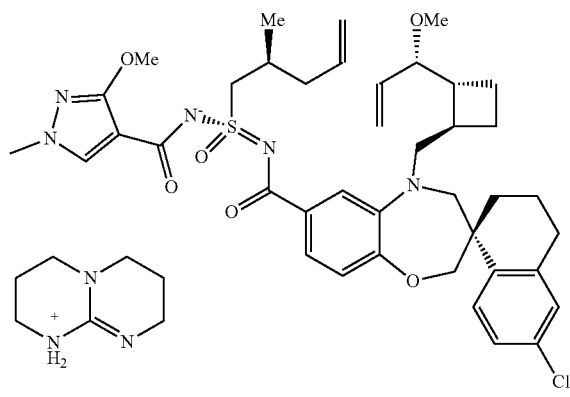

EX-73•TBD

A reaction vessel with EX-73 (1.0 equiv), methyl tert-butyl ether (10 volumes), and 1,5,7-triazabicyclo[4.4.0]dec-5-ene (1.0 equiv) was mixed at about 20° C. for about 3 days. The slurry was filtered, the flask was rinsed with methyl tert-butyl ether (4 volumes), then the cake was dried at about 60° C. in a vacuum oven for about 5 d to afford EX-73·TBD. $^1$H NMR (400 MHz, CDCl$_3$) δ 8.52 (s, 2H), 7.73 (s, 1H), 7.65-7.56 (m, 2H), 7.53 (dd, J=8.2, 1.8 Hz, 1H), 7.13 (dd, J=8.5, 2.4 Hz, 1H), 7.08 (d, J=2.3 Hz, 1H), 6.82 (d, J=8.2 Hz, 1H), 5.79 (ddt, J=17.1, 10.2, 7.0 Hz, 1H), 5.52 (ddd, J=17.2, 10.4, 7.8 Hz, 1H), 5.17-5.06 (m, 2H), 5.06-4.97 (m, 2H), 4.09 (d, J=11.9 Hz, 1H), 3.98 (d, J=11.8 Hz, 1H), 3.93 (s, 3H), 3.77-3.68 (m, 1H), 3.69 (s, 3H), 3.60 (dd, J=13.8, 7.3 Hz, 1H), 3.52-3.43 (m, 2H), 3.45-3.40 (m, 1H), 3.40-3.29 (m, 5H), 3.29-3.16 (m, 8H), 2.76 (t, J=4.8 Hz, 2H), 2.54-2.28 (m, 3H), 2.17-2.04 (m, 2H), 1.95 (dp, J=11.9, 5.8 Hz, 5H), 1.85 (s, 2H), 1.72 (dd, J=19.5, 9.5 Hz, 1H), 1.67-1.60 (m, 2H), 1.55 (q, J=9.9, 9.3 Hz, 1H), 1.19 (s, 1H), 1.12 (d, J=6.7 Hz, 3H).

Salt Formation of Intermediate
EX-73·(−)-Cinchonidine

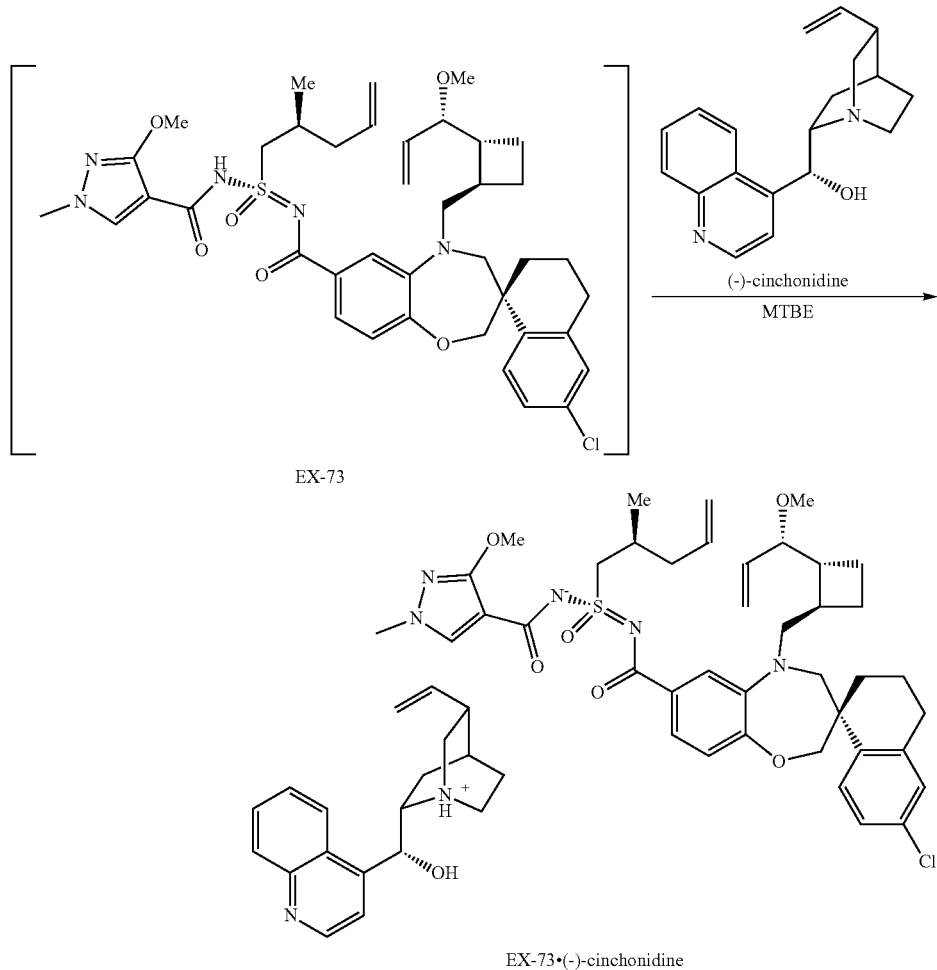

A reaction vessel with EX-73 (1.0 equiv), methyl tert-butyl ether (10 volumes), and (−)-cinchonidine (1.0 equiv) was stirred at about 20° C. for about 3 days. The slurry was filtered, the flask was rinsed with methyl tert-butyl ether (4 volumes), then the cake was dried at about 60° C. in a vacuum oven for about 5 days to afford EX-73·(−)-Cinchonidine. $^1$H NMR (400 MHz, Chloroform-d) δ 8.91 (d, J=4.5 Hz, 1H), 8.38 (d, J=8.4 Hz, 1H), 8.09 (dd, J=8.5, 1.3 Hz, 1H), 7.74 (d, J=4.5 Hz, 1H), 7.72-7.59 (m, 3H), 7.57 (d, J=1.9 Hz, 1H), 7.55-7.46 (m, 2H), 7.15 (dd, J=8.5, 2.4 Hz, 1H), 7.08 (d, J=2.3 Hz, 1H), 6.94 (d, J=8.1 Hz, 1H), 6.55 (s, 1H), 5.83 (ddt, J=17.3, 10.3, 7.1 Hz, 1H), 5.62-5.42 (m, 2H), 5.15-4.98 (m, 5H), 4.94 (dt, J=10.4, 1.2 Hz, 1H), 4.35 (s, 1H), 4.11 (d, J=12.0 Hz, 1H), 4.02 (d, J=11.9 Hz, 1H), 3.87 (s, 3H), 3.67 (d, J=10.3 Hz, 1H), 3.61 (s, 3H), 3.56-3.22 (m, 5H), 3.20 (s, 3H), 2.76 (t, J=7.1 Hz, 2H), 2.59 (s, 1H), 2.52 (dt, J=12.6, 6.4 Hz, 1H), 2.38 (s, 1H), 2.46-2.30 (m, 1H), 2.24-2.12 (m, 1H), 2.07 (d, J=8.5 Hz, 1H), 2.03 (s, 3H), 2.01-1.83 (m, 2H), 1.79-1.55 (m, 2H), 1.49-1.38 (m, 1H), 1.19 (d, J=6.8 Hz, 3H).

Salt Formation of Intermediate EX-73·(−)-Quinine

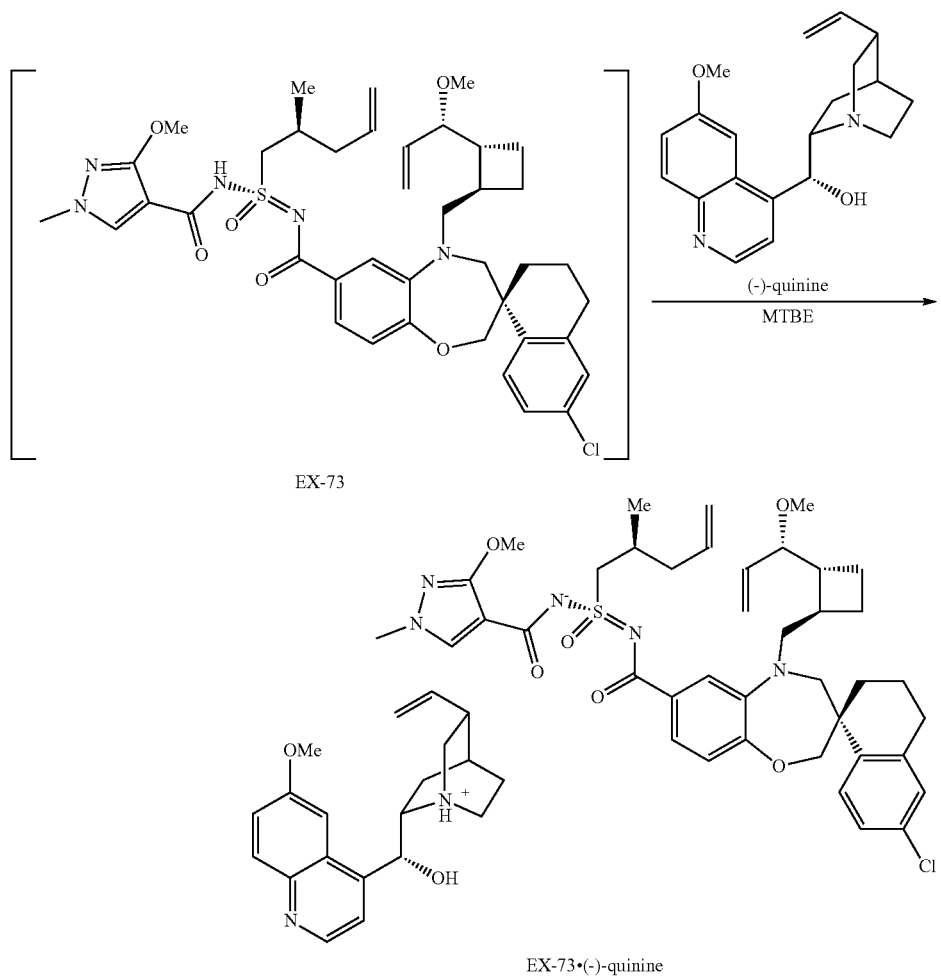

A reaction vessel was charged with EX-73 (1.0 equiv) and methyl tert-butyl ether (20 volumes) and (−)-quinine (1.0 equiv) and stirred at about 50° C. for about 1 day. The reaction mixture was cooled to about 20° C. and stirred for about 3 days. The reaction mixture was cooled to about 20° C. and stirred for about 3 days. The slurry was filtered then the cake was dried at about 60° C. in a vacuum oven for about 3 d to afford EX-73·(−)-Quinine. $^1$H NMR (400 MHz, Chloroform-d) δ 8.76 (d, J=4.5 Hz, 1H), 7.99 (d, J=9.2 Hz, 1H), 7.68-7.61 (m, 2H), 7.55 (d, J=1.9 Hz, 1H), 7.52-7.45 (m, 2H), 7.37 (s, 1H), 7.33 (dd, J=9.2, 2.6 Hz, 1H), 7.17 (dd, J=8.5, 2.4 Hz, 1H), 7.11 (d, J=2.3 Hz, 1H), 6.86 (d, J=8.2 Hz, 1H), 6.62 (s, 1H), 5.83 (ddt, J=17.4, 10.4, 7.1 Hz, 1H), 5.64 (ddd, J=17.1, 10.4, 6.7 Hz, 1H), 5.51 (ddd, J=17.1, 10.4, 7.8 Hz, 1H), 5.15 (dd, J=10.4, 1.9 Hz, 1H), 5.13-5.00 (m, 5H), 4.46 (s, 1H), 4.13 (d, J=12.0 Hz, 1H), 4.03 (d, J=11.9 Hz, 1H), 3.81 (s, 3H), 3.75 (s, 3H), 3.57 (s, 2H), 3.50 (d, J=14.2 Hz, 1H), 3.43 (s, 7H), 3.44-3.33 (m, 2H), 3.35-3.26 (m, 2H), 3.21 (s, 3H), 2.80 (d, J=6.3 Hz, 2H), 2.64 (s, 1H), 2.58-2.30 (m, 2H), 2.17 (dt, J=14.2, 7.4 Hz, 1H), 2.12-1.91 (m, 2H), 1.87 (s, 1H), 1.79-1.70 (m, 1H), 1.67-1.56 (m, 1H), 1.59-1.45 (m, 1H), 1.40 (s, 1H), 1.20 (d, J=6.8 Hz, 3H).

Salt-Break of Intermediate EX-73·DCA to EX-73

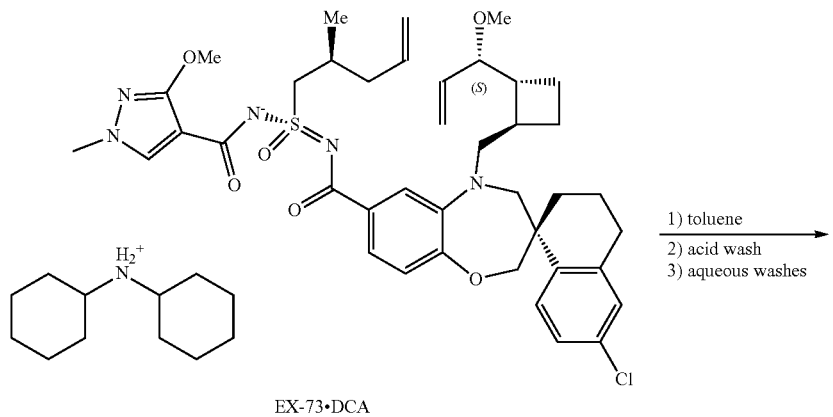

EX-73·DCA

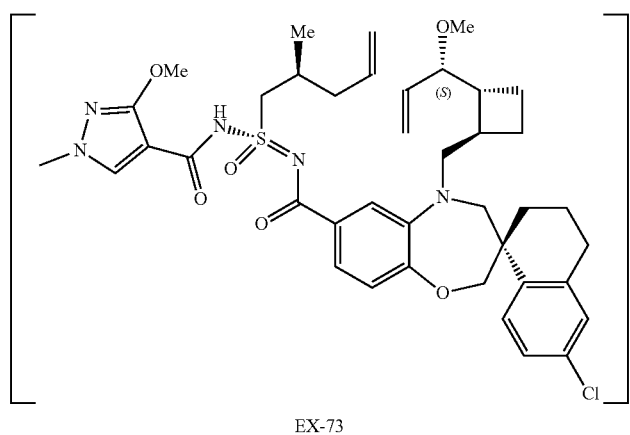

EX-73

A reaction vessel was charged with EX-73·DCA (1.0 equiv, scaling factor) and toluene (75 volumes) and stirred at about 20° C. to achieve a solution. Aqueous hydrochloric acid (75 volumes) was charged to the vessel, the resulting biphasic mixture was stirred, and the layers were separated. Water (75 volumes) was charged to the vessel containing the organic layer, the resulting biphasic mixture was stirred, and the layers were separated. Aqueous sodium chloride (75 volumes) was charged to the vessel containing the organic layer, the resulting biphasic mixture was stirred, and the layers were separated. Aqueous sodium chloride (75 volumes) was charged to the vessel containing the organic layer, the resulting biphasic mixture was stirred, and the layers were separated. The organic layer was carried forward without isolation into the next step.

Salt-Break of Intermediate EX-73·TBD to EX-73

A reaction vessel was charged with EX-73·TBD (1.0 equiv, scaling factor) and toluene (75 volumes) and stirred at elevated temperature to achieve a solution. Aqueous hydrochloric acid (75 volumes) was charged to the vessel, the resulting biphasic mixture was stirred, and the layers were separated. Water (75 volumes) was charged to the vessel containing the organic layer, the resulting biphasic mixture was stirred, and the layers were separated. Aqueous sodium chloride (75 volumes) was charged to the vessel containing the organic layer, the resulting biphasic mixture was stirred, and the layers were separated. Aqueous sodium chloride (75 volumes) was charged to the vessel containing the organic layer, the resulting biphasic mixture was stirred, and the layers were separated. The organic layer was carried forward without isolation into the next step.

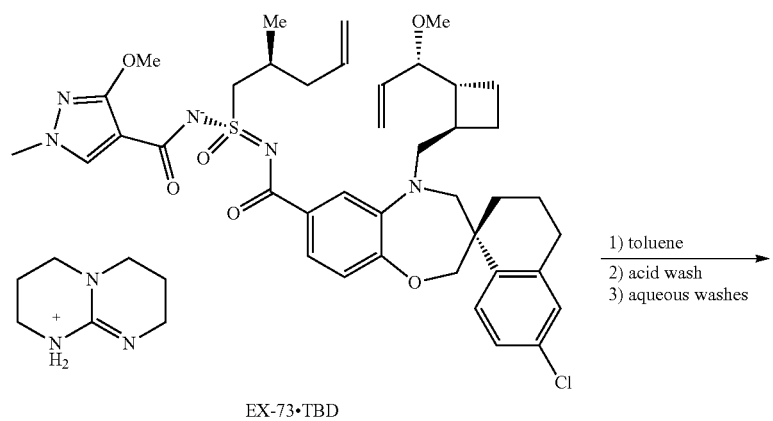
EX-73•TBD
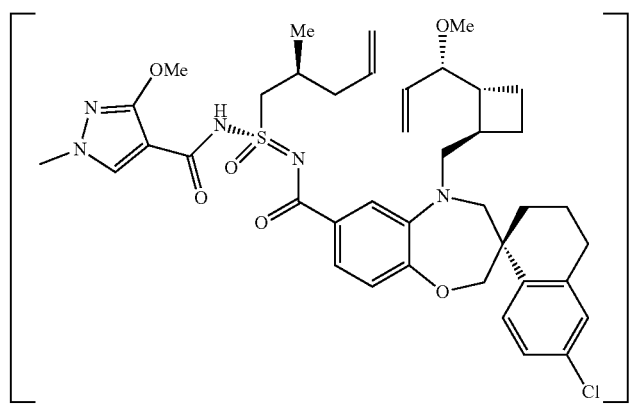
EX-73
Salt-break of Intermediate EX-73·(−)-Cinchonidine to EX-73
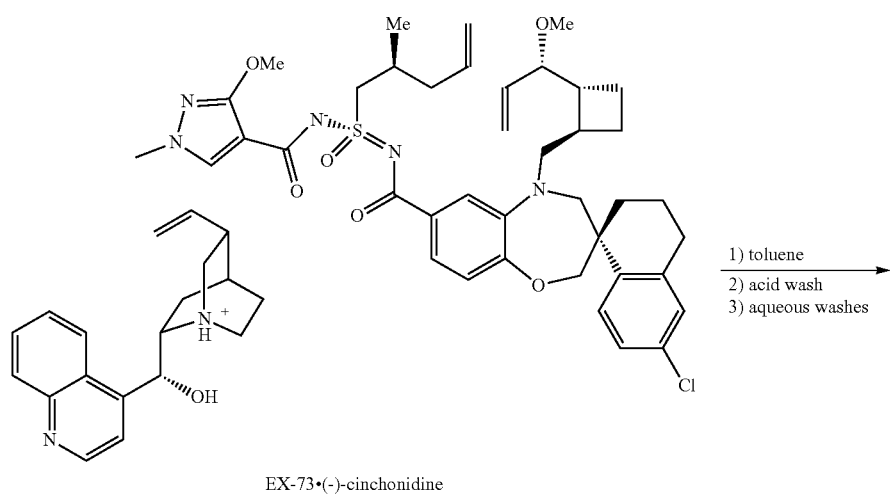
EX-73•(-)-cinchonidine

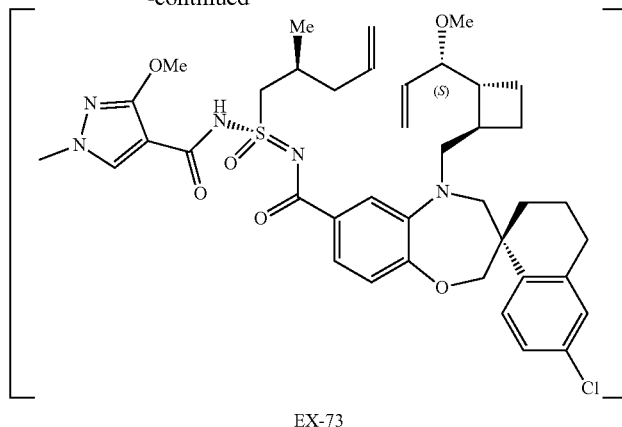

EX-73

A reaction vessel was charged with EX-73·(−)-Cinchonidine (1.0 equiv, scaling factor) and toluene (75 volumes) and stirred at about 20° C. to achieve a solution. Aqueous hydrochloric acid (75 volumes) was charged to the vessel, the resulting biphasic mixture was stirred, and the layers were separated. Water (75 volumes) was charged to the vessel containing the organic layer, the resulting biphasic mixture was stirred, and the layers were separated. Aqueous sodium chloride (75 volumes) was charged to the vessel containing the organic layer, the resulting biphasic mixture was stirred, and the layers were separated. Aqueous sodium chloride (75 volumes) was charged to the vessel containing the organic layer, the resulting biphasic mixture was stirred, and the layers were separated. The organic layer was carried forward without isolation into the next step.

Reductive Amination of methyl 3-amino-4-fluorobenzoate with EX-11 to EX-78 acetonitrile (30 volumes), and EX-11 (scaling factor, 1.00 equiv) as a solution in dichloromethane (12 volumes). The mixture was agitated at about 20° C. for approximately 0.5 h, then triethylsilane (2 equiv) and trifluoroacetic acid (2 equiv) were added. The mixture was agitated for approximately 17 h at about 20° C. Once the reaction was deemed complete, the mixture was filtered, concentrated and purified by chromatography with hexanes and EtOAc to afford EX-78. $^1$H NMR (400 MHz, CDCl$_3$): δ 7.34-7.21 (m, 2H), 6.96 (dd, J=11.2, 8.2 Hz, 1H), 5.76 (br s, 1H), 5.57-5.43 (m, 1H), 5.28-5.15 (m, 2H), 3.30 (s, 3H), 3.45-3.34 (m, 4H), 3.30 (dd, J=11.0, 4.4 Hz, 1H), 2.93-2.81 (m, 1H), 2.55-2.40 (m, 1H), 2.19-1.97 (m, 2H), 1.92-1.80 (m, 1H), 1.76-1.49 (m, 2H).

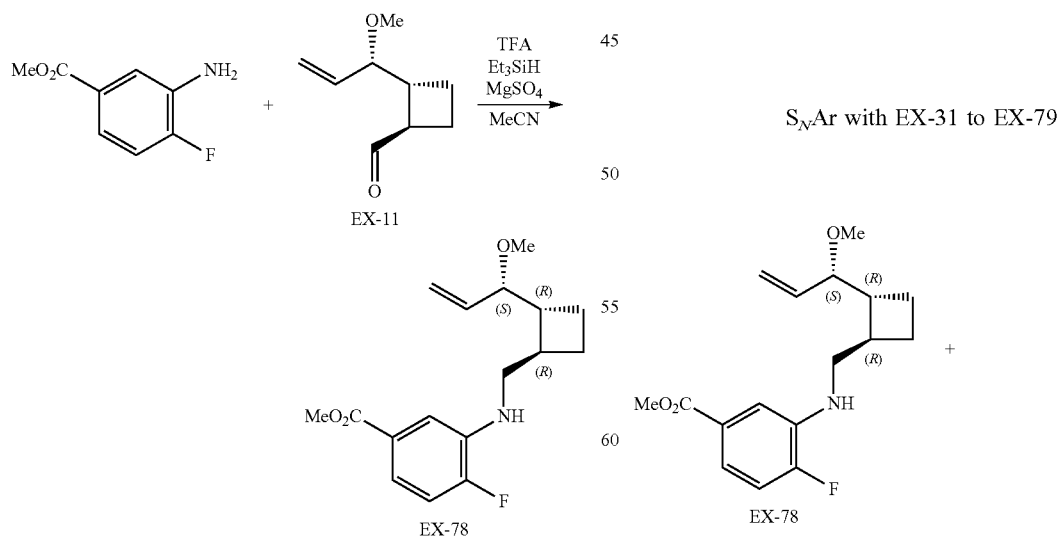

S$_N$Ar with EX-31 to EX-79

A reaction vessel was charged with methyl 3-amino-4-fluorobenzoate (1.0 equiv), magnesium sulfate (1.3 equiv),

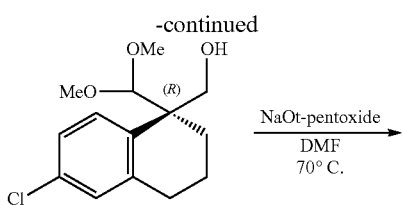

EX-31

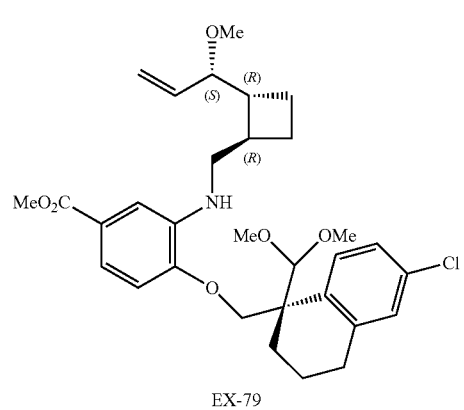

EX-79

Ester Hydrolysis EX-79 to EX-80

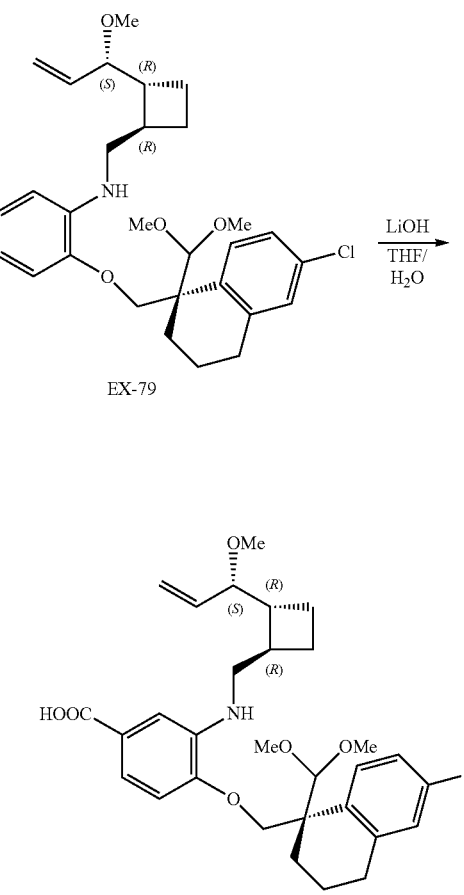

A reaction vessel was charged with EX-31 (1.1 equiv) and N,N-dimethylformamide (10 volumes). To this vessel was added sodium tert-pentoxide (40 wt % in toluene, 1.5 equiv). The mixture was stirred at about 20° C. for approximately 10 min, then a solution of EX-78 (scaling factor, 1.00 equiv) in N,N-dimethylformamide (10 volumes) was charged. The mixture was agitated at about 70° C. for approximately 1 h. Once the reaction was deemed complete, the mixture was charged to a vessel containing water (200 volumes) and 2-methyltetrahydrofuran (200 volumes). The phases were allowed to separate and the aqueous layer was partitioned. The aqueous phase was extracted with 2-methyltetrahydrofuran (100 volumes). The phases were allowed to separate and the aqueous layer was partitioned. The combined organic phases were washed with water (200 volumes). The phases were allowed to separate, and the aqueous layer was partitioned. The organic layer was dried over magnesium sulfate, filtered, concentrated and purified via chromatography with hexanes and EtOAc to give EX-79. $^1$H NMR (400 MHz, CDCl$_3$): δ 7.61-7.51 (m, 1H), 7.43-7.32 (m, 1H), 7.21 (br s, 1H), 7.16-7.06 (m, 2H), 6.76 (d, J=8.4 Hz, 1H), 5.63-5.49 (m, 1H), 5.26-5.16 (m, 2H), 4.53 (s, 1H), 4.26-4.02 (m, 3H), 3.86 (s, 3H), 3.50-3.35 (m, 7H), 3.33-3.17 (m, 4H), 3.07 (dd, J=11.7, 7.7 Hz, 1H), 2.85-2.67 (m, 2H), 2.49-2.36 (m, 1H), 2.18-1.84 (m, 6H), 1.82-1.71 (m, 1H), 1.71-1.61 (m, 1H), 1.60-1.48 (m, 1H).

A reaction vessel was charged with EX-79 (scaling factor, 1.00 equiv), tetrahydrofuran (20 volumes), and water (20 volumes). Lithium hydroxide monohydrate (11 equiv) was charged. The mixture was agitated at about 70° C. for approximately 22 h. Once the reaction was deemed complete, the mixture was cooled to about 20° C. and acidified to approximately pH 1 with 1 M aqueous hydrochloric acid. The mixture was then extracted with 2-methyltetrahydrofuran (40 volumes). The layers were allowed to separate and the aqueous phase was partitioned. The organics were concentrated, and purified via chromatography with hexanes and EtOAc to give EX-80. $^1$H NMR (400 MHz, CDCl$_3$): δ 7.60-7.53 (m, 1H), 7.50-7.39 (m, 1H), 7.31-7.15 (m, 1H—overlaps with solvent peak), 7.14-7.06 (m, 2H), 6.80 (d, J=8.2 Hz, 1H), 5.63-5.49 (m, 1H), 5.28-5.16 (m, 2H), 4.54 (s, 1H), 4.29-4.13 (m, 2H), 3.51-3.36 (m, 7H), 3.33-3.15 (m, 4H), 3.08 (dd, J=11.6, 7.6 Hz, 1H), 2.86-2.69 (m, 2H), 2.54-2.39 (m, 1H), 2.18-2.02 (m, 3H), 2.00-1.84 (m, 3H), 1.83-1.73 (m, 1H), 1.72-1.62 (m, 1H), 1.60-1.48 (m, 1H).

Coupling of EX-80 and EX-51 to EX-81

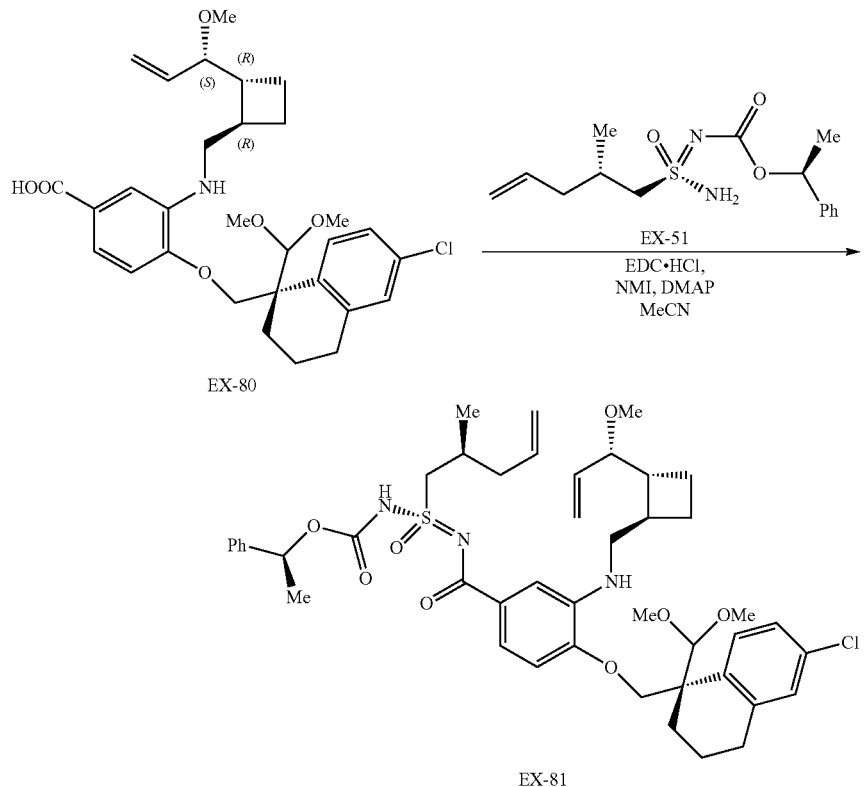

A reaction vessel was charged with EX-80 (1.00 equiv, scaling factor), acetonitrile (50 volumes), N-methylimidazole (3 equiv), 4-dimethylaminopyridine (1 equiv), and 1-(3-dimethylaminopropyl)-2-ethylcarbodiimide hydrochloride (1.3 equiv) and the contents were agitated. EX-51 (1.1 equiv) was charged to the vessel and the contents were agitated at about 20° C. for approximately 20 h. When the reaction was deemed complete the contents were diluted with ethyl acetate (150 volumes) and 5% aqueous citric acid (100 volumes). The contents were agitated and the layers allowed to separate. The aqueous layer was partitioned and the organics were washed with 0.5 M aqueous sodium hydroxide (100 volumes). The contents were agitated and the layers allowed to separate. The aqueous layer was partitioned and the organics were washed with water (100 volumes). The contents were agitated and the layers allowed to separate. The aqueous layer was partitioned and the organics concentrated and purified via chromatography with hexanes and EtOAc to yield EX-81. $^1$H NMR (400 MHz, CDCl$_3$) δ 7.65-7.53 (m, 1H), 7.46-7.37 (m, 1H), 7.34-7.28 (m, 1H), 7.25-7.19 (m, 2H), 7.19-7.02 (m, 5H), 6.62 (d, J=8.4 Hz, 1H), 5.67-5.42 (m, 3H), 5.25-5.12 (m, 2H), 5.01-4.87 (m, 2H), 4.54 (s, 1H), 4.19-3.86 (m, 3H), 3.45-3.33 (m, 7H), 3.23 (s, 3H), 3.19-2.99 (m, 4H), 2.83-2.67 (m, 2H), 2.42-2.30 (m, 1H), 2.14-1.98 (m, 5H), 1.97-1.79 (m, 5H), 1.78-1.68 (m, 1H), 1.67-1.57 (m, 1H), 1.54-1.44 (m, 1H), 1.34 (d, J=6.1 Hz, 3H), 0.92 (d, J=6.1 Hz, 3H).

Acetal Hydrolysis, Carbamate Cleavage, Reductive Amination to Form EX-62

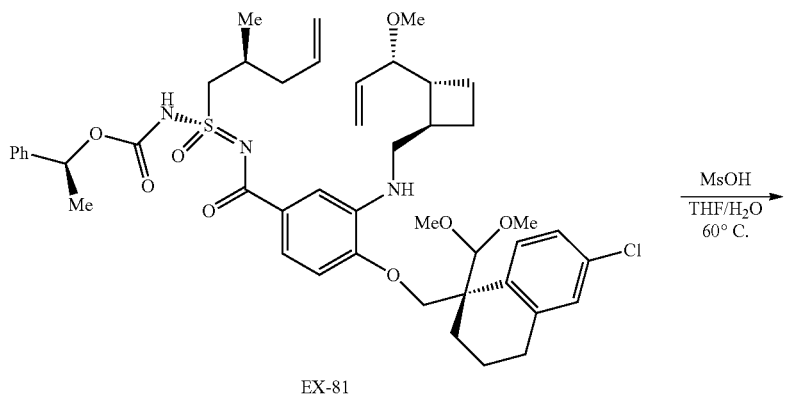

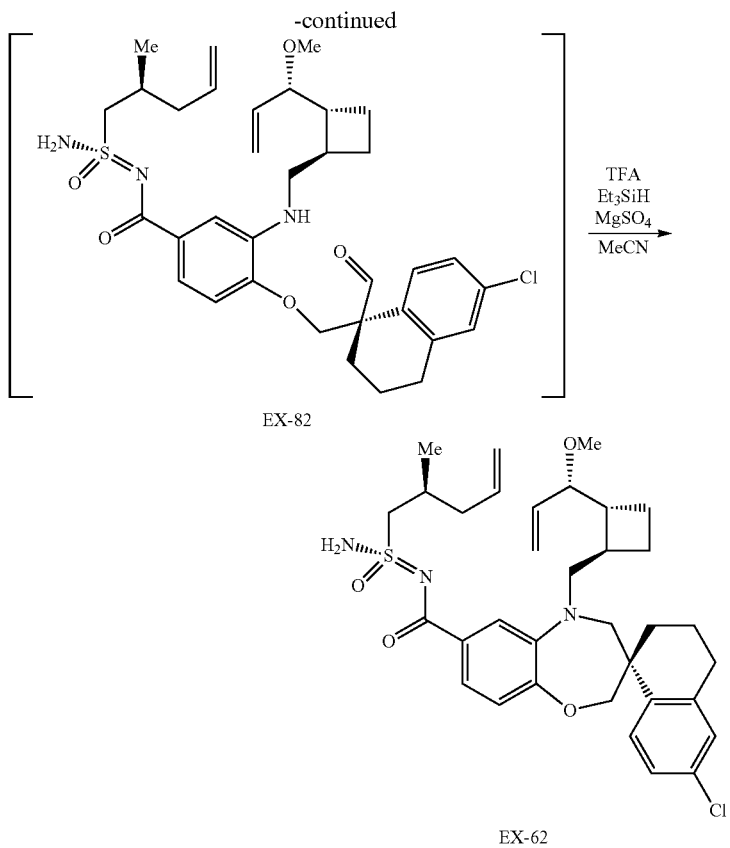

EX-82

EX-62

A reaction vessel was charged with EX-81 (1.00 equiv, scaling factor), tetrahydrofuran (20 volumes), and water (4 volumes) and the contents were agitated. Methanesulfonic acid (10 equiv) was charged to the vessel and the contents were agitated at about 65° C. for approximately 18 h. When the reaction was deemed complete the contents were diluted with saturated aqueous sodium bicarbonate (40 volumes) and 2-methyltetrahydrofuran (80 volumes). The contents were agitated and the layers allowed to separate. The aqueous layer was partitioned and the organics were washed with water (80 volumes). The contents were agitated and the layers allowed to separate. The aqueous layer was partitioned, the organics were concentrated and used immediately without further purification. A reaction vessel was charged with EX-82 (1 equiv, scaling factor is EX-81 from previous step), acetonitrile (20 volumes), and magnesium sulfate (17 equiv) and the contents were agitated. Triethylsilane (8 equiv) and trifluoroacetic acid (20 equiv) were charged to the vessel and the contents were agitated at about 20° C. for approximately 46 h. When the reaction was deemed complete the contents were filtered, concentrated and purified via chromatography with hexanes and EtOAc to yield EX-62. $^1$H NMR (400 MHz, CDCl$_3$): δ 7.70 (d, J=8.4 Hz, 1H), 7.49-7.55 (m, 2H), 7.17 (dd, J=8.8, 2.4 Hz, 1H), 7.09 (d, J=2.0 Hz, 1H), 6.91 (d, J=8.0 Hz, 1H), 5.70-5.83 (m, 3H), 5.59 (ddd, J=16.8, 10.4, 7.6 Hz, 1H), 5.04-5.22 (m, 4H), 4.12, 4.06 (ABq, J=12.0 Hz, 2H), 3.57-3.69 (m, 2H), 3.41-3.54 (m, 2H), 3.17-3.36 (m, 6H), 2.70-2.84 (m, 2H), 2.48-2.59 (m, 1H), 2.31-2.40 (m, 1H), 2.08-2.29 (m, 3H), 1.95-2.06 (m, 2H), 1.46-1.94 (m, 6H), 1.15 (d, J=6.8 Hz, 3H).

Coupling of 4-fluoro-3-nitrobenzoic Acid and EX-51 to EX-83

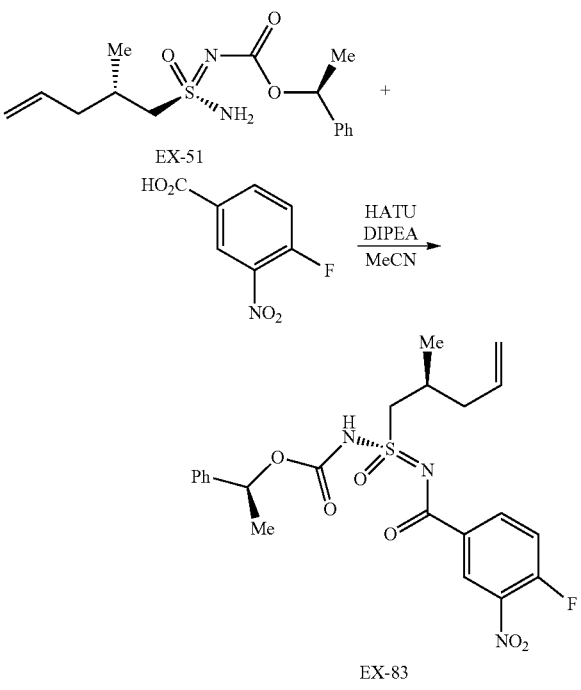

A reactor was charged with EX-51 (1.0 equiv., scaling factor), 4-fluoro-3-nitrobenzoic acid (1.2 equiv.), N,N-diisopropylamine (3.0 equiv.), HATU (1.2 equiv.,) and acetonitrile (10 volumes). The mixture was stirred at about 20° C. for about 15 hours. The reaction mixture was diluted with ethyl acetate (50 volumes) and the organic layer was washed with 5 wt % aqueous citric acid (25 volumes), and water (25 volumes). The organic layer was dried over sodium sulfate, filtered, concentrated and purified by chromatography to afford EX-83. $^1$H NMR (400 MHz, CDCl$_3$) δ 9.91 (s, 1H), 8.78 (dd, J=7.3, 2.2 Hz, 1H), 8.35 (ddd, J=8.7, 4.3, 2.2 Hz, 1H), 7.40-7.26 (m, 6H), 5.90 (q, J=6.6 Hz, 1H), 5.68 (ddt, J=17.2, 10.2, 7.1 Hz, 1H), 5.14-5.02 (m, 2H), 3.77 (dd, J=14.5, 4.4 Hz, 1H), 3.57 (dd, J=14.5, 7.9 Hz, 1H), 2.33 (ddd, J=13.6, 7.0, 4.4 Hz, 1H), 2.17 (t, J=6.6 Hz, 2H), 1.64 (d, J=6.6 Hz, 3H), 1.15 (d, J=6.7 Hz, 3H).

S$_N$Ar of EX-31 and EX-83 to EX-84 Followed by Deprotection to EX-85

A reactor was charged with EX-83 (1.0 equiv., scaling factor), EX-31 (1.2 equiv.), and tetrahydrofuran (15 volumes). The reaction mixture was charged with a solution of potassium tert-butoxide in tetrahydrofuran (2.5 equiv.) over about 10 minutes. The reaction mixture was agitated at about 20° C. for about 1 hour. The reaction mixture was quenched with 5% aqueous acetic acid (130 volumes) and extracted with ethyl acetate (160 volumes). The organic layer was washed with water (130 volumes), dried over sodium sulfate, filtered, and concentrated. The crude product was dissolved in 10% water in tetrahydrofuran (25 volumes). The solution was charged with methanesulfonic acid (2 volumes) and agitated at about 65° C. for about 3 hours. The reaction mixture was cooled to about 20° C. and diluted with ethyl acetate (160 volumes). The organic layer was washed with 20 wt % aqueous potassium carbonate (130 volumes) and water (130 volumes). The organic layer was dried over sodium sulfate, filtered, and concentrated to dryness. The crude product was purified by chromatography using ethyl acetate and heptane to afford EX-85. $^1$H NMR (400 MHz, CDCl$_3$) δ 9.55 (s, 1H), 8.60 (d, J=2.2 Hz, 1H), 8.26 (dd, J=8.7, 2.2 Hz, 1H), 7.23-7.17 (m, 2H), 7.10 (t, J=8.5 Hz, 2H), 5.82-5.67 (m, 3H), 5.17-5.04 (m, 2H), 4.57 (d, J=9.1 Hz, 1H), 4.25 (d, J=9.1 Hz, 1H), 3.46 (dd, J=14.4, 4.3 Hz, 1H), 3.28 (dd, J=14.4, 8.1 Hz, 1H), 2.86 (q, J=5.6 Hz, 2H), 2.31 (dddd, J=20.7, 10.8, 8.7, 5.6 Hz, 2H), 2.22-2.14 (m, 3H), 1.95 (q, J=7.0 Hz, 2H), 1.14 (dd, J=6.8, 1.8 Hz, 3H).

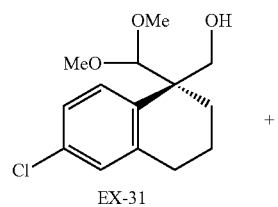

EX-31

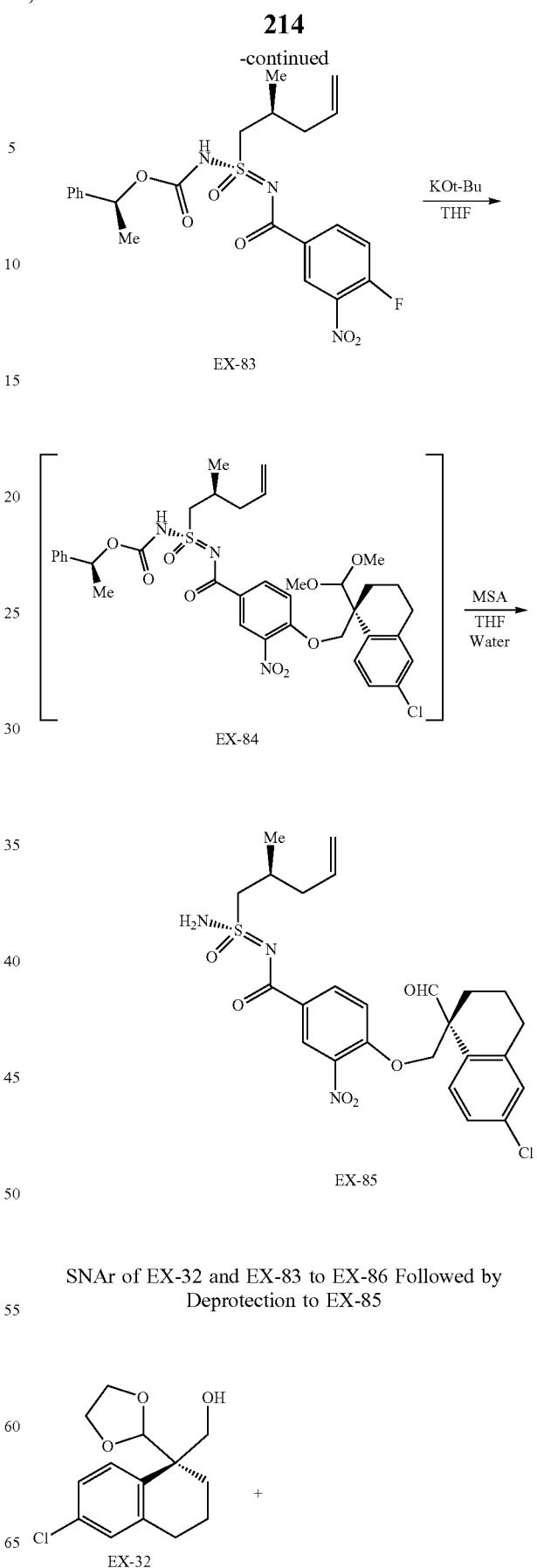

EX-83

EX-84

EX-85

SNAr of EX-32 and EX-83 to EX-86 Followed by Deprotection to EX-85

EX-32

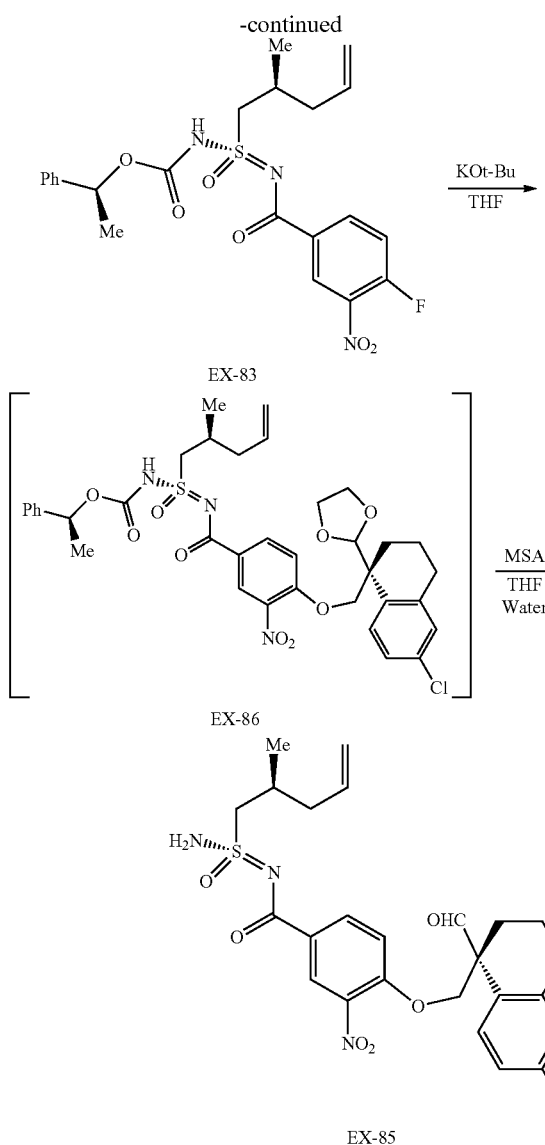

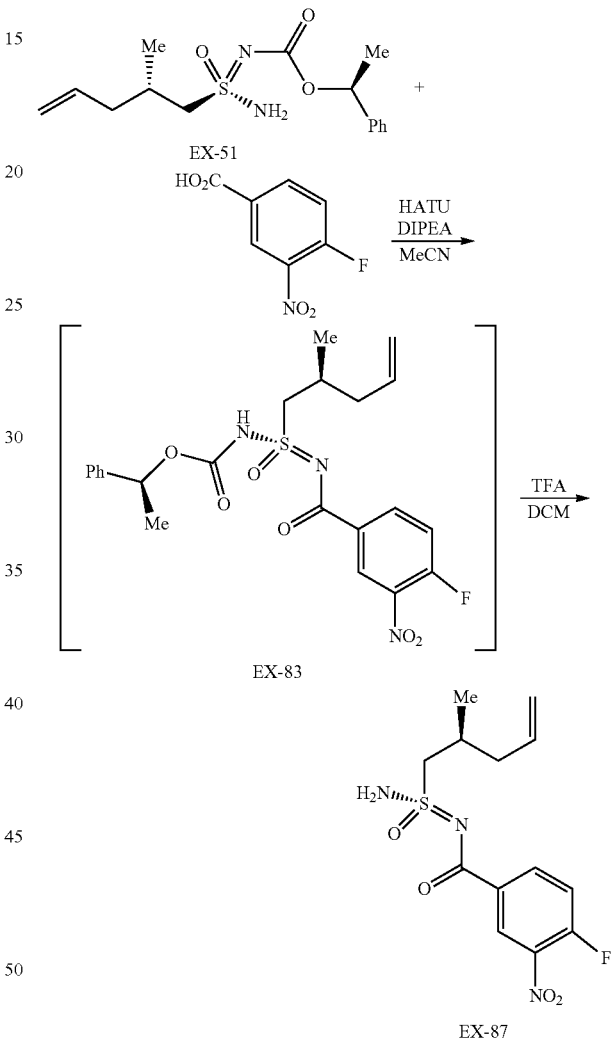

J=8.5 Hz, 2H), 5.82-5.67 (m, 3H), 5.17-5.04 (m, 2H), 4.57 (d, J=9.1 Hz, 1H), 4.25 (d, J=9.1 Hz, 1H), 3.46 (dd, J=14.4, 4.3 Hz, 1H), 3.28 (dd, J=14.4, 8.1 Hz, 1H), 2.86 (q, J=5.6 Hz, 2H), 2.31 (dddd, J=20.7, 10.8, 8.7, 5.6 Hz, 2H), 2.22-2.14 (m, 3H), 1.95 (q, J=7.0 Hz, 2H), 1.14 (dd, J=6.8, 1.8 Hz, 3H).

Coupling of 4-fluoro-3-nitrobenzoic Acid and EX-51 to EX-83 Followed by Deprotection to EX-87

A reactor was charged with EX-83 (1.0 equiv., scaling factor), EX-32 (1.5 equiv.), and tetrahydrofuran (15 volumes). The reaction mixture was charged with a solution of potassium tert-butoxide in tetrahydrofuran (2.5 equiv.) over about 10 minutes. The reaction mixture was agitated at about 20° C. for about 1 hour. The reaction mixture was quenched with 5% aqueous acetic acid (160 volumes) and extracted with ethyl acetate (160 volumes). The organic layer was washed with water (160 volumes), dried over sodium sulfate, filtered, and concentrated. The crude product was dissolved in 10% water in tetrahydrofuran (30 volumes). The solution was charged with methanesulfonic acid (2 volumes) and agitated at about 65° C. for about 21 hours. The reaction mixture was cooled to about 20° C. and diluted with ethyl acetate (160 volumes). The organic layer was washed with 20 wt % aqueous potassium carbonate (160 volumes) and water (160 volumes). The organic layer was dried over sodium sulfate, filtered, and concentrated to dryness. The crude product was purified by chromatography using ethyl acetate and heptane to afford EX-85. $^1$H NMR (400 MHz, CDCl$_3$) δ 9.55 (s, 1H), 8.60 (d, J=2.2 Hz, 1H), 8.26 (dd, J=8.7, 2.2 Hz, 1H), 7.23-7.17 (m, 2H), 7.10 (t, A reactor was charged with EX-51 (1.0 equiv., scaling factor), 4-fluoro-3-nitrobenzoic acid (1.2 equiv.), N,N-diisopropylamine (3.0 equiv.), HATU (1.2 equiv., and acetonitrile (20 volumes). The mixture was stirred at about 20° C. for about 15 hours. The reaction mixture was diluted with ethyl acetate (200 volumes) and the organic layer was washed with 5% aqueous citric acid (100 volumes), and water (100 volumes). The organic layer was dried over sodium sulfate, filtered, and concentrated to dryness. The crude material was diluted with dichloromethane (20 volumes) and trifluoroacetic acid (30.0 equiv.) and the mixture stirred for about 3 hours. The reaction mixture was diluted with ethyl acetate (200 volumes) and washed with water (100 volumes). The aqueous layer was neutralized to about pH 6 with 10 wt % aqueous citric acid and extracted with ethyl acetate (100 volumes). The combined organic layers were dried over sodium sulfate, filtered, and concentrated to dryness. The crude product was purified by chromatography using ethyl acetate and heptane to afford EX-87. $^1$H NMR (400 MHz, CDCl$_3$) δ 8.78 (dd, J=7.3, 2.2 Hz, 1H), 8.36 (ddd, J=8.7, 4.3, 2.2 Hz, 1H), 7.32 (dd, J=10.3, 8.7 Hz, 1H), 5.92-5.80 (m, 2H), 5.80-5.67 (m, 1H), 5.16-5.05 (m, 2H), 3.50 (dd, J=14.4, 4.3 Hz, 1H), 3.30 (dd, J=14.4, 8.0 Hz, 1H), 2.35 (ddt, J=12.9, 10.9, 6.8 Hz, 1H), 2.19 (t, J=6.9 Hz, 2H), 1.16 (d, J=6.7 Hz, 3H).

S$_N$Ar of EX-31 and EX-87 to EX-88

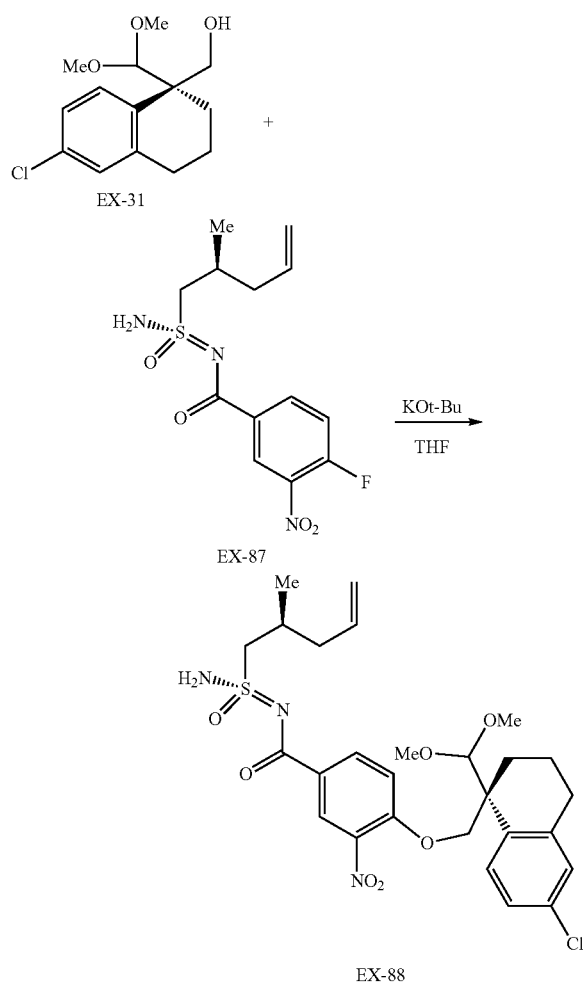

A reactor was charged with EX-87 (1.0 equiv., scaling factor), EX-31 (1.2 equiv.), and tetrahydrofuran (10 volumes). The reaction mixture was charged with a solution of potassium tert-butoxide in tetrahydrofuran (2.5 equiv.) over about 5 minutes. The reaction mixture was agitated at about 20° C. for about 30 minutes. The reaction mixture was quenched with 5 wt % aqueous acetic acid (10 volumes), and ethyl acetate (20 volumes). The aqueous layer was extracted with ethyl acetate (20 volumes). The organic layers were washed with saturated aqueous sodium chloride (10 volumes), dried over sodium sulfate, filtered, and concentrated. The crude product was purified by chromatography using ethyl acetate and heptane to afford EX-88. $^1$H NMR (400 MHz, CDCl$_3$) δ 8.63 (d, J=2.2 Hz, 1H), 8.25 (dd, J=8.8, 2.2 Hz, 1H), 7.71 (d, J=8.5 Hz, 1H), 7.18-6.94 (m, 3H), 5.86-5.61 (m, 3H), 5.21-5.02 (m, 2H), 4.76 (s, 1H), 4.25 (d, J=8.6 Hz, 1H), 4.15 (d, J=8.7 Hz, 1H), 3.45 (d, J=28.5 Hz, 7H), 3.28 (dd, J=14.3, 8.1 Hz, 1H), 2.85-2.69 (m, 2H), 2.33 (ddd, J=13.3, 6.6, 3.4 Hz, 1H), 2.23-2.16 (m, 2H), 2.11 (t, J=10.7 Hz, 1H), 1.93 (d, J=10.9 Hz, 2H), 1.79-1.64 (m, 1H), 1.15 (d, J=6.7 Hz, 3H).

Deprotection of EX-88 to EX-85

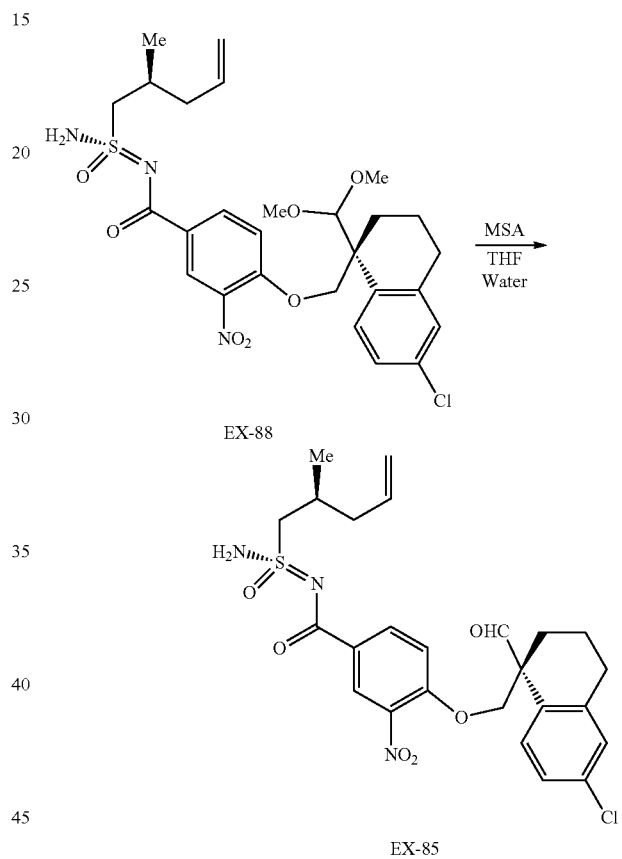

A reactor was charged with EX-88 (1.0 equiv., scaling factor) and 15% water in tetrahydrofuran (20 volumes). The solution was charged with methanesulfonic acid (0.5 volume) and agitated at about 65° C. for about 4 hours. The reaction mixture was cooled to about 20° C. and diluted with ethyl acetate (80 volumes). The organic layer was washed with 20 wt % aqueous potassium carbonate (20 volumes) and water (20 volumes). The organic layer was dried over sodium sulfate, filtered, and concentrated to dryness. The crude product was purified by chromatography using ethyl acetate and heptane to afford EX-85. $^1$H NMR (400 MHz, CDCl$_3$) δ 9.55 (s, 1H), 8.60 (d, J=2.2 Hz, 1H), 8.26 (dd, J=8.7, 2.2 Hz, 1H), 7.23-7.17 (m, 2H), 7.10 (t, J=8.5 Hz, 2H), 5.82-5.67 (m, 3H), 5.17-5.04 (m, 2H), 4.57 (d, J=9.1 Hz, 1H), 4.25 (d, J=9.1 Hz, 1H), 3.46 (dd, J=14.4, 4.3 Hz, 1H), 3.28 (dd, J=14.4, 8.1 Hz, 1H), 2.86 (q, J=5.6 Hz, 2H), 2.31 (dddd, J=20.7, 10.8, 8.7, 5.6 Hz, 1H), 2.22-2.14 (m, 3H), 1.95 (q, J=7.0 Hz, 2H), 1.14 (dd, J=6.8, 1.8 Hz, 3H).

Acylation of EX-51 and Oxidative Cleavage to EX-89

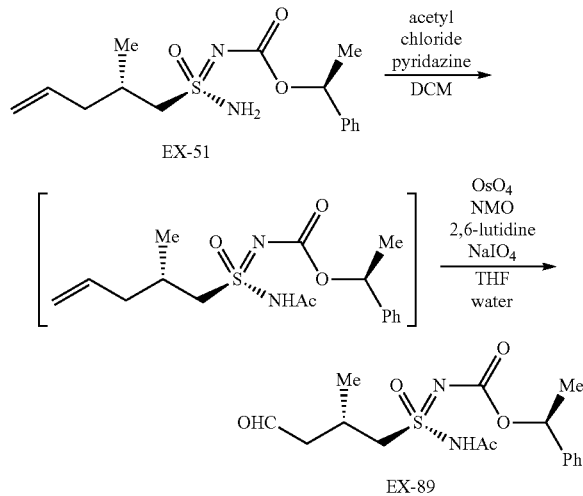

A reactor was charged with EX-51 (1.0 equiv., scaling factor), pyridazine (1.5 equiv.), acetyl chloride (1.5 equiv.), and acetonitrile (10 volumes). The mixture was stirred at about 20° C. for about 15 hours. The reaction mixture was diluted with ethyl acetate (20 volumes) and washed with three portions of water (10 volumes). The organic layer was dried over sodium sulfate, filtered, and concentrated. The crude material was dissolved in tetrahydrofuran:water (10:1 v/v, 10 volumes) and 4-methylmorpholine (1.5 equiv.) was added. 2,6-lutidine (2.0 equiv.) and osmium tetraoxide (4 wt % in water, 0.02 equiv.) were added and the mixture was stirred at about 20° C. for about 15 hours. Sodium periodate (2.0 equiv.) was added and the mixture was stirred for about 30 minutes. The reaction mixture was diluted with 5 wt % aqueous acetic acid (20 volumes) and water (40 volumes) and the aqueous layer was extracted with five portions of ethyl acetate (20 volumes). The combined organic layers were washed with two portions of water (10 volumes), dried over sodium sulfate, filtered, and concentrated. The crude product was purified by chromatography using ethyl acetate, heptane, and acetic acid to afford EX-89. $^1$H NMR (400 MHz, CDCl$_3$) δ 9.70 (s, 1H), 7.38-7.27 (m, 5H), 6.14 (s, 1H), 5.74 (dq, J=23.3, 6.6 Hz, 1H), 3.72-3.53 (m, 1H), 3.07-2.92 (m, 1H), 2.83-2.64 (m, 1H), 2.54 (s, 2H), 2.16-2.07 (m, 3H), 1.64-1.52 (m, 3H), 1.19-1.07 (m, 3H).

Seyferth-Gilbert Homologation of EX-89 to EX-90

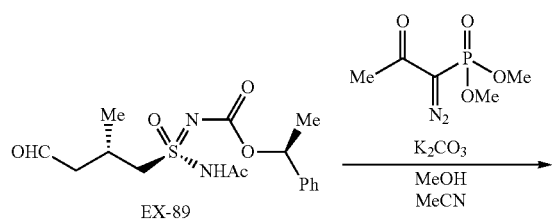

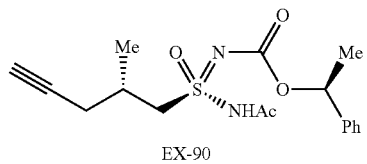

To a reactor was charged EX-89 (1.0 equiv., scaling factor), potassium carbonate (3.0 equiv.), and methanol (10 volumes). Dimethyl(1-diazo-2-oxopropyl)phosphonate (10 wt % in acetonitrile, 2.0 equiv.) was added and the mixture was stirred at about 20° C. for about 8 hours. The reaction mixture was diluted with ethyl acetate (20 volumes) washed with two portions of water (10 volumes). The aqueous layer was acidified to pH 4 with acetic acid and extracted with two portions of ethyl acetate (10 volumes). The combined organic layers were dried over sodium sulfate, filtered, and concentrated to afford EX-90. $^1$H NMR (400 MHz, CDCl$_3$) δ 7.39-7.28 (m, 5H), 5.77 (q, J=6.6 Hz, 1H), 3.80-3.75 (m, 1H), 3.55 (dd, J=14.5, 6.3 Hz, 1H), 2.49-2.34 (m, 2H), 2.33-2.22 (m, 1H), 2.12 (s, 3H), 1.98 (d, J=2.8 Hz, 1H), 1.58 (d, J=6.6 Hz, 3H), 1.19 (d, J=6.5 Hz, 3H):

Deprotection of EX-90 to EX-91

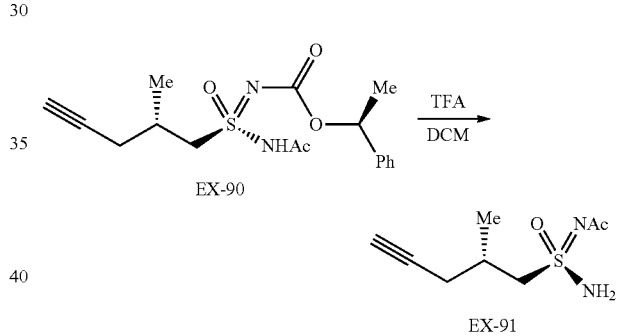

To a reactor was charged EX-90 (1.0 equiv., scaling factor), dichloromethane (20 volumes), and trifluoroacetic acid (15.0 equiv.). The mixture was heated to about 40° C. and stirred for about 1 hour. The reaction mixture was concentrated and the crude product was purified by chromatography using ethyl acetate and heptane to afford EX-91. $^1$H NMR (400 MHz, CDCl$_3$) δ 5.57 (s, 2H), 3.52 (dd, J=14.3, 5.6 Hz, 1H), 3.30 (dd, J=14.4, 6.4 Hz, 1H), 2.52-2.25 (m, 3H), 2.11 (s, 3H), 2.06 (t, J=2.5 Hz, 1H), 1.21 (d, J=6.7 Hz, 3H).

Hydroboration of EX-51 to EX-92

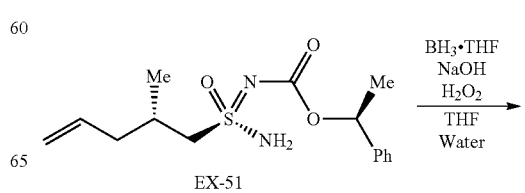

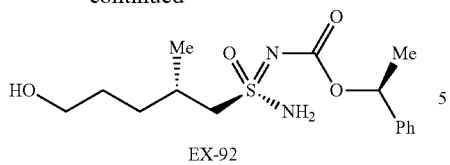

EX-92

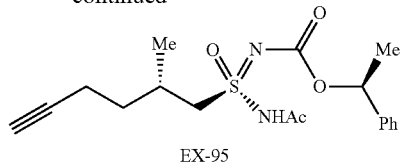

EX-95

A reactor was charged with EX-51 (1.0 equiv., scaling factor) and tetrahydrofuran (20 volumes). The mixture was cooled in an ice water bath and borane-THF complex (1 M in tetrahydrofuran, 1.2 equiv.) was added in about 1 minute. The mixture was warmed to about 20° C. and was stirred for about 30 minutes. Additional borane-THF complex (1 M in tetrahydrofuran, 1.2 equiv.) was added in about 1 minute and the mixture was stirred for about 15 minutes. The reaction mixture was cooled in an ice water bath and 6 M sodium hydroxide (20.0 equiv.) was added. Hydrogen peroxide (30 wt % in water, 20.0 equiv.) was added. The reaction mixture was warmed to about 20° C. and stirred for about 30 minutes. The reaction mixture was acidified to pH 4 with acetic acid and diluted with ethyl acetate (100 volumes). The organic layer was washed with 10 wt % aqueous sodium thiosulfate (20 volumes), water (20 volumes), dried over sodium sulfate, filtered, and concentrated and the crude product was purified by chromatography using ethyl acetate, heptane, and acetic acid to afford EX-92. $^1$H NMR (400 MHz, CDCl$_3$) δ 7.41-7.30 (m, 4H), 7.30-7.27 (m, 1H), 5.72 (q, J=6.6 Hz, 1H), 3.57 (t, J=5.9 Hz, 2H), 3.38 (dd, J=14.4, 5.5 Hz, 1H), 3.13 (dd, J=14.3, 6.9 Hz, 1H), 2.17 (dt, J=12.7, 6.6 Hz, 1H), 1.63-1.41 (m, 6H), 1.37-1.28 (m, 1H), 1.09 (d, J=6.7 Hz, 3H).

Acetylation of EX-92 to EX-93, Parikh-Doering Oxidation of EX-93 to EX-94 and Seyferth-Gilbert Homologation to EX-95

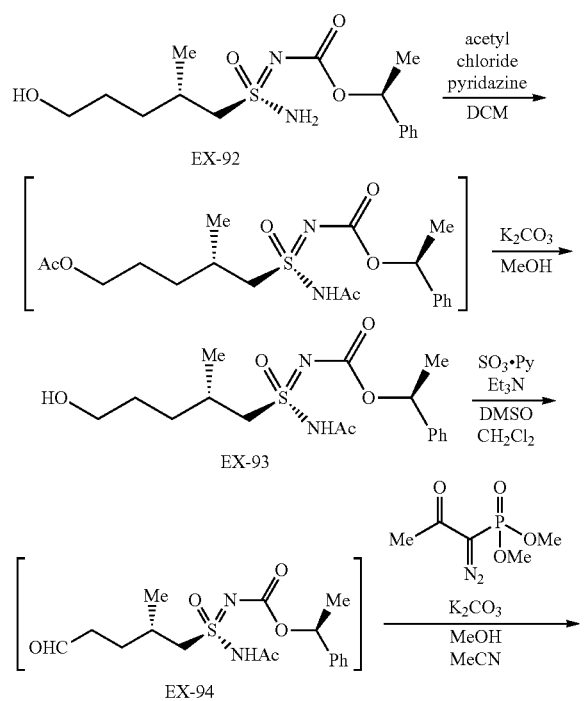

A reactor was charged with EX-92 (1.0 equiv., scaling factor) and acetonitrile (10 volumes). Pyridazine (1.5 equiv.) and acetyl chloride (1.5 equiv.) were added and the reaction mixture was stirred at about 20° C. for about 5 hours. The reaction mixture was diluted with ethyl acetate (100 volumes) and with two portions of water (50 volumes). The organic layer was dried over sodium sulfate, filtered, and concentrated. The crude product was charged with methanol (10 volumes) and potassium carbonate (5.0 equiv.) was added. The reaction mixture was stirred at about 20° C. for about 2 hours. The reaction mixture was diluted with ethyl acetate (100 volumes) and 5 wt % aqueous acetic acid (50 volumes). The aqueous layer was extracted with two portions of ethyl acetate (50 volumes). The combined organic layers were washed with water (50 volumes), dried over sodium sulfate, filtered, and concentrated to afford EX-93 (1.0 equiv., scaling factor) which was then charged to a reactor with sulfur trioxide-pyridine complex (3.0 equiv.), dichloromethane (100 volumes), dimethylsulfoxide (5 volumes), and triethylamine (3.0 equiv.) and the reaction mixture was stirred at about 20° C. for about 3 hours. The reaction mixture was diluted with ethyl acetate and 5 wt % aqueous acetic acid (500 volumes). The organic layer was washed with two portions of 10 wt % sodium chloride (500 volumes), dried over sodium sulfate, filtered, and concentrated to afford EX-94. The crude material was diluted with methanol (1000 volumes). Potassium carbonate (5.0 equiv.), and dimethyl(1-diazo-2-oxopropyl)phosphonate (10 wt % in acetonitrile, 2.0 equiv.) were charged and the reaction mixture was stirred at about 20° C. for about 4 hours. The reaction mixture was diluted with ethyl acetate (1000 volumes) and 5 wt % aqueous acetic acid (500 volumes). The organic layer was washed with two portions of 10 wt % sodium chloride (500 volumes), dried over sodium sulfate, filtered, and concentrated to afford EX-95. $^1$H NMR (400 MHz, CDCl$_3$) δ 7.37-7.28 (m, 5H), 5.76 (q, J=6.7 Hz, 1H), 3.70-3.56 (m, 1H), 3.54-3.41 (m, 1H), 2.32 (dt, J=12.0, 5.4 Hz, 1H), 2.20 (tdd, J=7.2, 4.3, 2.7 Hz, 2H), 2.14-2.07 (m, 3H), 1.92 (t, J=2.6 Hz, 1H), 1.76-1.63 (m, 1H), 1.57 (d, J=6.8 Hz, 3H), 1.48 (dt, J=14.3, 7.1 Hz, 1H), 1.10 (t, J=6.5 Hz, 3H).

Wittig Olefination of EX-89 with Ethyltriphenylphosphonium Iodide to EX-96

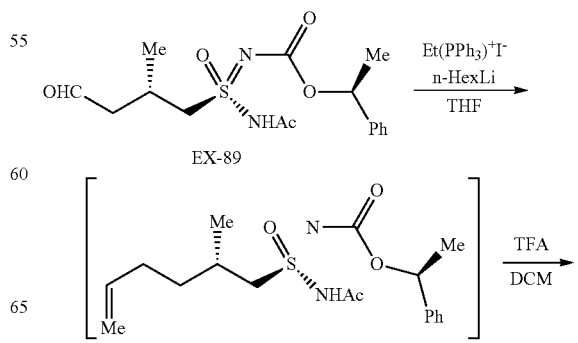

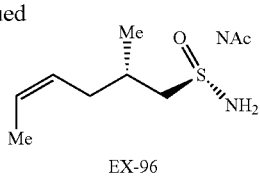

EX-96

A reactor was charged with ethyltriphenylphosphonium iodide (2.0 equiv.) and tetrahydrofuran (20 volumes). The reaction mixture was cooled to about −78° C. and n-hexyl-lithium (2.3 M in hexane, 2.0 equiv.) was added. The reaction mixture was warmed to about 20° C. and stirred for about 30 minutes. The reaction mixture was cooled to about −78° C. and EX-89 (1.0 equiv., scaling factor) was added as a solution in tetrahydrofuran (20 volumes). The reaction mixture was warmed to about 20° C. and stirred for about 1 hour. The reaction mixture was quenched with 5 wt % aqueous acetic acid (50 volumes) and ethyl acetate (100 volumes). The organic layer was washed with two portions of water (20 volumes), dried over sodium sulfate, filtered, and concentrated. The crude product was charged with dichloromethane (15 volumes) and trifluoroacetic acid (3 volumes). The reaction mixture was heated to about 40° C. and stirred for about 2 hours. The reaction mixture was concentrated. The crude product was diluted with 2-methyltetrahydrofuran (30 volumes) and the organic layer was extracted with three portions of 0.5 M aqueous sodium hydroxide (30 volumes). The combined aqueous layers were washed with methyl tert-butyl ether (20 volumes) and then acidified to pH 4 with acetic acid. The aqueous layer was extracted with three portions of ethyl acetate (50 volumes) and the combined organic layer were washed with two portions of water (10 volumes). The combined organic layers were dried over sodium sulfate, filtered, and concentrated and purified by chromatography using ethyl acetate, heptane, and acetic acid to afford EX-96. $^1$H NMR (400 MHz, CDCl$_3$) δ 5.68-5.55 (m, 1H), 5.36 (dtd, J=10.9, 7.3, 1.8 Hz, 1H), 3.34 (dd, J=14.3, 4.2 Hz, 1H), 3.26-3.11 (m, 1H), 2.33-2.12 (m, 3H), 2.11 (s, 3H), 1.61 (ddt, J=6.8, 1.8, 0.9 Hz, 3H), 1.17-1.09 (m, 3H).

Bromination of EX-96 and Subsequent Double Elimination to EX-97

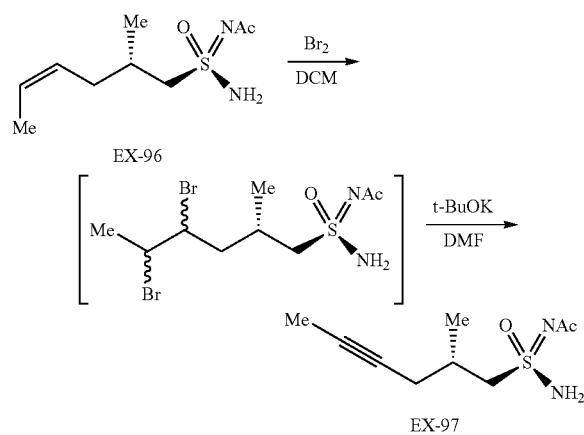

A reactor was charged with EX-96 (1.0 equiv., scaling factor) and dichloromethane (10 volumes). The reaction mixture was cooled to about −78° C. Bromine (1.2 equiv.) was added and the reaction mixture was warmed to about 0° C. The reaction mixture was stirred for about 30 minutes and then quenched with 10 wt % aqueous sodium thiosulfate (10 volumes). The mixture was further diluted with 5 wt % aqueous acetic acid (20 volumes) and the aqueous layer was extracted with three portions of dichloromethane (50 volumes). The combined organic layers were dried over sodium sulfate, filtered, and concentrated. The crude product was charged with dimethylformamide (10 volumes) and the reaction mixture was cooled to about 0° C. Potassium tert-butoxide (7.0 equiv.) was added in portions and the reaction mixture was warmed to about 20° C. The reaction mixture was stirred for about 1 hour and quenched with 5 wt % aqueous acetic acid (50 volumes). The aqueous layer was extracted with four portions of ethyl acetate (50 volumes). The combined organic layers were washed with three portions of 5 wt % aqueous lithium chloride (20 volumes), dried over sodium sulfate, filtered, and concentrated. The crude product was purified by chromatography using ethyl acetate, heptane, and acetic acid to afford EX-97. $^1$H NMR (400 MHz, CDCl$_3$) δ 3.53 (dd, J=14.4, 5.1 Hz, 1H), 3.27 (dd, J=14.3, 6.7 Hz, 1H), 2.37 (ddddd, J=13.8, 11.7, 6.8, 5.2, 2.0 Hz, 2H), 2.28-2.17 (m, 1H), 2.11 (s, 3H), 1.80 (t, J=2.4 Hz, 3H), 1.19 (d, J=6.6 Hz, 3H).

Oxidative Cleavage of EX-52 to EX-98

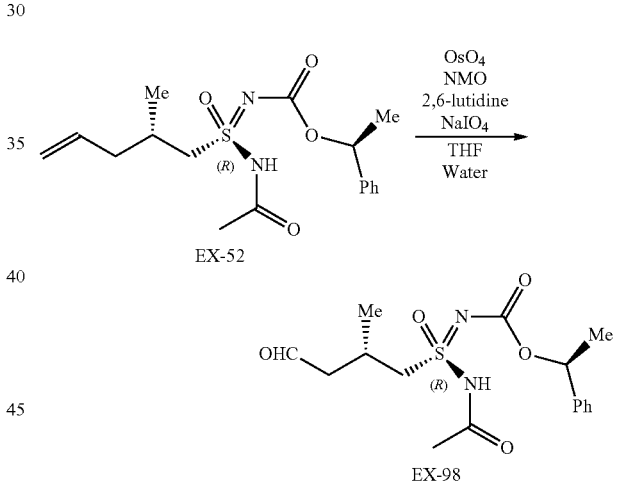

A reactor was charged with EX-52 (1.0 equiv., scaling factor), tetrahydrofuran:water (10:1 v/v, 10 volumes) and 4-methylmorpholine (1.5 equiv.). 2,6-lutidine (2.0 equiv.) and osmium tetraoxide (4 wt % in water, 0.02 equiv.) were added and the mixture was stirred at about 20° C. for about 18 hours. Sodium periodate (1.3 equiv.) was added and the mixture was stirred for about 30 minutes. The reaction mixture was diluted with 5 wt % aqueous acetic acid (15 volumes) and water (15 volumes) and the aqueous layer was extracted with five portions of ethyl acetate (15 volumes). The combined organic layers were washed with two portions of water (10 volumes), dried over sodium sulfate, filtered, concentrated and the crude product was purified by chromatography using ethyl acetate, heptane, and acetic acid to afford EX-98. $^1$H NMR (400 MHz, CDCl$_3$) δ 9.68 (s, 1H), 7.35 (dd, J=21.4, 4.7 Hz, 5H), 5.79 (q, J=6.5 Hz, 1H), 3.66 (s, 2H), 2.74 (s, 2H), 2.51 (t, J=10.9 Hz, 1H), 2.13 (d, J=9.1 Hz, 3H), 1.60 (d, J=6.6 Hz, 3H), 1.17 (d, J=6.6 Hz, 3H).

Wittig reaction of EX-98 with Ethyltriphenylphosphonium Iodide to EX-99

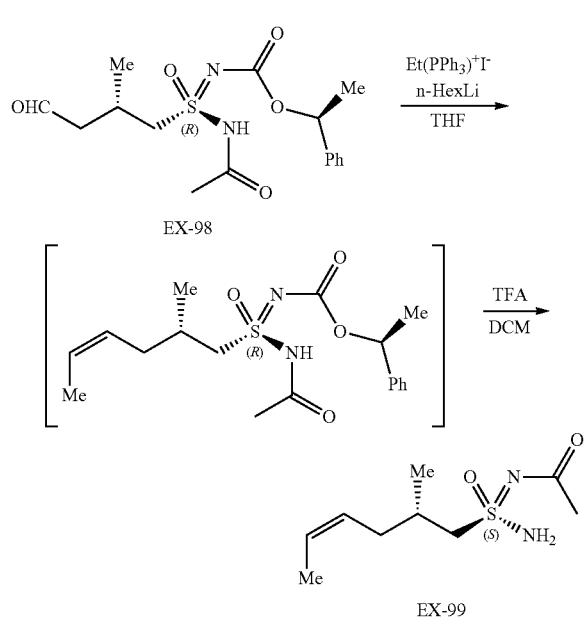

Bromination of EX-99 and Subsequent Double Elimination to EX-100

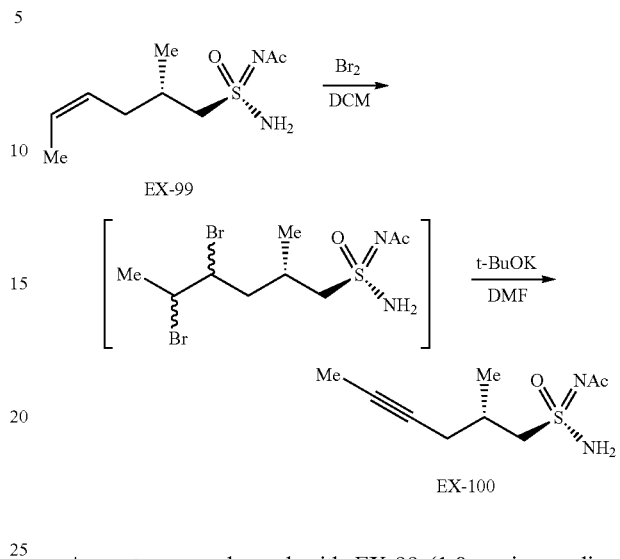

A reactor was charged with ethyltriphenylphosphonium iodide (2.0 equiv.) and tetrahydrofuran (30 volumes). The reaction mixture was cooled to about −78° C. and n-hexyllithium (2.3 M in hexane, 2.0 equiv.) was added. The reaction mixture was warmed to about 20° C. and stirred for about 30 minutes. The reaction mixture was cooled to about −78° C. and EX-98 (1.0 equiv., scaling factor) was added as a solution in tetrahydrofuran (30 volumes). The reaction mixture was warmed to about 20° C. and stirred for about 1 hour. The reaction mixture was quenched with 5 wt % aqueous acetic acid (30 volumes) and the aqueous layer was extracted with two portions of ethyl acetate (50 volumes). The organic layer was washed with two portions of water (15 volumes), dried over sodium sulfate, filtered, and concentrated. The crude product was charged with dichloromethane (12 volumes) and trifluoroacetic acid (3 volumes). The reaction mixture was heated to about 40° C. and stirred for about 2 hours. The reaction mixture was concentrated. The crude product was diluted with 2-methyltetrahydrofuran (10 volumes) and the organic layer was extracted with three portions of 0.5 M aqueous sodium hydroxide (15 volumes). The combined aqueous layers were washed with methyl tert-butyl ether (10 volumes) and then acidified to pH 4 with acetic acid. The aqueous layer was extracted with three portions of ethyl acetate (25 volumes) and the combined organic layer were washed with two portions of water (3 volumes). The combined organic layers were dried over sodium sulfate, filtered, concentrated and the crude product was purified by chromatography using ethyl acetate, heptane, and acetic acid to afford EX-99. $^1$H NMR (400 MHz, CDCl$_3$) δ 5.72 (s, 2H), 5.67-5.54 (m, 1H), 5.34 (dtd, J=10.7, 7.2, 1.8 Hz, 1H), 3.43 (dd, J=14.3, 4.4 Hz, 1H), 3.11 (dd, J=14.3, 7.4 Hz, 1H), 2.30-2.04 (m, 6H), 1.64-1.57 (m, 3H), 1.15 (d, J=6.5 Hz, 3H).

A reactor was charged with EX-99 (1.0 equiv., scaling factor) and dichloromethane (20 volumes). The reaction mixture was cooled to about −78° C. Bromine (1.2 equiv.) was added and the reaction mixture was warmed to about 0° C. The reaction mixture was stirred for about 30 minutes and then quenched with 10 wt % aqueous sodium thiosulfate (10 volumes). The mixture was further diluted with 5 wt % aqueous acetic acid (20 volumes) and the aqueous layer was extracted with three portions of dichloromethane (30 volumes). The combined organic layers were dried over sodium sulfate, filtered, and concentrated. The crude product was charged with dimethylformamide (30 volumes) and the reaction mixture was cooled to about 0° C. Potassium tert-butoxide (6.0 equiv.) was added in portions and the reaction mixture was warmed to about 20° C. The reaction mixture was stirred for about 1 hour and quenched with cold water (40 volumes) and 5 wt % aqueous acetic acid (60 volumes). The aqueous layer was extracted with three portions of ethyl acetate (60 volumes). The combined organic layers were washed with three portions of 5 wt % aqueous lithium chloride (30 volumes), dried over sodium sulfate, filtered, and concentrated. The crude product was purified by chromatography using ethyl acetate, heptane, and acetic acid to afford EX-100. $^1$H NMR (400 MHz, CDCl$_3$) δ 5.76 (s, 2H), 3.64 (dd, J=14.3, 6.0 Hz, 1H), 3.16 (dd, J=14.3, 6.3 Hz, 1H), 2.49-2.28 (m, 2H), 2.22 (ddq, J=16.1, 5.0, 2.5 Hz, 1H), 2.12 (s, 3H), 1.79 (t, J=2.5 Hz, 3H), 1.19 (d, J=6.7 Hz, 3H).

Coupling of EX-63 and EX-96 and Deprotection to EX-101

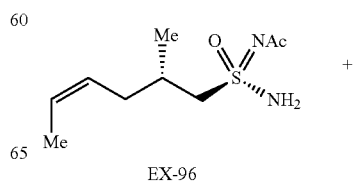

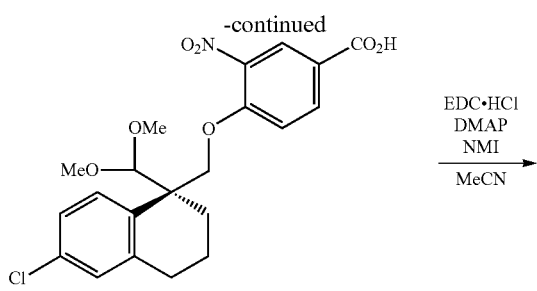

EX-63

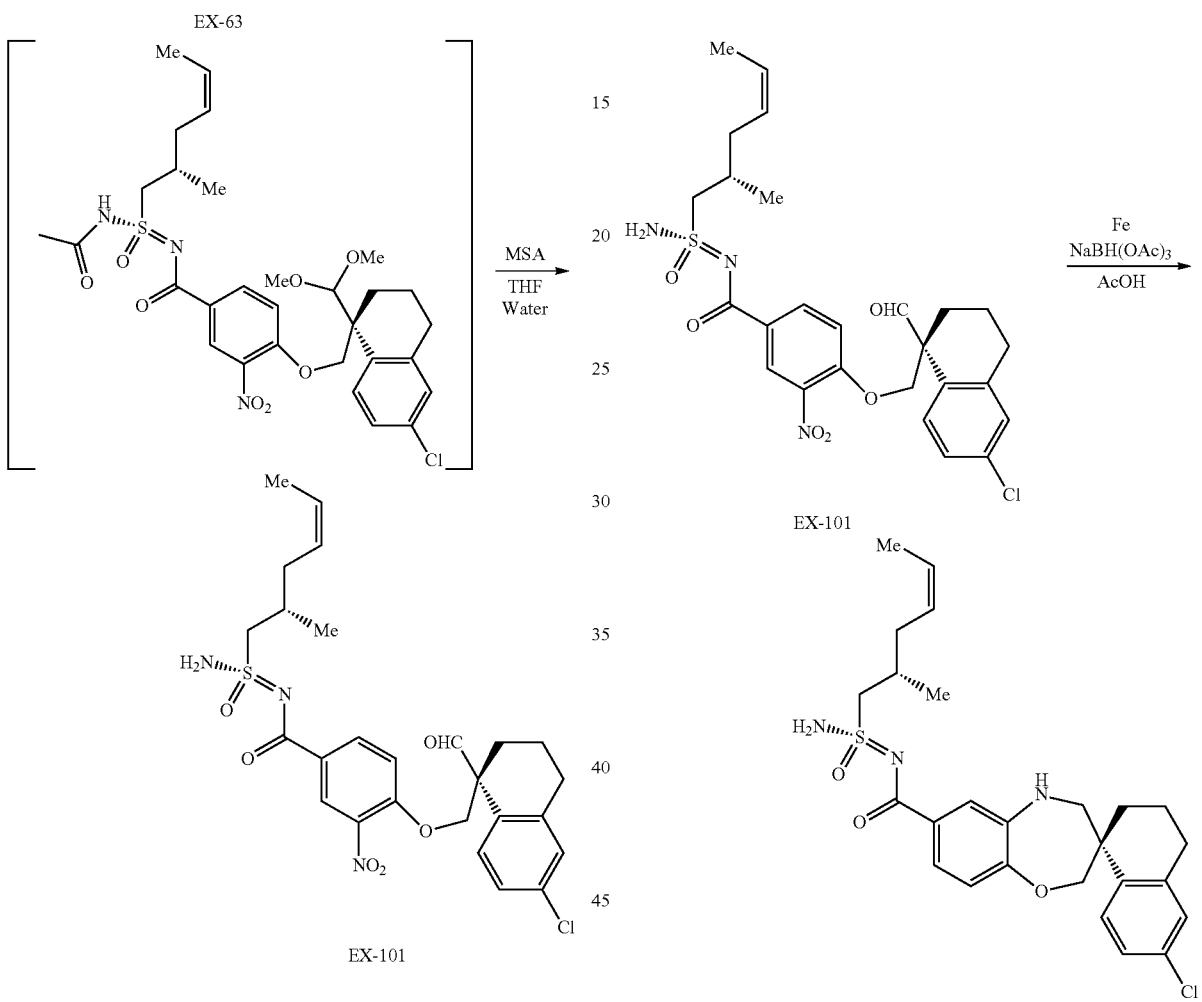

EX-101. ¹H NMR (400 MHz, CDCl₃) δ 9.56 (s, 1H), 8.62-8.50 (m, 1H), 8.30-8.19 (m, 1H), 7.24-7.02 (m, 4H), 5.71 (s, 2H), 5.67-5.58 (m, 1H), 5.37 (dtd, J=10.9, 7.4, 1.8 Hz, 1H), 4.57 (d, J=9.0 Hz, 1H), 4.25 (d, J=9.0 Hz, 1H), 3.44 (dd, J=14.3, 4.3 Hz, 1H), 3.39-3.23 (m, 1H), 2.86 (q, J=5.5 Hz, 2H), 2.37-2.08 (m, 5H), 1.95 (s, 2H), 1.64-1.56 (m, 3H), 1.13 (t, J=6.5 Hz, 3H).

Reductive Cyclization of EX-101 to EX-102

A reactor was charged with EX-63 (1.0 equiv., scaling factor), EDC.HCl (1.3 equiv.), DMAP (1.1 equiv.), acetonitrile (10 volumes), NMI (3.5 equiv.), and EX-96 (1.1 equiv.). The mixture was agitated at about 20° C. for about 3 hours. The mixture was diluted with ethyl acetate (10 volumes) and the organic layer was washed with 5 wt % aqueous acetic acid (5 volumes), 10% aqueous sodium hydroxide (5 volumes), and water (5 volumes). The organic layer was dried over sodium sulfate, filtered, and concentrated. The crude product was charged with 15 v/v % water in tetrahydrofuran (10 volumes). The solution was charged with methanesulfonic acid (2 volumes) and agitated at about 65° C. for about 2 hours. The reaction mixture was cooled to about 20° C. and diluted with ethyl acetate (60 volumes). The organic layer was washed with three portions of water (10 volumes). The organic layer was dried over sodium sulfate, filtered, and concentrated to dryness. The crude product was purified by chromatography using ethyl acetate and heptane to afford A reactor was charged with EX-101 (1.0 equiv., scaling factor), iron (10.0 equiv.), and acetic acid (10 volumes). The mixture was agitated at about 70° C. for about 1 hour. The reaction mixture was cooled to about 20° C. and charged with sodium triacetoxyborohydride (3.0 equiv.). The mixture was agitated at about 20° C. for approximately 30 minutes. The reaction mixture was diluted with ethyl acetate (100 volumes) and filtered through Celite. The organic layer was washed with two portions of water (25 volumes). The organic layer was dried over sodium sulfate, filtered, concentrated to dryness and the crude product was purified by chromatography using ethyl acetate and heptane to afford EX-102. ¹H NMR (400 MHz, CDCl₃) δ 7.87 (d, J=8.5 Hz, 1H), 7.51 (dd, J=8.3, 2.0 Hz, 1H), 7.46 (d, J=2.0 Hz, 1H), 7.16 (dd, J=8.5, 2.4 Hz, 1H), 7.07 (d, J=2.3 Hz, 1H), 6.89 (d, J=8.3 Hz, 1H), 5.82-5.67 (m, 2H), 5.67-5.55 (m, 1H), 5.43-5.28 (m, 1H), 4.25-4.07 (m, 2H), 3.50-3.37 (m, 2H), 3.37-3.25 (m, 2H), 2.73 (t, J=6.2 Hz, 2H), 2.37-2.26 (m, 1H), 2.17 (dtd, J=27.4, 13.8, 13.2, 6.7 Hz, 2H), 1.95-1.72 (m, 3H), 1.72-1.64 (m, 1H), 1.64-1.57 (m, 3H), 1.14 (d, J=6.7 Hz, 3H).

Coupling of EX-102 and EX-11 to EX-103

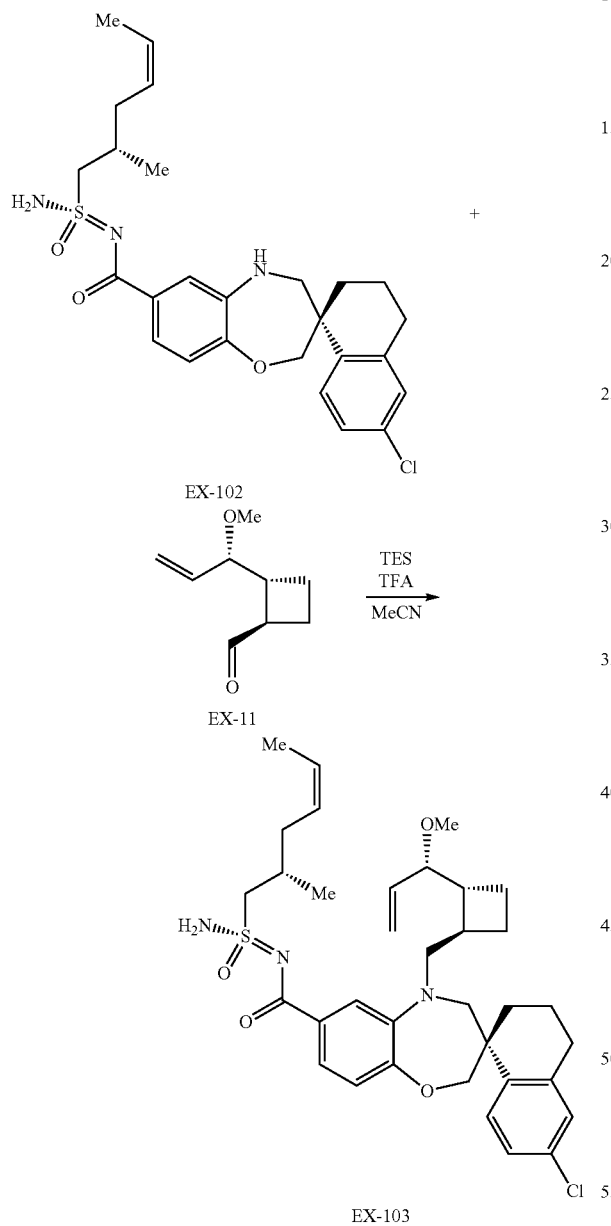

5.58-5.51 (m, 1H), 5.41-5.32 (m, 1H), 5.19 (d, J=2.7 Hz, 1H), 5.16 (d, J=10.1 Hz, 1H), 4.11 (d, J=12.2 Hz, 1H), 4.05 (d, J=11.9 Hz, 1H), 3.64 (d, J=10.5 Hz, 1H), 3.60 (d, J=9.9 Hz, 1H), 3.50 (d, J=7.8 Hz, 1H), 3.47-3.38 (m, 1H), 2.76 (q, J=6.0, 5.5 Hz, 2H), 7.68 (d, J=8.4 Hz, 1H), 7.60-7.47 (m, 2H), 7.16 (dd, J=8.5, 2.4 Hz, 1H), 7.08 (d, J=2.4 Hz, 1H), 6.90 (d, J=8.2 Hz, 1H), 3.38-3.18 (m, 6H), 2.57-2.48 (m, 1H), 2.31 (q, J=6.3 Hz, 1H), 2.16 (ddt, J=36.2, 16.1, 7.6 Hz, 4H), 2.01 (dt, J=19.7, 7.3 Hz, 2H), 1.86 (s, 1H), 1.80-1.72 (m, 1H), 1.67 (d, J=9.1 Hz, 1H), 1.60 (s, 3H), 1.58-1.47 (m, 2H), 1.16 (dd, J=6.7, 3.7 Hz, 4H).

Coupling of EX-103 and EX-72 to EX-104

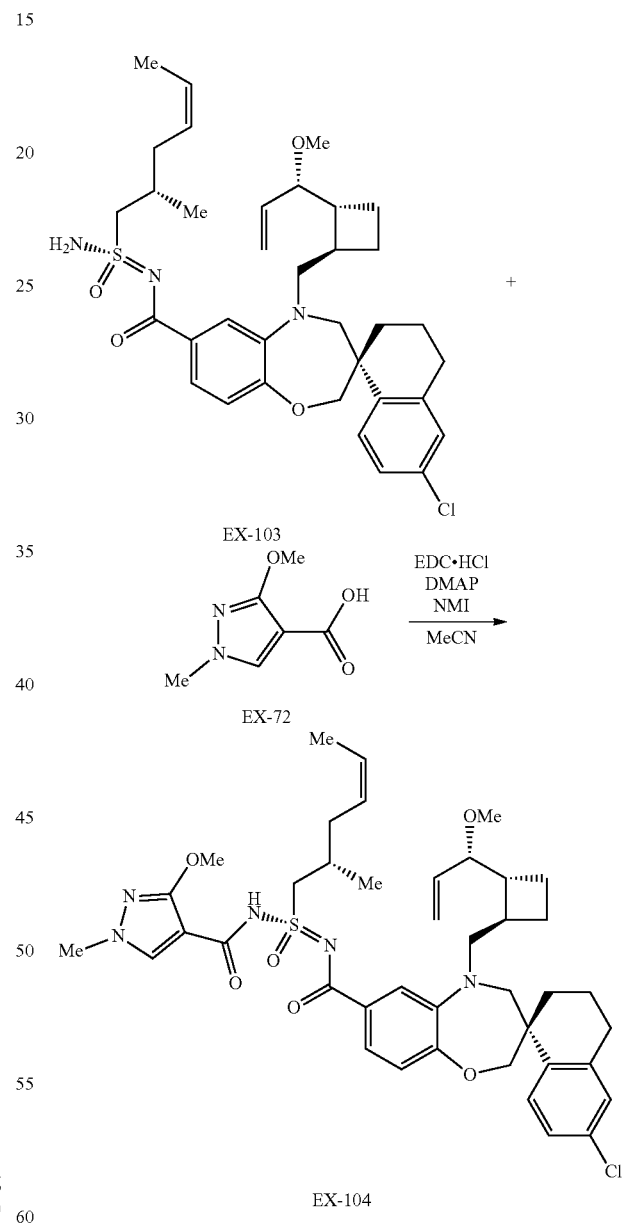

A reactor was charged with EX-102 (1.0 equiv., scaling factor), EX-11 (1.4 equiv.), magnesium sulfate (200 wt %) and acetonitrile (10 volumes). The reaction mixture was charged with triethylsilane (2.0 equiv.) and TFA (2.0 equiv.) and agitated at about 20° C. for about 5 hours. The reaction mixture was filtered through Celite, concentrated and the crude product was purified by chromatography using ethyl acetate and heptane to afford EX-103. ¹H NMR (400 MHz, CDCl₃) δ 5.69 (d, J=31.4 Hz, 1H), 5.65-5.58 (m, 1H), A reactor was charged with EX-103 (1.0 equiv., scaling factor), EDC.HCl (1.2 equiv.), DMAP (1.0 equiv.), acetonitrile (10 volumes), NMI (3.0 equiv.), and EX-72 (1.2 equiv.). The mixture was agitated at about 20° C. for about 15 hours. The mixture was diluted with ethyl acetate (100 volumes) and the organic layer was washed with 5 wt % aqueous acetic acid (30 volumes) and water (15 volumes). The organic layer was dried over sodium sulfate, filtered, concentrated and the crude product was purified by chromatography using dichloromethane and methanol to afford EX-104. ¹H NMR (400 MHz, CDCl₃) δ 7.77 (s, 1H), 7.68 (d, J=8.5 Hz, 1H), 7.57-7.47 (m, 2H), 7.16 (dd, J=8.5, 2.3 Hz, 1H), 7.08 (d, J=2.3 Hz, 1H), 6.91 (d, J=8.2 Hz, 1H), 5.66-5.48 (m, 2H), 5.38 (dtd, J=10.9, 7.3, 1.8 Hz, 1H), 5.21-5.10 (m, 2H), 4.13 (d, J=11.9 Hz, 1H), 4.07 (d, J=8.5 Hz, 4H), 3.84 (dd, J=14.3, 4.7 Hz, 1H), 3.78 (s, 4H), 3.64-3.54 (m, 2H), 3.46 (t, J=7.9 Hz, 1H), 3.37-3.22 (m, 5H), 2.77 (t, J=5.0 Hz, 2H), 2.51 (td, J=8.5, 4.0 Hz, 1H), 2.40 (dq, J=13.3, 6.8 Hz, 1H), 2.27 (dt, J=14.0, 6.7 Hz, 1H), 2.20-1.95 (m, 4H), 1.87 (s, 2H), 1.73 (dq, J=35.2, 9.1, 8.5 Hz, 2H), 1.62-1.47 (m, 5H), 1.15 (d, J=6.7 Hz, 3H).

Ring Closing Metathesis of EX-104 to Compound 1

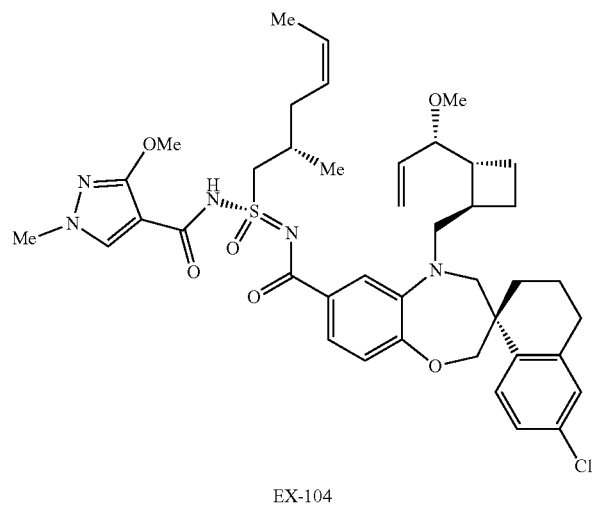

EX-104

Hydrosilylation of EX-100 to EX-105

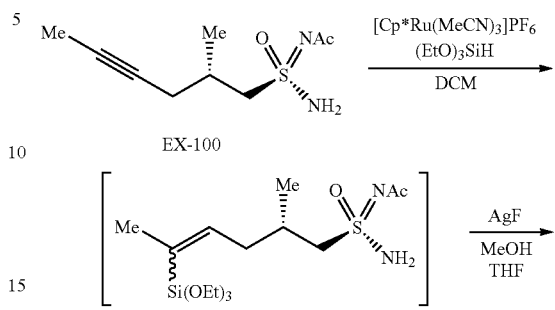

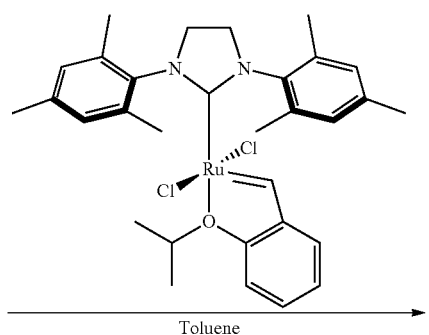

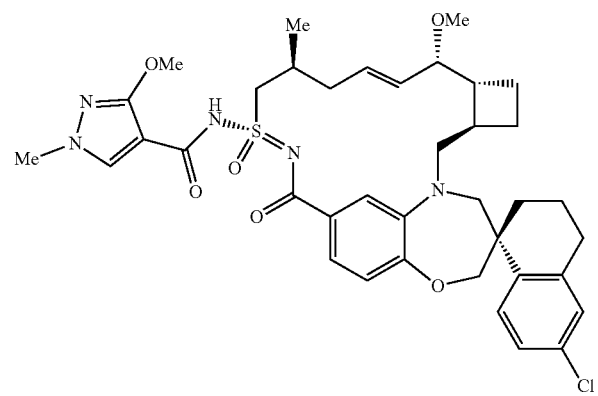

COMPOUND 1

A reactor was charged with EX-104 (1.0 equiv., scaling factor), Hoveyda Grubbs II catalyst (0.10 equiv.) and toluene (200 volumes). The contents were heated to about 80° C. and agitated for about 30 minutes. The reaction mixture was cooled to about 20° C. and acetonitrile (50 volumes) was charged. The contents were concentrated and purified by chromatography using dichloromethane and methanol to afford Compound 1.

-continued

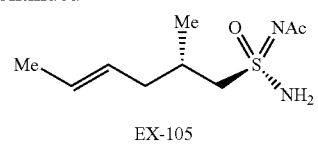

EX-105

A reactor was charged with EX-100 (1.0 equiv., scaling factor), tris(acetonitrile)cyclopenta-dienylruthenium(II) hexafluorophosphate (0.05 equiv.), and dichloromethane (10 volumes). The reaction mixture was cooled to about 0° C. and triethoxysilane (1.3 equiv.) was added. The reaction mixture was stirred for about 15 minutes and tris(hydroxymethyl)phosphine (0.5 equiv.) was added. The reaction mixture was warmed to about 20° C. and stirred for about 15 minutes. Florisil (500 mass %) was added, the reaction mixture was filtered, and the filtrate was concentrated. The crude product was charged in 1:1 v/v tetrahydrofuran:methanol (20 volumes) and silver fluoride (2.5 equiv.) was added. The reaction mixture was stirred for about 3 hours and N-acetyl-L-cysteine (5 equiv.) and water (20 volumes) were added. The reaction mixture was diluted with ethyl acetate (100 volumes) and filtered through Celite. The filtrate was washed with 5 wt % aqueous acetic acid (50 volumes). The organic layer was dried over sodium sulfate, filtered, and concentrated. The crude product was purified by chromatography using ethyl acetate, heptane, and acetic acid to afford EX-105. $^1$H NMR (400 MHz, CDCl$_3$) δ 5.88-5.58 (m, 2H), 5.49 (dt, J=14.7, 6.6 Hz, 1H), 5.45-5.28 (m, 1H), 3.44 (ddd, J=14.4, 4.7, 2.3 Hz, 1H), 3.06 (ddd, J=14.2, 7.6, 2.2 Hz, 1H), 2.20 (dd, J=13.0, 6.6 Hz, 1H), 2.10 (d, J=2.2 Hz, 5H), 1.66 (d, J=6.4 Hz, 3H), 1.12 (dd, J=6.7, 2.3 Hz, 3H).

Coupling of EX-100 and EX-60 to EX-106

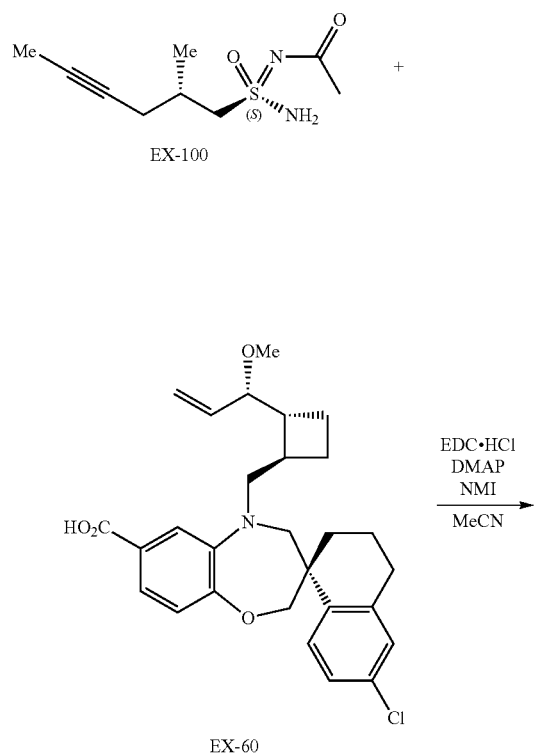

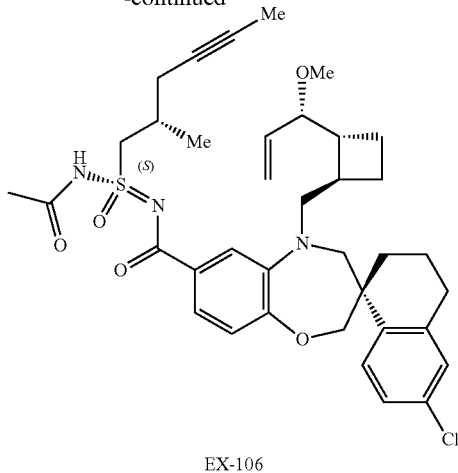

A reactor was charged with EX-60 (1.0 equiv., scaling factor), EDC.HCl (1.3 equiv.), DMAP (1.1 equiv.), acetonitrile (10 volumes), NMI (3.5 equiv.), and EX-100 (1.1 equiv.). The mixture was agitated at about 20° C. for about 3 hours. The mixture was diluted with ethyl acetate (10 volumes) and the organic layer was washed with 5 wt % aqueous acetic acid (30 volumes). The organic layer was dried over sodium sulfate, filtered, and concentrated to afford EX-106. $^1$H NMR (400 MHz, CDCl$_3$) δ 7.69 (d, J=8.5 Hz, 1H), 7.47 (s, 1H), 7.44-7.37 (m, 1H), 7.16 (dd, J=8.5, 2.4 Hz, 1H), 7.12 (s, OH), 7.08 (d, J=2.3 Hz, 1H), 6.91 (d, J=8.2 Hz, 1H), 5.64-5.51 (m, 1H), 5.23-5.13 (m, 2H), 4.17-4.04 (m, 2H), 3.92 (dd, J=14.4, 5.1 Hz, 1H), 3.74-3.58 (m, 3H), 3.51 (t, J=8.0 Hz, 1H), 3.29 (s, 5H), 2.76 (q, J=6.0, 5.5 Hz, 2H), 2.52 (td, J=8.4, 3.7 Hz, 1H), 2.47-2.34 (m, 2H), 2.33-2.23 (m, 1H), 2.21 (s, 3H), 2.15-2.07 (m, 1H), 2.07-1.95 (m, 2H), 1.91-1.77 (m, 5H), 1.61 (ddt, J=40.5, 17.4, 9.0 Hz, 4H), 1.30-1.18 (m, 3H).

Hydrosilylation of EX-106 and Deprotection to EX-107

A reactor was charged with EX-106 (1.0 equiv., scaling factor), tris(acetonitrile)cyclopenta-dienylruthenium(II) hexafluorophosphate (0.05 equiv.), and dichloromethane (10 volumes). The reaction mixture was cooled to about 0° C. and triethoxysilane (1.3 equiv.) was added. The reaction mixture was stirred for about 30 minutes and tris(hydroxymethyl)phosphine (0.5 equiv.) was added. The reaction mixture was warmed to about 20° C. and stirred for about 1 hour. Florisil (300 mass %) was added, the reaction mixture was filtered, and the filtrate was concentrated. The crude product was charged in 1:1 v/v tetrahydrofuran:methanol (20 volumes) and silver fluoride (3.5 equiv.) was added. The reaction mixture was stirred for about 5 hours and N-acetyl-L-cysteine (5.0 equiv.) and water (30 volumes) were added. The reaction mixture was diluted with ethyl acetate (30 volumes) and filtered through Celite. The filtrate was washed with 5 wt % aqueous acetic acid (30 volumes) and saturated aqueous sodium chloride (30 volumes). The aqueous layer was extracted with three portions of ethyl acetate (100 volumes). The combined organic layers were dried over sodium sulfate, filtered, and concentrated. The crude product was diluted with 2-propanol (50 volumes), and sodium isopropoxide (20 wt % in tetrahydrofuran, 55 volumes). The reaction mixture was heated to about 60-70° C.

and stirred for about 9 hours. The reaction mixture was cooled to about 20° C. and diluted with ethyl acetate (250 volumes). The pH was adjusted to about 4 with acetic acid and the aqueous layer was extracted with ethyl acetate (50 volumes). The combined organic layers were washed with water (50 volumes), dried over sodium sulfate, filtered, and concentrated. The crude product was purified by chromatography using ethyl acetate and heptane to afford EX-107. $^1$H NMR (400 MHz, CDCl$_3$) δ 7.68 (d, J=8.5 Hz, 1H), 7.57-7.47 (m, 2H), 7.16 (dd, J=8.5, 2.4 Hz, 1H), 7.08 (d, J=2.3 Hz, 1H), 6.90 (d, J=8.2 Hz, 1H), 5.64-5.43 (m, 2H), 5.36 (dt, J=15.1, 7.0 Hz, 1H), 5.22-5.12 (m, 2H), 4.11 (d, J=12.0 Hz, 1H), 4.05 (d, J=11.9 Hz, 1H), 3.62 (dd, J=14.5, 10.7 Hz, 2H), 3.53-3.39 (m, 2H), 3.34 (s, 1H), 3.30 (s, 3H), 3.28-3.21 (m, 2H), 2.76 (q, J=5.9, 5.4 Hz, 2H), 2.57-2.48 (m, 1H), 2.33-2.25 (m, 1H), 2.22-2.02 (m, 4H), 2.02-1.94 (m, 2H), 1.87 (s, 1H), 1.83-1.54 (m, 7H), 1.13 (d, J=6.8 Hz, 3H).

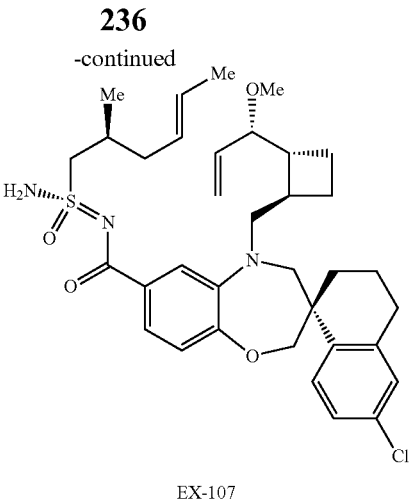

EX-107

Coupling of EX-107 and EX-72 to EX-108

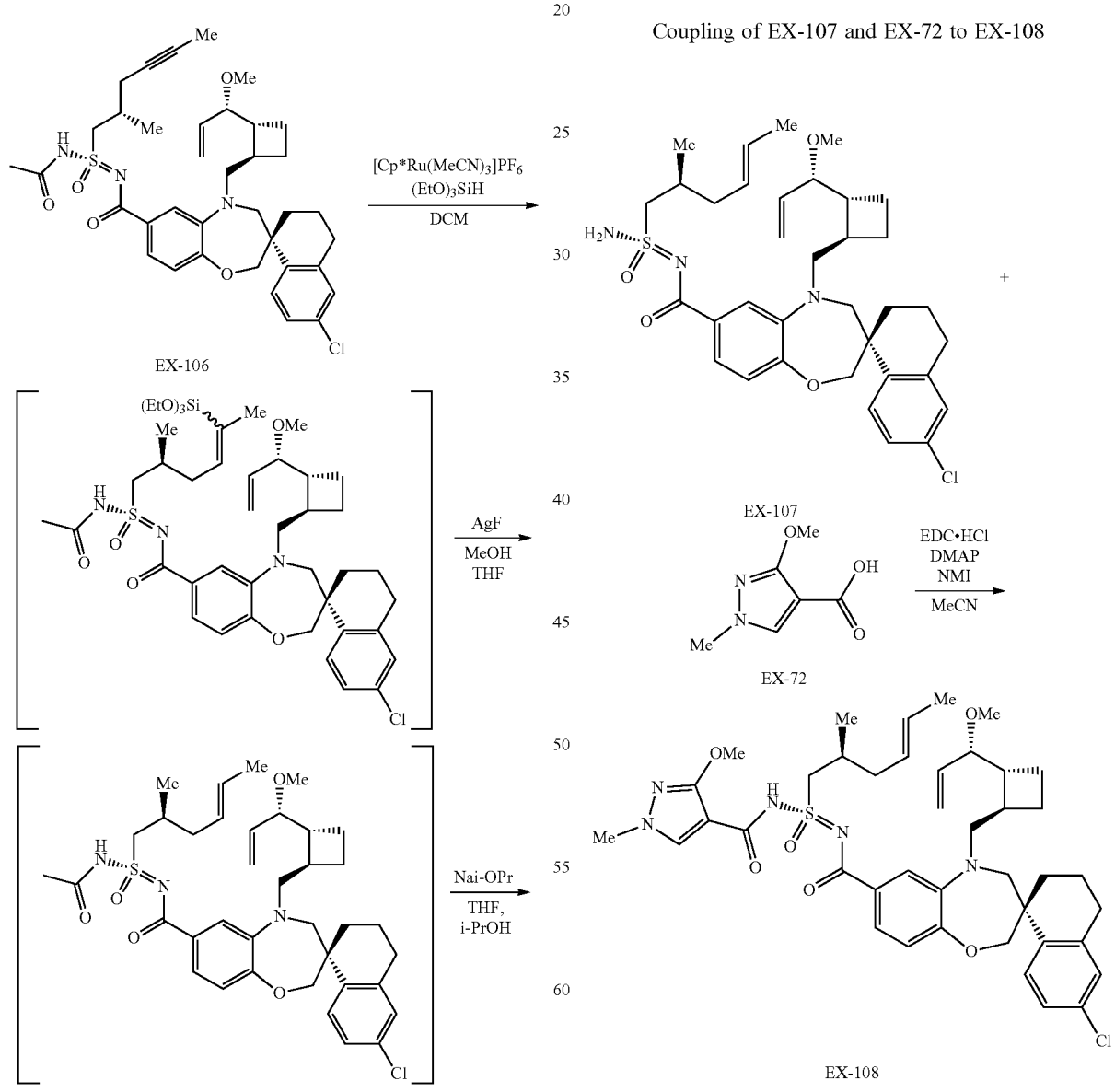

A reactor was charged with EX-107 (1.0 equiv., scaling factor), EDC.HCl (1.2 equiv.), DMAP (1.0 equiv.), acetonitrile (20 volumes), NMI (3.0 equiv.), and EX-72 (1.2 equiv.). The mixture was agitated at about 20° C. for about 15 hours. The mixture was diluted with ethyl acetate (300 volumes) and the organic layer was washed with 5 wt % aqueous acetic acid (50 volumes), dried over sodium sulfate, filtered, and concentrated. The crude product was purified by chromatography using dichloromethane and methanol to afford EX-108. $^1$H NMR (400 MHz, CDCl$_3$) δ 7.76 (d, J=8.8 Hz, 1H), 7.68 (d, J=8.5 Hz, 1H), 7.56-7.46 (m, 2H), 7.16 (dd, J=8.5, 2.4 Hz, 1H), 7.08 (d, J=2.4 Hz, 1H), 6.90 (d, J=8.2 Hz, 1H), 5.61-5.42 (m, 2H), 5.42-5.28 (m, 1H), 5.21-5.10 (m, 2H), 4.13 (d, J=12.0 Hz, 1H), 4.10-4.03 (m, 4H), 3.83 (dd, J=14.3, 4.5 Hz, 1H), 3.78 (s, 3H), 3.69 (dd, J=14.3, 7.9 Hz, 1H), 3.64-3.54 (m, 2H), 3.46 (t, J=7.9 Hz, 1H), 3.37-3.24 (m, 5H), 2.77 (s, 2H), 2.51 (d, J=4.0 Hz, 1H), 2.36 (q, J=6.4 Hz, 1H), 2.13 (dt, J=16.4, 7.4 Hz, 3H), 2.00 (s, 1H), 1.87 (s, 1H), 1.76 (t, J=8.9 Hz, 1H), 1.71-1.63 (m, 4H), 1.56 (d, J=29.1 Hz, 4H), 1.13 (d, J=6.8 Hz, 3H).

Ring Closing Metathesis of EX-108 to Compound 1

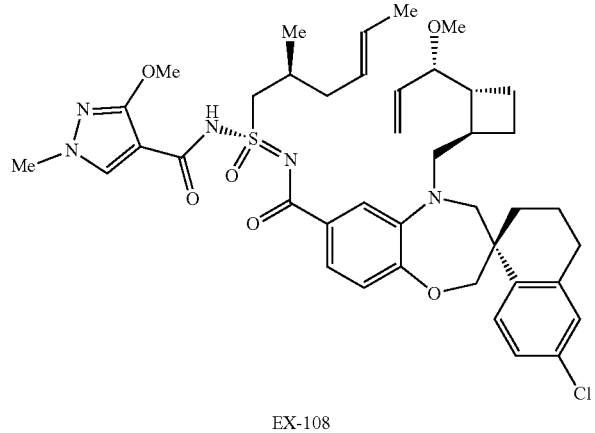

EX-108

A reactor was charged with EX-108 (1.0 equiv., scaling factor), Hoveyda Grubbs II catalyst (0.10 equiv.) and toluene (200 volumes). The contents were heated to about 80° C. and agitated for about 30 minutes. The reaction mixture was cooled to about 20° C. and acetonitrile (50 volumes) was charged. The contents were concentrated and purified by chromatography using dichloromethane and methanol to afford Compound 1.

Esterification of EX-132 to EX-133

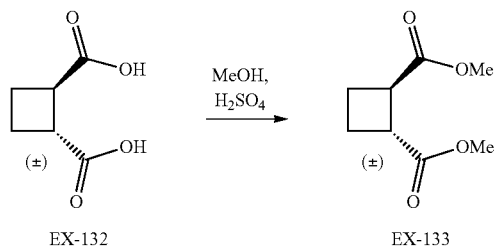 [SMILES: O=C(O)[C@@H]1CC[C@H]1C(=O)O ; COC(=O)[C@@H]1CC[C@H]1C(=O)OC]

EX-132          EX-133

A reaction vessel was charged with EX-132 (1.0 equiv, scaling factor), methanol (5 volumes, and sulfuric acid (0.02 volumes). The resulting solution was then warmed to about

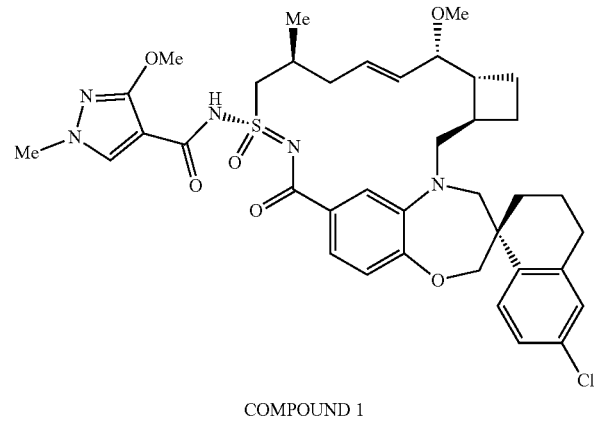

COMPOUND 1

60° C. and stirred overnight. The reaction mixture was concentrated to dryness under vacuum. The residue was then diluted with methyl tert-butyl ether (5 volumes) followed by the addition of ~0.5 M potassium carbonate (5 volumes). The layers were separated, the organic layer was washed with saturated sodium chloride (2.5 volumes), then dried over magnesium sulfate. The drying agent was removed via filtration then the filtrate was concentrated and purified on silica gel affording EX-133. $^1$H NMR (300 MHz, Chloroform-d) δ 3.68 (s, 6H), 3.44-3.38 (m, 2H), 2.18-2.16 (m, 4H)

Enzymatic Hydrolysis of EX-133 to EX-134

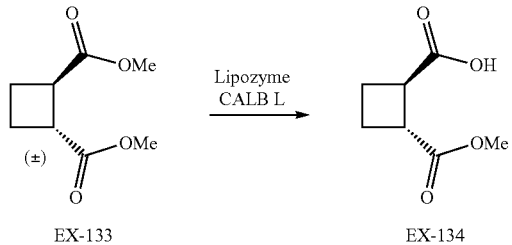 [SMILES: COC(=O)[C@@H]1CC[C@H]1C(=O)OC ; COC(=O)[C@@H]1CC[C@H]1C(=O)O]

A reactor was charged with EX-133 (1.0 equiv, scaling factor), acetone (2 volumes), 0.1 M pH 7 phosphate buffer (18 volumes), and Lipozyme CALB L (0.05 volumes). The reaction mixture was warmed to 30° C. and the pH was maintained between 7.0-7.5 via the addition of 1 N NaOH. After about 4 h, the reaction mixture was diluted with methyl tert-butyl ether (10 volumes) and the layers were separated. The aqueous layer was back-extracted with methyl tert-butyl ether (5 volumes). The organic layers were combined and washed with 0.5 M potassium carbonate (5 V). The aqueous layer was separated then adjusted to ~pH 1 with concentrated HCl (1 volumes). The aqueous layer was extracted twice with ethyl acetate (5 volumes), the organic layer was washed with saturated sodium chloride (5 volumes), then dried over magnesium sulfate. The drying agent was removed via filtration then the filtrate was concentrated to dryness under vacuum affording EX-134. $^1$H NMR (300 MHz, Chloroform-d) δ 3.70 (s, 3H), 3.47-3.41 (m, 2H), 2.25-2.16 (m, 4H).

Reduction of EX-134 to EX-1

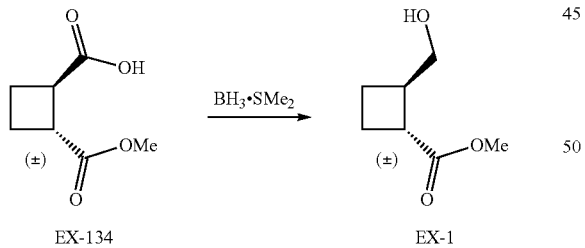

To a reactor was charged with EX-134 (1.0 equiv, scaling factor) and 2-methyltetrahydrofuran (10 volumes). The resulting solution was cooled to about 0° C. followed by the addition of borane dimethyl sulfide complex in tetrahydrofuran (1.5 equiv) at such a rate to maintain the internal temperature below about 10° C. Once the addition was complete, the reaction mixture was warmed to about room temperature and stirred for about 1 h. The reaction mixture was quenched by the slow addition of 3 M aqueous HCl (5 equiv) followed by the addition of saturated sodium chloride (3.3 volumes) and ethyl acetate (10 volumes). The biphasic reaction mixture was then gently warmed, and the layers were separated. The aqueous layer was back-extracted with ethyl acetate (5 volumes), the organic layers were combined, dried over magnesium sulfate. The drying agent was removed via filtration, the filtrate was concentrated and purified on silica gel affording EX-1. $^1$H NMR (300 MHz, Chloroform-d) δ 3.68-3.57 (m, 5H), 2.94 (q, J=9.0 Hz, 1H), 2.79-2.67 (m, 1H), 2.25-2.02 (m, 2H), 1.97-1.86 (m, 1H), 1.79-1.66 (m, 2H).

What is claimed is:

1. A method comprising converting a compound of formula 10-E, or a salt thereof, to a compound of formula 9-B, or a salt thereof:

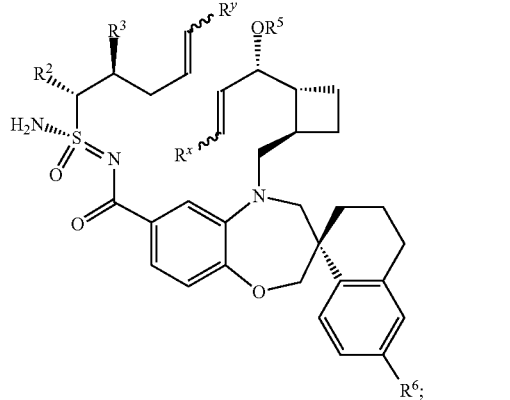

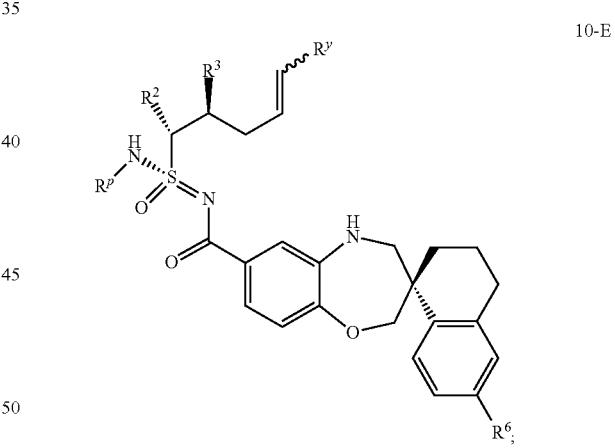

wherein $R^2$ and $R^3$ are independently H or $C_{1-6}$alkyl;

$R^5$ is $C_{1-6}$ alkyl;

$R^6$ is halogen;

wherein $R^x$ and $R^y$ are each independently H or $C_{1-6}$ alkyl; and wherein $R^p$ is H.

2. The method of claim 1, further comprising converting a compound of formula 10-C, or a salt thereof to the compound of formula 10-E, or a salt thereof:

10-E
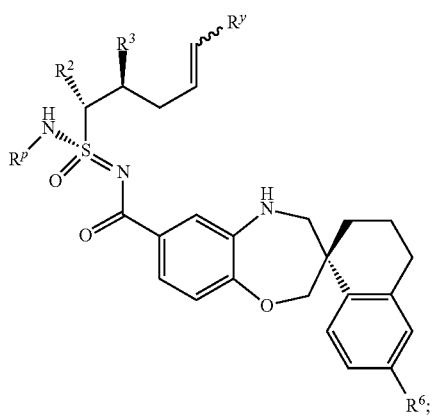
3. The method of claim 1, wherein 10-E is selected from
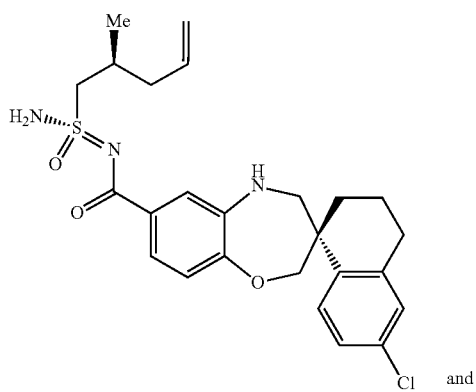
and
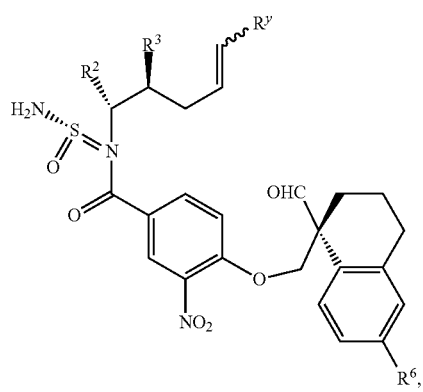
or a salt thereof.
4. A method comprising converting a compound of formula 10-B, or a salt thereof to a compound of formula 10-E, or a salt thereof:
10-C
10-E
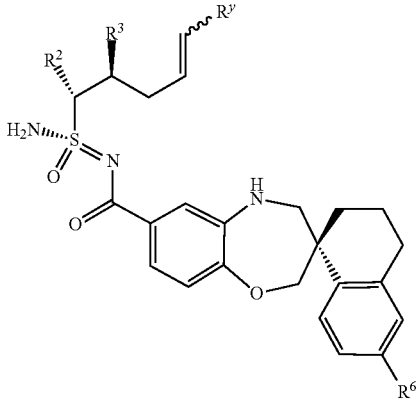
10-B
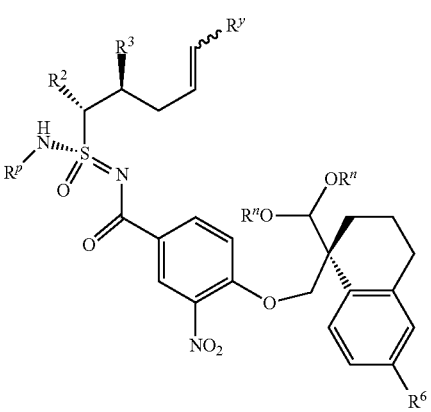
wherein $R^p$ is H;
wherein $R^y$ is H;
wherein $R^2$ and $R^3$ are independently H or $C_{1-6}$alkyl; and
wherein $R^6$ is halogen; and wherein each R" is independently $C_{1-6}$ alkyl, or the two R" moieties join together to form a $C_{2-4}$ alkyl bridge, wherein the bridge is optionally substituted by one to four groups independently selected from $C_{1-3}$ alkyl and phenyl.

5. The method of claim 1, wherein $R^2$ is H.
6. The method of claim 1, wherein $R^3$ is methyl.
7. The method of claim 1, wherein $R^5$ is methyl.
8. The method of claim 1, wherein $R^6$ is chloro.
9. The method of claim 4, wherein $R^2$ is H.
10. The method of claim 4, wherein $R^3$ is methyl.
11. The method of claim 4, wherein $R^6$ is chloro.
12. A method of preparing formula 10-B comprising reacting formula 10-A, or a salt thereof with formula 5-E, or a salt thereof:

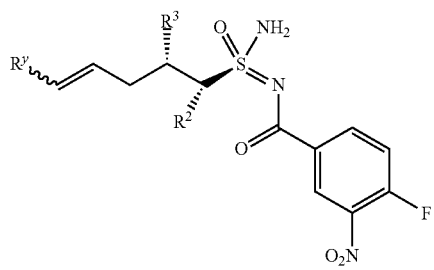

10-A

5-E

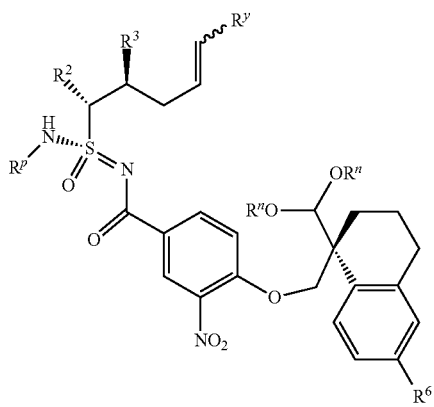

10-B wherein each R" is independently $C_{1-6}$ alkyl, or the two R" moieties join together to form a $C_{2-4}$ alkyl bridge, wherein the bridge is optionally substituted by one to four groups independently selected from $C_{1-3}$ alkyl and phenyl;
wherein $R^p$ is H;
wherein $R^y$ is H;
wherein $R^2$ and $R^3$ are independently H or $C_{1-6}$ alkyl; and
wherein $R^6$ is halogen.

13. The method of claim 12, wherein $R^2$ is H.
14. The method of claim 12, wherein $R^3$ is methyl.
15. The method of claim 12, wherein $R^6$ is chloro.

* * * * *